(12) United States Patent
Matsui et al.

(10) Patent No.: US 8,481,696 B2
(45) Date of Patent: Jul. 9, 2013

(54) GLYCOSYLATED GLYCOPEPTIDE ANTIBIOTIC DERIVATIVES

(75) Inventors: Kouhei Matsui, Osaka (JP); Kazuyuki Minagawa, Osaka (JP); Osamu Yoshida, Osaka (JP); Kenji Morimoto, Osaka (JP); Yuuki Ogata, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 339 days.

(21) Appl. No.: 12/810,507

(22) PCT Filed: Dec. 25, 2008

(86) PCT No.: PCT/JP2008/073511
§ 371 (c)(1),
(2), (4) Date: Jun. 24, 2010

(87) PCT Pub. No.: WO2009/081958
PCT Pub. Date: Jul. 2, 2009

(65) Prior Publication Data
US 2010/0286364 A1 Nov. 11, 2010

(30) Foreign Application Priority Data
Dec. 26, 2007 (JP) ................... 2007-333408

(51) Int. Cl.
*A61K 31/7032* (2006.01)
*A61K 31/7048* (2006.01)
*C07H 15/203* (2006.01)
*C07H 15/24* (2006.01)

(52) U.S. Cl.
USPC ............... 536/6.5; 514/25; 514/31; 536/16.8; 536/17.4

(58) Field of Classification Search
None
See application file for complete search history.

(56) References Cited

U.S. PATENT DOCUMENTS

| | | | |
|---|---|---|---|
| 4,497,802 | A | 2/1985 | Debono |
| 4,639,433 | A | 1/1987 | Hunt et al. |
| 4,643,987 | A | 2/1987 | Nagarajan et al. |
| 4,698,327 | A | 10/1987 | Nagarajan et al. |
| 5,591,714 | A | 1/1997 | Nagarajan et al. |
| 5,840,684 | A | 11/1998 | Cooper et al. |
| 5,843,889 | A | 12/1998 | Cooper et al. |
| 2003/0068669 | A1 | 4/2003 | Thorson |
| 2004/0259228 | A1 | 12/2004 | Thorson |
| 2005/0239689 | A1 | 10/2005 | Thorson |
| 2005/0266523 | A1 | 12/2005 | Thorson |

FOREIGN PATENT DOCUMENTS

| | | |
|---|---|---|
| EP | 0 273 727 A2 | 7/1988 |
| EP | 0 287 110 A2 | 10/1988 |
| EP | 0 301 785 A2 | 2/1989 |
| EP | 0 435 503 B1 | 7/1991 |
| EP | 0 801 075 A1 | 10/1997 |
| EP | 0 802 199 B1 | 12/1999 |
| EP | 0 667 353 B1 | 10/2003 |
| EP | 1 818 340 A1 | 8/2007 |
| JP | 1-240196 | 9/1989 |
| JP | 2000-302687 | 10/2000 |
| JP | 2001-163898 | 6/2001 |
| JP | 2003-26725 | 1/2003 |
| WO | WO 93/03060 | 2/1993 |
| WO | WO 96/30401 | 10/1996 |
| WO | WO 97/28812 | 8/1997 |
| WO | WO 97/38702 | 10/1997 |
| WO | WO 98/52589 | 11/1998 |
| WO | WO 98/52592 | 11/1998 |
| WO | WO 00/04044 | 1/2000 |
| WO | WO 00/39156 | 7/2000 |
| WO | WO 00/41710 | 7/2000 |
| WO | WO 00/42067 | 7/2000 |
| WO | WO 00/59528 | 10/2000 |
| WO | WO 00/69893 | 11/2000 |
| WO | WO 01/81372 A2 | 11/2001 |
| WO | WO 01/81373 A2 | 11/2001 |

(Continued)

OTHER PUBLICATIONS

Yoshida et al., "Novel Semi-Synthetic Glycopeptide Antibiotics Active Against Methicillin-Resistant *Staphylococcus aureus* (MRSA) and Vancomycin-Resistant Enterococci (VRE): Doubly-Modified Water-Soluble Derivatives of Chloroorienticin B" Bioorganic and Medicinal Chemistry Letters (2002) vol. 12 pp. 3027-3031.*

(Continued)

*Primary Examiner* — Eric S Olson
(74) *Attorney, Agent, or Firm* — Finnegan, Henderson, Farabow, Garrett & Dunner, LLP

(57) ABSTRACT

The present invention provides novel glycopeptides antibiotic derivatives comprising a sugar residue (I) represented by the formula:

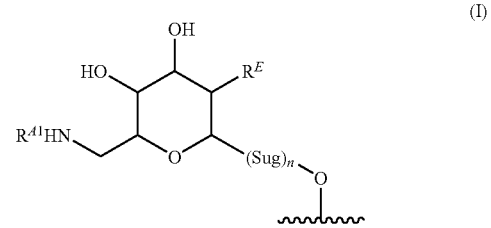

(I)

(wherein n is an integer of 1 to 5: Sugs are each independently a monosaccharide, (Sug)$_n$ is a divalent sugar residue formed by binding of same or different 1 to 5 monosaccharides; R$^{A1}$ is optionally substituted lower alkyl, optionally substituted lower alkenyl, or optionally substituted cycloalkyl; and R$^E$ is OH or NHAc (Ac is acetyl)) is bound to an aromatic ring of the fourth amino acid residue in the glycopeptide skeleton. These derivatives have antibacterial activity against vancomycin-resistant bacteria.

39 Claims, No Drawings

FOREIGN PATENT DOCUMENTS

| WO | WO 2004/019970 A2 | 3/2004 |
|---|---|---|
| WO | WO 2004/044222 A2 | 5/2004 |
| WO | WO 2005/018743 A1 | 3/2005 |
| WO | WO 2005/025599 A1 | 3/2005 |
| WO | WO 2006/003456 A2 | 1/2006 |
| WO | WO 2006/057288 A1 | 6/2006 |

OTHER PUBLICATIONS

Weingarten et al., "Facile Formation of Novel Carbohydrate-Amino Acid Conjugates by Reductive Amination" Synlett (2003) No. 7 pp. 1052-1054.*

Qian et al., "Chemoenzymatic Synthesis of beta-(1-3)-Gal(NAc)-Terminating Glycosides of Complex Tertiary Sugar Alcohols" J. Am. Chem. Soc. (1999) vol. 121 pp. 12063-12072.*

Wu et al., "Differential flexibilities in three branches of an N-linked triantennary glycopeptide" Proc. Natl. Acad. Sci. USA (1991) vol. 88 pp. 9355-9359.*

Oberthür, M. et al., "A Systematic Investigation of the Synthetic Utility of Glycopeptide Glycosyltransferases," J. Am. Chem. Soc., vol. 127, pp. 10747-10752, (2005).

Lu, W. et al., "Characterization of a Regiospecific Epivancosaminyl Transferase GtfA and Enzymatic Reconstitution of the Antibiotic Chloroeremomycin," PNAS, vol. 101, No. 13, pp. 4390-4395, (2004).

Thayer, D. A. et al., "Vancomycin Analogues Containing Monosaccharides Exhibit Improved Antibiotic Activity: A Combined One-Pot Enzymatic Glycosylation and Chemical Diversification Strategy," Chem. Asian J., vol. 1, pp. 445-452, (2006).

Griffith, B. R. et al., "Sweetening Natural Products via Glycorandomization," Current Opinion in Biotechnology, vol. 16, pp. 622-630, (2005).

Fu, X. et al., "Antibiotic Optimization via in vitro Glycorandomization," Nature Biotechnology, vol. 21, No. 12, pp. 1467-1469, (2003).

Melançon III, C. et al., "Glyco-Stripping and Glyco-Swapping," ACS Chemical Biology, vol. 1, No. 8, pp. 499-504, (2006).

Balzarini, J. et al., "Inhibition of Feline (FIPV) and Human (SARS) Coronavirus by Semisynthetic Derivatives of Glycopeptide Antibiotics," Antiviral Research, vol. 72, pp. 20-33, (2006).

Maffioli, S. I. et al., "Synthesis and Antibacterial Activity of Alkyl Derivatives of the Glycopeptide Antibiotic A40926 and Their Amides," Bioorganic & Medicinal Chemistry Letters, vol. 15, pp. 3801-3805, (2005).

Fu, X. et al., "Diversifying Vancomycin via Chemoenzymatic Strategies," Organic Letters, vol. 7, No. 8, pp. 1513-1515, (2005).

Kruger, R. G. et al., "Tailoring of Glycopeptide Scaffolds by the Acyltransferases from the Teicoplanin and A-40,926 Biosynthetic Operons," Chemistry & Biology, vol. 12, pp. 131-140, (2005).

Ritter, R. K. et al., "A Programmable One-Pot Oligosaccharide Synthesis for Diversifying the Sugar Domains of Natural Products: A case Study of Vancomycin," Angew. Chem. Intr. Ed., vol. 42, pp. 4657-4660, (2003).

Balzarini, J. et al., "Antiretroviral Activity of Semisynthetic Derivatives of Glycopeptide Antibiotics," J. Med. chem., vol. 46, pp. 2755-2764, (2003).

Chen, Z. et al., "Structural Requirements for VanA Activity of Vancomycin Analogues," Tetrahedron, vol. 58, pp. 6585-6594, (2002).

Blizzard, T. A. et al., "Antibacterial Activity of G6-Quaternary Ammonium Derivatives of Lipophilic Vancomycin Analogue," Bioorganic & Medicinal Chemistry Letters, vol. 12, pp. 849-852, (2002).

Unverzagt, C., "Chemoenzymatic Synthesis of a Sialylated Diantennary N-Glycan Linked to Asparagine," Carbohydrate Research, vol. 305, pp. 423-431, (1998).

Unverzagt, C. et al., "Chemoenzymatic Synthesis of Deca and Dodecasaccharide N-Glycans of the 'Bisecting' Type," Tetrahedron Letters, vol. 41, pp. 45449-4553, (2000).

Van Bambeke, F., "Glycopeptides: How Can a Structural Modification Bring to a New Life an Old Family of Antibiotics?" Pharmacologie Catholique de Louvain, Brussels, Belgium, 69 pages (Dec. 13, 2003).

Booth, P. M. et al., "Preparation and Conformational Analysis of Vancomycin Hexapeptide and Aglucovancomycin Hexapeptide," J. Chem. Soc. Perkin Trans., vol. 1, pp. 2335-2339, (1989).

Gerhard, U. et al., "The Role of the Sugar and Chlorine Substituents in the Dimerization of Vancomycin Antibiotics," J. Am. Chem. Soc., vol. 115, pp. 232-237, (1993).

Mackay, J. P. et al., "Glycopeptide Antibiotic Activity and the Possible Role of Dimerization: A Model for Biological Signaling," J. Am. Chem. Soc., vol. 116, pp. 4581-4590, (1994).

Pearce, C. M. et al., "Complete Assignment of the $^{13}$C NMR Spectrum of Vancomycin," J. Am. Soc. Perkin Trans., vol. 2, pp. 153-157, (1995).

Westwell, M. S. et al., "Cooperativity in Ligand Binding Expressed at a Model Cell Membrane by the Vancomycin Group Antibiotics," Chem. Commun., pp. 589-590, (1996).

Cooper, M. A. et al., "Surface Plasmon Resonance Analysis of Glycopeptide Antibiotic Activity at a Model Membrane Surface," Chem. Commun., pp. 1625-1626, (1997).

Bardsley, B. et al., "Measurement of the Different Affinities of the Two Halves of Glycopeptide Dimers for Acetate," Chem. Commun., pp. 1049-1050, (1997).

Sharman, G. J. et al., "Common Factors in the Mode of Action of Vancomycin Group Antibiotics Active Against Resistant Bacteria," Chem. Commun., pp. 723-724, (1997).

Van Wageningen, A. M. A. et al., "Binding of D-Serine-Terminating Cell-Wall Analogues to Glycopeptide Antibiotics," Chem. Commun., pp. 1171-1172, (1998).

Bardsley, B. et al., "An Illustration of the Expression of Cooperative Binding Energy in Arrays of Non-Covalent Interactions," Chem. Commun., pp. 2305-2306, (1998).

Bardsley, B. et al., "Cooperativity Between Ligand Binding and Dimerisation in a Derivative of Ristocetin A," J. Chem. Soc., Perkin Trans., vol. 2, pp. 1925-1929, (1998).

Williams, D. H. et al., "The Vancomycin Group of Antibiotics and the Fight Against Resistant Bacteria," Angew. Chem. Int. Ed., vol. 38, pp. 1172-1193, (1999).

Staroske, T. et al., "Synthesis of Extended Bacterial Cell-Wall Precursor Analogues for Ligand Binding Studies with Glycopeptide Antibiotics," J. Chem. Soc., Perkin Trans., vol. 1, pp. 1105-1107, (1999).

Van Bambeke, F. et al., "Glycopeptide Antibiotics from Conventional Molecules to New Derivatives," Drugs, vol. 64, No. 9, pp. 913-936, (2004).

Hubbard, B. K. et al., "Vancomycin Assembly: Nature's Way," Angew. Chem. Int. Ed., vol. 42, No. 7, pp. 730-765, (2003).

Kahne, D. et al., "Glycopeptide and Lipoglycopeptide Antibiotics," Chem. Rev., vol. 105, No. 2, pp. 425-448, (2005).

Malabarba, A. et al., "Glycopeptide Resistance in Multiple Antibiotic-Resistant Gram-Positive Bacteria: A Current Challenge for Novel Semi-Synthetic Glycopeptide Derivatives," Eur. J. Med. Chem., vol. 32, pp. 459-478, (1997).

Malabarba, A. et al., "Structural Modifications of Glycopeptide Antibiotics," Medicinal Research Reviews, vol. 17, No. 1, pp. 69-137, (1997).

Van Bambeke, F., "Glycopeptides: How Can a Structural Modification Bring to a New Life an Old Family of Antibiotics?" Pharmacologie Catholique de Louvain, Brussels, Belgium, 69 pages, (2004).

Nicolaou, K. C. et al., "Chemistry, Biology, and Medicine of the Glycopeptide Antibiotics," Angew. Chem. Int. Ed., vol. 38, pp. 2096-2152, (1999).

Pace, J. L. et al., "Glycopeptides: Update on an Old Successful Antibiotic Class," Biochemical Pharmacology, vol. 71, pp. 968-980, (2006).

Ge, M. et al., "Reconstruction of Vancomycin by Chemical Glycosylation of the Pseudoaglycon," J. Am. Chem.. Soc., vol. 120, No. 42, pp. 11014-11015, (1998).

Thompson, C. et al., "Synthesis of Vancomycin from the Aglycon," J. Am. Chem. Soc., vol. 121, No. 6, pp. 1237-1244, (1999).

Ge, M. et al., "Vancomycin Derivatives That Inhibit Peptidoglycan Biosynthesis Without Binding D-Ala-D-Ala," Science, vol. 284, 507-511, (1999).

Eggert, U. S. et al., "Genetic Basis for Activity Differences Between Vancomycin and Glycolipid Derivatives of Vancomycin," Science, vol. 294, pp. 361-364, (2001).

Chen, L. et al., "Vancomycin Analogues Active Against VanA-Resistant Strains Inhibit Bacterial Transglycosylase Without Binding Substrate," PNAS, vol. 100, No. 10, pp. 5658-5663, (2003).

Leimkuhler, C. et al., "Differential Inhibition of *Staphylococcus aureus* PBP2 by Glycopeptide Antibiotics," J. Am. Chem. Soc., vol. 127, No. 10, pp. 3250-3251, (2005).

Barrett, D. et al., "Kinetic Characterization of the Glycosyltransferase Module of *Staphylococcus aureus* PBP2," Journal of Bacteriology, vol. 187, No. 6, pp. 2215-2217, (2005).

Adachi, M. et al., "Degradation and Reconstruction of Moenomycin A and Derivatives: Dissecting the Function of the Isoprenoid Chain," J. Am. Chem. Soc., vol. 128, No. 43, pp. 14012-14013, (2006).

Taylor, J. G. et al., "The Total Synthesis of Moenomycin A," J. Am. Chem. Soc., vol. 128, No. 47., pp. 15084-15085, (2006).

Dong, S. D. et al., "The Structural Basis for induction of VanB Resistance," J. Am. Chem. Soc., vol. 124, No. 31, pp. 9064-9065, (2002).

Leimkuhler, C. et al., "Glycosylation of Glycopeptides: a Comparison of Chemoenzymatic and Chemical Methods," Tetrahedron: Asymmetry, vol. 16, pp. 599-603, (2005).

Howard-Jones, A. R. et al., "Kinetic Analysis of Teicoplanin Glycosyltransferases and Acyltransferase Reveal Ordered Tailoring of Aglycone Scaffold to Reconstitute Mature Teicoplanin," J. Am. Chem. Soc., vol. 129, No. 33, pp. 10082-10083, (2007).

Cooper, R. D. G. et al., "Reductive Alkylation of Glycopeptide Antibiotics: Synthesis and Antibacterial Activity," The Journal of Antibiotics, vol. 49, No. 6, pp. 575-581, (1996).

Allen, N. E. et al., "The Role of Hydrophobic Side Chains as Determinants of Antibacterial Activity of Semisynthetic Glycopeptide Antibiotics," The Journal of Antibiotics, vol. 50, No. 8, pp. 677-684, (1997).

Rodriguez, M. et al., "Novel Glycopeptide Antibiotics: N-Alkylated Derivatives Active Against Vancomycin-Resistant Enterococci," The Journal of Antibiotics, vol. 51, No. 6, pp. 560-569, (1998).

Allen, N. E. et al., "Mechanism of Action of Oritavancin and Related Glycopeptide Antibiotics," FEMS Microbiology Reviews, vol. 26, pp. 511-532, (2003).

Ward, K. E. et al., "Oritavancin—an Investigational Glycopeptide Antibiotic," Expert Opin. Investig. Drugs, vol. 15, No. 4, pp. 417-429, (2006).

Poulakou, G. et al., "Oritavancin: A New Promising Agent in the Treatment of Infections due to Gram-Positive Pathogens," Expert Opin. Investig. Drugs, vol. 17, No. 2, pp. 225-243, (2008).

Tsuji, N. et al., "New Glycopeptide Antibiotics: II. The Isolation and Structures of Chloroorienticins," The Journal of Antibiotics, vol. XLI, No. 10, pp. 1506-1510, (1988).

Tsuji, N. et al., New Glycopeptide Antibiotics I. The Structures of Orienticins, The Journal of Antibiotics, vol. XLI, No. 6, pp. 819-822, (1988).

Yoshida, O. et al., "Novel Semi-Synthetic Glycopeptide Antibiotics Active Against Methicillin-Resistant *Staphylococcus aureus* (MRSA) and Vancomycin-Resistant Enterococci (VRE): Doubly-Modified Water-Soluble Derivatives of Chloroorienticin B," Bioorganic & Medicinal Chemistry Letters, vol. 12, pp. 3027-3031, (2002).

Yasukata, T. et al., "An Efficient and Practical Method for Solid-Phase Synthesis of Tripeptide-Bearing Glycopeptide Antibiotics: Combinatorial Parallel Synthesis of Carboxamide Derivatves of Chloroorienticin B," Bioorganic & Medicinal Chemistry Letters, vol. 12, pp. 3033-3036, (2002).

Pace, J. L. et al., "In Vitro Activity of TD-6424 Against *Staphylococcus aureus*," Antimicrobial Agents and Chemotherapy, vol. 47, No. 11, pp. 3602-3604, (2003).

Judice, J. K. et al., "Semi-Synthetic Glycopeptide Antibacterials," Bioorganic & Medicinal Chemistry Letters, vol. 13, pp. 4165-4168, (2003).

Laohavaleeson, S. et al., "Telavancin: A Novel Lipoglycopeptide for Serious Gram-Positive Infections," Expert Opin. Investig. Drugs, vol. 16, No. 3, pp. 347-357, (2007).

Nannini, E. C. et al., "A New Lipoglycopeptide: Telavancin," Expert Opin. Pharmacother., vol. 9, No. 12, pp. 2197-2207, (2008).

Plavlov, A. Y. et al., "A New Type of Chemical Modification of Glycopeptides Antibiotics: Aminomethylated Derivatives of Eremomycin and their Antibacterial Activity," The Journal of Antibiotics, vol. 50, No. 6, pp. 509-513, (1997).

Griffith, B. R. et al., "'Sweetening' Natural Products via Glycorandomization," Current Opinion in Biotechnology, vol. 16, pp. 622-630, (2005).

Kodama, H. et al., Synthesis of UDP-6-Deoxy-and-6-Fluoro-D-Galactoses and Their Enzymatic Glycosyl Transfer to Mono-and Biantennary Carbohydrate Chains, Tetrahedron Letters, vol. 34, No. 40, pp. 6419-6422, (1993).

Nishida, Y. et al., "Extension of the βGall, 1-Transfer to N-Acetyl 5-Thio-Gentosamine by Galactosyltransferase," Tetrahdedron Letters, vol. 34, No. 18, pp. 2905-2906, (1993).

Unverzagt, C., "Chemoenzymatische Synthese eines sialylierten Undecasaccharid-Asparagins," Angew Chem., vol. 108, No. 20, pp. 2507-2510, (1996).

Křen, V. et al., "Ergot Alkaloid Glycosides with Immunomodulatory Activities," Bioorganic & Medicinal Chemistry, vol. 4, No. 6, pp. 869-876, (1996).

Yamada, K. et al., "High Performance Polymer Supports for Enzyme-Assisted Synthesis of Glycoconjugates," Carbohydrate Research, vol. 305, pp. 443-461, (1998).

Seifert, J. et al., "Synthesis of Three Biantennary N-Glycans Containing the α-1,6 Core-Fucosyl Motif," Tetrahedron Letters, vol. 38, No. 45, pp. 7857-7860, (1997).

Niggermann, J. et al., "β-1,4-Galactosyltransferase-Catalyzed Synthesis of the Branched Tetrasaccharide Repeating Unit of *Streptococcus pneumoniae* Type 14," Bioorganic & Medicinal Chemistry, vol. 6, pp. 1605-1612, (1998).

Mazur, A. W. et al., "Chemoenzymic Approaches to the Preparation of 5-C-(Hydroxymethyl)hexoses," J. Org. Chem., vol. 62, No. 13, pp. 4471-4475, (1997).

Liu, X. C. et al., "Sugar-Containing Polyamines Prepared Using Galactose Oxidase Coupled With Chemical Reduction," J. Am. Chem. Soc., vol. 121, No. 2, pp. 466-467, (1999).

Andreana, P. R. et al., "Chemo-Enzymatic Synthesis of Polyhydroxyazepanes," Tetrahedron Letters, vol. 43, pp. 6526-6528, (2002).

Van Wijk, A. et al., "Enzymatically Oxidized Lactose and Derivatives Thereof as Potential Protein Cross-Linkers," Carbohydrate Research, vol. 341, pp. 2921-2926, (2006).

Maradufu, A. et al., "Dimeric Nature of the Aldehyde Produced from Methyl β-D-Galactopyranoside by D-Galactose Oxidase," Carbohydrate Research, vol. 32, pp. 127-136, (1974).

Rokhsana, D. et al., "Structure of the Oxidized Active Site of Galactose Oxidase from Realistic in Silico Models," J. Am. Chem. Soc., vol. 128, pp. 15550-15551, (2006).

Bütler, T. et al., "Chemoenzymatic Synthesis of Biotinylated Nucleotide Sugars as Substrates for Glycosyltransferases," Chembiochem, vol. 2, pp. 884-894, (2001).

Wang, L. X. et al., "Chemoenzymatic Synthesis of HIV-1 gp41 Glycopeptides: Effects of Glycosylation on the Anti-HIV Activity and α-Helix Bundle-Forming Ability of Peptide C34," ChemBioChem, vol. 6, pp. 1068-1074, (2005).

Hang, H. C. et al., "The Chemistry and Biology of Mucin-Type O-Linked Glycosylation," Bioorganic & Medicinal Chemistry, vol. 13, pp. 5021-5034, (2005).

Nicolaou, K. C. et al., "Solid- and Solution-Phase Synthesis of Vancomycin and Vancomycin Analogues with Activity Against Vancomycin-Resistant Bacteria," Chem. Eur. J. vol. 7, No. 17, pp. 3798-3823, (2001).

Kerns, R. et al., "The Role of Hydrophobic Substituents in the Biological Activity of Glycopeptide Antibiotics," J. Am. Chem. Soc., vol. 122, pp. 12608-12609, (2000).

Pavlov, A. Y. et al., "Synthesis and Antibacterial Activity of Derivatives of the Glycopeptide Antibiotic A-40926 N-Alkylated at the Aminoglucuronyl Moiety," The Journal of Antibiotics, vol. 51, No. 5, pp. 525-527, (1998).

Preobrazhenskaya, M. N. et al., "Patients of Glycopeptides of the Vancomycin Family and Their Derivatives as Antimicrobials: Jan. 1999-Jun. 2003," Expert Opinion on Therapeutic Patents, vol. 14, No. 2, pp. 141-173, (2004).

Salas, J. A. et al., "Engineering the Glycosylation of Natural Products in Actinomycetes," Trends in Microbiology, vol. 15, No. 5, pp. 219-232, (2007).

Mulichak, A. M. et al., "Structure of the UDP-Glucosyltransferase GtfB That Modifies the Heptapeptide Aglycone in the Biosynthesis of Vancomycin Group Antibiotics," Structure, vol. 9, pp. 547-557, (2001).

Grdadolnik, S. G. et al., "Vancomycin: Conformational Consequences of the Sugar Substituent," J. Med. Chem., vol. 41, pp. 2090-2099, (1998).

Griffith, B. R. et al., "Model for Antibiotic Optimization via Neoglycosylation: Synthesis of Liponeoglycopeptides Active Against VRE," J. Am. Chem. Soc., vol. 129, pp. 8150-8155, (2007).

Sundram, U. et al., "Novel Vancomycin Dimers with Activity Against Vancomycin-Resistant Enterococci," J. Am. Chem. Soc., vol. 118, pp. 13107-13108, (1996).

Sharman, G. J. et al., "The Roles of Dimerization and Membrane Anchoring in Activity of Glycopeptide Antibiotics Against Vancomycin-Resistant Bacteria," J. Am. Chem. Soc., vol. 119, pp. 12041-12047, (1997).

Mackay, J. P. et al., "Dissection of the Contributions Toward Dimerization of Glycopeptide Antibiotics," J. Am. Chem. Soc., vol. 16, pp. 4573-4580, (1994).

Marshall, F. J., "Structure Studies on Vancomycin," J. Medicinal Chem., vol. 8, pp. 18-22, (1965).

Nagarajan, R. et al., "Selective Cleavage of Vancosamine, Glucose, and N-Methyl-Leucine from Vancomycin and Related Antibiotics," J. Chem. Soc., Chem. Commun. pp. 1306-1307, (1988).

Losey, H. C. et al., "Tandem Action of Glycosyltransferases in the Maturation of Vancomycin and Teicoplanin Aglycones: Novel Glycopeptides," Biochemistry, vol. 40, pp. 4754-4755, (2001).

Nagarajan, R., "Structure-Activity Relationships of Vancomycin-Type Glycopeptide Antibiotics," The Journal of Antibiotics, vol. 46, No. 8, pp. 1181-1195, (1993).

Nagarajan, R. et al., "The Structural Relationships of A82846B and its Hydrolysis Products with Chloroorienticins A, B and C," The Journal of Antibiotics, vol. 42, No. 9, pp. 1438-1440, (1989).

* cited by examiner

GLYCOSYLATED GLYCOPEPTIDE ANTIBIOTIC DERIVATIVES

TECHNICAL FIELD

The present invention relates to glycosylated glycopeptide antibiotic derivatives, a process for producing the same, and their intermediates thereof.

BACKGROUND ART

A glycopeptide antibiotic is an antibiotic having a complicated polycyclic peptide structure which is produced by a variety of microorganisms, and is provided as an antibacterial agent effective for most of Gram-positive bacteria. In recent years, penicillin and cephalosporin resistant bacteria have appeared, and infection with multidrug resistant bacteria and methicillin-resistant *Staphylococcus aureus* (MRSA) lead to important problems in the medical field. A glycopeptide-based antibiotic such as vancomycin is typically effective for such microorganisms, and vancomycin has become the last resort drug for infection with MRSA and other resistant bacteria. However, particular microorganism such as vancomycin-resistant Enterococci (VRE) have begun to obtain resistance to vancomycin. In addition, recently, *Staphylococcus aureus* (VRSA) which has acquired VRE resistance has been found out.

Vancomycin has a structure represented by the following formula:

[Chemical formula 1]

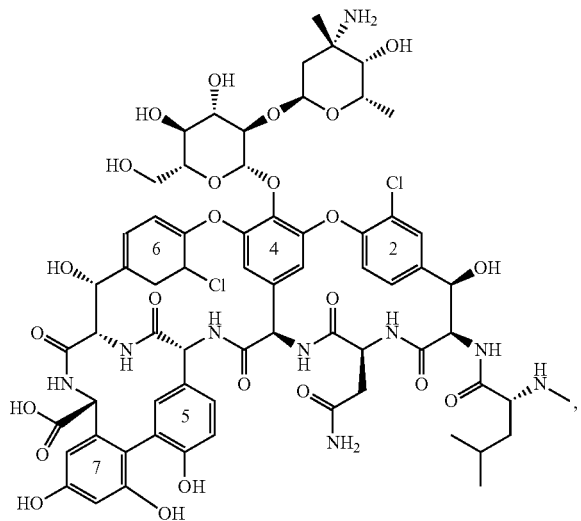

more specifically, the following formula:

[Chemical formula 2]

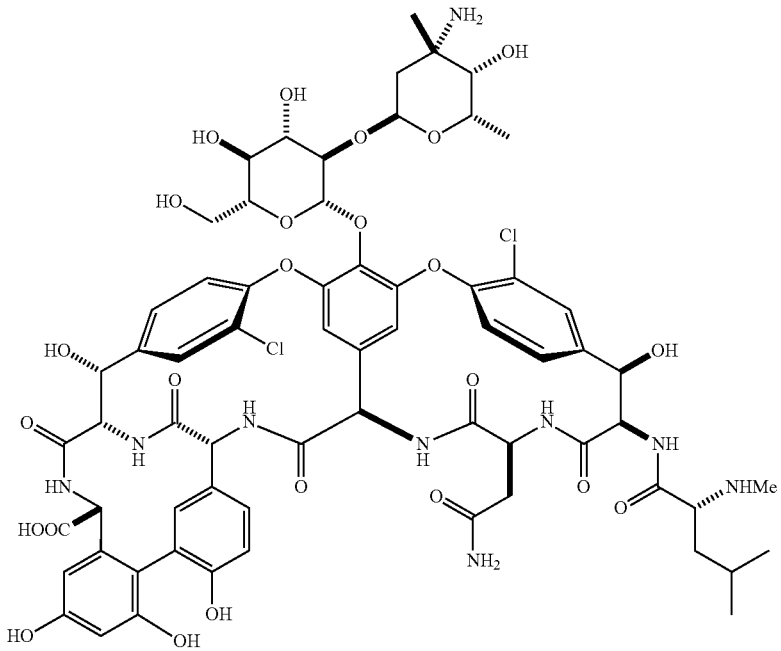

and the aromatic ring of amino acid residues which are the second and sixth position from N-terminal is substituted with a chlorine atom. Vancomycin derivatives are generally also termed glycopeptide antibiotics and, more academically, a generic name of dalbaheptides derived from D-alanyl-D-alanine binding antibiotics with a heptapeptidic structure has been proposed. The dalbaheptide has a peptide chain consisting of seven amino acids including aromatic amino acids as a common fundamental skeleton.

Previously, vancomycin, and other glycopeptide antibiotics having these common peptide chain as fundamental skeleton have been variously modified. For example, chloroorienticin B having the following structure (Patent Literature 1: JP-A No. 1-240196) and derivatives thereof (Patent Literature 2: JP-A No. 2001-163898) are known.

[Chemical formula 3]

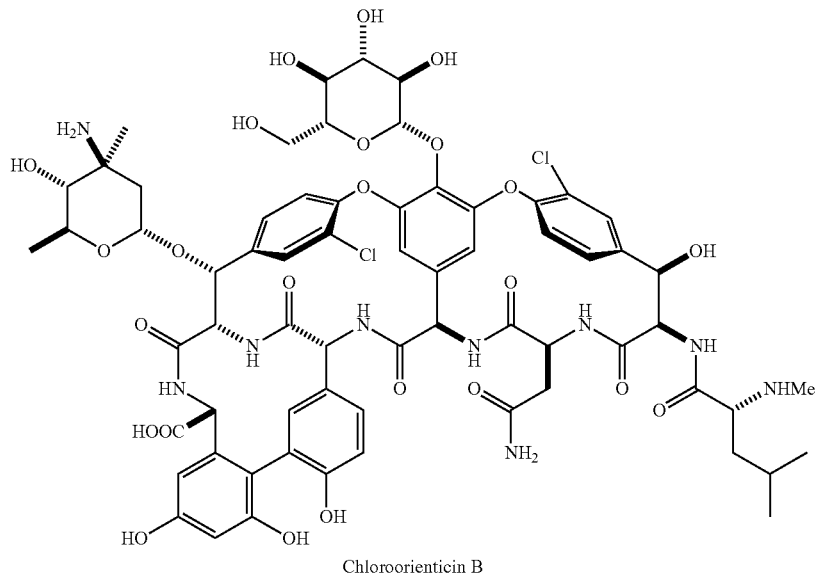

Chloroorienticin B

[Chemical formula 4]

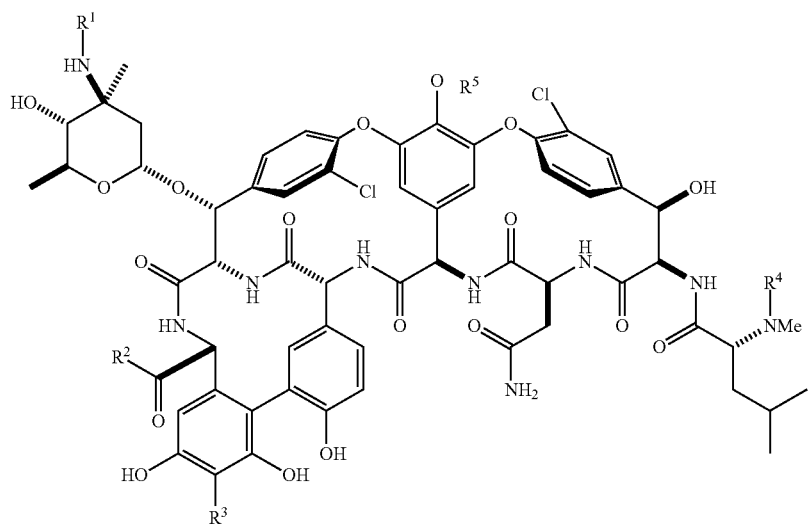

(wherein $R^5$ is hydrogen, glucosyl, or (4-epi-vancosaminyl)-O-glucosyl)

As other glycopeptide antibiotics, for example, the following compounds are known.

[Chemical formula 5]
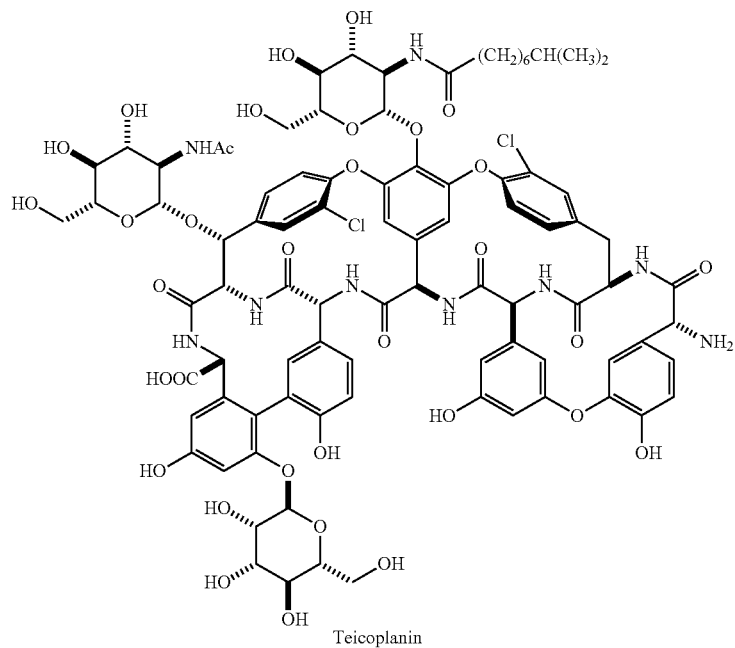
Teicoplanin
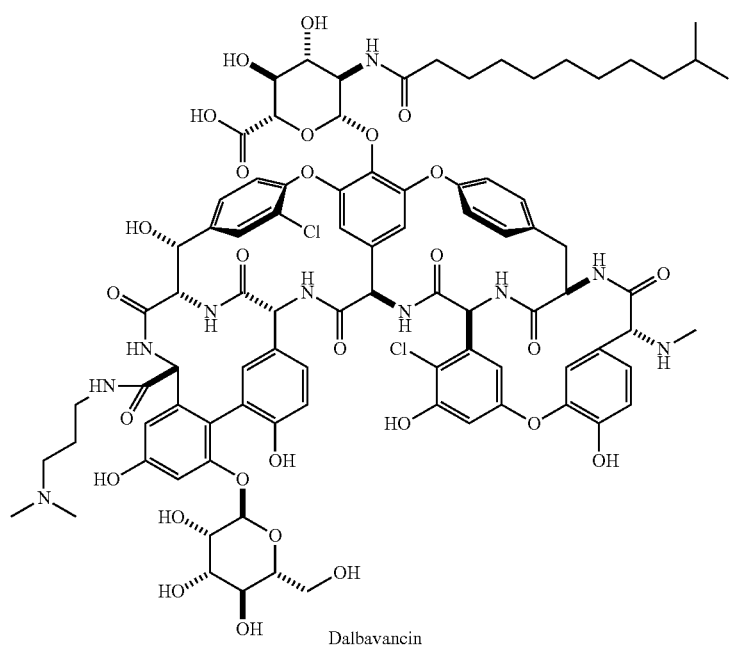
Dalbavancin

-continued

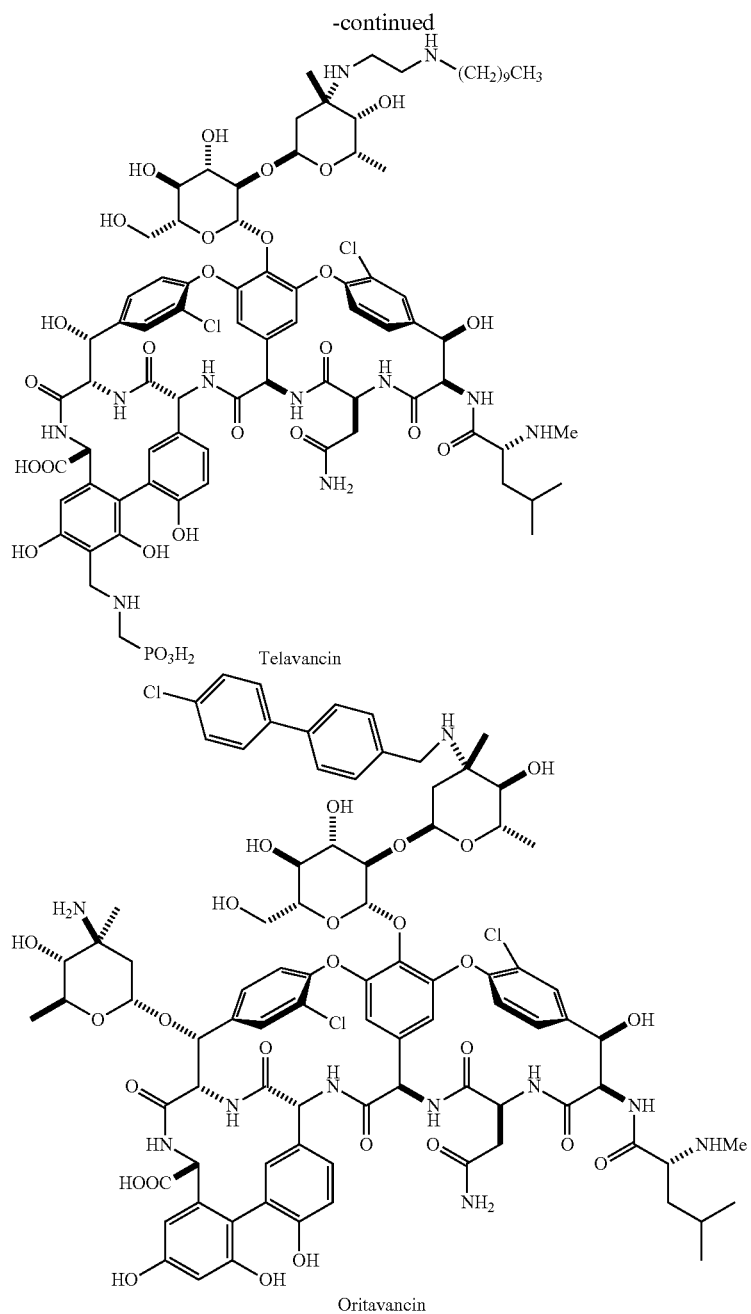

Telavancin

Oritavancin

In addition, glycopeptide compounds in which the amino sugar of vancomycin is modified are also known (e.g., Patent Literature 18).

However, development of antibacterial agents with novel structure in which antibacterial activity to drug-resistant bacteria, water solubility, distribution, safety and the like are further improved is desired.

On the other hand, as methods of chemically modifying glycopeptide antibiotics, methods using various glycosylase have been reported (e.g., Patent Literature 3, Non-Patent Literatures 1 to 5).

In addition, a glycopeptide compounds in which a sugar side chain consisting of 1 or 2 sugars, to which an aminomethylene-type substituent is bound, is bound to the aromatic ring part of the fourth amino acid residue of the glycopeptide antibiotic are known (e.g., Patent Literatures 4 to 17, Non-Patent Literatures 5 to 17).

Among them, in Non-Patent Literature 11 (Angewandte Chemie, International Edition (2003), 42(38), 4657-4660), a vancomycin derivative in which —$CH_2$ $NH_2$ is bound to galactose at the sugar chain terminal is described, but no compound in which the amino group is further chemically modified is described.

In addition, recent trend of study regarding glycopeptide compounds has been reported (e.g., Non-Patent Literature 18)

[Patent Literature 1] JP-A No. 1-240196
[Patent Literature 2] JP-A No. 2001-163898
[Patent Literature 3] WO2006003456

[Patent Literature 4] US2005239689A1
[Patent Literature 5] US2003068669A1
[Patent Literature 6] US2004259228A1
[Patent Literature 7] US2005266523A1
[Patent Literature 8] WO2004019970
[Patent Literature 9] WO2001081373
[Patent Literature 10] WO2001081372
[Patent Literature 11] WO2000069893
[Patent Literature 12] WO2000059528
[Patent Literature 13] WO2000042067
[Patent Literature 14] WO2000004044
[Patent Literature 15] WO9303060
[Patent Literature 16] EP301785A1
[Patent Literature 17] EP273727A1
[Patent Literature 18] WO2006057303
[Non-Patent Literature 1] Journal of the American Chemical Society (2005), 127(30), 10747-10752
[Non-Patent Literature 2] Proceedings of the National Academy of Sciences of the United States of America (2004), 101(13), 4390-4395
[Non-Patent Literature 3] Chemistry—An Asian Journal (2006), 1, 445-452
[Non-Patent Literature 4] Current Opinion in Biotechnology 2005, 16:622-630
[Non-Patent Literature 5] Nature Biotechnology (2003), 21(12), 1467-1469
[Non-Patent Literature 6] ACS Chemical Biology (2006), 1(8), 499-504
[Non-Patent Literature 7] Activity Research (2006), 72(1) 20-33
[Non-Patent Literature 8] Bioorganic & Medical Chemistry Letters (2005), 15(16), 3801-3805
[Non-Patent Literature 9] Organic Letters (2005), 7(8), 1513-1515
[Non-Patent Literature 10] Chemistry & Biology (2005), 12(1), 131-140
[Non-Patent Literature 11] Angewandte Chemie, International Edition (2003), 42(38), 4657-4660
[Non-Patent Literature 12] Journal of Medicinal Chemistry (2003), 46(13), 2755-2764
[Non-Patent Literature 13] Tetrahedron (2002), 58(32), 6585-6594
[Non-Patent Literature 14] Bioorganic & Medicinal Chemistry Letters (2002), 12(6), 849-852
[Non-Patent Literature 15] Chemistry—A European Journal (2001), 7(17), 3798-3823
[Non-Patent Literature 16] Journal of the American Chemical Society (2000), 122(50), 12608-12609
[Non-Patent Literature 17] Journal of Antibiotics (1998), 51(5), 525-527
[Non-Patent Literature 18] Expert Opinion on Therapeutic Patents (2004) 14(2) 141-173

DISCLOSURE OF THE INVENTION

Problems to be Solved by the Invention

The present invention provides novel glycopeptide compounds having antibacterial activities. The present invention provides glycopeptide compounds which are preferably also effective for drug-resistant bacteria (e.g., VRSA, VRE), and are further preferably excellent in water solubility, distribution, safety or the like. Further, the present invention provides a method of glycosylating glycopeptide antibiotics utilizing glycosyltransferase and a process for producing glycopeptide compounds utilizing the same, as well as their intermediates therefor.

Means to Solve the Problems

The present inventors have intensively studied and, as a result, succeeded in further glycosylation by performing an enzymatic reaction on a sugar which binds to an aromatic ring of a fourth amino acid residue of a glycopeptide antibiotic such as chloroorienticin B, and the like. The present inventors have succeeded in introducing an amino side chain regioselectively by oxidizing hydroxymethylene at the further glycosylated sugar chain terminal into aldehyde by an enzymatic reaction, or the like, and chemically modifying the aldehyde group.

The greatest characteristic of the glycopeptide compounds of the present invention is in that the compounds have a partial structure including aromatic ring of the fourth amino acid residue of the glycopeptide antibiotic, and two or more connected sugars are bound to the aromatic ring via an ether bond.

In the glycopeptide compound of the present invention, preferably, among two or more connected sugars, a sugar which is bound to an aglycone of a glycopeptide antibiotic is a β-D-glucosyl group and, more preferably, a sugar at the terminal is a β-D-galactosyl group.

In the glycopeptide compounds of the present invention, more preferably, —CH$_2$OH or —COH is bound to the sugar at the terminal and, further preferably, an optionally substituted aminomethylene group formed by chemical modification of them is bound thereto.

Therefore, according to the present invention, various glycopeptide compounds in which a side chain containing the glycosylated sugar on aromatic ring of the fourth amino acid residue of the glycopeptide antibiotics is bound via an ether bond are provided.

The present invention specifically provides the following compounds.

(1) A glycopeptide compound, a pharmaceutically acceptable salt thereof, or a solvate thereof, which is characterized in that a sugar residue (I) represented by the formula:

[Chemical formula 6]

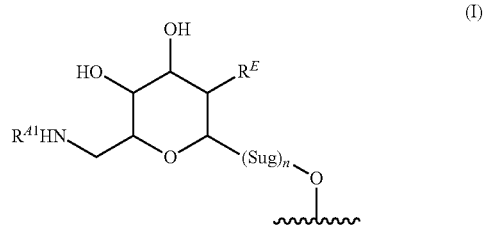

wherein
n is an integer of 1 to 5;
Sugs are each independently a monosaccharide, (Sug)$_n$ is a divalent sugar residue formed by binding same or different 1 to 5 monosaccharides;
$R^{41}$ is optionally substituted lower alkyl, optionally substituted lower alkenyl, or optionally substituted cycloalkyl; and
$R^E$ is OH or NHAc (Ac is acetyl);
is bound to an aromatic ring of the fourth amino acid residue in a glycopeptide skeleton.

More particularly, the present invention provides compounds represented by the following (2) to (32).

(2) The glycopeptide compound, a pharmaceutically acceptable salt thereof, or a solvate thereof according to above (1), wherein the monosaccharide is selected from the group consisting of glucose, galactose, fructose, fucose, mannose, rhamnose, galactosamine, glucosamine, N-acetylgalactosamine, N-acetylglucosamine, vancosamine, epi-vancosamine, glucuronic acid, sialic acid, deoxyglucose, and deoxygalactose.

(3) The glycopeptide compound, a pharmaceutically acceptable salt thereof, or a solvate thereof according to above (1), wherein the monosaccharide is glucose.

(4) The glycopeptide compound, a pharmaceutically acceptable salt thereof, or a solvate thereof according to any one of above (1) to (3), wherein n is 1 or 2.

(5) The glycopeptide compound, a pharmaceutically acceptable salt thereof, or a solvate thereof according to above (1), wherein the monosaccharide is glucose; and n is 1 or 2.

(6) The glycopeptide compound, a pharmaceutically acceptable salt thereof, or a solvate thereof according to above (1), wherein the sugar residue (I) is a sugar residue (I-0) represented by the formula:

[Chemical Formula 7]

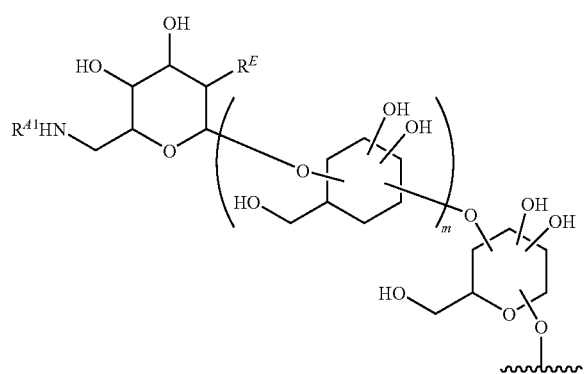

(I-0)

wherein
m is an integer of 0 to 4; and
$R^{A1}$ and $R^E$ are each as defined in above (1).

(7) The glycopeptide compound, a pharmaceutically acceptable salt thereof, or a solvate thereof according to above (1), wherein the sugar residue (I) is a sugar residue (I-1) represented by the formula:

[Chemical formula 8]

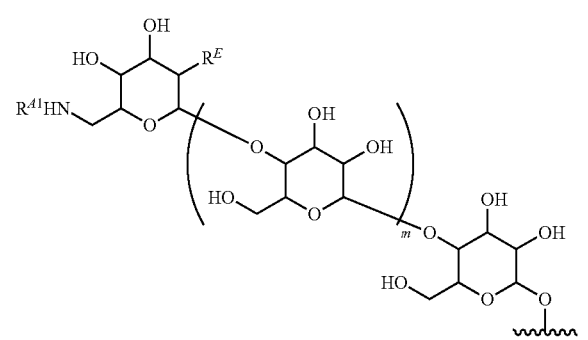

(I-1)

wherein
m is an integer of 0 to 4; and
$R^{A1}$ and $R^E$ are each as defined in above (1).

(8) The glycopeptide compound, a pharmaceutically acceptable salt thereof, or a solvate thereof according to above (1), wherein the sugar residue (I) is a sugar residue (I-2) represented by the formula;

[Chemical formula 9]

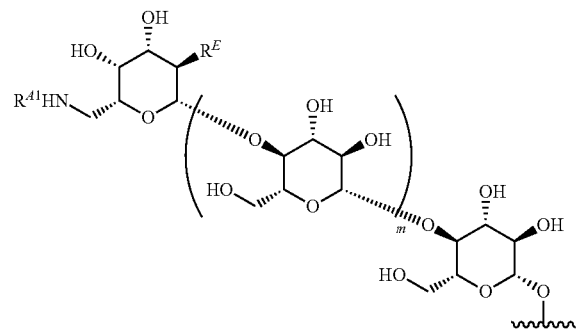

(I-2)

wherein
m is an integer of 0 to 4; and
$R^{A1}$ and $R^E$ are each as defined in above (1).

(9) The glycopeptide compound, a pharmaceutically acceptable salt thereof, or a solvate thereof according to any one of above (1) to (8), wherein the compound has a partial structure (II) represented by the formula;

[Chemical formula 10]

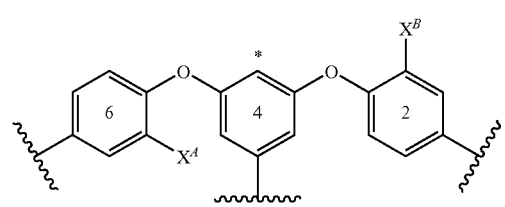

(II)

wherein the ring 2, the ring 4 and the ring 6 represent aromatic rings of the second, fourth and sixth amino acid residues of a glycopeptide antibiotic, respectively; $X^A$ and $X^B$ each represent independently hydrogen or halogen; and * represents a binding position with a sugar residue.

(10) The glycopeptide compound, a pharmaceutically acceptable salt thereof, or a solvate thereof according to above (1), wherein the compound has a partial structure (III) represented by the formula:

[Chemical formula 11]

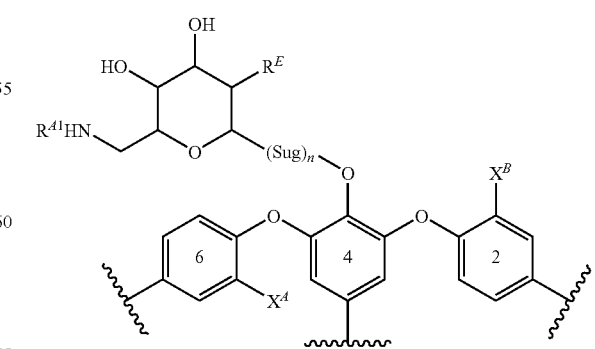

(III)

wherein the ring 2, the ring 4 and the ring 6 represent aromatic rings of the second, fourth and sixth amino acid residues of a glycopeptide antibiotic, respectively; $X^A$ and $X^B$ each represent independently hydrogen or halogen; and other symbols are each as defined in above (1).

(11) The glycopeptide compound, a pharmaceutically acceptable salt thereof, or a solvate thereof according to above (10), wherein the partial structure (III) is a partial structure (III-0) represented by the formula:

[Chemical formula 12]

(III-0)

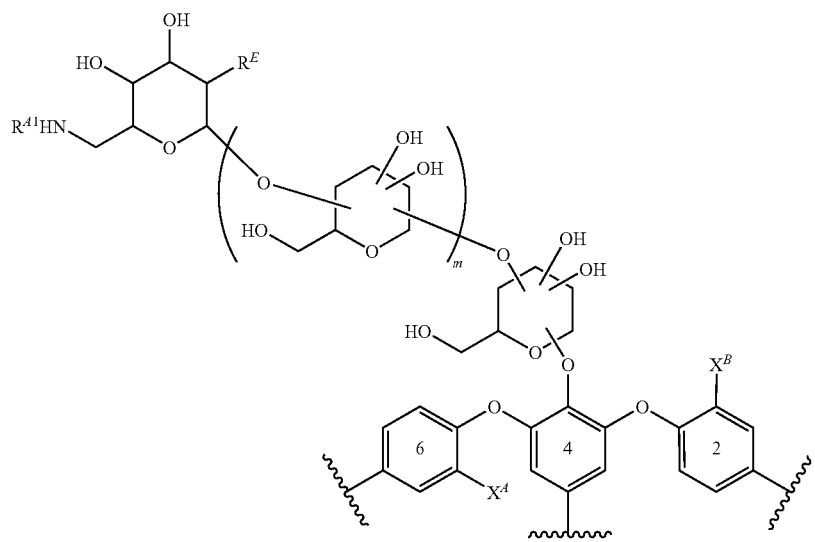

wherein the ring 2, the ring 4 and the ring 6 represent aromatic rings of the second, fourth and sixth amino acid residues of a glycopeptide antibiotic; $X^A$ and $X^B$ each represent independently hydrogen or halogen; m is an integer of 0 to 4; and $R^{41}$ and $R^E$ are each as defined in above (1).

(12) The glycopeptide compound, a pharmaceutically acceptable salt thereof, or a solvate thereof according to above (10), wherein the partial structure (III) is a partial structure (III-1) represented by the formula:

[Chemical formula 13]

(III-1)

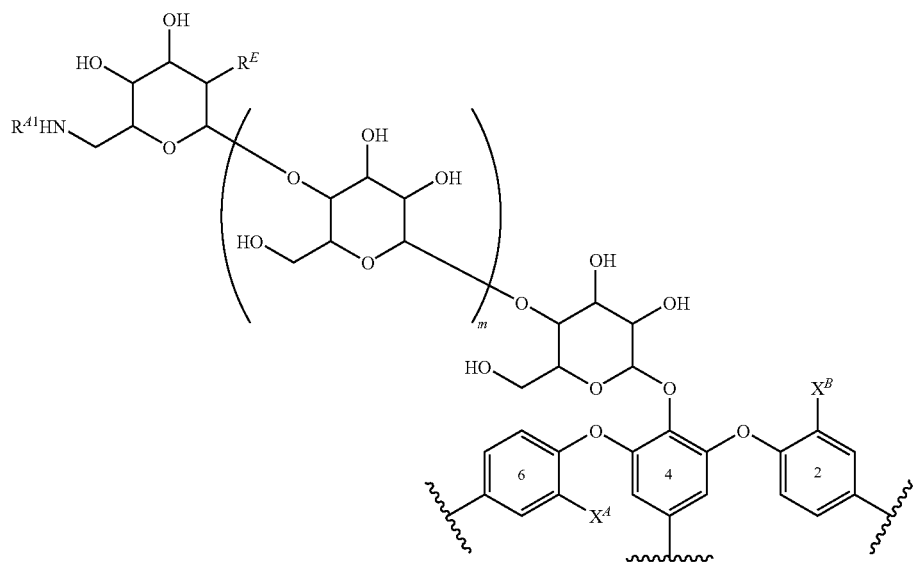

wherein the ring 2, the ring 4 and the ring 6 represent aromatic rings of the second, fourth and sixth amino acid residue of a glycopeptides antibiotic, respectively; $X^A$ and $X^B$ each represents independently hydrogen or halogen; m is an integer of 0 to 4; and $R^{A1}$ and $R^E$ are each as defined in above (1).

[Chemical formula 14]

(13) The glycopeptide compound, a pharmaceutically acceptable salt thereof, or a solvate thereof according to above (10), wherein the partial structure (III) is a partial structure (III-2) represented by the formula:

(III-2)

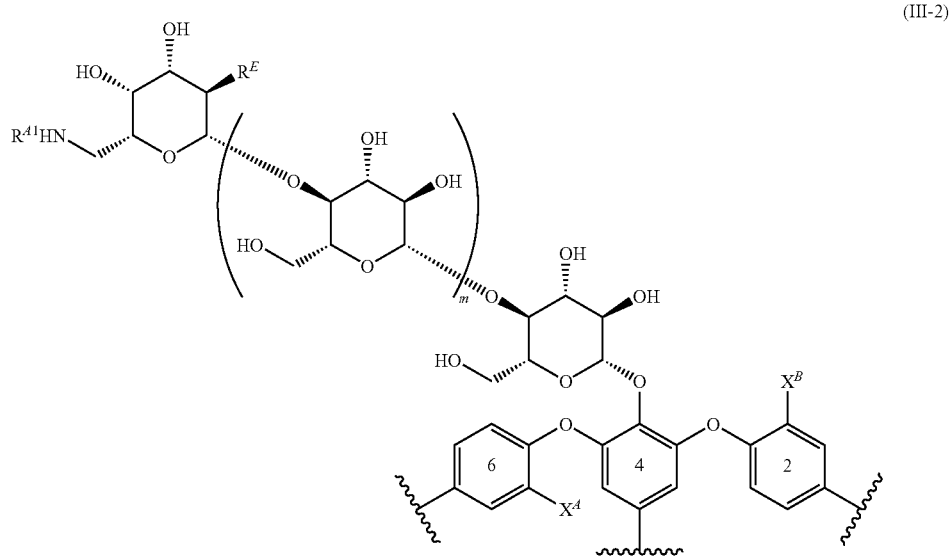

wherein the ring 2, the ring 4 and the ring 6 represent aromatic rings of the second, fourth and sixth amino acid residues of a glycopeptide antibiotic, respectively; $X^A$ and $X^B$ each represent independently hydrogen or halogen; m is an integer of 0 to 4; and $R^{A1}$ and $R^E$ are each as defined in above (1).

(14) The compound, a pharmaceutically acceptable salt thereof, or a solvate thereof according to any one of above (1) to (13), wherein the glycopeptide compound is a chlorooreinticin B derivative or a vancomycin derivative.

(15) The compound, a pharmaceutically acceptable salt thereof, or a solvate thereof according to above (1), wherein the compound is represented by the formula:

[Chemical formula 15]

(IV)

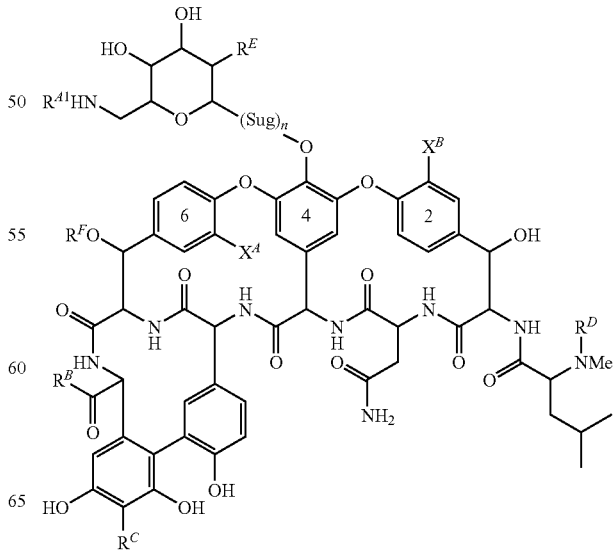

wherein

R$^F$ is hydrogen or a sugar residue;

R$^B$ is —OH, —NR$^5$R$^{5'}$ (wherein R$^5$ and R$^{5'}$ are each independently hydrogen, optionally substituted lower alkyl, optionally substituted lower alkyloxy, or optionally substituted amino or amino acid residue) or —OR$^6$ (wherein R$^6$ is optionally substituted lower alkyl (a hetero atom group may intervene in the lower alkyl part));

R$^C$ is hydrogen or optionally substituted alkyl (a hetero atom group may intervene in the lower alkyl part);

R$^D$ is hydrogen or lower alkyl; and other symbols are each as defined in above (1).

(16) The compound, a pharmaceutically acceptable salt thereof, or a solvate thereof according to above (15), wherein the compound is represented by the formula:

[Chemical formula 16]

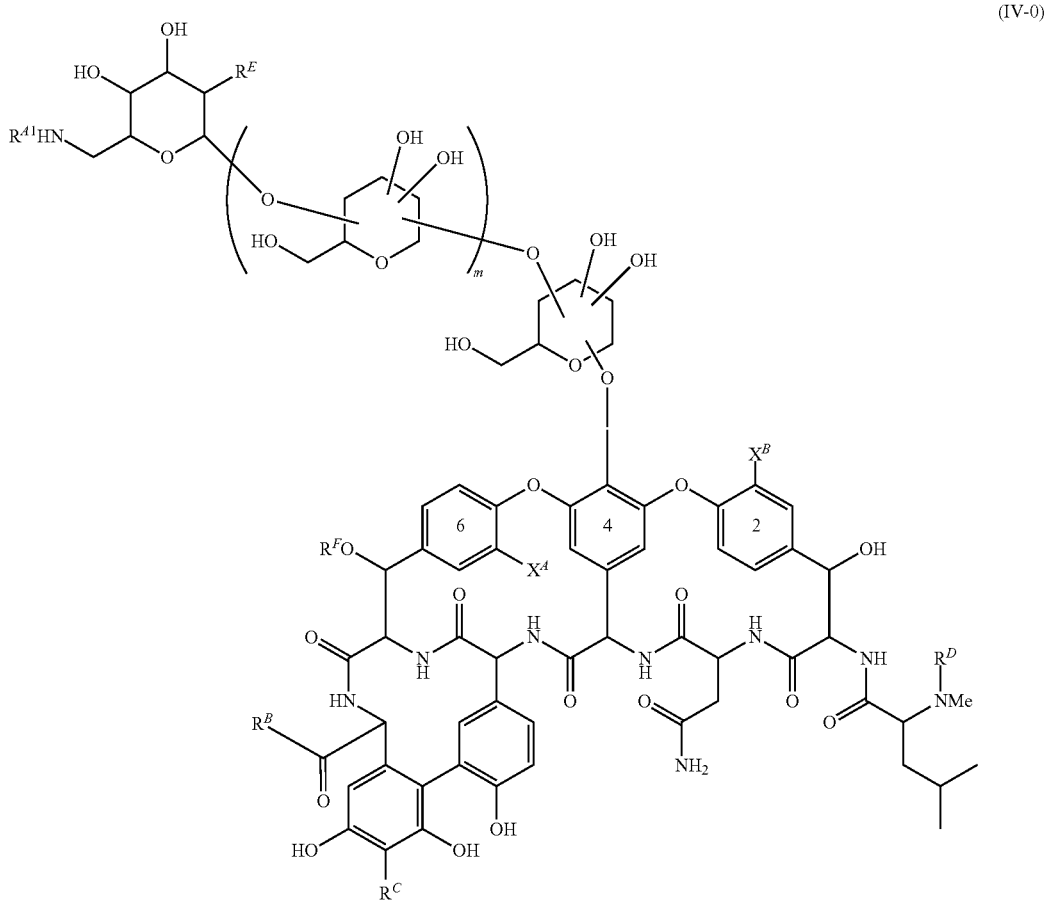

(IV-0)

wherein m is an integer of 0 to 4; and other symbols are each as defined in above (15).

(17) The compound, a pharmaceutically acceptable salt thereof, or a solvate thereof according to above (16), wherein the compound is represented by the formula:

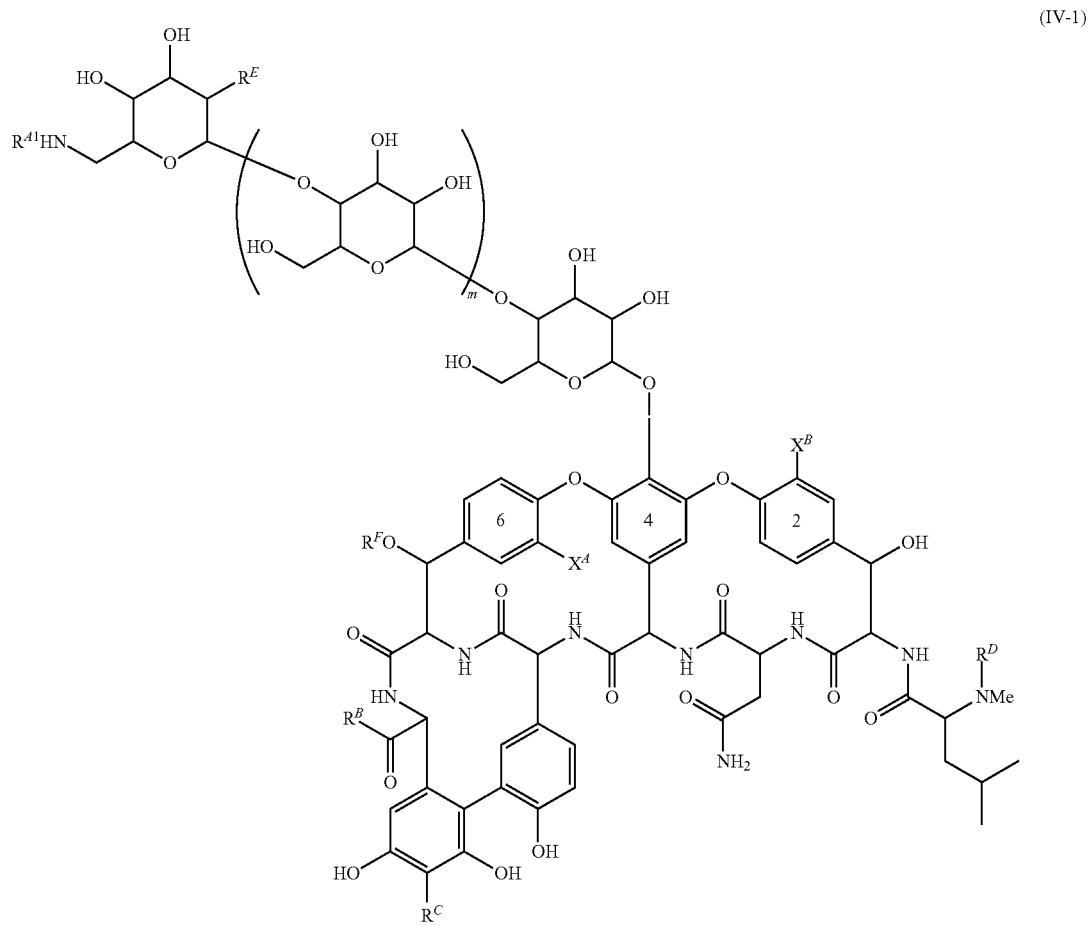
(IV-1)
wherein respective symbols are each as defined in above (16).
(18) The compound, a pharmaceutically acceptable salt thereof, or a solvate thereof according to above (16), wherein the compound is represented by the formula:
[Chemical formula 18]
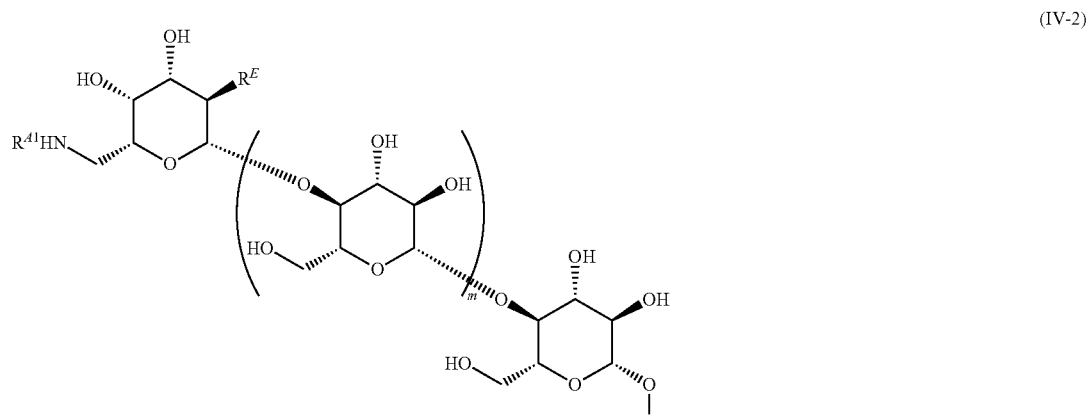
(IV-2)

-continued

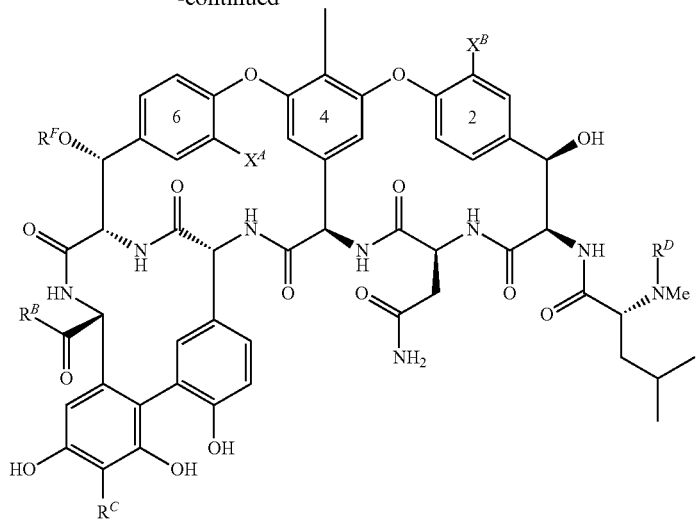

wherein respective symbols are each as defined in above (16).

(19) The compound, a pharmaceutically acceptable salt thereof, or a solvate thereof according to above (1), wherein the compound is represented by the formula:

[Chemical formula 19]

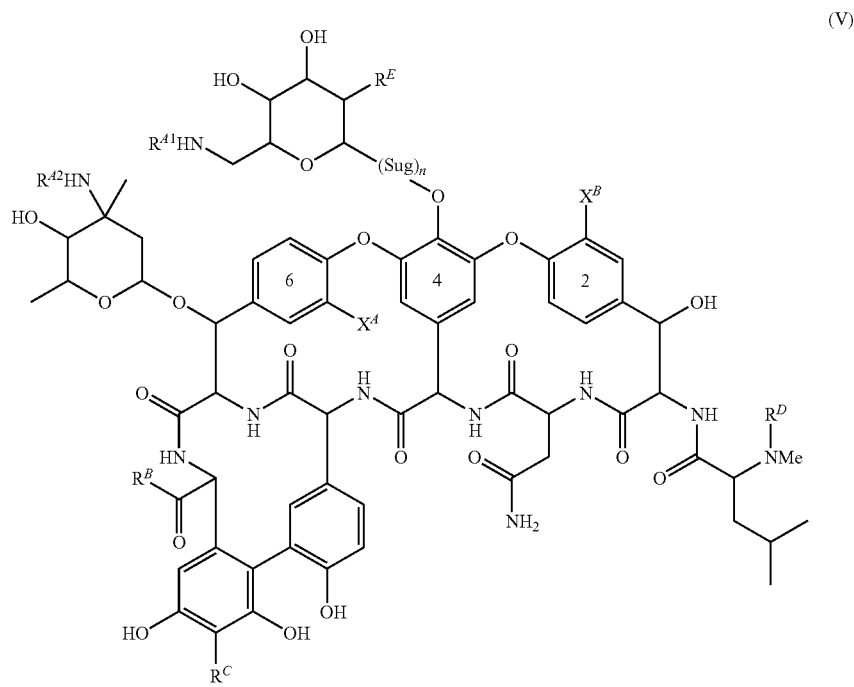

(V)

wherein $R^{A2}$ is hydrogen or optionally substituted lower alkyl;

$R^B$ is —OH, —NR$^5$R$^{5'}$ (wherein R$^5$ and R$^{5'}$ are each independently hydrogen, optionally substituted lower alkyl, optionally substituted lower alkyloxy, optionally substituted amino or amino sugar residue) or a —OR$^6$ (wherein R$^6$ is optionally substituted lower alkyl (a hetero atom group may intervene in the lower alkyl part));

$R^C$ is hydrogen or optionally substituted lower alkyl (a hetero atom group may intervene in the lower alkyl part);

$R^D$ is hydrogen or lower alkyl;

$X^A$ and $X^B$ are each independently hydrogen or halogen; and other symbols are each as defined in above (1).

(20) The compound according to above (19), wherein the compound is represented by the formula:

[Chemical formula 20]
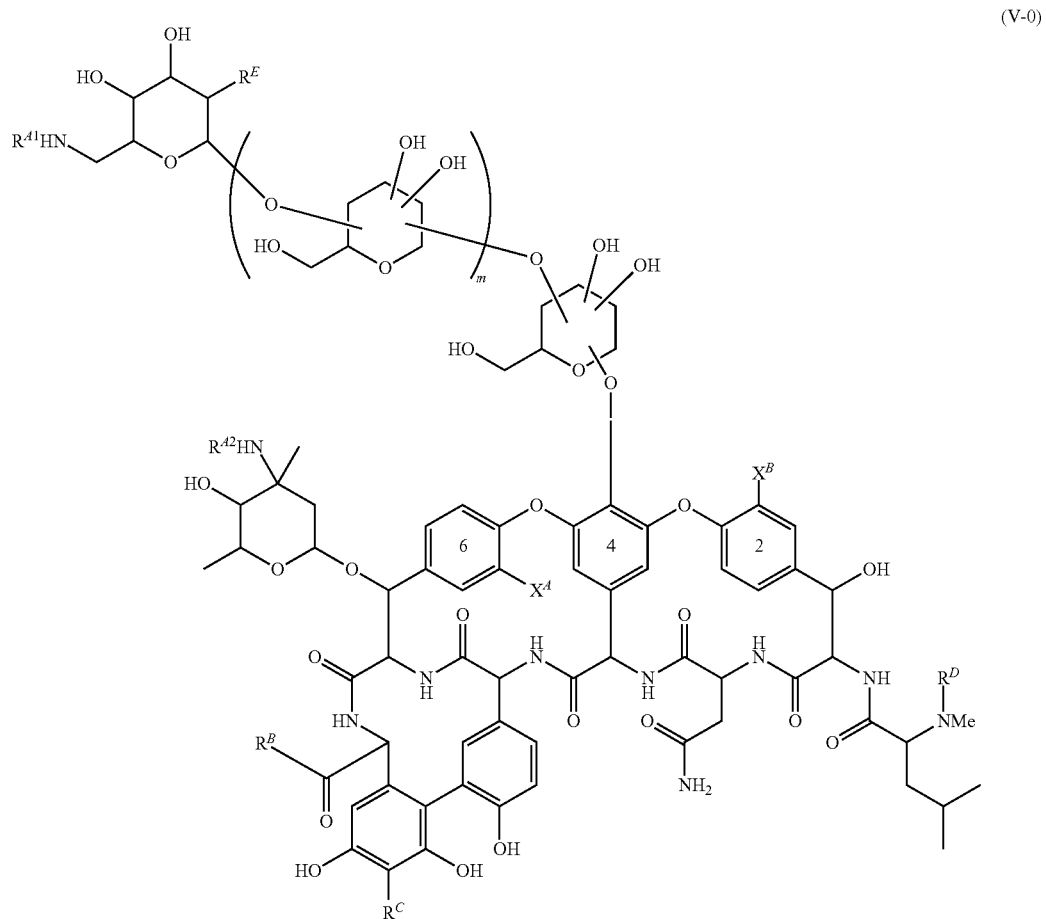
(V-0)
wherein
m is an integer of 0 to 4; and
other symbols are each as defined in above (19).
(21) The compound according to above (20), wherein the compound is represented by the formula:
[Chemical formula 21]
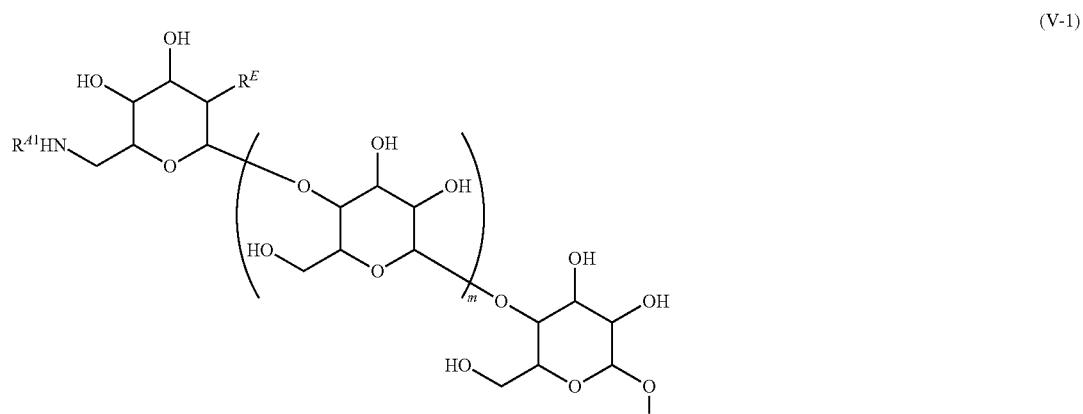
(V-1)

-continued

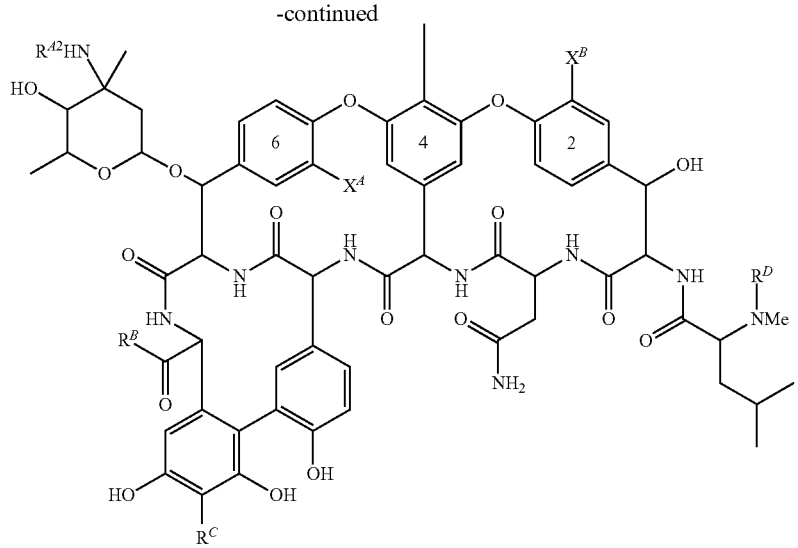

wherein respective symbols are as defined in above (20).

(22) The compound, a pharmaceutically acceptable salt thereof, or a solvate thereof according to above (20), wherein the compound is represented by the formula:

[Chemical formula 22]

(V-2)

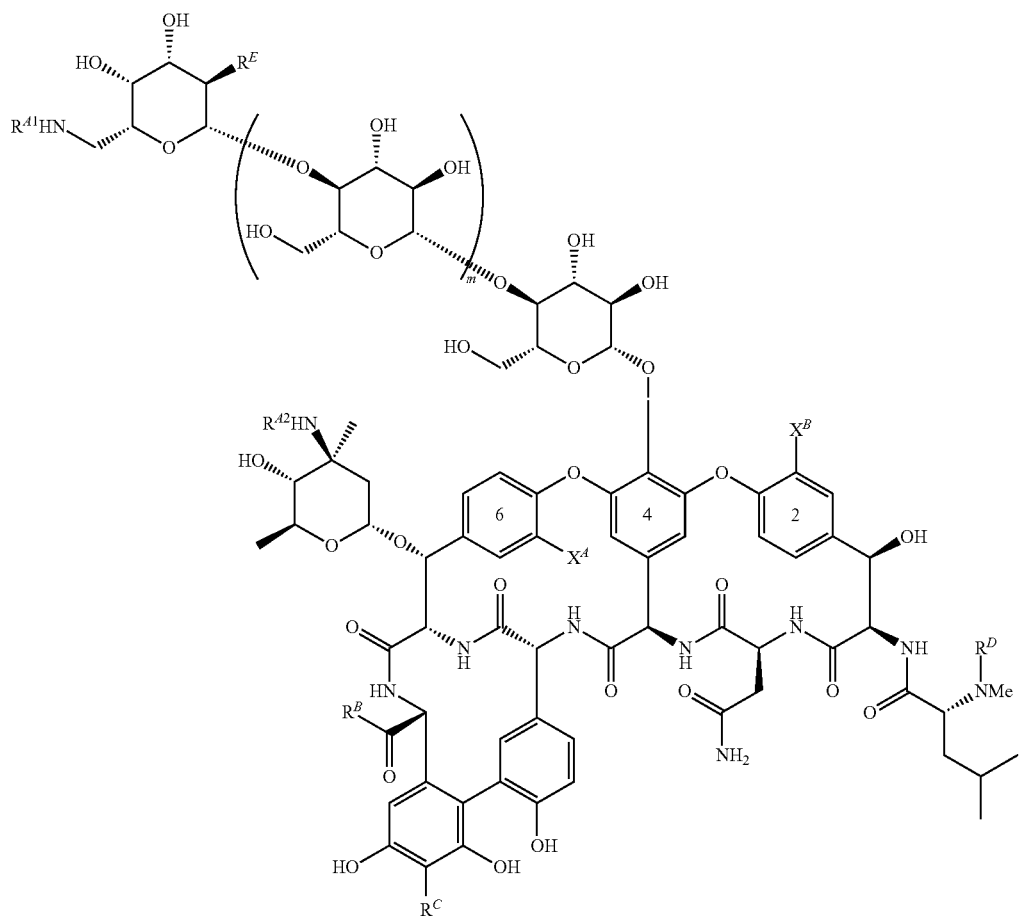

wherein respective symbols are each as defined in above (20).

(23) The compound, a pharmaceutically acceptable salt thereof, or a solvate thereof according to above (1), wherein the compound is represented by the formula:

[Chemical formula 23]

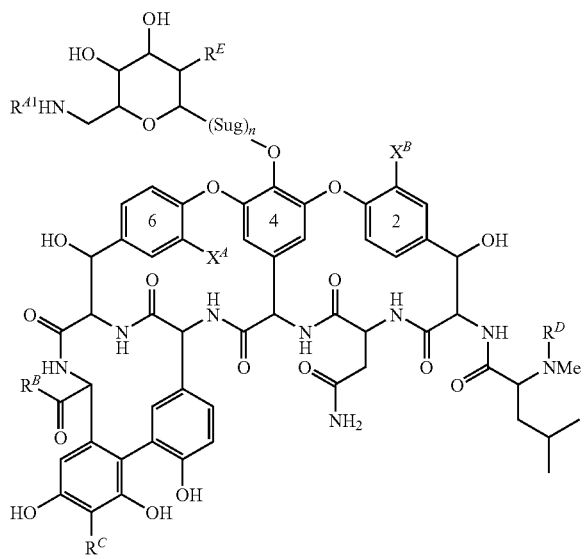

(VI)

wherein $R^B$ is —OH, —$NR^5R^{5'}$ (wherein $R^5$ and $R^{5'}$ are each independently hydrogen, optionally substituted with lower alkyl, optionally substituted lower alkyloxy, or optionally substituted amino or amino sugar residue) or —$OR^6$ (wherein $R^6$ is optionally substituted lower alkyl (a hetero atom group may intervene in the lower alkyl part));

$R^C$ is hydrogen or optionally substituted lower alkyl (a hetero atom group may intervene in the lower alkyl part);

$R^D$ is hydrogen or lower alkyl; and $X^A$ and $X^B$ are each independently hydrogen or halogen; and other symbols are as defined in above (1).

(24) The compound, a pharmaceutically acceptable salt thereof, or a solvate thereof according to above (23), wherein the compound is represented by the formula:

[Chemical formula 24]

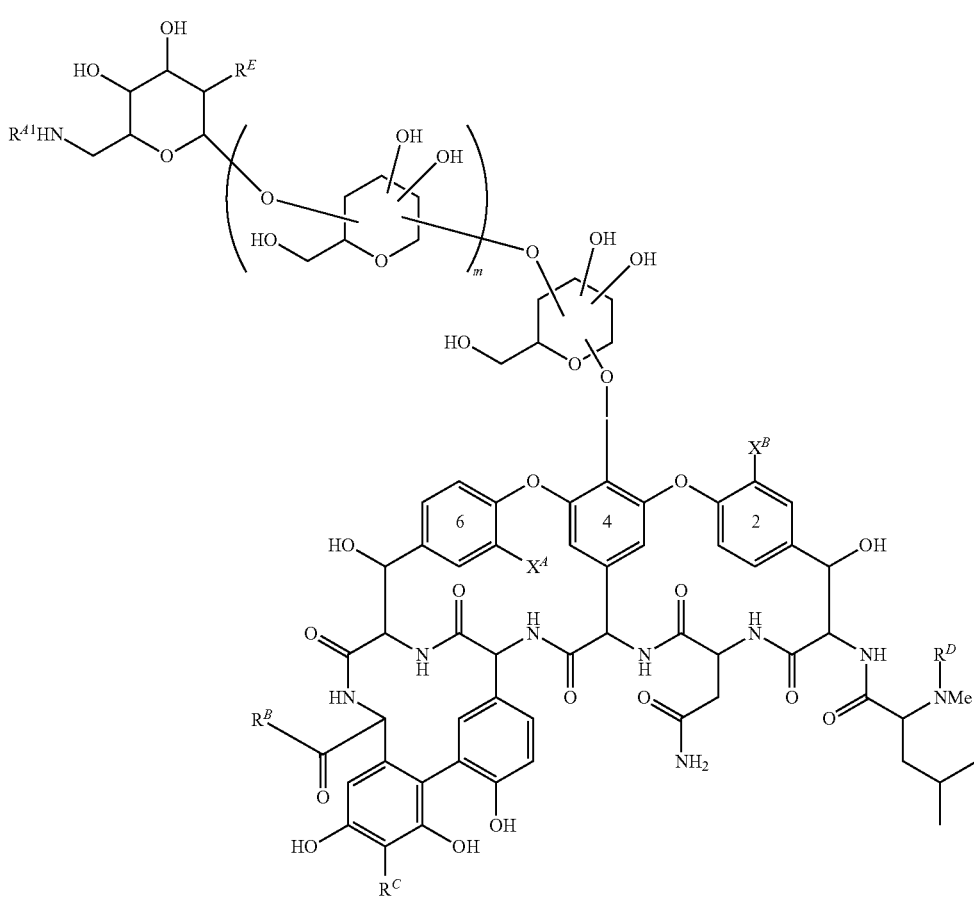

(VI-0)

wherein
m is an integer of 0 to 4; and
other symbols are each as defined in above (23).

(25) The compound, a pharmaceutically acceptable salt thereof, or a solvate thereof according to above (24), wherein the compound is represented by the formula:

[Chemical formula 25]

(VI-1)

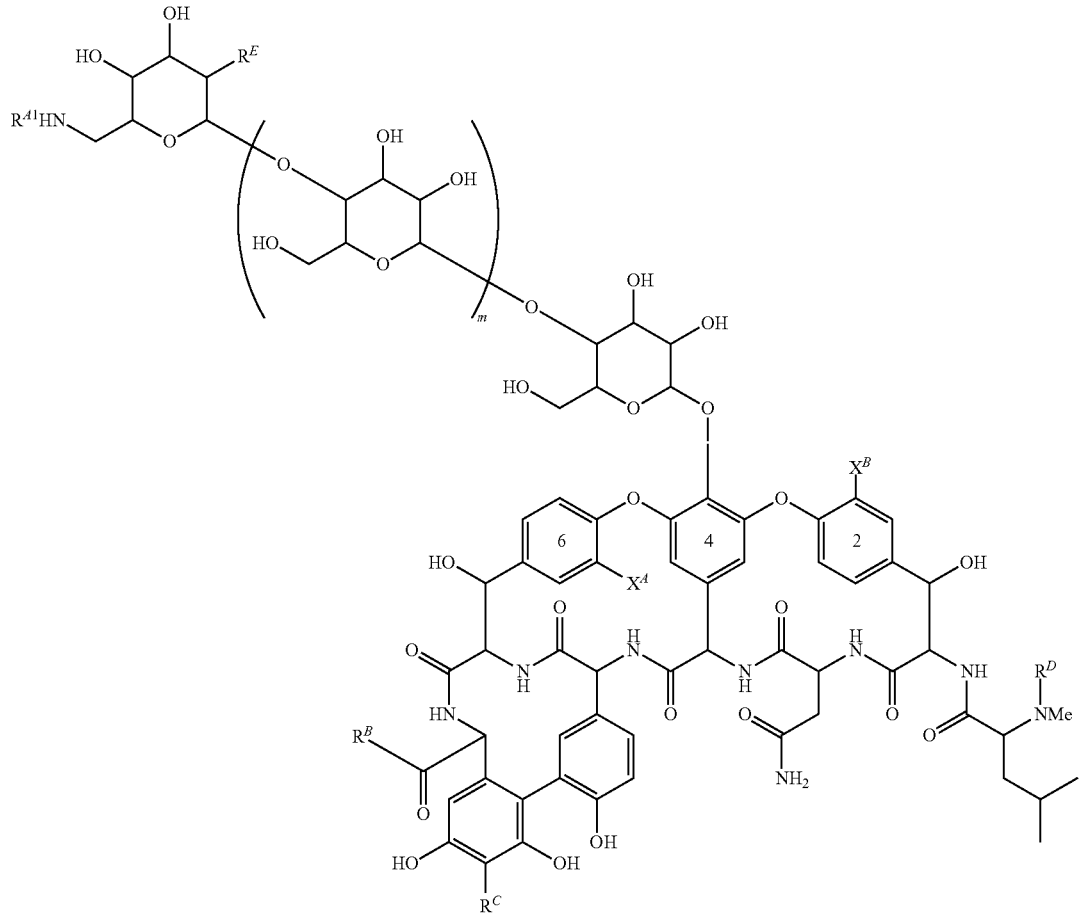

wherein respective symbols are as defined in above (24).

(26) The compound, a pharmaceutically acceptable salt thereof, or a solvate thereof according to above (24), wherein the compound is represented by the formula:

[Chemical formula 26]

(VI-2)

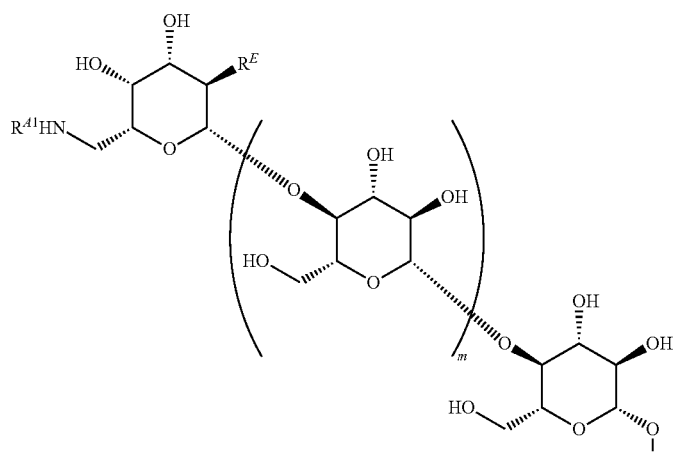

-continued

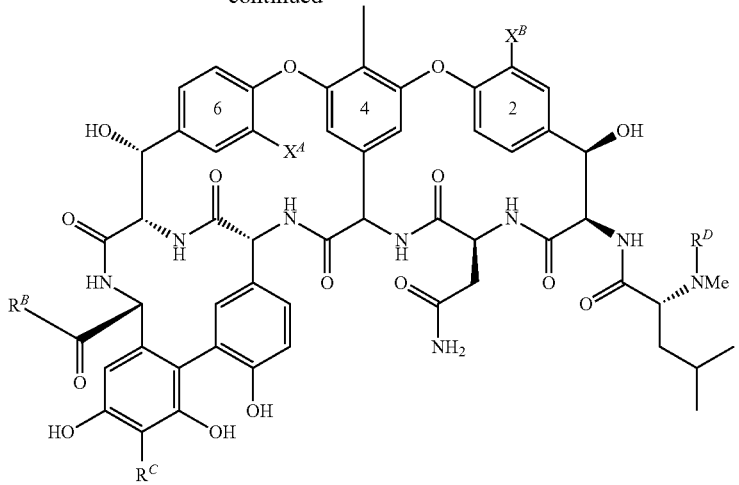

wherein respective symbols are each as defined in above (24).

(27) The compound, a pharmaceutically acceptable salt thereof, or a solvate thereof according to any one of above (6) to (8), (11) to (13), (16) to (18), (20) to (22), and (24) to (26), wherein m is 0 or 1.

(28) The compound, a pharmaceutically acceptable salt thereof, or a solvate thereof according to any one of above (1) to (27), wherein $R^E$ is OH.

(29) The compound, a pharmaceutically acceptable salt thereof, or a solvate thereof according to any one of above (1) to (28), wherein each substituents in optionally substituted lower alkyl, optionally substituted lower alkenyl, or optionally substituted cycloalkyl, of $R^{A1}$ are selected from the following Substituent group A.

Substituent group A: optionally substituted aryl, optionally substituted heteroaryl, optionally substituted heterocycle, optionally substituted aralkylthio, optionally substituted heteroaralkylthio, optionally substituted cycloalkyl, optionally substituted lower alkyloxy, optionally substituted aralkyloxy, optionally substituted aryloxy, optionally substituted arylsulfonylamino, and optionally substituted amino

(30) The compound, a pharmaceutically acceptable salt thereof, or a solvate thereof according to above (29), wherein each substituents of "optionally substituted" groups in Substituent group A of above (29) are selected from the following Substituent group B.

Substituent group B: optionally substituted arylaminocarbonylamino, optionally substituted arylcarbonylamino, oxo, halogen, optionally substituted aryl, optionally substituted aryloxy, optionally substituted arylthio, optionally substituted arylsulfonyl, optionally substituted lower alkyl, optionally substituted aralkyl, optionally substituted amino, optionally substituted aralkylcarbonylamino, optionally substituted aralkylaminocarbonyl, optionally substituted aralkylsulfinyl, optionally substituted arylsulfonylamino, optionally substituted aralkylthio, halo lower alkyl, halo lower alkyloxy, optionally substituted heteroaryl, optionally substituted heteroaryloxy, and optionally substituted aryl lower alkenyl (30') The compound, a pharmaceutically acceptable salt thereof, or a solvate thereof according to above (29), wherein each substituent of "optionally substituted" groups in Substituent group A of above (29) is selected from the following Substituent group B.

Substituent group B: optionally substituted arylaminocarbonylamino, optionally substituted arylaminocarbonyl, optionally substituted arylcarbonyl, optionally substituted arylcarbonylamino, optionally substituted arylcarbonylaminoalkyl, oxo, halogen, optionally substituted aryl, optionally substituted aryloxy, optionally substituted arylthio, optionally substituted arylamino, optionally substituted arylaminoalkyl, optionally substituted arylaminocarbonylalkyl, optionally substituted arylsulfonyl, optionally substituted lower alkyl, optionally substituted aralkyl, optionally substituted amino, optionally substituted aralkylcarbonylamino, optionally substituted aralkylamino, optionally substituted aralkylaminocarbonyl, optionally substituted aralkylsulfinyl, optionally substituted arylsulfonylamino, optionally substituted arylaminosulfonyl, optionally substituted aralkylthio, halo lower alkyl, lower alkyloxy, lower alkylamino, halo lower alkyloxy, optionally substituted heteroaryl, optionally substituted heteroarylalkyl, optionally substituted heteroarylcarbonyl, optionally substituted heteroaryloxy, optionally substituted heteroarylthio, optionally substituted aryl lower alkenyl, optionally substituted heteroaryl lower alkenyl, optionally substituted cycloalkyl, optionally substituted cycloalkyloxy, optionally substituted cycloalkylthio, optionally substituted cycloalkylaminocarbonyl, optionally substituted cycloalkyl lower alkenyl, optionally substituted cycloalkylsulfonyl, optionally substituted cycloalkylaminocarbonylamino, optionally substituted cycloalkylaminoalkyl, optionally substituted cycloalkyl lower alkylamino, optionally substituted cycloalkylamino, optionally substituted cycloalkyl lower alkyl, optionally substituted cycloalkylcarbonyl, optionally substituted cycloalkyl lower alkylcarbonylamino, optionally substituted cycloalkylcarbonylamino, optionally substituted cycloalkylcarbonylaminoalkyl, optionally substituted cycloalkyl lower alkylaminocarbonyl, optionally substituted cycloalkylsulfonylamino, optionally substituted cycloalkylaminocarbonylalkyl, and optionally substituted cycloalkylaminosulfonyl

(31) The compound, a pharmaceutically acceptable salt thereof, or a solvate thereof according to above (30) or (30'), wherein each substituents of "optionally substituted" groups in Substituent group B of above (30) or (30') are selected from the following Substituent group C.

Substituent group C: lower alkyl, lower alkyloxy, lower alkylsulfonyl, nitro, aralkyloxy, halogen, cyano, halo lower alkyl, halo lower alkyloxy, and di-lower alkylamino

(32) The compound, a pharmaceutically acceptable salt thereof, or a solvate thereof according to any one of above (15) to (31), and (30'), wherein $R^B$ is OH; $R^C$ is H; and $R^D$ is H.

In addition, the present invention provides a process for producing the compounds described in above (1) to (32), and (30'), shown in the following (33) to (38).

(33) A process for producing the glycopeptide compound, a pharmaceutically acceptable salt thereof, or a solvate thereof as defined in above (6) including the following steps:

(Step 1)

a step converting a sugar residue (VI) represented by the formula:

[Chemical formula 27]

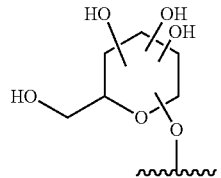
(VI)

into a group (VII) represented by the formula:

[Chemical formula 28]

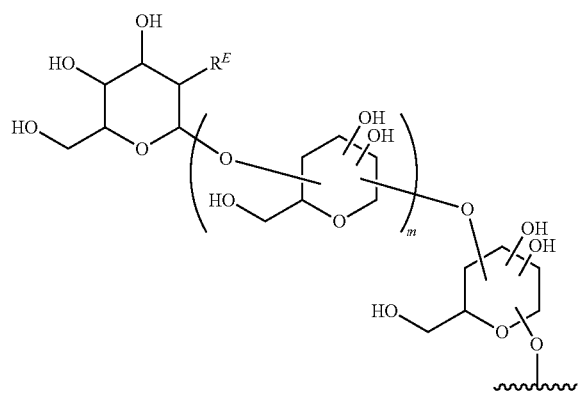
(VII)

wherein $R^E$ is OH or NHAc; and m is an integer of 0 to 2;

by performing 1+m (m is an integer of 0 to 2) times of glycosylating reaction in the presence of glycosyltransferase and a sugar donor using a glycopeptide compound, a salt thereof, or a solvate thereof as a raw material, wherein the aromatic ring of the fourth amino acid residue is substituted with the sugar residue (VI).

(Step 2)

a step converting the hydroxymethylene part in the sugar at the end of the group (VII) into a group (VIII) represented by the formula:

[Chemical formula 29]

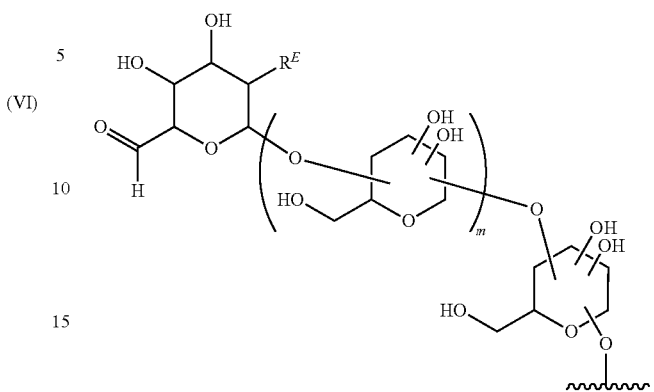
(VIII)

wherein respective symbols are as defined above;
by an oxidation reaction; and
(Step 3)
a step converting the group (VIII) into a sugar residue (I-0) represented by the formula:

[Chemical formula 30]

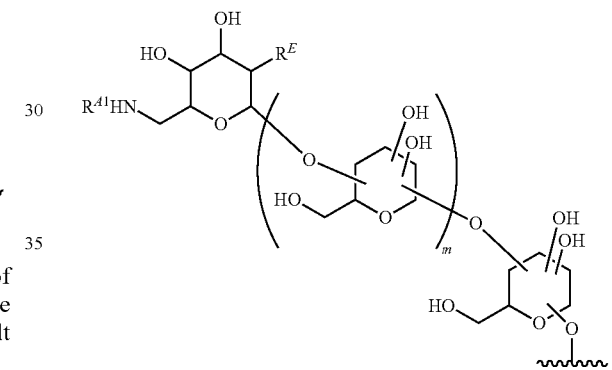
(I-0)

wherein respective symbols are as defined above
by reductive amination reaction of the aldehyde group of the group (VIII) with a compound (A) represented by the formula $R^{41}NH_2$.

(34) A process for producing the compound (IV-0), a pharmaceutically acceptable salt thereof or a solvate thereof as defined in above (16) represented by the formula:

[Chemical formula 34]

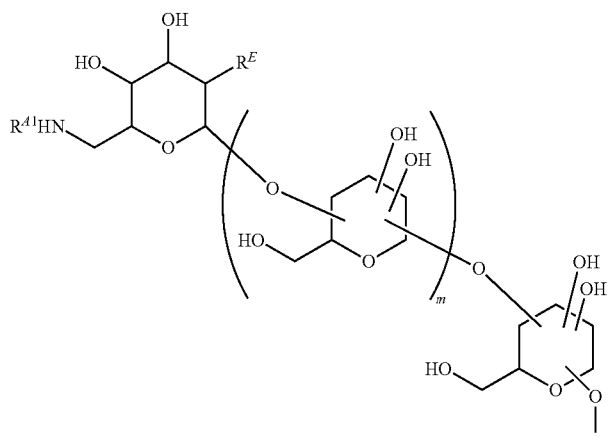
(IV-0)

-continued

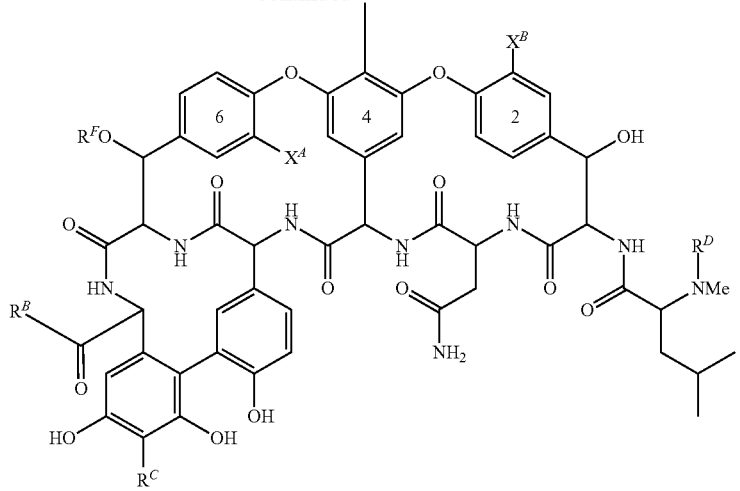

wherein respective symbols are as defined below,
including the following steps:

(Step 1)

a step of reacting 1+m (m is an integer of 0 to 2) times of glycosylating reaction in the presence of glycosyltransferase and a sugar donor using a compound (VII-1) as a raw material represented by the formula:

[Chemical formula 31]

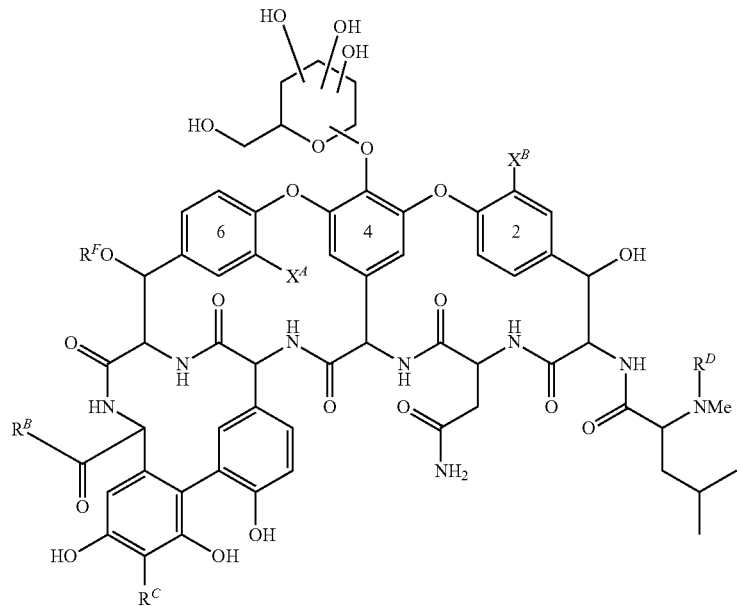

(VII-1)

wherein respective symbols are as defined in above (15), to obtain a compound (VIII-1), a salt thereof, or a solvate thereof represented by the formula:

[Chemical formula 32]
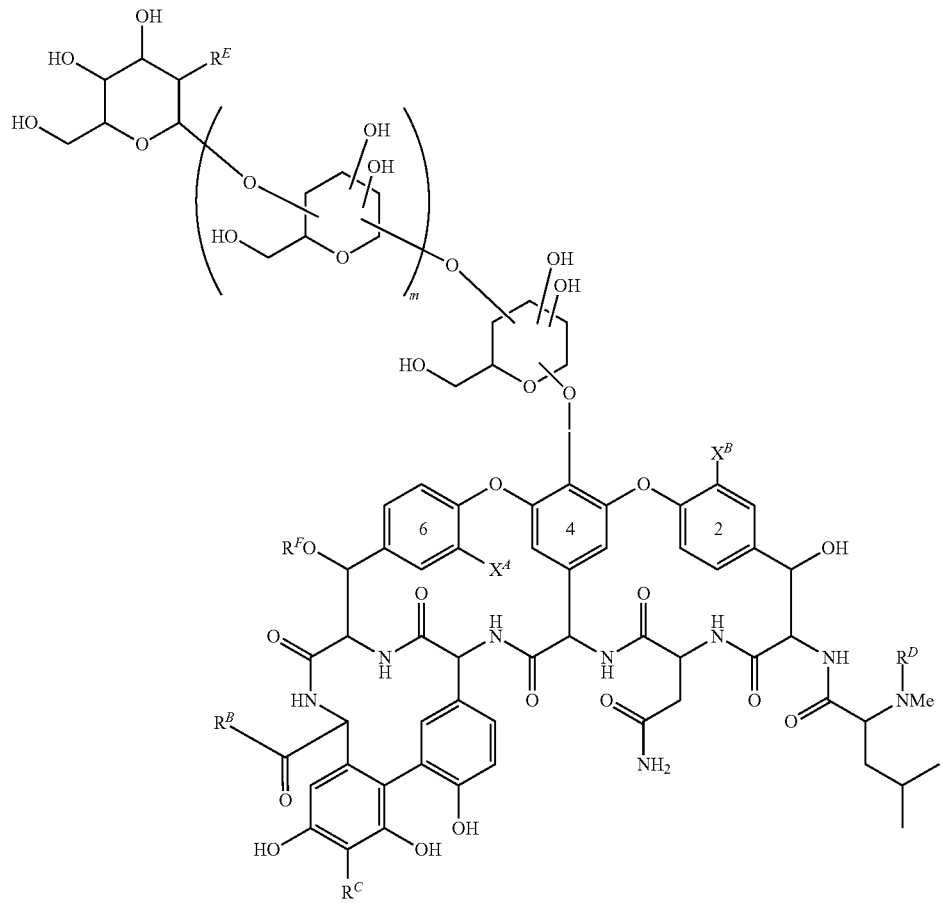
(VIII-1)
wherein $R^E$ is OH or NHAc; and other symbols are as defined above,
(Step 2)
a step of subjecting the compound (VIII-1), a salt thereof, or a solvate thereof to an oxidation reaction to obtain a compound (IX-1), a salt thereof, or a solvate thereof represented by the formula:
[Chemical formula 33]
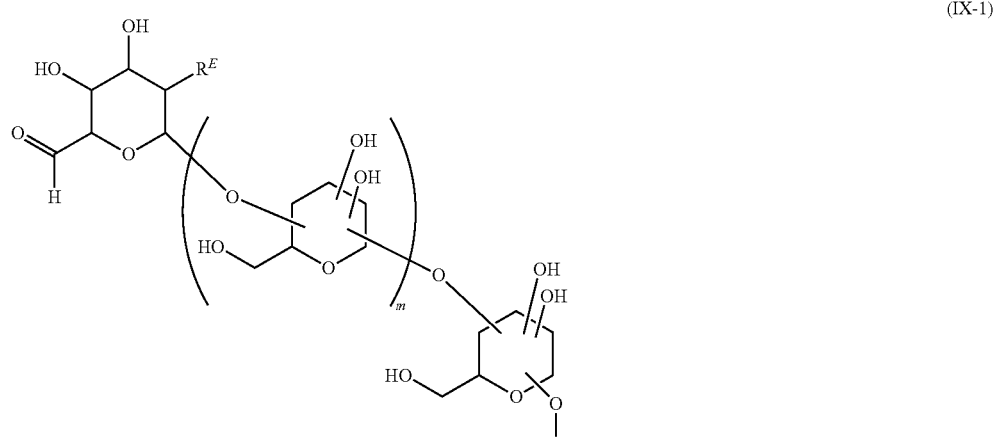
(IX-1)

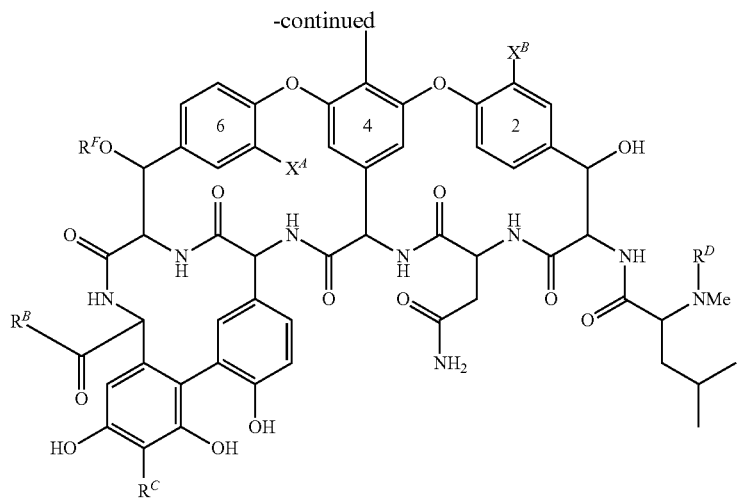

wherein respective symbols are as defined above,
and
(Step 3)
a step of subjecting the compound (IX-1), a salt thereof, or a solvate thereof to a reductive amination reaction with a compound (A) represented by the formula: $R^{A1}NH_2$.
(35) A process for producing a compound (IV-1), a pharmaceutically acceptable salt, or a solvate thereof, as defined in above (17) represented by the formula:

[Chemical formula 38]

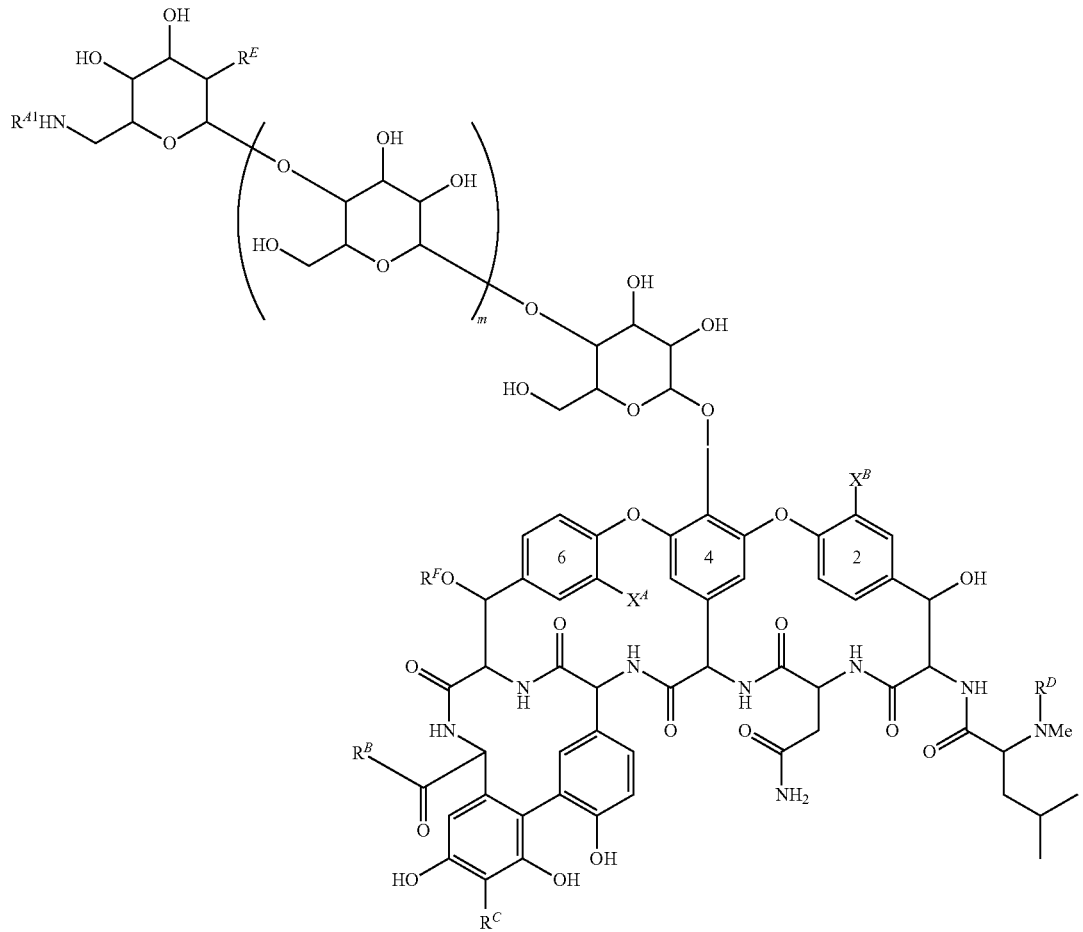

(IV-1)

wherein respective symbols are as defined below,
including the following steps:
(Step 1)
a step of reacting 1+m (m is an integer of 0 to 2) times of glycosylating reaction in the presence of glycosyltransferase and a sugar donor using a compound (VII-1) as a raw material represented by the formula:

[Chemical formula 35]

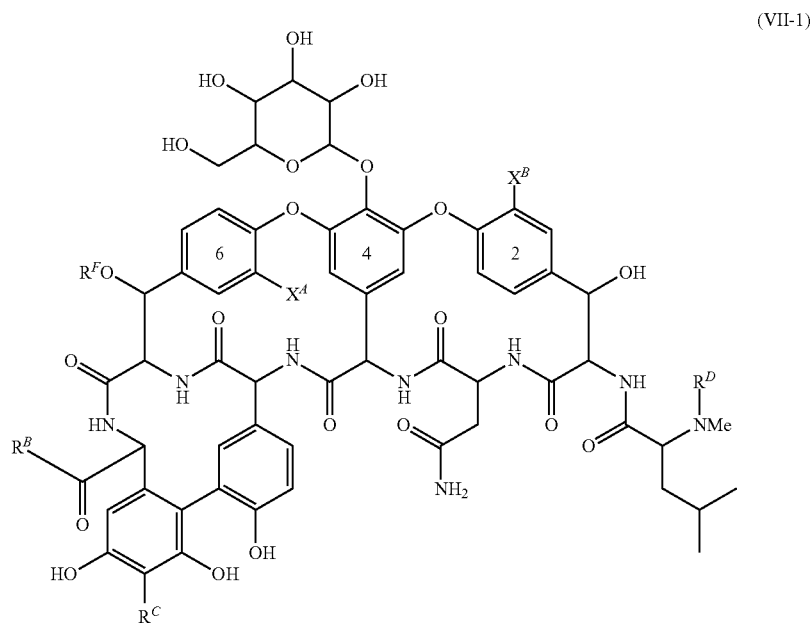

(VII-1)

wherein respective symbols are as defined in above (15), to obtain a compound (VIII-2), a salt thereof, or a solvate thereof, represented by the formula:

[Chemical formula 36]

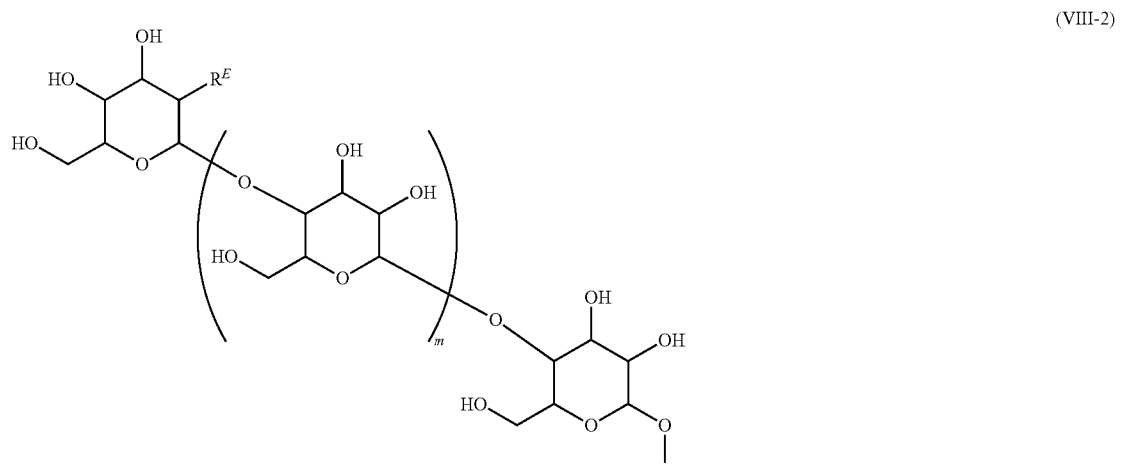

(VIII-2)

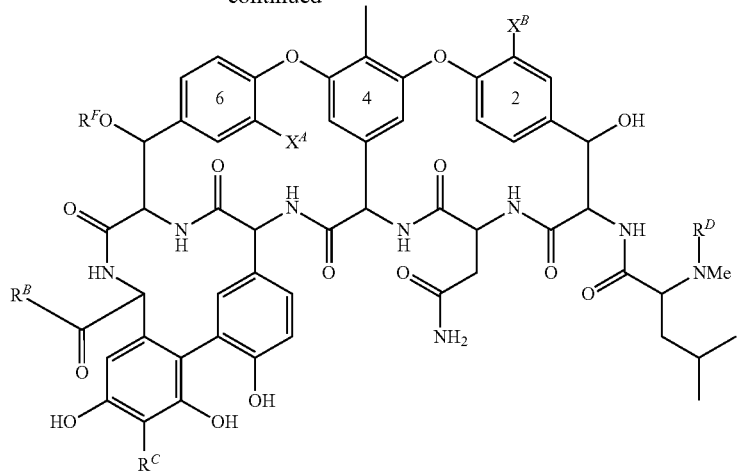
wherein $R^E$ is OH or NHAc; and other symbols are as defined above,
(Step 2)
a step of subjecting the compound (VIII-2), a salt thereof, or a solvate thereof to an oxidation reaction to obtain a compound (IX-2), a salt thereof, or a solvate thereof represented by the formula:
[Chemical formula 37]
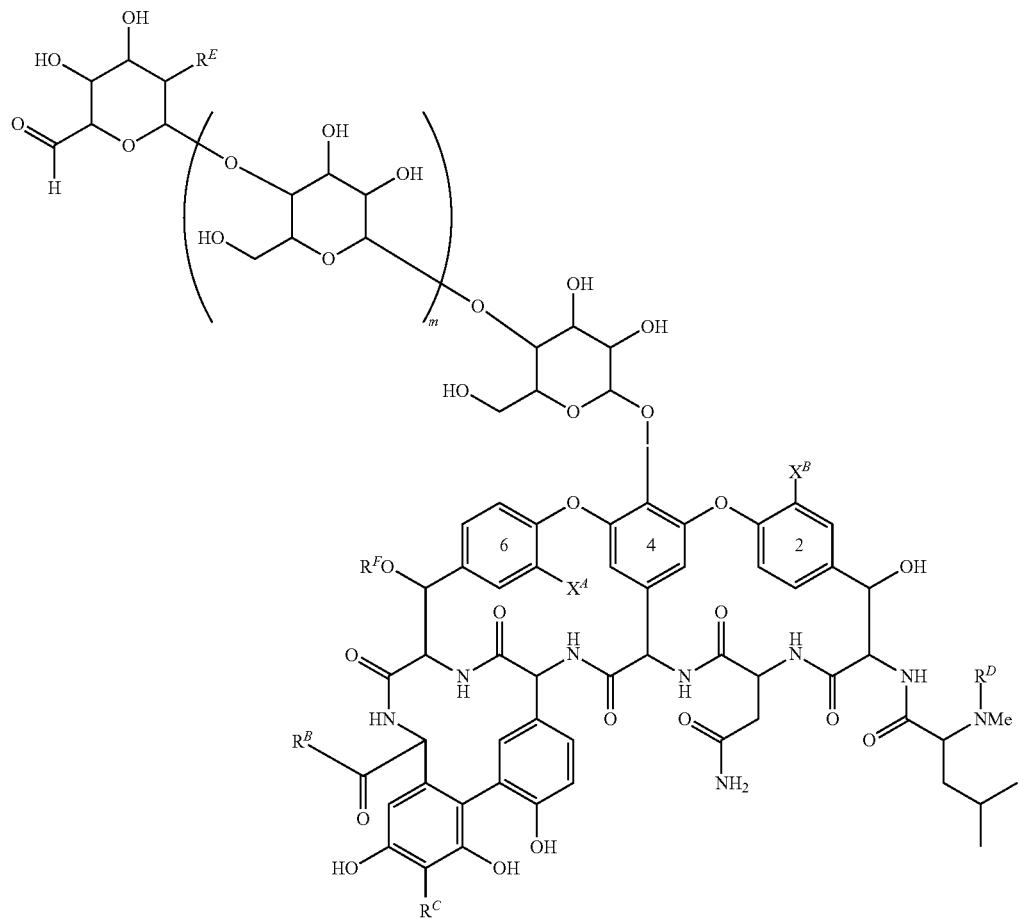
(IX-2)
wherein respective symbols are as defined above; and (Step 3)

a step of subjecting the compound (IX-2), a salt thereof, or a solvate thereof to a reductive amination reaction with a compound (A) represented by the formula: $R^{41}NH_2$.

(36) A process for producing a compound (IV-2), a pharmaceutically acceptable salt thereof, or a solvate thereof, as defined in above (18) represented by the formula:

[Chemical formula 42]

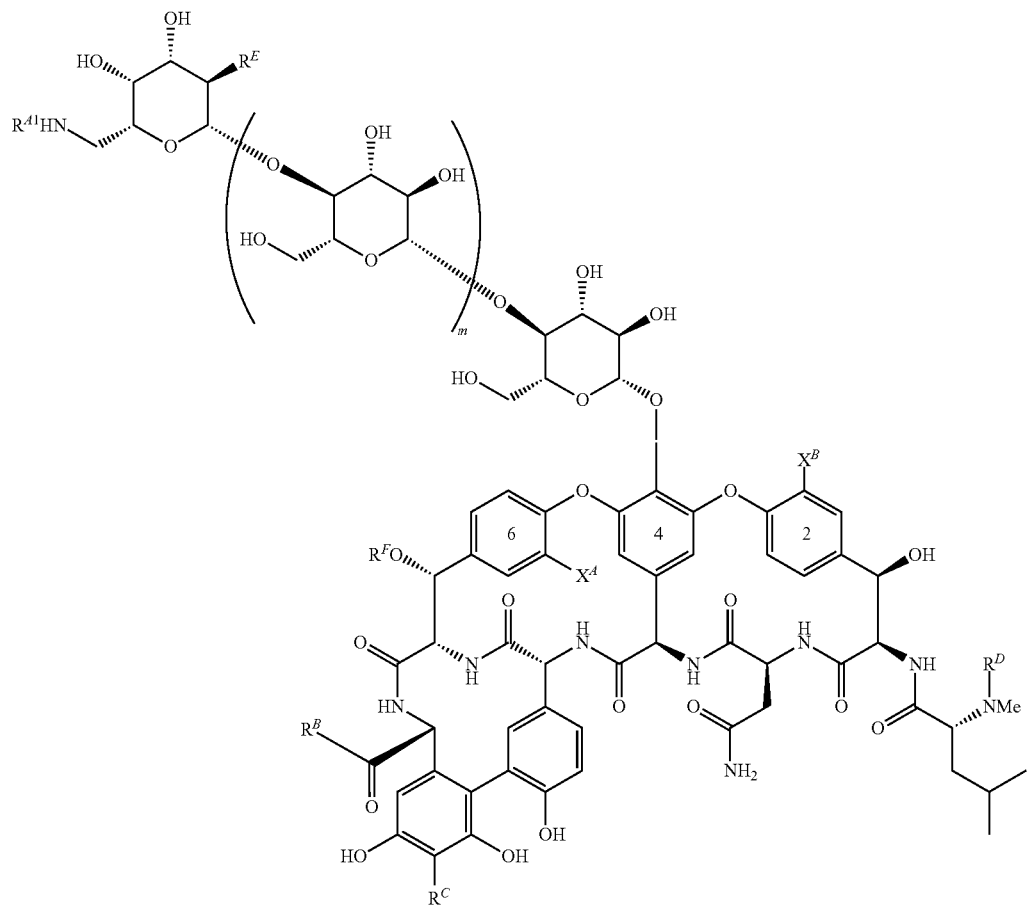

(IV-2)

wherein respective symbols are as defined below;

including the following steps:

(Step 1)

a step of reacting 1+m (m is an integer of 0 to 2) times of glycosylating reaction in the presence of glycosyltransferase and a sugar donor using a compound (VII-2) as a raw material represented by the formula:

[Chemical formula 39]
(IV-2)
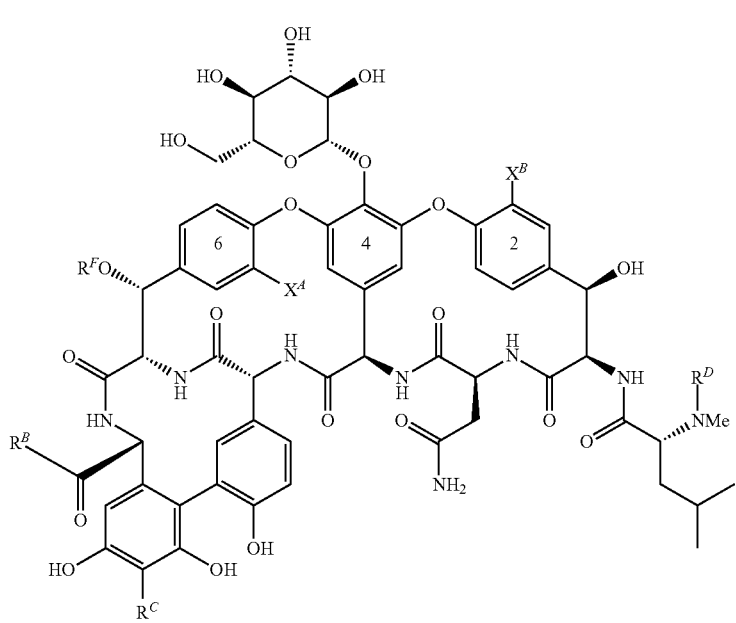
wherein respective symbols are as defined in above (15), to obtain a compound (VIII-3), a salt thereof, or a solvate thereof represented by the formula:
[Chemical formula 40]
(VIII-3)
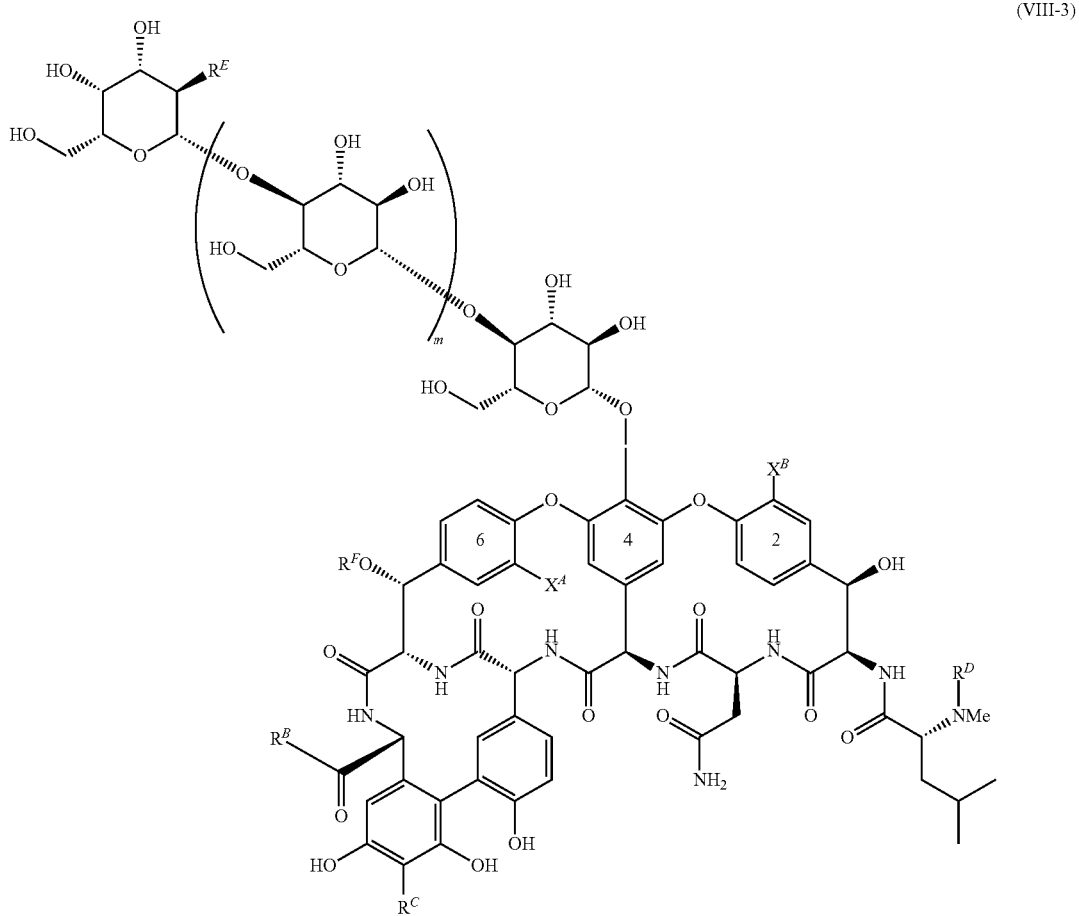

wherein $R^E$ is OH or NHAc; and other symbols are as defined above, (Step 2)

a step of subjecting the compound (VIII-3), a salt thereof, or a solvate thereof to an oxidation reaction to obtain a compound (IX-3), a salt thereof, or a solvate thereof represented by the formula:

[Chemical formula 41]

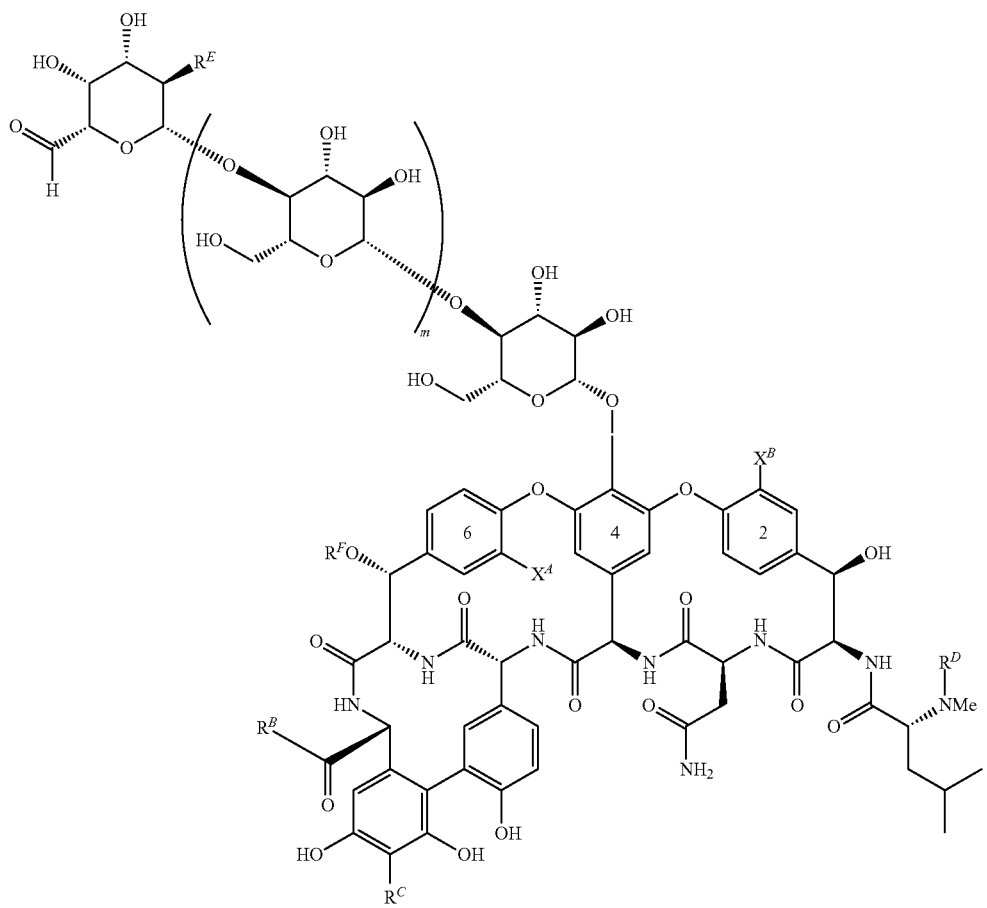

(IX-3)

wherein respective symbols are as defined above, and (Step 3)

a step of subjecting the compound (IX-3), a salt thereof, or a solvate thereof to a reductive amination reaction with a compound (A) represented by the formula: $R^{A1}NH_2$.

(37) The process according to any one of above (33) to (36), wherein in the step 1, the glycosyltransferase is galactosyltransferase; a sugar of the sugar donor is the same or different 1 to 3 sugars selected from glucose, galactose, N-acetylgalactosamine, deoxyglucose, and deoxygalactose; and, in the step 2, the oxidation reaction is performed with galactose oxidase.

(38) The process according to any one of above (33) to (36), wherein in the step 1, the glycosyltransferase is galactosyltransferase; and, after addition of glucose by an optional first glycosylating reaction, galactose is further added by a second glycosylating reaction; and, in the step 2, the oxidation reaction is performed with galactose oxidase.

Further, the present invention also provides compounds shown by the following above (39) and (40), which are useful as an intermediate for producing the compounds as defined in any one of above (1) to (32), and (30').

(39) The compound (VIII-1), a salt thereof, or a solvate thereof as defined in above (34).

(40) The compound (IX-1), a salt thereof, or a solvate thereof as defined in (34).

The present invention further provides following dehydrated material of a sugar at the side chain terminal.

(41) A compound, a pharmaceutically acceptable salt thereof, or a solvate thereof represented by the formula:
[Chemical formula 43]
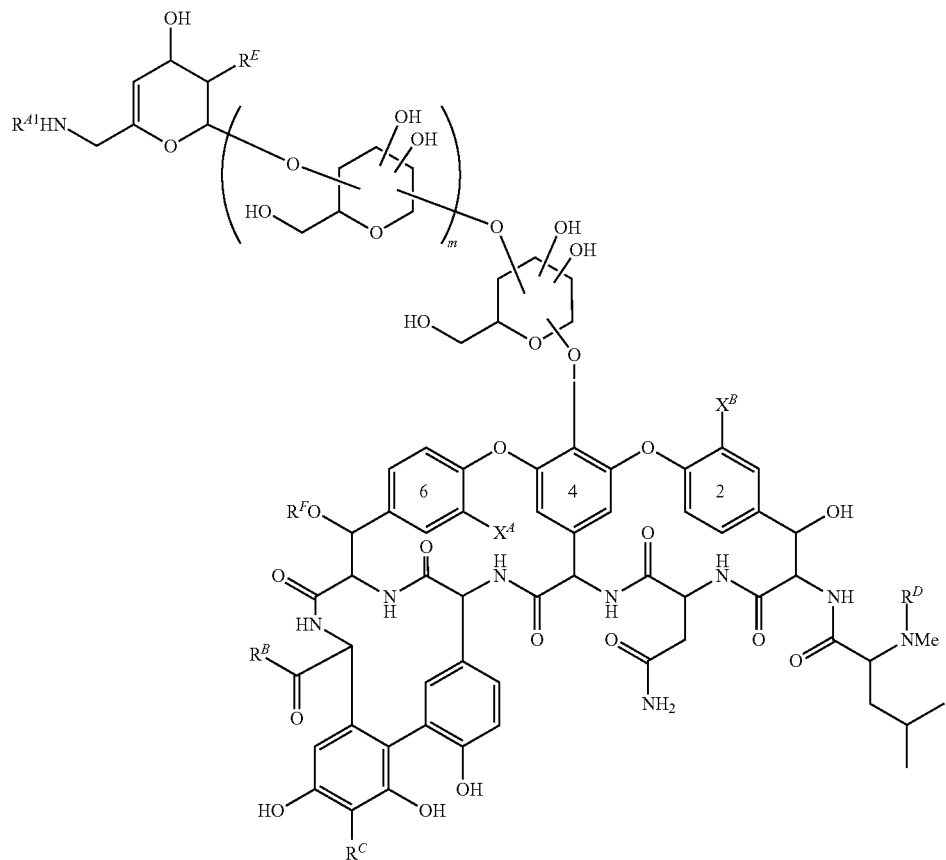
(X-1)
wherein respective symbols are each as defined in above (16).
(42) A compound, a pharmaceutically acceptable salt thereof, or a solvate thereof represented by the formula:
[Chemical formula 44]
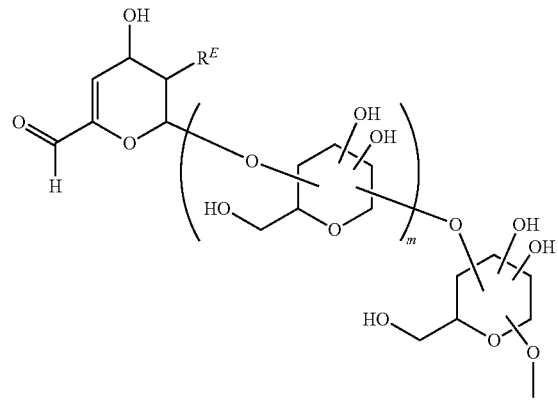
(XI-1)

-continued

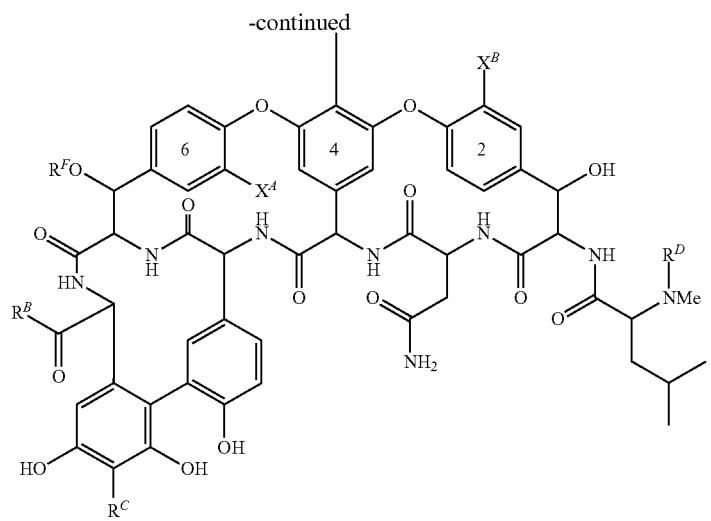

wherein respective symbols are as defined above.

(43) A pharmaceutical composition containing the compound as defined in any one of above (1) to (32), (30'), and (39) to (42), or a pharmaceutically acceptable salt thereof, or a solvate thereof.

Effects of the Invention

The glycopeptide antibiotic derivative of the present invention, a pharmaceutically acceptable salt thereof, or a solvate thereof exhibits an antibacterial activity in an In Vitro and/or In Vivo test against various bacterium such as *Staphylococcus* including MRSA, *Streptococcus, Pneumococcus, Enterococcus*, and the like. Particularly, the compound of the present invention is also effective for vancomycin-resistant bacterium derived therefrom and, particularly, for vancomycin-resistant *Enterococcus* (VRE) and vancomycin-resistant *Staphylococcus aureus* (VRSA). Therefore, the compound of the present invention is useful for treating or preventing various bacterial infections such as complicated skin and skin tissue infection, meningitis, sepsis, pneumonia, arthritis, peritonitis, bronchitis, empyema, endocarditis, catheter bloodstream infection and the like. In addition, the more preferable compound of present invention has high water solubility, is better in disposition, and/or is safe in toxicity (renal toxicity, hepatic toxicity, histamine freeing activity, hERG channel inhibition, antigenicity, etc.).

BEST MODE FOR CARRYING OUT THE INVENTION

Herein, the "glycopeptide antibiotic" means an arbitrary glycopeptide compound having a peptide chain consisting of seven amino acids including an aromatic amino acid as a common fundamental skeleton, and a derivative thereof, represented by vancomycin and chloroorienticins. In addition, the "glycopeptide skeleton" means a cyclic fundamental structure consisting of the peptide chain which is commonly possessed by glycopeptide antibiotics. Examples of the known glycopeptide antibiotics are disclosed in JP-A No. 61-251699 gazette, JP-A No. 7-258289 gazette, International Publication WO 96/30401 pamphlet, International Publication WO 00/39156 pamphlet, JP-A No. 2000-302687 gazette, International Publication WO 2004/44222 pamphlet; U.S. Pat. Nos. 4,639,433; 4,643,987; 4,497,802; 4,698,327; 5,591, 714; 5,840,684; and 5,843,889; EP0802199; EP0801075; EP0667353; WO 97/28812; WO 97/38702; WO 98/52589; WO 98/52592; as well as J. Am. Chem. Soc., 1996, 118, 13107-13108; J. Am. Chem. Soc., 1997, 119, 12041-12047; and J. Am. Chem. Soc., 1994, 116, 4573-4580.

More specific examples of the glycopeptide antibiotics include vancomycin, teicoplanin, ristomycin, ristocetin, actaplanin, actinoidin, ardacin, avoparcin, azureomycin, balhimycin, chloroorienticin A, chloroorienticin B, chloropolyspoin, decaplanin, N-demethylvancomycin, eremomycin, galacardin, helvecardin, izupeptin, kibdelin, mannopeptin, orienticin, parvodicin, synmonicin, oritavancin, telavancin (TD-6424), dalbavancin, and A-40926.

In the present invention, the "glycopeptide skeleton" preferably has the following partial structure (II) as an aglycone part,

[Chemical formula 45]

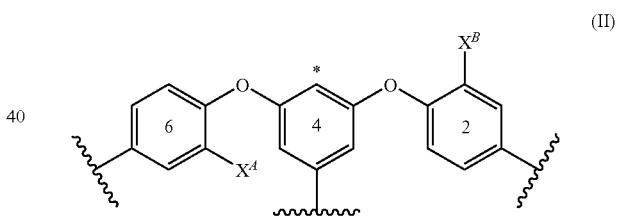

(II)

(wherein the ring 2, the ring 4 and the ring 6 represent aromatic rings of the second, fourth and sixth amino acid residues of a glycopeptide antibiotic, respectively; $X^A$ and $X^B$ are each independently hydrogen or halogen; and * represents a binding position with a sugar residue).

$X^A$ and $X^B$ are preferably both halogen, further preferably Cl.

Further preferably, the glycopeptides skeleton has the following partial structure (II-0);

[Chemical formula 46]

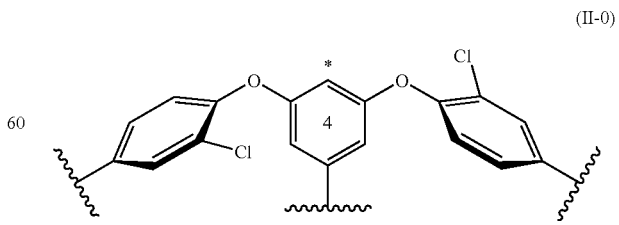

(II-0)

(wherein the ring 4 represents an aromatic ring of the fourth amino acid residue of a glycopeptide antibiotic; and * represents a binding position with a sugar residue).

Further preferably, the glycopeptide skeleton has the following partial structure (II-1);

[Chemical formula 47]

(II-1)

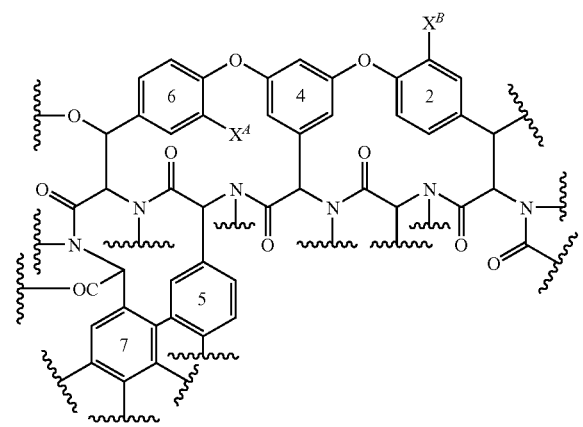

(wherein the rings 2, 4, 5, 6 and 7 represent aromatic rings at the second, fourth, fifth, sixth and seventh amino acid residues of a glycopeptide antibiotic, respectively; $X^A$ and $X^B$ are each independently hydrogen or halogen; and * represents a binding position with a sugar residue).

Further preferably, the glycopeptide skeleton has the following partial structure (II-2):

[Chemical formula 48]

(II-2)

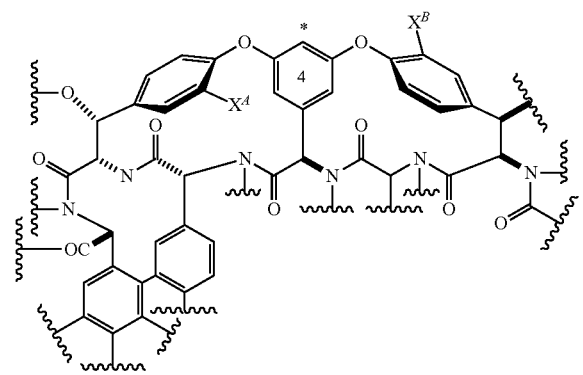

(wherein, respective symbols are as defined above).

The aglycone part may be optionally substituted with a substituent which is well-known to a person skilled in the art or can be synthesized by a person skilled in the art. For example, a C-terminal, an N-terminal, a resorcinol part or the like in a vancomycin derivative, a teicoplanin derivative, a chloroorienticin B derivative or the like may be optionally chemically modified. In addition, a sugar may be bound to a part other than carbon represented by *.

Further preferably, the glycopeptide skeleton has the following partial structure (IV'):

[Chemical formula 49]

(IV')

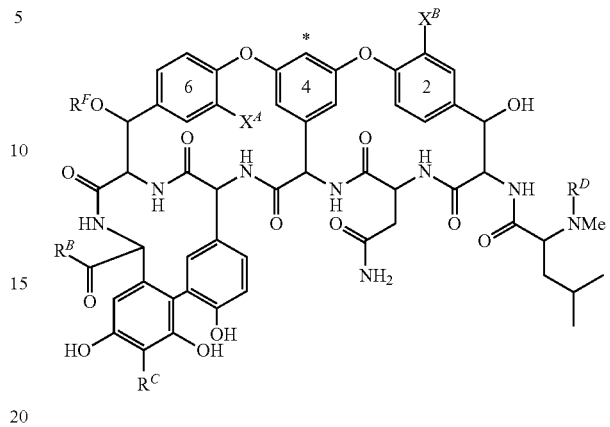

(wherein $R^F$ is hydrogen or a sugar residue;

$R^B$ is —OH, —$NR^5R^{5'}$ (wherein $R^5$ and $R^{5'}$ are each independently hydrogen, optionally substituted lower alkyl, optionally substituted lower alkyloxy, optionally substituted amino or amino sugar residue) or —$OR^6$ (wherein $OR^6$ is optionally substituted lower alkyl (a hetero atom group may intervene in the lower alkyl part));

$R^C$ is hydrogen or optionally substituted lower alkyl (a hetero atom group may intervene in the lower alkyl part);

$R^D$ is hydrogen or lower alkyl;

other symbols are as defined above; and $R^F$ is preferably a sugar residue, more preferably a sugar residue represented by the formula:

[Chemical formula 50]

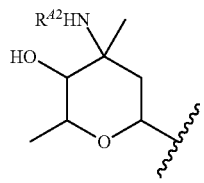

(wherein $R^{42}$ is hydrogen or optionally substituted lower alkyl), still more preferably a sugar residue represented by the formula:

[Chemical formula 51]

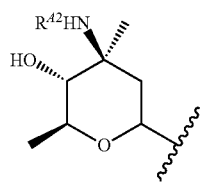

(wherein respective symbols are as defined above).

$R^{42}$ is preferably hydrogen; or lower alkyl optionally substituted with optionally substituted aryl, optionally substituted heteroaryl, or optionally substituted heterocycle or hydroxyl. As a substituent of the "optionally substituted aryl", the "optionally substituted heteroaryl", or the "optionally substituted heterocycle", arylcarbonylamino optionally substituted with halo lower alkyloxy is preferable. $R^{A2}$ is more preferably hydrogen).

$R^B$ is preferably —OH, or —NHR$^5$ (wherein R$^5$ is lower alkyl optionally substituted with hydroxyl or dialkylamino, lower alkyloxy optionally substituted with lower alkyloxy, or lower alkylamino). More preferably, $R^B$ is —OH.

$R^C$ is preferably hydrogen, or lower alkyl optionally substituted with optionally substituted amino. As a substituent of the "optionally substituted amino", SO$_3$H, hydroxy, or lower alky optionally substituted with tri-lower alkylammonium; or heteroaralkyl is preferable. $R^C$ is more preferably hydrogen.

$R^D$ is preferably hydrogen.

Further preferably, the glycopeptide skeleton has the following partial structure (IV"):

[Chemical formula 52]

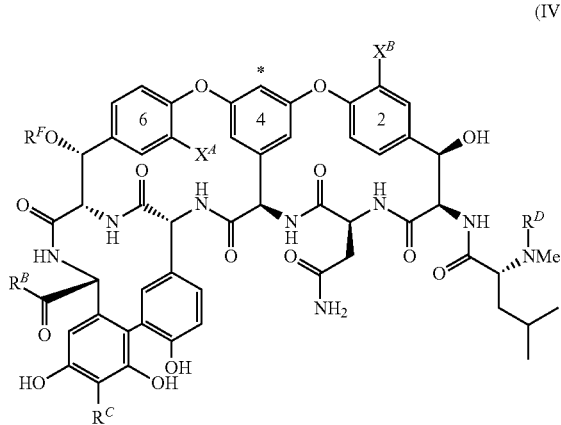

(IV")

(wherein respective symbols are as defined above).

The present compound has an aglycone represented by the partial structure. The compound is a glycopeptide compound in which, further, various sugar residues are bound to the aromatic ring of the fourth amino acid residue in the glycopeptide skeleton. The sugar residue is represented by the following structure:

[Chemical formula 53]

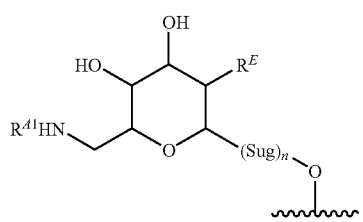

(I)

(wherein
n is an integer of 1 to 5;
Sugs are each independently a monosaccharide, (Sug)$_n$ is a divalent sugar residue formed by binding same or different 1 to 5 monosaccharides;
$R^{A1}$ is optionally substituted lower alkyl, optionally substituted lower alkenyl, or optionally substituted cycloalkyl; and
$R^E$ is OH or NHAc (Ac is acetyl)).
n is preferably 1 or 2.

Sug is preferably glucose, galactose, fructose, fucose, mannose, rhamnose, galactosamine, glucosamine, N-acetylgalactosamine, N-acetylglucosamine, vancosamine, epi-vancosamine, glucuronic acid, sialic acid, deoxyglucose, or deoxygalactose. More preferable is glucose (e.g., β-D-glucose) or galactose (e.g., β-D-galactose).

When n is 1, Sug is further preferably glucose (e.g., β-D-glucose).

When n is 2, it is particularly preferable that two Sugs are glucose (e.g., β-D-glucose) at the same time.

$R^{A1}$ is preferably optionally substituted lower alkyl, or optionally substituted cycloalkyl, more preferably optionally substituted lower alkyl.

$R^E$ is preferably OH.

The sugar residue (I) is preferably the following sugar residue (I-0);

[Chemical formula 54]

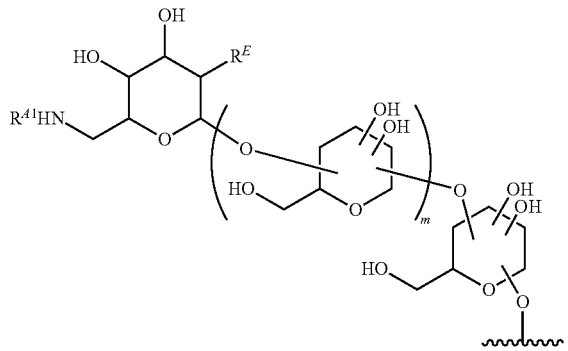

(I-0)

(wherein
m is an integer of 0 to 4; and
$R^{A1}$ and $R^E$ are each as defined above).

In the formula (I-0), positions of two hydroxyl groups which bind to each monosaccharide other than the terminal sugar are not particularly limited, but each hydroxyl group is preferably bound to the 2-position and the 3-position of one monosaccharide. In addition, the binding manner of two adjacent monosaccharides is not particularly limited, but monosaccharides are preferably bound to the 1-position and the 4-position. In addition, the binding position of the sugar which binds to an aglycone part is also not particularly limited, but the sugar preferably forms a glycoside bond with an aglycone at the 1-position of the monosaccharide.

m is preferably 0 or 1.

The sugar residue (I-0) is preferably the following sugar residue (I-1):

[Chemical formula 55]

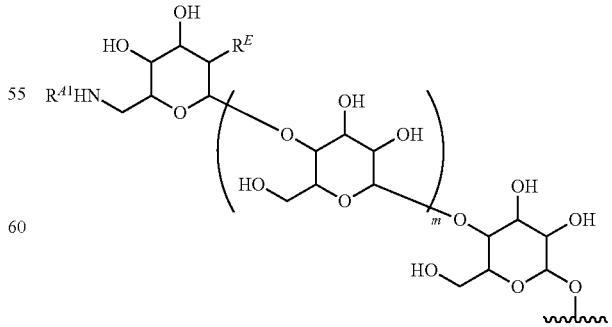

(I-1)

(wherein respective symbols are as defined above).

A monosaccharide adjacent to an aglycone is preferably glucose (e.g., β-D-glucose).

A monosaccharide situated at the terminal is preferably a monosaccharide in which the 6-positional hydroxyl of galactose or N-acetylgalactosamine is substituted with optionally substituted amino. More preferable is a monosaccharide in which the 6-positional hydroxyl of galactose (e.g., β-D-galactose) is substituted with optionally substituted amino.

A monosaccharide constituting other sugar residue is preferably glucose or galactose, more preferably glucose (e.g., β-D-glucose).

The sugar residue (I-1) is preferably the following sugar residue (I-2):

[Chemical formula 56]

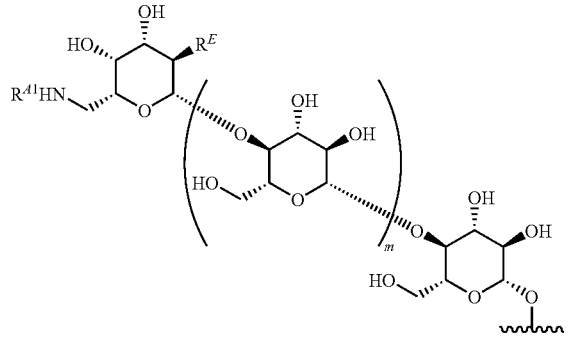

(I-2)

(wherein respective symbols are as defined above).

In the glycopeptide compound of the present invention, the sugar residue exemplified above is bound to carbon represented by * of the aglycone exemplified above.

The present compound preferably has the following partial structure (III):

[Chemical formula 57]

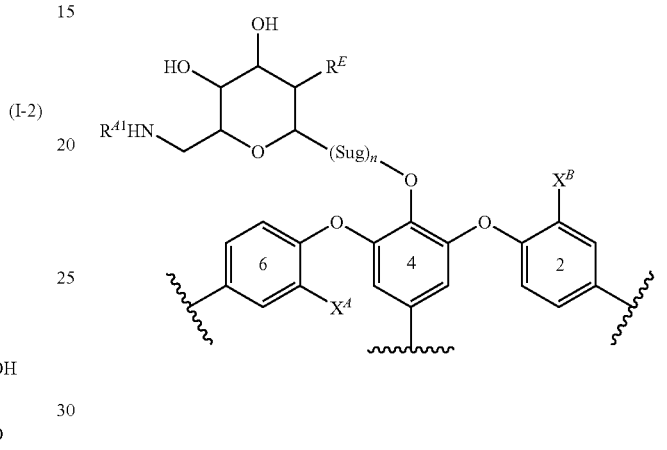

(III)

(wherein respective symbols are as defined above).

The partial structure (III) is preferably the following partial structure (III-0):

[Chemical formula 58]

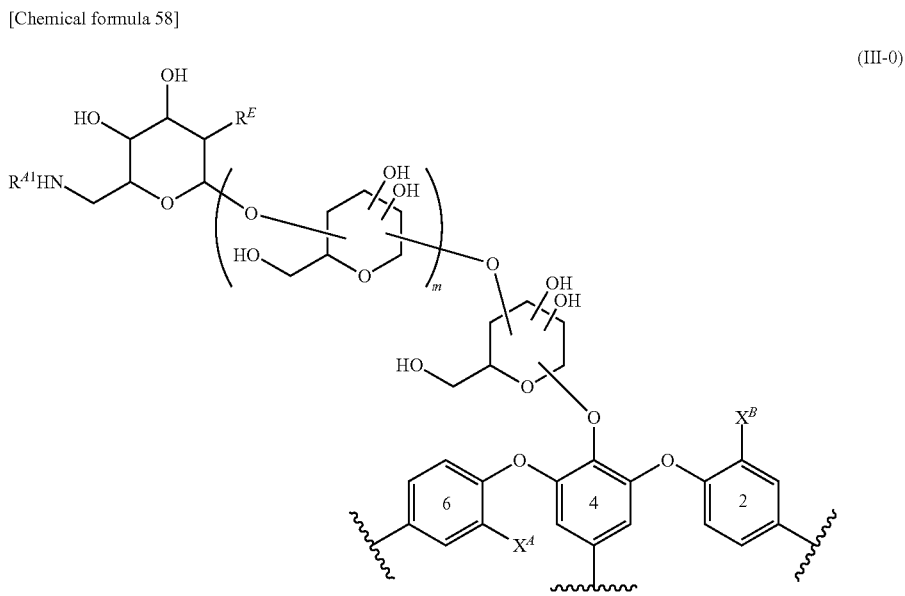

(III-0)

(wherein respective symbols are as defined above).

The partial structure (III-0) is preferably the following partial structure (III-1):

[Chemical formula 59]
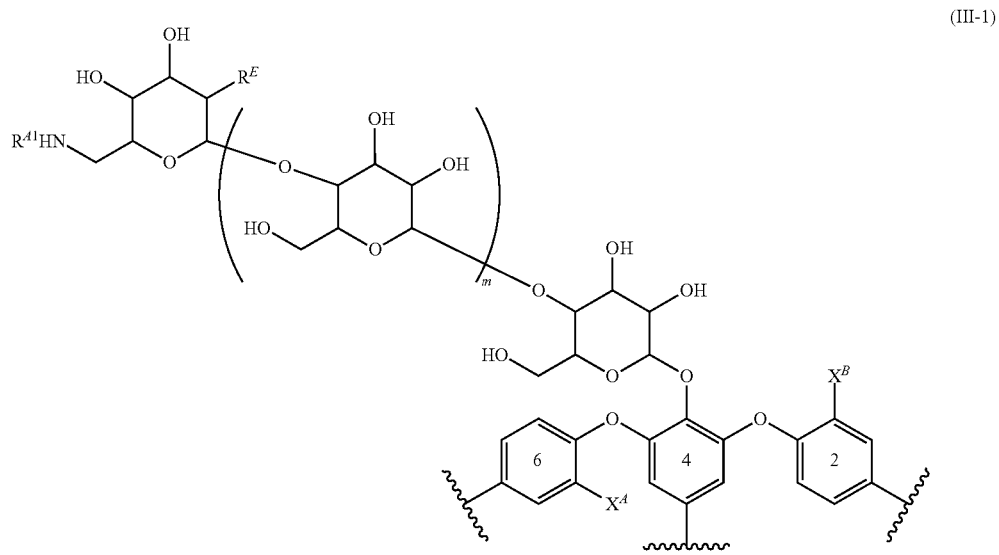
(III-1)
(wherein respective symbols are as defined above).
The partial structure (III-1) is preferably the following structure (III-2):
[Chemical formula 60]
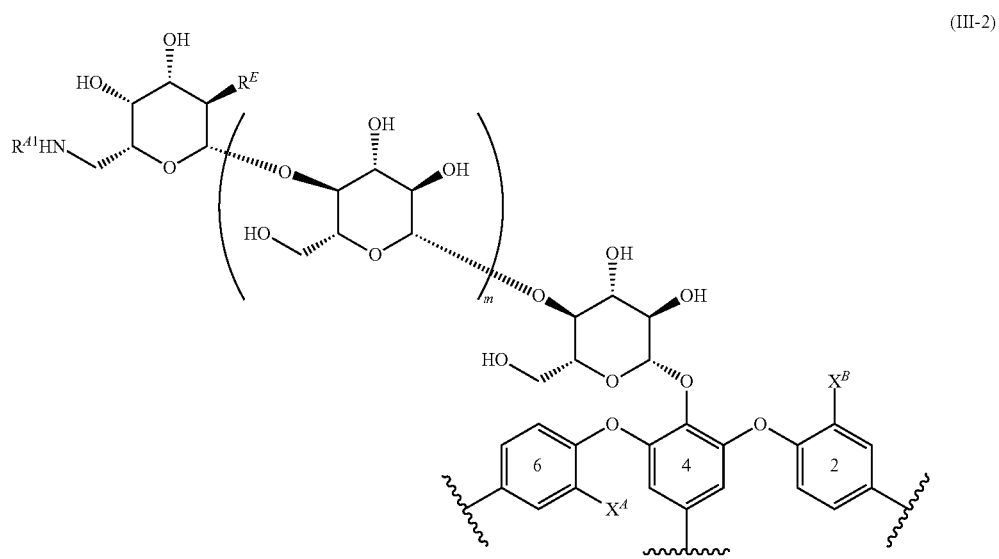
(III-2)
(wherein respective symbols are as defined above).
The compound (X-1) is preferably the following compound (X-2):

[Chemical formula 61]
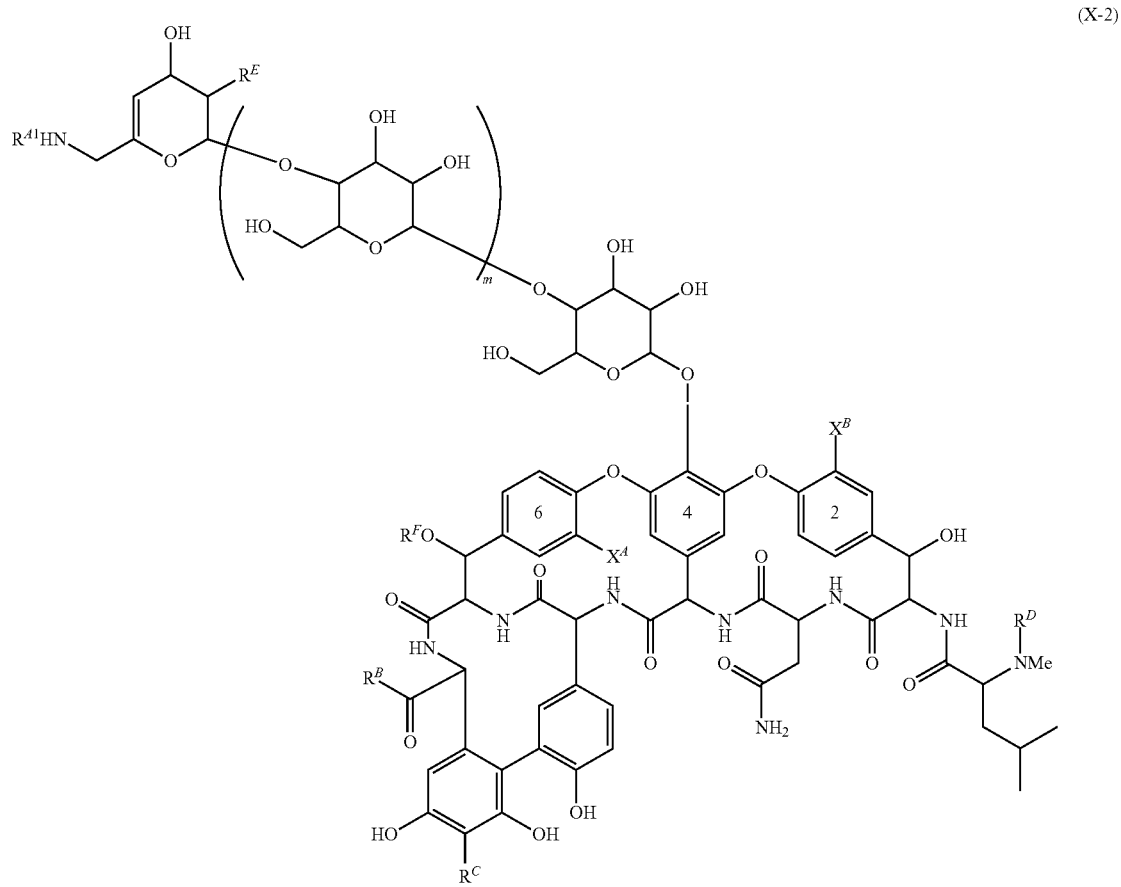
(X-2)
(wherein respective symbols are as defined above),
further preferably a compound (X-3):
[Chemical formula 62]
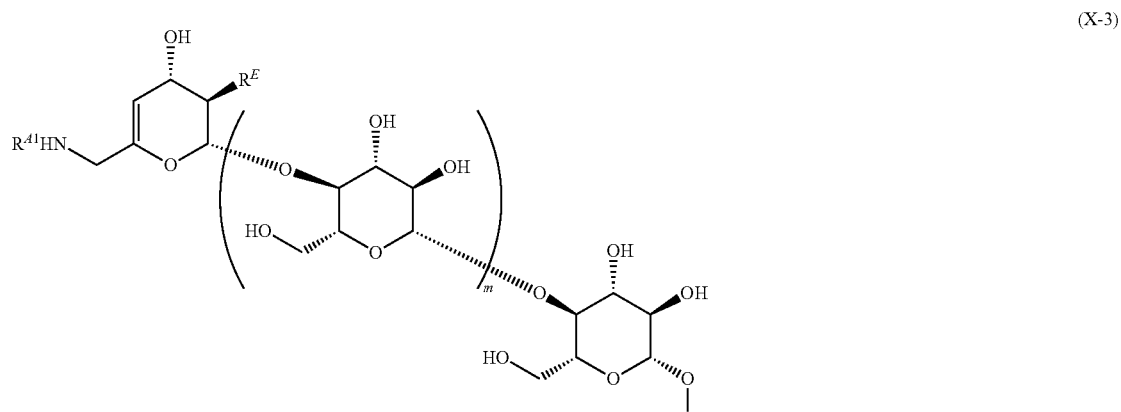
(X-3)

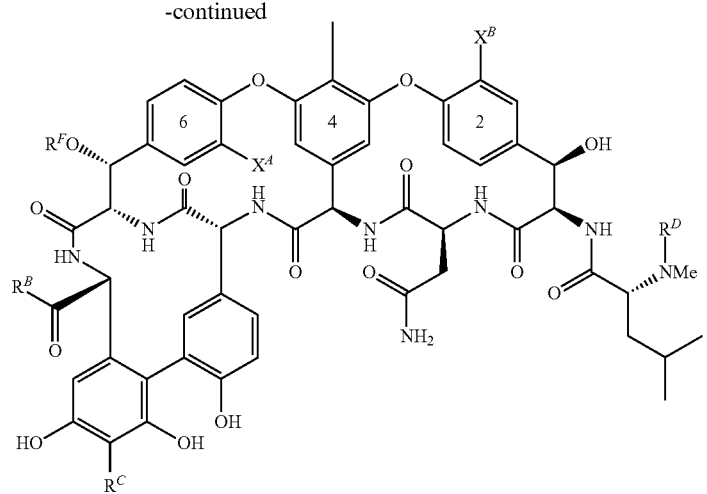
(wherein respective symbols are as defined above).
The compound (XI-1) is preferably the following compound (XI-2):
[Chemical formula 63]
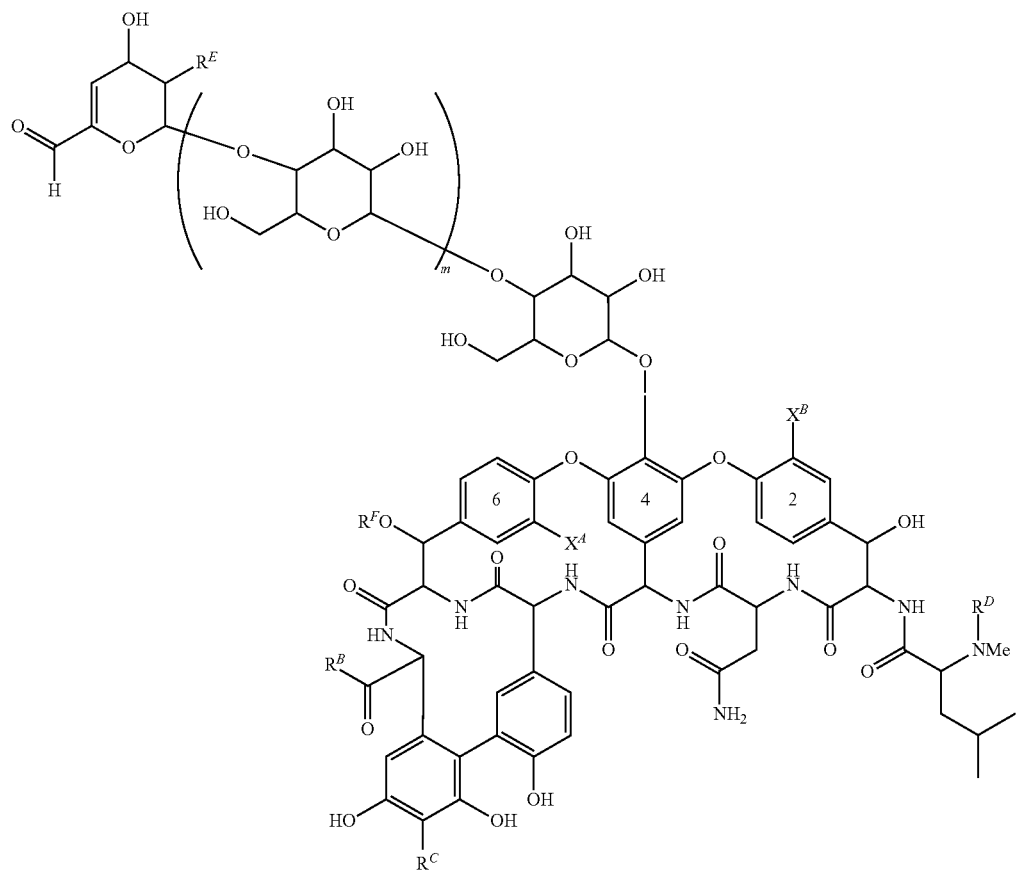
(XI-2)
(wherein respective symbols are as defined above), further preferably a compound (XI-3):

[Chemical formula 64]

(XI-3)

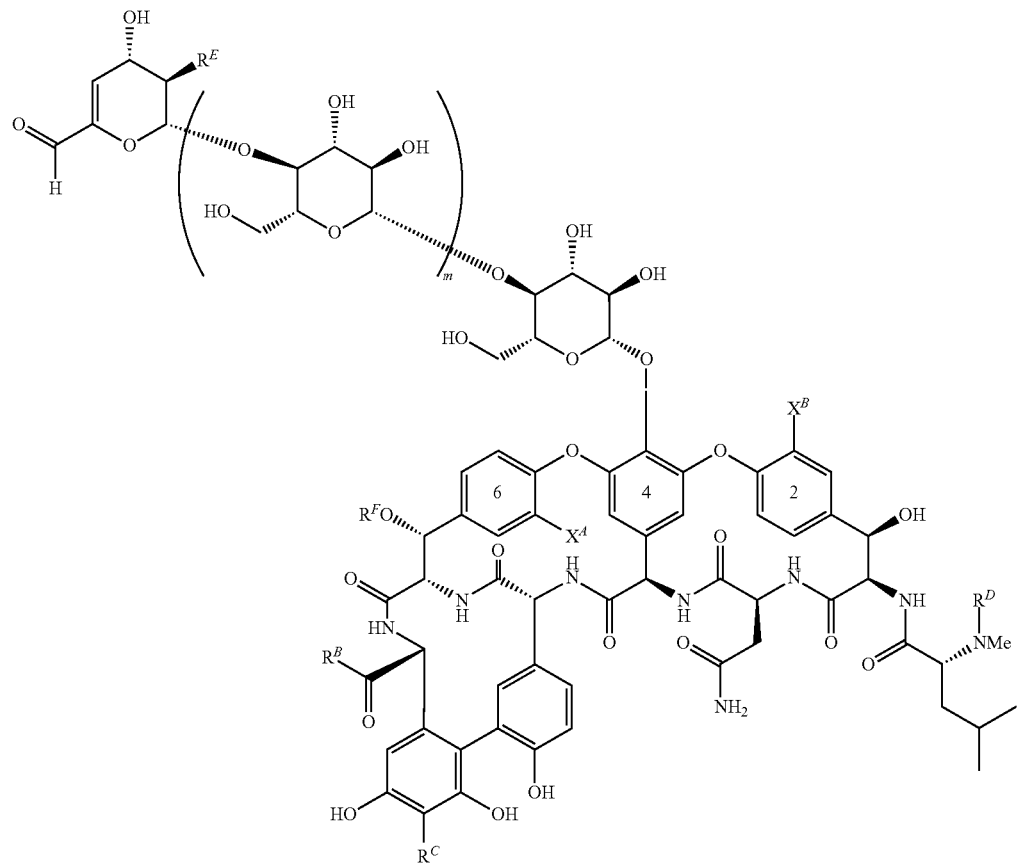

(wherein respective symbols are as defined above).

The present compound further preferably includes a structure in which the sugar residue (I), (I-0), (I-1) or (I-2) is bound to the partial structure (II-0).

The present compound further preferably includes a structure in which the sugar residue (I), (I-0), (I-1) or (I-2) is bound to the partial structure (II-1).

The present compound further preferably includes a structure in which the sugar residue (I), (I-0), (I-1) or (I-2) is bound to the partial structure (II-2).

The present compound further preferably includes a structure in which the sugar residue (I), (I-0), (I-1) or (I-2) is bound to the partial structure (IV').

The present compound further preferably includes a structure in which the sugar residue (I), (I-0), (I-1) or (I-2) is bound to the partial structure (IV").

In addition, the compounds (IV-0) and (X-1), the compounds (IV-1) and (X-2), the compounds (IV-2) and (X-3), the compounds (IX-1) and (XI-1), the compounds (IX-2) and (XI-2), as well as the compounds (IX-3) and (XI-3) may be each a composition consisting of the mixture.

As used herein, the "sugar residue" means a remaining part when one OH is removed from a monosaccharide, or a polysaccharide in which the same or different plural monosaccharides are connected in straight or branched manner.

As used herein, as the "monosaccharide", glucose, galactose, fructose, fucose, mannose, rhamnose, galactosamine, glucosamine, N-acetylgalactosamine, N-acetylglucosamine, vancosamine, epi-vancosamine, glucuronic acid, sialic acid, deoxyglucose, and deoxygalactose are preferably. As a monosaccharide constituting a root part of a sugar residue which binds to the aromatic ring of the fourth amino acid residue of a glycopeptide skeleton, glucose (e.g., β-D-glucose) is particularly preferable. As a monosaccharide constituting the terminal part of a sugar residue which binds to the aromatic ring of the fourth amino acid residue of a glycopeptide skeleton, galactose or N-acetylgalactosamine is more preferable. Particularly, galactose (e.g., β-D-galactose) is preferable.

As used herein, the "amino sugar residue" expresses the "sugar residue" having an amino group or a substituted amino group. Examples of the representative amino sugar residue include L-vancosaminyl, 3-desmethyl-vancosaminyl, 3-epi-vancosaminyl, 4-epi-vancosaminyl, 4-keto-vancosaminyl, acosaminyl, actinosaminyl, daunosaminyl, 3-epi-daunosaminyl, ristosaminyl, N-methyl-D-glucaminyl, N-acetyl-D-glucosamyl, or N-acyl-D-glucosamyl. Actinosaminyl, acosaminyl, 4-epi-vancosaminyl, 4-keto-vancosaminyl, ristosaminyl, or vancosaminyl is preferable. Particularly, L-4-epi-vancosaminyl is preferable.

As used herein, the term "lower alkyl" which is used alone or in combination with other terms includes straight or branched monovalent hydrocarbon group, having 1 to 15, preferably 1 to 10 carbon atoms. Examples include methyl, ethyl, n-propyl, isopropyl, n-butyl, isobutyl, sec-butyl, t-butyl, n-pentyl, isopentyl, neo-pentyl, n-hexyl, isohexyl, n-heptyl, n-octyl and the like. More preferably, examples include C1-C6 alkyl. Further preferably, examples include C1-C3 alkyl.

As used herein, the "lower alkenyl" which is used alone or in combination with other terms includes straight or branched monovalent hydrocarbon group having 2 to 15, preferably 2 to 10 carbon atoms, and one or two or more double bonds. Examples include vinyl, allyl, 1-propenyl, 2-propenyl, crotonyl, isopentenyl, various butenyl isomers and the like. Preferably, examples include C2-C6 alkenyl. Preferably, a double bond exists between the 1-positional and the 2-positional carbon atoms. Further preferably, examples include C2-C4 alkenyl.

As used herein, examples of the "lower alkyloxy" include methyloxy, ethyloxy, n-propyloxy, isopropyloxy, n-butyloxy, isobutyloxy, s-butyloxy, t-butyloxy, n-pentyloxy, n-hexyloxy and the like. Preferably, examples include C1-C6 alkyloxy. Further preferably, examples include C1-C3 alkyloxy.

As used herein, the "cycloalkyl" which is used alone or in combination with other terms includes cycloalkyl having 3 to 8 carbon atoms. Examples include cyclopropyl, cyclobutyl, cyclopentyl, cyclohexyl, cycloheptyl, and cyclooctyl. Preferably, examples include C3-C6 cycloalkyl. These may be cross-linked via 1 to 3 carbon atoms between two carbon atoms which constitute ring and are not adjacent.

As cycloalkyl in $R^{41}$, cyclopropyl and cyclopentyl are particularly preferable.

As cycloalkyl in the substituent group A, cross-linked cyclohexyl is preferable.

As used herein, the "aryl" which is used alone or in combination with other terms includes monocyclic or condensed cyclic aromatic hydrocarbon group having 6 to 14 carbon numbers. Examples include phenyl, 1-naphthyl, 2-naphthyl, anthryl and the like. Preferably, examples include phenyl, 1-naphthyl, and 2-naphtyl. Further preferably, examples include phenyl, and 2-naphthyl.

As used herein, the "heteroaryl" which is used alone or in combination with other terms means, for example, monocyclic aromatic heterocyclic group and condensed aromatic heterocyclic group containing hetero atom selected from nitrogen atom, sulfur atom and oxygen atom in the ring. The monocyclic aromatic heterocyclic group means group optionally having bond at a replaceable optional position, which is derived from 5- to 8-membered aromatic ring optionally containing 1 to 4 of oxygen atom, sulfur atom and/or nitrogen atom in the ring. The condensed aromatic heterocyclic group means group optionally having bond at a replaceable optional position, in which 5- to 8-membered aromatic ring optionally containing 1 to 4 of oxygen atom, sulfur atom, and/or nitrogen atom in the ring is condensed with 1 to 4 of 5- to 8-membered aromatic carbocycles or other 5- to 8-membered aromatic heterocycles.

Examples of the specific "heteroaryl" include furyl (e.g., 2-furyl, 3-furyl), thienyl 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4 imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl).

As the "heteroaryl" in the substituent group A, a 5- or 6-membered ring (e.g., thienyl, furyl, oxazolyl, isoxazolyl, thiazolyl, oxadiazolyl, pyridyl, pyrimidinyl, pyridazinyl, pyrazinyl, indolyl) is preferable.

As the "heteroaryl" in the substituent group B, 5- or 6-membered ring (e.g., thienyl, pyrrolyl, pyridyl) is preferable.

As the "heteroaryl" as a substituent of "optionally substituted lower alkyl" in $R^{42}$, 5- or 6-membered ring (e.g., imidazolyl, pyridyl) is preferable.

As used herein, the "heterocycle" means, for example, monocyclic non-aromatic heterocyclic group and condensed non-aromatic heterocyclic group containing hetero atom selected from nitrogen atom, sulfur atom and oxygen atom in the ring. The monocyclic non-aromatic heterocyclic group means group optionally having bond at a replaceable optional position, which is derived from 5- to 8-membered non-aromatic ring optionally containing 1 to 4 of oxygen atom, sulfur atom and/or nitrogen atom in the ring. The condensed non-aromatic heterocyclic group means group optionally having bond at a replaceable optional position, in which 5- to 8-membered non-aromatic ring optionally containing 1 to 4 of oxygen atom, sulfur atom and/or nitrogen atom in the ring is condensed with 1 to 4 of 5- to 8-membered aromatic carbocycle, 5- to 8-membered aromatic heterocycle, 5- to 8-membered non-aromatic carbocycle, or another 5- to 8-membered non-aromatic heterocycle.

Examples of the specific "heterocycle" include pyrrolidinyl (e.g., 1-pyrrolidinyl, 2-pyrrolidinyl, pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., isoindolinyl (e.g., isoindolinyl), morpholinyl (e.g., morpholino, 3-morpholinyl), dihydropyridyl, tetrahydropyridyl, tetrahydroquinolyl, tetrahydrofuryl, dihydropyranyl, tetrahydropyranyl, 1,3-benzodioxolanyl, 1,4-benzodioxanyl, 1-benzoxolanyl, oxetanyl, azetidinyl, diazetidinyl, chromanyl and the like.

As the "heterocycle" in the substituent group A, 5- or 6-membered ring (e.g., piperidyl, piperazinyl, morpholinyl) is preferable.

As the "heterocycle" as the substituent of "optionally substituted lower alkyl" in $R^{42}$, 5- or 6-membered ring (e.g., morpholinyl) is preferable.

Examples of the "aryloxy" used herein include phenyloxy, naphthyloxy, and the like. Preferably, examples include phenyloxy.

Examples of the "arylsulfonylamino" used herein include phenylsulfonylamino, naphthylsulfonylamino and the like. Preferably, examples include naphthylsulfonylamino.

Examples of the "arylcarbonylamino" used herein include benzoylamino, naphthylcarbonylamino and the like. Preferably, examples include benzoylamino.

Examples of the "arylaminocarbonylamino" used herein include phenylaminocarbonylamino, naphthylaminocarbonylamino and the like. Preferably, examples include phenylaminocarbonylamino.

Examples of the "heteroaryloxy" used herein include pyridyloxy, furyloxy, pyrrolyloxy, thienyloxy and the like. Preferably, examples include pyridyloxy.

Examples of the "arylaminocarbonyl" used herein include phenylaminocarbonyl, naphthylaminocarbonyl and the like. Preferably, examples include phenylaminocarbonyl.

Examples of the "arylcarbonyl" used herein include phenylcarbonyl, naphthylcarbonyl and the like. Preferably, examples include phenylcarbonyl.

Examples of the "arylthio" used herein include phenylthio, naphthylthio and the like. Preferably, examples include phenylthio.

Examples of the "arylamino" used herein include phenylamino, naphtylamino, phenylmethylamino and the like. Preferably, examples include phenylamino.

Examples of the "arylaminoalkyl" used herein include phenylamino lower alkyl, naphthylamino lower alkyl, phenylmethylamino lower alkyl and the like. Preferably, examples include phenylamino lower alkyl.

Examples of the "arylsulfonyl" used herein include phenylsulfonyl, naphthylsulfonyl and the like. Preferably, examples include phenylsulfonyl.

Examples of the "arylaminosulfonyl" used herein include phenylaminosulfonyl, naphthylaminosulfonyl and the like. Preferably, examples include phenylaminosulfonyl.

Examples of the "heteroarylalkyl" used herein include pyridyl lower alkyl, furyl lower alkyl, pyrrolyl lower alkyl, thienyl lower alkyl and the like. Preferably, examples include pyridyl lower alkyl, and thienyl lower alkyl.

Examples of the "heteroarylcarbonyl" used herein include pyridylcarbonyl, furylcarbonyl, pyrrolylcarbonyl, thienylcarbonyl and the like. Preferably, examples include pyridylcarbonyl, and thienylcarbonyl.

Examples of the "heteroarylthio" used herein include pyridylthio and the like.

As used herein, the "aralkyl" which is used alone or in combination with other terms is the "lower alkyl" substituted with one or more of the "aryl"s, and these can replace at all possible positions. Examples include benzyl, phenylethyl (e.g., 2-phenylethyl etc.), phenylpropyl (e.g., 3-phenylpropyl etc.), naphthylmethyl (e.g., 1-naphthylmethyl, 2-naphthylmethyl etc.), anthrylmethyl (e.g., 9-anthrylmethyl etc.), biphenylmethyl (e.g., 4-biphenylmethyl etc.) and the like. Preferably, examples include benzyl, and phenylethyl. More preferably, examples include benzyl.

As used herein, the "heteroaralkyl" which is used alone or in combination with other term is the "lower alkyl" substituted with one or two or more of "heteroaryl"s at an optional position, and these can replace at all possible positions. Examples include oxazolylmethyl (e.g., 2-oxazolylmethyl, 4-oxazolylmethyl), thiazolylmethyl (e.g., 2-thiazolylmethyl, 4-thiazolylmethyl), oxazolylethyl (e.g., 5-oxazolyl-2-ethyl), thiazolylethyl (e.g., 5-thiazolyl-2-ethyl), benzoxazolylmethyl (e.g., benzoxazol-2-ylmethyl), benzothiazolylmethyl (e.g., benzothiazol-2-ylmethyl), indolylmethyl (e.g., indol-3-ylmethyl), imidazolylmethyl (e.g., 4-imidazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., benzimidazol-2-methyl), pyridylmethyl (e.g., 4-pyridylmethyl), furylmethyl (e.g., furan-2-ylmethyl), thienylmethyl (e.g., thiophen-2-ylmethyl) and the like.

A substituent of the "optionally substituted lower alkyl" in $R^C$ is preferably "optionally substituted amino". A substituent of the "optionally substituted amino" is preferably heteroaralkyl (e.g., pyridylethyl).

Examples of the "aralkyloxy" used herein include phenyl C1-C3 alkyloxy, naphthyl C1-C3 alkyloxy and the like. Preferably, examples include benzyloxy.

Examples of the "aralkylthio" used herein include phenyl C1-C3 alkylthio, naphthyl C1-C3 alkylthio and the like. Preferably, examples include benzylthio.

Examples of the "aralkylamino" used herein include phenyl C1-C3 alkylamino, naphthyl C1-C3 alkylamino and the like. Preferably, examples include benzylamino.

Examples of the "aralkylcarbonylamino" used herein include phenyl C1-C3 alkylcarbonylamino, naphthyl C1-C3 alkylcarbonylamino and the like. Preferably, examples include benzylcarbonylamino.

Examples of the "aralkylaminocarbonyl" used herein include phenyl C1-C3 alkylaminocarbonyl, naphthyl C1-C3 alkylaminocarbonyl and the like. Preferably, examples include benzylaminocarbonyl.

Examples of the "aralkylsulfinyl" used herein include phenyl C1-C3 alkylsulfinyl, naphthyl C1-C3 alkylsulfinyl and the like. Preferably, examples include benzylsulfinyl.

Examples of the "heteroaralkylthio" used herein include pyridyl C1-C3 alkylthio, furyl C1-C3 alkylthio, pyrrolyl C1-C3 alkylthio, thienyl C1-C3 alkylthio and the like. Preferably, examples include furylmethylthio.

Examples of the "aryl lower alkenyl" used herein include phenyl C2-C4 alkenyl, naphthyl C2-C4 alkenyl and the like. Preferably, examples include 2-phenylethenyl.

As used herein, the "halogen" means fluorine, chlorine, bromine, and iodine. Preferably, examples include fluorine, chlorine and bromine.

As used herein, a term "halo lower alkyl" which is used alone or in combination with other term includes the "lower alkyl" substituted with the "halogen" at 1 to 8 places, preferably 1 to 5 places. Examples include trifluoromethyl, trichloromethyl, difluoromethyl, trifluoroethyl, dichloroethyl, trichloroethyl and the like. Preferably, examples include C1-C3 alkyl substituted with the "halogen" at 1 to 5 places. Particularly preferably, examples include trifluoromethyl.

As used herein, as the "halo lower alkyloxy", C1-C3 alkyloxy substituted with the "halogen" at 1 to 5 places is preferable. Particularly preferably, examples include trifluoromethyloxy.

Examples of the "di-lower alkylamino" used herein include dimethylamino, diethylamino, di-n-propylamino, diisopropylamino, ethylmethylamino, methyl n-propylamino, methylisopropylamino, ethyl n-propylamino, ethylisopropylamino and the like. Preferably, examples include dimethylamino.

Examples of a substituent of the "optionally substituted lower alkyl", the "optionally substituted alkenyl", the "optionally substituted aryl", the "optionally substituted heteroaryl", the "optionally substituted cycloalkyl", the "optionally substituted heterocycle", the "optionally substituted aralkyl", the "optionally substituted aralkylthio", the "optionally substituted heteroaralkylthio", the "optionally substituted lower alkyloxy", the "optionally substituted aralkyloxy", the "optionally substituted aryloxy", the "optionally substituted arylsulfonylamino", the "optionally substituted arylaminocarbonylamino", the "optionally substituted arylcarbonylamino", the "optionally substituted aralkylcarbonylamino, the "optionally substituted aralkylaminocarbonyl", the "optionally substituted aralkylsulfinyl", the "optionally substituted heteroaryloxy", the "optionally substituted arylaminocarbonyl", the "optionally substituted arylcarbonyl", the "optionally substituted arylthio", the "optionally substituted arylamino", the "optionally substituted arylaminoalkyl", the "optionally substituted arylsulfonyl", the "optionally substituted aralkylamino", the "optionally substituted arylaminosulfonyl", the "optionally substituted heteroarylalkyl", the "optionally substituted heteroarylcarbonyl", the "optionally substituted heteroarylthio", the "optionally substituted aryl lower alkenyl", and the "optionally substituted amino" include hydroxy, carboxy, halogen (F, Cl, Br, I), halo lower alkyl (e.g., $CF_3$, $CH_2CF_3$, $CH_2CCl_3$), C1-C6 alkyl (e.g., methyl, ethyl, isopropyl, tert-butyl), C2-C6 alkenyl (e.g., C3-C6 alkynyl (e.g., ethynyl), cycloalkyl (e.g., cyclopropyl, cyclobutyl, cyclopentyl, cyclohexyl), cycloalkenyl (e.g., cyclopropenyl), alkoxy (e.g., methoxy, ethoxy, propoxy, butoxy), alkenyloxy (e.g., vinyloxy, allyloxy etc.), alkoxycarbonyl (e.g., methoxycarbonyl, ethoxycarbonyl, tert-butoxycarbonyl etc.), nitro, nitroso, optionally substituted amino (e.g., amino, lower alkylamino (e.g., methylamino, ethylamino, dimethylamino), acylamino (e.g., acetylamino, benzoylamino), aralkylamino (e.g., benzylamino, tritylamino), hydroxyamino), azido, aryl (e.g., phenyl), aralkyl (e.g., benzyl), cyano, isocyano, isocyanato, thiocyanato, isothiocyanato, mercapto, lower alkylthio (e.g., methylthio), lower alkylsulfonyl (e.g., methanesulfonyl, ethanesulfonyl), optionally substituted carbamoyl (e.g., lower alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazine, azido, ureido, amidino, guanidino, phthalimido, oxo, optionally substituted aryl (e.g., phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-aminophenyl, 3-aminophenyl, 4-aminophenyl, 1-naphthyl, 2-naphthyl), optionally substituted heteroaryl (e.g., pyridin-2-yl, pyridin-3-yl, pyridin-4-yl, pyrimidin-2-yl, pyrimidin-4-yl, pyrimidin-5-yl, isoxazol-3-yl, isoxazol-5-yl, pyrrol-2-yl, pyrazol-3-yl, furan-2-yl, furan-3-yl, thiophen-2-yl, thiophen-3-yl, imidazol-2-yl, oxazol-2-yl, thiazol-2-yl and the like).

Examples of a substituent of the "optionally substituted aryl", the "optionally substituted heteroaryl", the "optionally substituted cycloalkyl", the "optionally substituted heterocycle", the "optionally substituted aralkyl", the "optionally substituted aralkylthio", the "optionally substituted heteroaralkylthio", the "optionally substituted aralkyloxy", the "optionally substituted aryloxy", the "optionally substituted arylsulfonylamino", the "optionally substituted arylaminocarbonylamino", the "optionally substituted arylcarbonylamino", the "optionally substituted aralkylcarbonylamino", the "optionally substituted aralkylaminocarbonyl", the "optionally substituted aralkylsulfinyl", the "optionally substituted heteroaryloxy", the "optionally substituted arylaminocarbonyl", the "optionally substituted arylcarbonyl", the "optionally substituted arylthio", the "optionally substituted arylamino", the "optionally substituted arylaminoalkyl", the "optionally substituted arylsulfonyl", the "optionally substituted aralkylamino", the "optionally substituted arylaminosulfonyl", the "optionally substituted heteroarylalkyl", the "optionally substituted heteroarylcarbonyl", the "optionally substituted heteroarylthio", the "optionally substituted aryl lower alkenyl", and the "optionally substituted cycloalkyl" alone or in combination with other term include the above exemplified substituents. The aryl, the heteroaryl, the cycloalkyl, and the heterocycle may be substituted with these substituents at replaceable optional positions, and the number of substituents is 1 to 3.

$R^{A1}$ is preferably various lipophilic groups. More preferable is optionally substituted lower alkyl, optionally substituted lower alkenyl, or optionally substituted cycloalkyl. Further preferable is optionally substituted lower alkyl or optionally substituted cycloalkyl. Particularly preferable is optionally substituted lower alkyl. A substituent of the "optionally substituted" group is one or more same or different substituents selected from the substituent group A.

Substituent group A: optionally substituted aryl, optionally substituted heteroaryl, optionally substituted heterocycle, optionally substituted aralkylthio, optionally substituted heteroaralkylthio, optionally substituted cycloalkyl, optionally substituted lower alkyloxy, optionally substituted aralkyloxy, optionally substituted aryloxy, optionally substituted arylsulfonylamino, and optionally substituted amino.

A substituent of the "optionally substituted" group in the substituent group A is one or more same or different substituents selected from the substituent group B.

Substituent group B: optionally substituted arylaminocarbonylamino, optionally substituted arylaminocarbonyl, optionally substituted arylcarbonyl, optionally substituted arylcarbonylamino, optionally substituted arylcarbonylaminoalkyl, oxo, halogen, optionally substituted aryl, optionally substituted aryloxy, optionally substituted arylthio, optionally substituted arylamino, optionally substituted arylaminoalkyl, optionally substituted arylaminocarbonylalkyl, optionally substituted arylsulfonyl, optionally substituted lower alkyl, optionally substituted aralkyl, optionally substituted amino, optionally substituted aralkylcarbonylamino, optionally substituted aralkylamino, optionally substituted aralkylaminocarbonyl, optionally substituted aralkylsulfinyl, optionally substituted arylsulfonylamino, optionally substituted arylaminosulfonyl, optionally substituted aralkylthio, halo lower alkyl, lower alkyloxy, lower alkylamino, halo lower alkyloxy, optionally substituted heteroaryl, optionally substituted heteroarylalkyl, optionally substituted heteroarylcarbonyl, optionally substituted heteroaryloxy, optionally substituted heteroarylthio, optionally substituted aryl lower alkenyl, optionally substituted heteroaryl lower alkenyl, optionally substituted cycloalkyl, optionally substituted cycloalkyloxy, optionally substituted cycloalkylthio, optionally substituted cycloalkylaminocarbonyl, optionally substituted cycloalkyl lower alkenyl, optionally substituted cycloalkylsulfonyl, optionally substituted cycloalkylaminocarbonylamino, optionally substituted cycloalkylaminoalkyl, optionally substituted cycloalkyl lower alkylamino, optionally substituted cycloalkylamino, optionally substituted cycloalkyl lower alkyl, optionally substituted cycloalkylcarbonyl, optionally substituted cycloalkyl lower alkylcarbonylamino, optionally substituted cycloalkylcarbonylamino, optionally substituted cycloalkylcarbonylaminoalkyl, optionally substituted cycloalkyl lower alkylaminocarbonyl, optionally substituted cycloalkylsulfonylamino, optionally substituted cycloalkylaminocarbonylalkyl, and optionally substituted cycloalkylaminosulfonyl.

A substituent of the "optionally substituted" in the substituent group B is one or more same or different substituents selected from the substituent group C.

Substituent group C: lower alky, lower alkyloxy, lower alkylsulfonyl, nitro, aralkyloxy, halogen, cyano, halo lower alkyl, halo lower alkyloxy, and di-lower alkylamino.

A preferable embodiment of $R^{41}$ includes the following groups.

(1-1) —CH$_2$-(substituted)Ph-CONR-(substituted)Ph
(1-2) —CH$_2$-(substituted)Ph-NRCO-(substituted)Ph
(1-3) —CH$_2$-(substituted)Ph-CH$_2$—CONR-(substituted)Ph
(1-4) —CH$_2$-(substituted)Ph-CH$_2$—NRCO-(substituted)Ph
(1-5) —CH$_2$-(substituted)Ph-X—CONR-(substituted) Ph
(1-6) —CH$_2$-(substituted)Ph-X—NRCO-(substituted) Ph
(1-7) —CH$_2$-(substituted)Het-CONR-(substituted)Ph
(1-8) —CH$_2$-(substituted)Het-NRCO-(substituted)Ph
(1-9) —CH$_2$-(substituted)Ph-CONR—CH$_2$-(substituted)Ph
(1-10) —CH$_2$-(substituted)Ph-NRCO—CH$_2$-(substituted)Ph
(1-11) —CH$_2$-(substituted)Ph-CH$_2$—CONR—CH$_2$-(substituted)Ph
(1-12) —CH$_2$-(substituted)Ph-CH$_2$—NRCO—CH$_2$-(substituted)Ph
(1-13) —CH$_2$-(substituted)Ph-X—CONR—CH$_2$-(substituted)Ph
(1-14) —CH$_2$-(substituted)Ph-X—NRCO—CH$_2$-(substituted)Ph
(1-15) —CH$_2$-(substituted)Het-CONR—CH$_2$-(substituted)Ph
(1-16) —CH$_2$-(substituted)Het-NRCO—CH$_2$-(substituted)Ph
(1-17) —(CH$_2$)$_m$-(substituted)Ph-CONR-(substituted)Ph
(1-18) —(CH$_2$)$_m$-(substituted)Ph-NRCO-(substituted)Ph
(1-19) —(CH$_2$)$_m$-(substituted)Ph-CH$_2$—CONR-(substituted)Ph
(1-20) —(CH$_2$)$_m$-(substituted)Ph-CH$_2$—NRCO-(substituted)Ph
(1-21) —(CH$_2$)$_m$-(substituted)Ph-X—CONR-(substituted)Ph
(1-22) —(CH$_2$)$_m$-(substituted)Ph-X—NRCO-(substituted)Ph
(1-23) —(CH$_2$)$_m$-(substituted)Het-CONR-(substituted)Ph
(1-24) —(CH$_2$)$_m$-(substituted)Het-NRCO-(substituted)Ph
(1-25) —(CH$_2$)$_m$-(substituted)Het-X—CONR-(substituted)Ph
(1-26) —(CH$_2$)$_m$-(substituted)Het-X—NRCO-(substituted)Ph
(1-27) —(CH$_2$)$_m$—S—CH$_2$-(substituted)Ph
(1-28) —(CH$_2$)-(substituted)Het-(substituted)Ph
(1-29) —(CH$_2$)—CH[(substituted)Ph]$_2$
(1-30) -(substituted)cAlk-X—CH$_2$-(substituted)Ph
(1-31) —CH$_2$-(substituted)cAlk
(1-32) —(CH$_2$)$_m$—X—(CH$_2$)$_m$—H
(1-33) —(CH$_2$)$_m$—X-(substituted)Ph
(1-34) —CH$_2$-(substituted)Ph
(1-35) —CH$_2$-(substituted)Het-CH$_2$-(substituted)Ph
(1-36) —CH$_2$-(substituted)Ph-(substituted)Ph
(1-37) —(CH$_2$)$_m$—S—CH$_2$-(substituted)Het
(1-38) —CH$_2$-(substituted)Ph-X-(substituted)Ph
(1-39) —(CH$_2$)$_m$-(substituted)Het-CH$_2$-(substituted)Ph
(1-40) —CH$_2$-(substituted)Ph-X-(substituted)Het
(1-41) —CH$_2$-(substituted)Ph-(substituted)Het
(1-42) —(CH$_2$)$_m$-(substituted)Het
(1-43) —CH$_2$-(substituted)Ph-SO—CH$_2$-(substituted)Ph
(1-44) -(substituted)cAlk-(substituted)Ph
(1-45) —CH$_2$-(substituted)Ph-S—CH$_2$-(substituted)Ph
(1-46) —CH$_2$-(substituted)Het-(substituted)Het
(1-47) —CH$_2$-(substituted)Ph-CO-(substituted)Ph
(1-48) —CH$_2$-(substituted)Het-CO-(substituted)Ph
(1-49) —CH$_2$-(substituted)Het-CH=CH-(substituted)Ph
(1-50) —CH$_2$-(substituted)Het-X—CH$_2$-(substituted)Ph
(1-51) —CH$_2$-(substituted)Het-CH$_2$—X-(substituted)Ph
(1-52) —CH$_2$-(substituted)Het-SO$_2$-(substituted)Ph
(1-53) —CH$_2$-(substituted)Het-X-(substituted)Ph
(1-54) —CH$_2$—CH=CH-(substituted)Het-(substituted)Ph In the above formulas, Ph is phenyl; X is O, S or NR; R is hydrogen or lower alkyl; Het is optionally condensed heteroaryl or heterocycle (preferably 5- or 6-membered); cAlk is cycloalkyl (preferably 3- to 6-membered); m is 2 or 3; and (substituted) indicates optionally substituted.

Among the aforementioned groups, a particularly preferable embodiments of $R^{41}$ is (1-28).

Examples of chemical modification in $R^B$, $R^C$ and $R^D$ include substituents described in JP-A No. 2001-163898. Specifically, the following are exemplified.

$R^b$ is selected from the group consisting of the following (2-1) to (2-7);

(2-1) Hydroxy:

(2-2) Mono- or di-alkylamino optionally substituted (provided that (2-4) is excluded), wherein two alkyls may be bound to form a ring, the substituent is amino, monoalkylamino, dialkylamino, trialkylammonium, hydroxy, guanidino, carboxy, alkyloxycarbonyl, carbamoyl optionally substituted with by cyano, mono- or di-alkylcarbamoyl, mono- or di-arylcarbamoyl, aryl, alkylamide or arylamide, alkylurea or arylurea, —(C=O)N$^-$—N$^+$(R$^X$)$_3$, —N$^+$(R$^X$)$_2$(CH$_2$)$_m$COOR$^Y$, —N$^+$(R$^X$)$_2$(CH$_2$)$_m$N$^+$(R$^X$)$_3$, —SO$_2$—OR$^Y$ (wherein m is 1 to 3, R$^X$ is C1-C3 alkyl, and R$^Y$ is hydrogen or C1-C3 alkyl), or —P=O(OR$^Y$)$_2$ (wherein R$^Y$ is hydrogen or C1-C3 alkyl), or a combination thereof, wherein alkyl in the substituent may be further substituted with amino optionally substituted with alkyloxycarbonyl or aryloxycarbonyl, and an aryl ring in the substituent can be further substituted with halogen, nitro, amino, hydroxy, carboxy, alkyloxycarbonyl, alkyl optionally substituted with amino, or optionally acylated hydroxyalkyl or thioalkyl, or a combination thereof;

(2-3) Amino, or cycloalkylamino optionally substituted with hydroxy;

(2-4) Di-substituted methylamino-NHCHR$^6$R$^7$, wherein R$^6$ is selected from carboxy, alkyloxycarbonyl optionally having a substituent, carbamoyl, or monoalkylcarbamoyl optionally having a substituent, or cycloalkylcarbamoyl optionally having a substituent, wherein the substituent is amino, monoalkylamino, dialkylamino, trialkylammonium, carboxy, hydroxy, —(C=O)N$^-$—N$^+$(R$^X$)$_3$, aryl optionally substituted with —(CH$_2$)$_m$COOR$^X$ (wherein m is 1 to 3, R$^X$ is C1-C3 alkyl), —N$^+$(R$^X$)$_2$(CH$_2$)$_m$COOR$^Y$ (wherein R$^Y$ is hydrogen or C1-C3 alkyl), or —N$^+$(R$^X$)$_2$(CH$_2$)$_m$N$^+$(R$^X$)$_3$, or a combination thereof, R[7] is indole or thioindole in which a nitrogen is optionally substituted with C1-C3 alkyl, or imidazolyl;

(2-5) Tripeptide R-A[1]-A[2]-A[3]-; wherein A[1], A[2], and A[3] are an arbitrary amino acid unit, respectively, R represents hydroxy, amino, or mono- or di-alkylamino optionally substituted, at the carboxy terminal of the tripeptide, the substituent is amino, monoalkylamino, dialkylamino, trialkylammonium, guanidino, or aryl;

(2-6) Hydrazino optionally having a substituent, or hydroxamic acid, wherein the substituent is alkyl, or arylalkyl optionally substituted with alkyl; and (2-7) Alkoxy optionally having a substituent, wherein the substituent is arylcarbonyl optionally further substituted with nitro, hydroxamic acid, or alkyl;

provided that, in (2-2) to (2-7), the existing aryl ring may contain hetero atom, and the existing carbon-carbon single bond may be interrupted with hetero atom, or hetero group selected from —O(P=O) (OR$^F$) O— (wherein R$^F$ is hydrogen, alkyloxycarbonyl or aryloxycarbonyl), and imino, in some cases;

R$^B$ is preferably —OH, —NHR$^5$, or —NR$^5$R$^{5'}$ (wherein R$^5$ and R$^{5'}$ are hydrogen, optionally substituted lower alkyl, —NH—R, —NH—COR, —NH—CONHR, —O—R (each R is independently hydrogen or optionally substituted lower alkyl, respectively), or amino sugar residue). Preferably, one of R$^5$ and R$^{5'}$ is hydrogen. More preferable is —OH or —NHR$^5$ (wherein R$^5$ is substituted lower alkyl, or optionally substituted lower alkyloxy).

As a substituent of the optionally substituted lower alkyl and the optionally substituted lower alkyloxy, hydrophilic substituent is preferable. For example, the same or different 1 to 10, preferably 1 to 6 substituents selected from amino, mono- or di-lower alkylamino, tri-lower alkylamine, amino lower alkylamino, hydroxyl lower alkylamino, hydroxy, carboxy, lower alkoxycarbonyl, SO$_3$H, PO$_3$H$_2$, optionally substituted carbamoyl, quaternary ammonium group (e.g., tri-lower alkylamino (e.g., —N$^+$(CH$_3$)$_3$)), optionally substituted heterocyclic group (heterocycle or heteroaryl), optionally substituted heterocyclic thio, guanidino, NHSO$_2$NH$_2$, and hydroxy lower alkoxy are exemplified. An N atom part in the heterocycle may be quaternarized to form a salt. As a substituent of the optionally substituted heterocycle, hydroxy, amino, carboxy, amino lower alkyl, and quaternary ammonium lower alkyl are exemplified. Alternatively, a lower alkyl group on the quaternary ammonium group may be further substituted with the substituted lower alkyl (substituent; carboxy, hydroxy, quaternary ammonium group). More preferable is optionally substituted lower amino, hydroxy, or lower alkoxy.

R$^C$ is selected from the group consisting of the group (3-1) to (3-4);

(3-1) Hydrogen;

(3-2) Alkyl, cycloalkyl, or aminomethyl optionally substituted with alkylene, which may each have a substituent, wherein the substituent is amino optionally substituted with alkyloxycarbonyl or aryloxycarbonyl, monoalkylamino, dialkylamino, trialkylammonium, aryl optionally substituted with cycloalkyl, pyridyl, hydroxy, guanidino, —O—(P=O) (OH)$_2$, carboxy, SO$_3$H, —N$^+$(R$^X$)$_2$(CH$_2$)$_m$N$^+$(R$^X$)$_3$, or —(C=O)—N$^-$—N$^+$(R$^X$)$^3$ (wherein m is 1 to 3, R$^X$ is C1-C3 alkyl), or a combination thereof, wherein alkyl in the monoalkylamino or dialkylamino substituent may be further substituted with amino in some cases;

(3-3) Alkynyl optionally having a substituent, wherein the substituent is amino optionally substituted with alkyloxycarbonyl or aryloxycarbonyl, or aryl; and (3-4) Halogen;

provided that, in (3-2) and (3-3), an existing aryl ring may contain hetero atom, and an existing carbon-carbon single bond is interrupted with heteroatom, or hetero group selected from —O(P=O)(OR$^J$)O— (wherein R$^J$ is hydrogen, alkyloxycarbonyl or aryloxycarbonyl), amido and imino in some cases.

R$^C$ is preferably hydrogen or optionally substituted lower alkyl. A substituent of the optionally substituted lower alkyl is preferably the —NHR$^5$, or substituents of optionally substituted lower alkyl in R$^5$ are exemplified. More preferable is the —NHR$^5$. Herein, R$^5$ is preferably optionally substituted aralkyl, optionally substituted heteroaralkyl, or optionally substituted lower alkyl. A substituent of the optionally substituted aralkyl, the optionally substituted heteroaralkyl, or the optionally substituted lower alkyl is preferably —NH$_2$, —SO$_3$H, or —OH.

As a preferable combination of R$^B$ and R$^C$, the case where R$^B$ is —OH, —NHR$^5$ (R$^5$ is mono- or di-lower alkylamino lower alkyl, tri-lower alkylammonium lower alkyl, or amino sugar residue), —NR$^5$R$^{5'}$ (R$^5$ and R$^{5'}$ are both hydroxy lower alkyl), or —NHCH$_2$CON$^-$N$^+$(Me)$_3$, and R$^C$ is hydrogen, mono- or di-substituted amino lower alkyl (examples of substituent: lower alkyl, mono- or di-lower alkylamino lower alkyl, tri-lower alkylammonium lower alkyl, hydroxy lower alkyl, hydroxy lower alkoxy lower alkyl, —CH$_2$CON$^-$N$^+$(Me)$_3$, lower alkyl substituted with 1 to 6 hydroxys, and lower alkyl substituted with carboxy, hydroxy, oxo, optionally substituted carbamoyl, guanidido, sulfonic acid group, phosphoric acid group, NHCO$_2$NH$_2$ and/or amino, optionally substituted heterocyclic lower alkyl (substituent: amino lower alkyl), optionally substituted quaternary ammonium lower alkyl (substituent: carboxy, hydroxy, quaternary ammonium group)) is exemplified. Specifically, cases in Table 6 to Table 8 described later are exemplified.

As a particularly preferable combination of R$^B$ and R$^C$, R$^B$ is —OH, and R$^C$ is hydrogen.

R$^D$ is selected from the group consisting of the following (4-1) to (4-6):

(4-1) Hydrogen;

(4-2) Alkyl optionally substituted, wherein the substituent is alkyloxycarbonyl, amino, optionally alkylated aryl, arylcarbonyl, carbamoyl, mono- or di-alkylcarbamoyl or mono- or di-arylalkylcarbamoyl or a combination thereof, wherein alkyl or aryl in the substituent may be further substituted with amino optionally substituted with alkyloxycarbonyl or aryloxycarbonyl, or hydroxy;

(4-3) Alkyloxycarbonyl optionally substituted, wherein the substituent is optionally alkylated aryl;

(4-4) Arylamide or arylthioamide;

(4-5) Optionally alkylated amino or amidino; and (4-6) Nitroso; provided that in (4-2) to (4-5), aryl ring can have hetero atom, and carbon-carbon single bond is interrupted with hetero atom in some cases.

$R^D$ is preferably hydrogen or lower alkyl optionally having substituent. Particularly preferable is hydrogen.

Alternatively, an N-terminal part may be de-leucinated to convert it into —$NH_2$, or it may be further acylated according to a method described in the literature (e.g., Expert Opin. Ther. Patents (2004) 14, pp. 141-173), $R^F$ is hydrogen or sugar residue. Preferable is a sugar residue. More preferable is amino sugar residue. Further preferable is amino sugar residue represented by the following formula:

[Chemical formula 65]

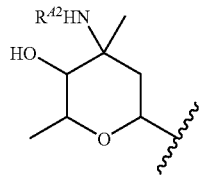

(wherein $R^{42}$ is hydrogen or optionally substituted lower alkyl).

Particularly preferable is amino sugar residue represented by the following formula:

[Chemical formula 66]

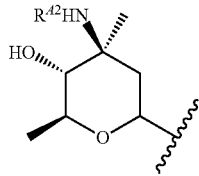

(wherein $R^{42}$ is as defined above).

Examples of a substituent of optionally substituted lower alkyl in $R^{42}$ include hydroxy, carboxy, halogen (F, Cl, Br, I), halo lower alkyl (e.g., $CF_3$, $CH_2CF_3$, $CH_2CCl_3$), C1-C6 alkyl (e.g., methyl, ethyl, isopropyl, tert-butyl) optionally substituted with hydroxy, C2-C6 alkenyl (e.g., vinyl), C3-C6 alkynyl (e.g., ethynyl), cycloalkyl (e.g., cyclopropyl, cyclobutyl, cyclopentyl, cyclohexyl), cycloalkenyl (e.g., cyclopropenyl), alkoxy (e.g., methoxy, ethoxy, propoxy, butoxy), alkenyloxy (e.g., vinyloxy, allyloxy etc.), alkoxycarbonyl (e.g., methoxycarbonyl, ethoxycarbonyl, tert-butoxycarbonyl etc.), nitro, nitroso, optionally substituted amino (e.g., amino, lower alkylamino (e.g., methylamino, ethylamino, dimethylamino), acylamino (e.g., acetylamino, benzoylamino), aralkylamino (e.g., benzylamino, tritylamino), hydroxyamino), azido, aryl (e.g., phenyl), aralkyl (e.g., benzyl), cyano, isocyano, isocyanato, thiocyanato, isothiocyanato, mercapto, lower alkylthio (e.g., methylthio), lower alkylsulfonyl (e.g., methanesulfonyl, ethanesulfonyl), optionally substituted carbamoyl (e.g., lower alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazine, azido, ureido, amidino, guanidino, phthalimido, oxo, optionally substituted aryl (e.g., phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-aminophenyl, 3-aminophenyl, 4-aminophenyl, 1-naphthyl, 2-naphthyl), optionally substituted heteroaryl (e.g., pyridin-2-yl, pyridin-3-yl, pyridin-4-yl, pyrimidin-2-yl, pyrimidin-4-yl, pyrimidin-5-yl, isoxazol-3-yl, isoxazol-5-yl, pyrrol-2-yl, pyrazol-3-yl, furan-2-yl, furan-3-yl, thiophen-2-yl, thiophen-3-yl, imidazol-2-yl, oxazol-2-yl, thiazol-2-yl), optionally substituted heterocycle (e.g., 1-pyrrolidinyl, 2-pyrrolidinyl, 3-pyrrolinyl, 2-imidazolidinyl, imidazolinyl, 1-pyrazolidinyl, 2-pyrazolidinyl, pyrazolinyl, piperidino, 2-piperidyl, 1-piperazinyl, morpholino, 3-morpholinyl, tetrahydrofuryl, tetrahydropyranyl) and the like. Preferable is hydroxy, optionally substituted aryl, optionally substituted heteroaryl, or optionally substituted heterocycle. More preferable is hydroxy, pyridin-3-yl, imidazol-2-yl, morpholino, or 3-(3-trifluoromethyloxybenzoylamino) phenyl.

A particularly preferable embodiment of $R^{42}$ is hydrogen.

Preferable compounds of the present invention can be classified into the following categories.

In a compound represented by the formula (IV-2):

[Chemical formula 67]

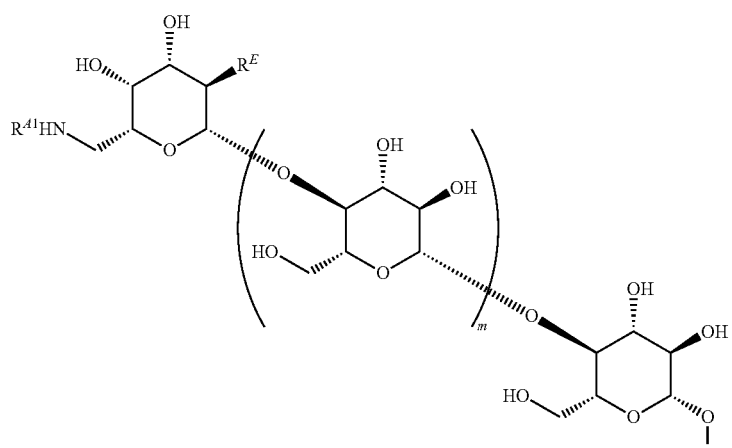

(IV-2)

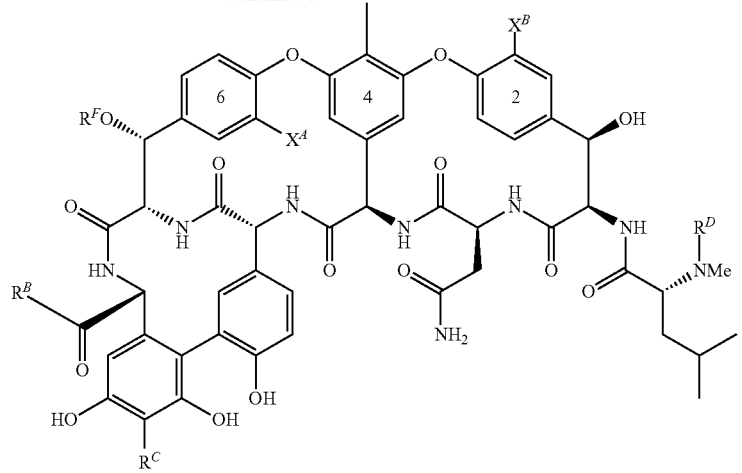

(wherein respective symbols are as defined above):
1) A compound, a pharmaceutically acceptable salt thereof, or a solvate thereof in which $R^{41}$ is optionally substituted lower alkyl;
2) The compound, a pharmaceutically acceptable salt thereof, or a solvate thereof according to 1), wherein $R^{41}$ is lower alkyl optionally substituted with a substituent selected from the following substituent group A;
Substituent group A: optionally substituted aryl, optionally substituted heteroaryl, optionally substituted heterocycle, optionally substituted aralkylthio, optionally substituted heteroaralkylthio, optionally substituted cycloalkyl, optionally substituted lower alkyloxy, optionally substituted aralkyloxy, optionally substituted aryloxy, optionally substituted arylsulfonylamino, and optionally substituted amino;
3) The compound, a pharmaceutically acceptable salt thereof, or a solvate thereof according to 2), wherein a substituent of the "optionally substituted" group in the substituent group A of 2) is selected from the following substituent group B;
Substituent group B: optionally substituted arylaminocarbonylamino, optionally substituted arylaminocarbonyl, optionally substituted arylcarbonyl, optionally substituted arylcarbonylamino, optionally substituted arylcarbonylaminoalkyl, oxo, halogen, optionally substituted aryl, optionally substituted aryloxy, optionally substituted arylthio, optionally substituted arylamino, optionally substituted arylaminoalkyl, optionally substituted arylaminocarbonylalkyl, optionally substituted arylsulfonyl, optionally substituted lower alkyl, optionally substituted aralkyl, optionally substituted amino, optionally substituted aralkylcarbonylamino, optionally substituted aralkylamino, optionally substituted aralkylaminocarbonyl, optionally substituted aralkylsulfinyl, optionally substituted arylsulfonylamino, optionally substituted arylaminosulfonyl, optionally substituted aralkylthio, halo lower alkyl, lower alkyloxy, lower alkylamino, halo lower alkyloxy, optionally substituted heteroaryl, optionally substituted heteroarylalkyl, optionally substituted heteroarylcarbonyl, optionally substituted heteroaryloxy, optionally substituted heteroarylthio, optionally substituted aryl lower alkenyl, optionally substituted heteroaryl lower alkenyl, optionally substituted cycloalkyl, optionally substituted cycloalkyloxy, optionally substituted cycloalkylthio, optionally substituted cycloalkylcarbonyl, optionally substituted cycloalkyl lower alkenyl, optionally substituted cycloalkylsulfonyl, optionally substituted cycloalkylaminocarbonylamino, optionally substituted cycloalkylaminoalkyl, optionally substituted cycloalkyl lower alkylamino, optionally substituted cycloalkylamino, optionally substituted cycloalkyl lower alkyl, optionally substituted cycloalkylcarbonyl, optionally substituted cycloalkyl lower alkylcarbonylamino, optionally substituted cycloalkylcarbonylamino, optionally substituted cycloalkylcarbonylaminoalkyl, optionally substituted cycloalkyl lower alkylaminocarbonyl, optionally substituted cycloalkylsulfonylamino, optionally substituted cycloalkylaminocarbonylalkyl, and optionally substituted cycloalkylaminosulfonyl;
4) The compound, a pharmaceutically acceptable salt thereof, or a solvate thereof according to 3), wherein a substituent of the "optionally substituted" group in the substituent group B of 3) is selected from the following substituent group C;
Substituent group C: lower alkyl, lower alkyloxy, lower alkylsulfonyl, nitro, aralkyloxy, halogen, cyano, halo lower alkyl, halo lower alkyloxy, and di-lower alkylamino;
5) A compound, a pharmaceutically acceptable salt thereof, or a solvate thereof in which $R^B$ is —OH, —NHR$^5$, or —NR$^5$R$^{5'}$ (wherein R$^5$ and R$^{5'}$ are hydrogen, optionally substituted lower alkyl, —NH—R, —NH—COR, —NH—CONHR, —O—R (each R are independently hydrogen or optionally substituted lower alkyl), or amino sugar residue);
6) The compound, a pharmaceutically acceptable salt thereof, or a solvate thereof according to 5), wherein R$^B$ is —OH or —NHR$^5$ (wherein R$^5$ is lower alkyl optionally substituted with same or different 1 to 6 substituents selected from the following substituent group D, or lower alkyloxy optionally substituted with same or different 1 to 6 substituents selected from the following substituent D;
Substituent group D: amino, mono- or di-lower alkylamino, tri-lower alkylamino, amino lower alkylamino, hydroxy lower alkylamino, hydroxy, carboxy, lower alkoxycarbonyl, $SO_3H$, $PO_3H_2$, optionally substituted carbamoyl, quaternary ammonium group, optionally substituted heterocyclic group, optionally substitute heterocyclic thio, guanidino, $NHSO_2NH_2$, and hydroxy lower alkoxy);
7) A compound, a pharmaceutically acceptable salt thereof, or a solvate thereof in which $R^C$ is hydrogen or optionally substituted lower alkyl;
8) The compound, a pharmaceutically acceptable salt thereof, or a solvate thereof according to 7), wherein $R^C$ is hydrogen, or lower alkyl optionally substituted with amino optionally substituted with a substituent selected from the following substituent group E;

Substituent group E: aralkyl optionally substituted —$NH_2$, —$SO_3H$, or —OH; heteroaralkyl optionally substituted —$NH_2$, —$SO_3H$, or —OH; or lower alkyl optionally substituted with —$NH_2$, —$SO_3H$, or —OH;

9) A compound, a pharmaceutically acceptable salt thereof, or a solvate thereof in which $R^D$ is hydrogen, or lower alkyl optionally having a substituent;

10) The compound, a pharmaceutically acceptable salt thereof, or a solvate thereof according to 9), wherein $R^D$ is hydrogen;

11) A compound, a pharmaceutically acceptable salt thereof, or a solvate thereof in which $R^F$ is hydrogen or a sugar residue;

12) The compound, a pharmaceutically acceptable salt thereof, or a solvate thereof according to 11), wherein $R^F$ is an amino sugar residue represented by the formula:

[Chemical formula 68]

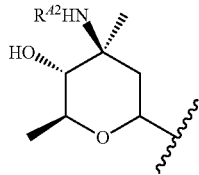

(wherein $R^{A2}$ is hydrogen or optionally substituted lower alkyl);

13) The compound, a pharmaceutically acceptable salt thereof, or a solvate thereof according to 12), wherein $R^F$ is an amino sugar residue represented by the formula:

[Chemical formula 69]

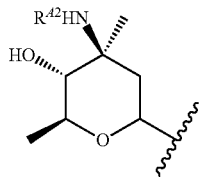

(wherein $R^{A2}$ is hydrogen, hydroxy, pyridin-3-yl, imidazol-2-yl, morpholino, or lower alkyl optionally substituted with 3-(3-trifluoromethyloxybenzoylamino)phenyl);

14) A compound, a pharmaceutically acceptable salt thereof, or a solvate thereof in which $X^A$ and $X^B$ are both Cl;

15) A compound, a pharmaceutically acceptable salt thereof, or a solvate thereof in which $R^E$ is —OH;

16) A compound, a pharmaceutically acceptable salt thereof, or a solvate thereof in which $R^E$ is —NHAc;

17) A compound, a pharmaceutically acceptable salt thereof, or a solvate thereof in which m is 0 or 1.

Each category of the 1) to 17) can optionally constitute a compound with a combination of two or more.

As a combination of $R^B$, $R^C$ and $R^D$, the case where $R^B$ is hydroxy, —$NHR^5$ ($R^5$ is mono- or di-lower alkylamino lower alkyl, tri-lower alkylammonium lower alkyl, or an amino sugar residue), —$NR^5R^{5'}$ ($R^5$ and $R^{5'}$ are both hydroxy lower alkyl), or —$NHCH_2CON^-N^+(Me)_3$, $R^C$ is hydrogen, mono- or di-substituted amino lower alkyl (examples of substituent: lower alkyl, mono- or di-lower alkylamino lower alkyl, tri-lower alkylammonium lower alkyl, hydroxy lower alkyl, hydroxy lower alkoxy lower alkyl, —$CH_2CON^-N^+(Me)_3$, lower alkyl optionally substituted with 1 to 6 of hydroxys, and lower alkyl substituted with carboxy, hydroxy, oxo, optionally substituted carbamoyl, guanidino, sulfonic acid residue, phosphoric acid group, $NHSO_2NH_2$ and for amino, optionally substituted with heterocyclic lower alkyl (substituent: amino lower alkyl), optionally substituted quaternary ammonium lower alkyl (substituent: carboxy, hydroxy, quaternary ammonium group)) and $R^D$ is hydrogen is exemplified. Specifically, the cases of Tables 1 to 8 are exemplified.

TABLE 1

| $R^B$ | $R^C$ | $R^D$ |
|---|---|---|
| —$NH(CH_2)_2NMe_2$ | H | H |
| —$NH(CH_2)_2N^+Me_3$ | H | H |
| —$NH(CH_2)_3NMe_2$ | H | H |
| —$NH(CH_2)_3N^+Me_3$ | H | H |
| —$NH(CH_2)_2NH(CH_2)_2NH_2$ | H | H |

TABLE 2

| $R^B$ | $R^C$ | $R^D$ |
|---|---|---|
| —$NH(CH_2)_2NH(CH_2)_2OH$ | H | H |
| —$N[(CH_2)_2OH]_2$ | H | H |
| —$NHCH_2CO_2H$ | H | H |
| —$NH(CH_2)_2CO_2H$ | H | H |
| —$NH(CH_2)_2SO_3H$ | H | H |
| —$NH(CH_2)_2PO_3H_2$ | H | H |
| (structure: glycyl cyanamide) | H | H |
| (structure: glycyl trimethylhydrazinium) | H | H |
| (structure: ethyl trimethylammonium carboxylate) | H | H |
| (structure: bis-trimethylammonium ethyl) | H | H |
| (structure: piperazinium ethylamine) | H | H |

TABLE 3

| $R^B$ | $R^C$ | $R^D$ |
|---|---|---|
| (structure: piperidinyl methyl amidine) | H | H |

TABLE 3-continued

| $R^B$ | $R^C$ | $R^D$ |
|---|---|---|
| | 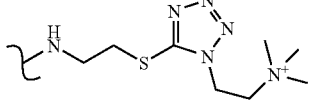 | H H |
| | 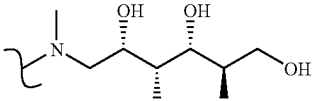 | H H |
| | 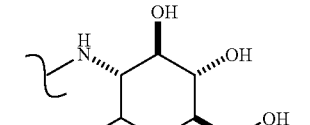 | H H |
| | 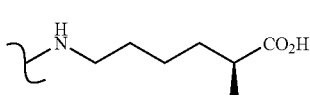 | H H |
| | 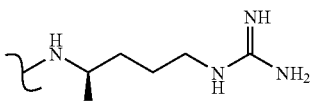 | H H |
| | 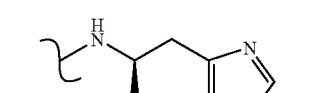 | H H |
| |  | H H |
| | 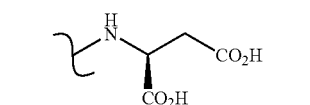 | H H |
| OH | —CH$_2$NHMe | H |
| OH | —CH$_2$NH(CH$_2$)$_2$NH$_2$ | H |

TABLE 4

| $R^B$ | $R^C$ | $R^D$ |
|---|---|---|
| OH | —CH$_2$NH(CH$_2$)$_2$NMe$_2$ | H |
| OH | —CH$_2$NH(CH$_2$)$_2$N$^+$Me$_3$ | H |
| OH | —CH$_2$N[(CH$_2$)$_2$OH]$_2$ | H |
| OH | —CH$_2$NHCH$_2$CO$_2$H | H |
| OH | —CH$_2$NH(CH$_2$)$_2$CO$_2$H | H |
| OH | —CH$_2$NH(CH$_2$)$_2$SO$_3$H | H |
| OH | —CH$_2$NHCH$_2$PO$_3$H$_2$ | H |
| OH | 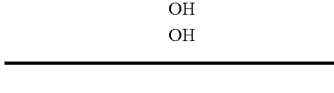 | H |

TABLE 4-continued

| $R^B$ | $R^C$ | $R^D$ |
|---|---|---|
| OH | 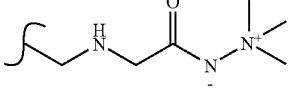 | H |
| OH | 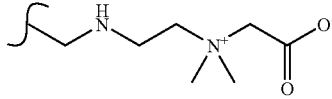 | H |
| OH | 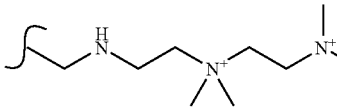 | H |

TABLE 5

| $R^B$ | $R^C$ | $R^D$ |
|---|---|---|
| OH | 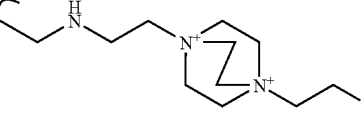 | H |
| OH |  | H |
| OH | 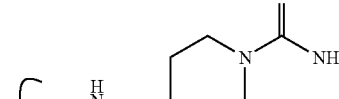 | H |
| OH | 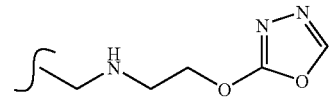 | H |
| OH | 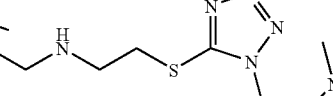 | H |
| OH | 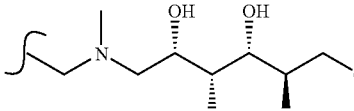 | H |
| OH | 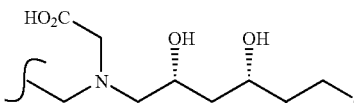 | H |

TABLE 5-continued

| $R^B$ | $R^C$ | $R^D$ |
|---|---|---|
| OH | 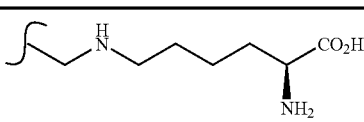 | H |
| OH | 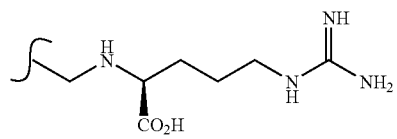 | H |
| OH | 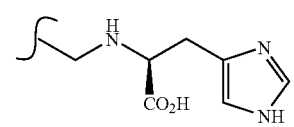 | H |
| OH | 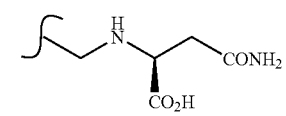 | H |

TABLE 6

| $R^B$ | $R^C$ | $R^D$ |
|---|---|---|
| —NH(CH$_2$)$_3$NMe$_2$ | —CH$_2$NH(CH$_2$)$_2$N$^+$Me$_3$ | H |
| —NH(CH$_2$)$_3$NMe$_2$ | —CH$_2$N[(CH$_2$)$_2$OH]$_2$ | H |
| —NH(CH$_2$)$_3$NMe$_2$ | 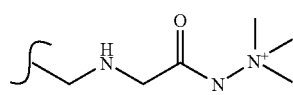 | H |

TABLE 6-continued

| $R^B$ | $R^C$ | $R^D$ |
|---|---|---|
| —NH(CH$_2$)$_3$NMe$_2$ | 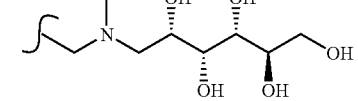 | H |
| —NH(CH$_2$)$_3$NMe$_2$ | 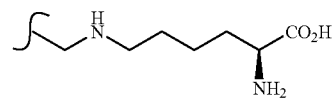 | H |
| —NH(CH$_2$)$_2$N$^+$Me$_3$ | —CH$_2$NH(CH$_2$)$_2$N$^+$Me$_3$ | H |
| —NH(CH$_2$)$_2$N$^+$Me$_3$ | —CH$_2$N[(CH$_2$)$_2$OH]$_2$ | H |
| —NH(CH$_2$)$_2$N$^+$Me$_3$ | 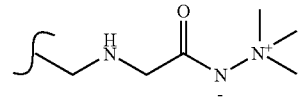 | H |
| —NH(CH$_2$)$_2$N$^+$Me$_3$ | 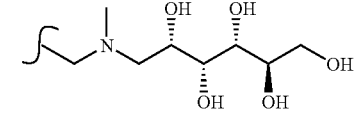 | H |
| —NH(CH$_2$)$_2$N$^+$Me$_3$ | 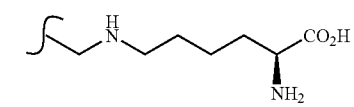 | H |
| —N[(CH$_2$)$_2$OH]$_2$ | —CH$_2$NH(CH$_2$)$_2$N$^+$Me$_3$ | H |

TABLE 7

| $R^B$ | $R^C$ | $R^D$ |
|---|---|---|
| —N[(CH$_2$)$_2$OH]$_2$ | —CH$_2$N[(CH$_2$)$_2$OH]$_2$ | H |
| —N[(CH$_2$)$_2$OH]$_2$ | 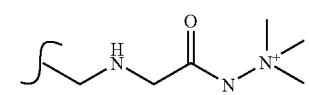 | H |
| —N[(CH$_2$)$_2$OH]$_2$ | 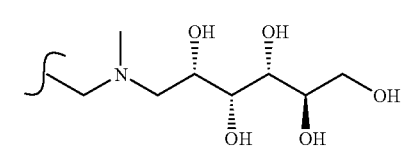 | H |
| —N[(CH$_2$)$_2$OH]$_2$ | 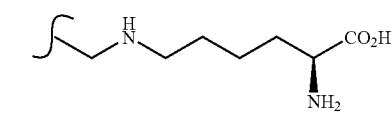 | H |
| —NH(CH$_2$)$_2$CO$_2$H | —CH$_2$NH(CH$_2$)$_2$N$^+$Me$_3$ | H |
| —NH(CH$_2$)$_2$CO$_2$H | —CH$_2$N[(CH$_2$)$_2$OH]$_2$ | H |
| —NH(CH$_2$)$_2$CO$_2$H | 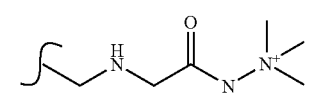 | H |

TABLE 7-continued
| $R^B$ | $R^C$ | $R^D$ |
|---|---|---|
| —NH(CH$_2$)$_2$CO$_2$H | 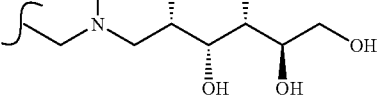 | H |
| —NH(CH$_2$)$_2$CO$_2$H | 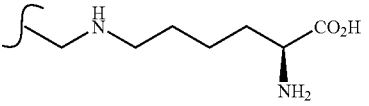 | H |
| 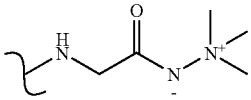 | —CH$_2$NH(CH$_2$)$_2$N$^+$Me$_3$ | H |
| 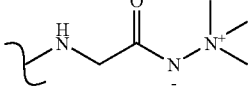 | —CH$_2$N[(CH$_2$)$_2$OH]$_2$ | H |
TABLE 8
| $R^B$ | $R^C$ | $R^D$ |
|---|---|---|
| 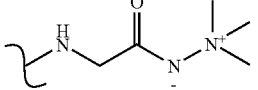 | 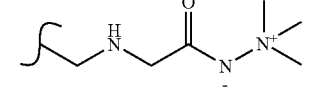 | H |
| 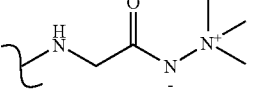 | 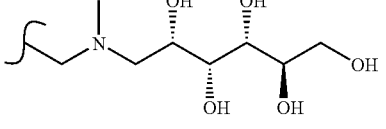 | H |
| 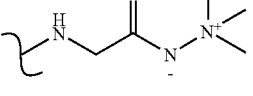 | 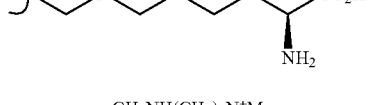 | H |
| 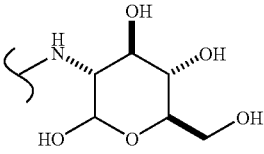 | —CH$_2$NH(CH$_2$)$_2$N$^+$Me$_3$ | H |
| 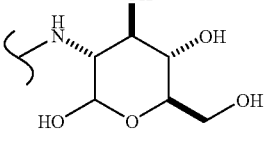 | —CH$_2$N[(CH$_2$)$_2$OH]$_2$ | H |
| 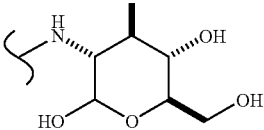 | 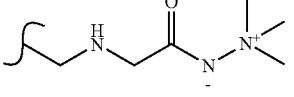 | H |

TABLE 8-continued
| $R^B$ | $R^C$ | $R^D$ |
|---|---|---|
| 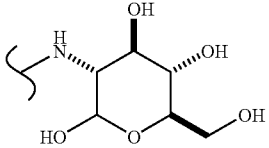 | 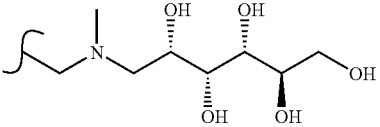 | H |
| 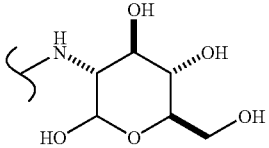 | 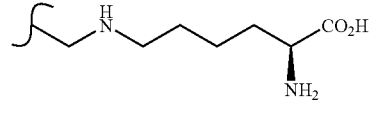 | H |
| OH | H | H |
More specific present compounds are exemplified below. Table 9 and Table 10 below are examples of $R^{41}$ which is composed of each combinations of $R^B$, $R^C$ and $R^D$.

TABLE 9

| Structural formula | $R^B$ | $R^C$ | $R^D$ |
|---|---|---|---|
| (glycopeptide core structure with $R^{A1}$, $R^B$, $R^C$, $R^D$ substituents) | OH | H | H |

$R^{A1}$ = (three aryl/heteroaryl amide substituent structures shown)

TABLE 9-continued
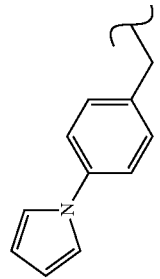 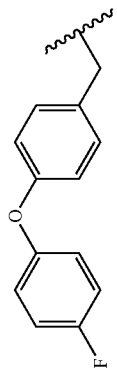 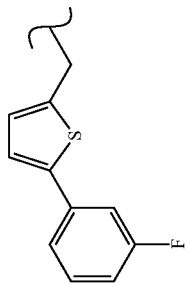 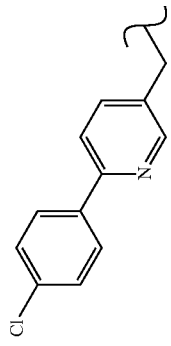
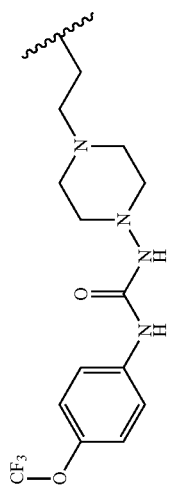 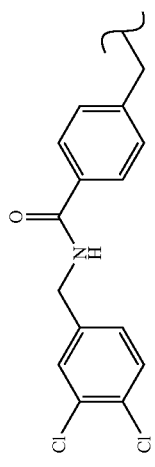 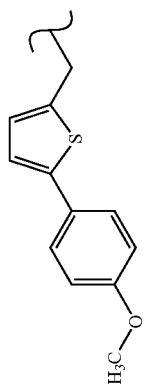 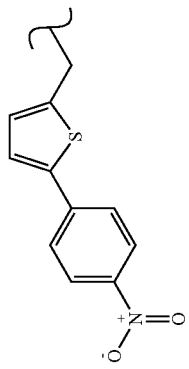
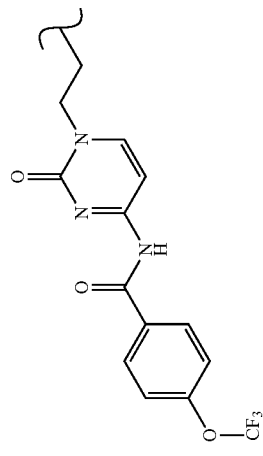 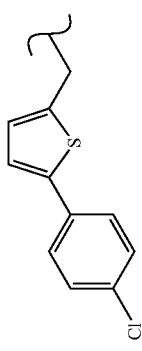 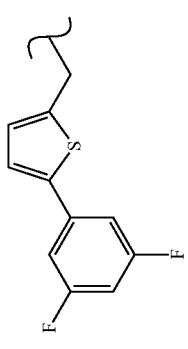 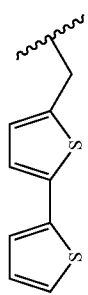

TABLE 9-continued
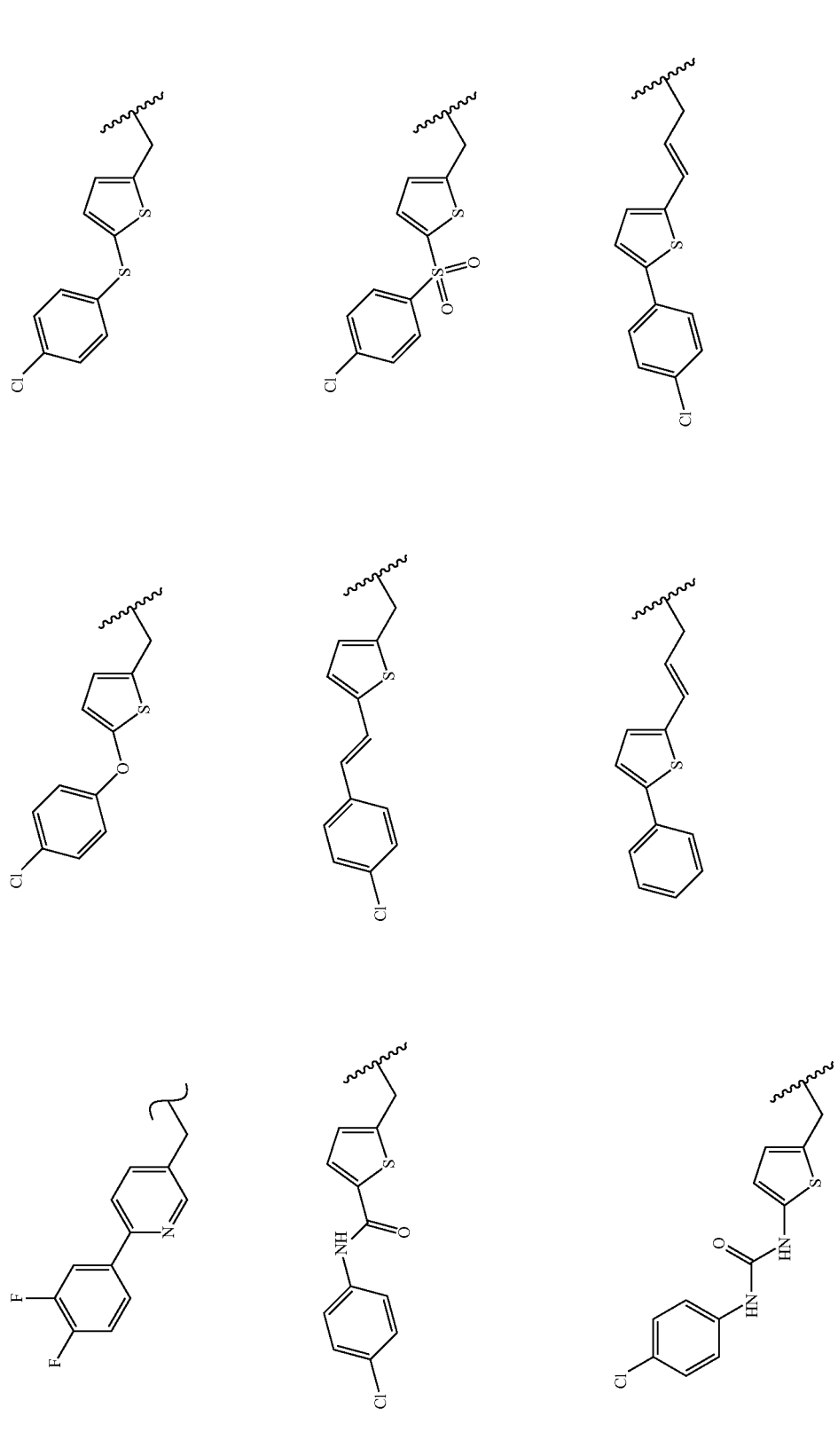

TABLE 10

| Structural formula | $R^B$ | $R^C$ | $R^D$ |
|---|---|---|---|
| (see structure) | OH | H | H |

$R^{41}$: (three structures shown)

TABLE 10-continued
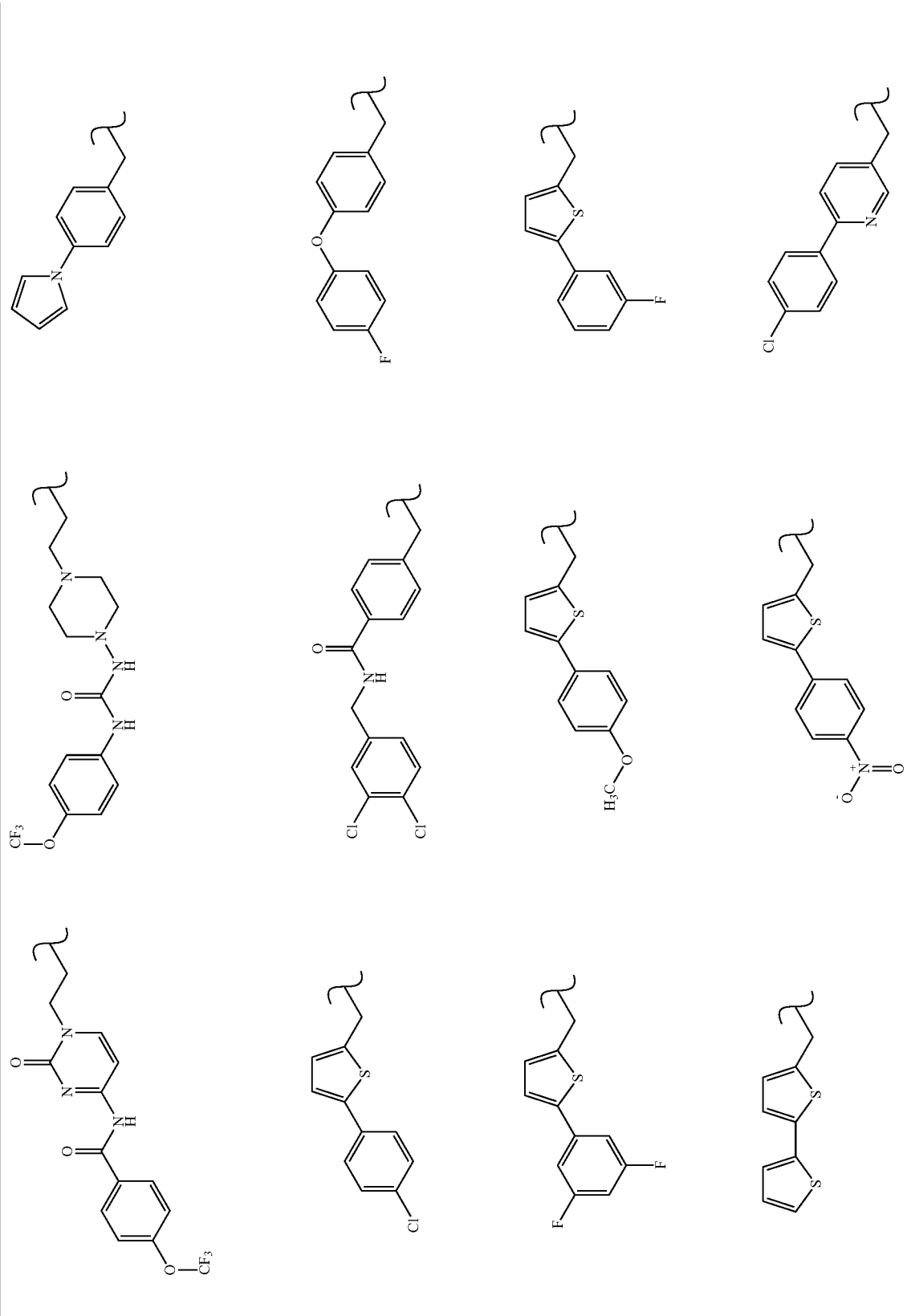

TABLE 10-continued
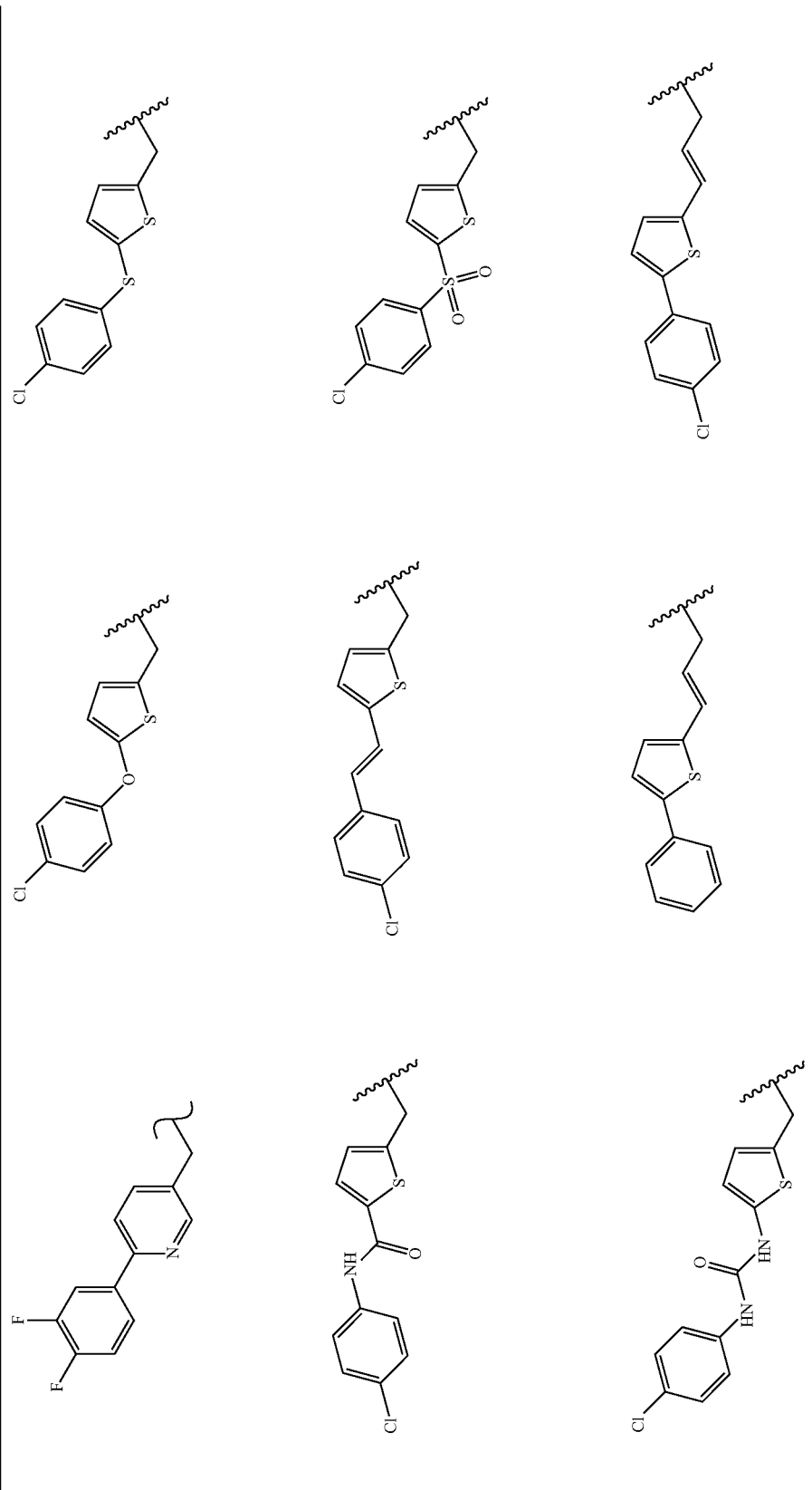

The present invention includes the aforementioned compounds, pharmaceutically acceptable salts thereof, and solvates thereof. Theoretically possible all tautomers, geometric isomers, and the like of the present compounds are within a scope of the present invention.

"Pharmaceutically acceptable" means not harmful preventively or therapeutically. Examples of the pharmaceutically acceptable salt of the present compound include, as basic salt, alkali metal salts such as sodium salt, potassium salt and the like; alkaline earth metal salts such as calcium salt, magnesium salt and the like; ammonium salt; aliphatic amine salts such as trimethylamine salt, triethylamine salt, dicyclohexylamine salt, ethanolamine salt, diethanolamine salt, triethanolamine salt, procaine salt, meglumine salt, diethanolamine salt and ethylenediamine salt; aralkylamine salts such as N,N-dibenzylethylenediamine salt, benethamine salt and the like; heterocyclic aromatic amine salts such as pyridine salt, picoline salt, quinoline salt, isoquinoline salt and the like; quaternary ammonium salts such as tetramethylammonium salt, tetraethylammonium salt, benzyltrimethylammonium salt, benzyltriethylammonium salt, benzyltributylammonium salt, methyltrioctylammonium salt, tetrabutylammonium salt and the like; and basic amino acid salts such as arginine salt, lysine salt and the like. Examples of acidic salt include inorganic acid salts such as hydrochloride, sulfate, nitrate, phosphate, carbonate, bicarbonate, perchlorate and the like; organic acid salts such as acetate, propionate, lactate, maleate, fumarate, tartarate, malate, citrate, ascorbate and the like; sulfonates such as methanesulfonate, isethionate, benzenesulfonate, p-toluenesulfonate and the like; and acidic amino acid salts such as aspartate, glutamate and the like.

In addition, a solvate, various solvates of the present compound are also within a scope of the present invention, and examples include monosolvate, disolvate, monohydrate, dihydrate and the like.

General Process

A representative process of the present compound is described below, but it is not particularly limited to the production process.

A starting material of the present invention can be prepared by variously chemically modifying an amino part ($R^{A2}$) of an amino sugar which binds to the sixth amino acid residue of a glycopeptides skeleton of chloroorienticin B or the known derivative thereof, or a C-terminal part ($R^B$), a resorcinol part ($R^C$), or an N-terminal part, a methylamino part ($R^D$) of chloroorienticin B, vancomycin or the known derivative thereof. Alternatively, an aglycone obtained by once eliminating a sugar side chain which binds to the aromatic ring of the fourth amino acid residue of a glycopeptide skeleton can be also used as a raw material. Alternatively, as a starting material, chloroorienticin B, vancomycin or the known derivative thereof may be used without chemical modification.

The chemical modification may be performed, for example, according to the method described in International Publication WO 2006/057303 pamphlet which constitutes a part of the present description. Specifically, the chemical modification is as follows.

1) Modification of $R^{A2}$ Part

Representatively, using chloroorienticin B as a raw material, corresponding various aldehydes are reacted with an amino part of an amino sugar optionally in the presence of an acid or a base to form a Schiff base which is an intermediate, this may be subsequently reduced to be N-alkylated, thereby to form an objective secondary amine.

More particularly, a reaction of forming a Schiff base is performed at a temperature of about 0° C. to about 100° C. optionally in the presence of an acid or a base in a polar solvent such as dimethyl sulfoxide, dimethylformamide, methanol, acetonitrile or water, or a mixed solvent thereof, optionally under the inert atmosphere such as nitrogen or argon. Preferably, the reaction is performed at a temperature of about 20° C. to about 40° C. for about 1 minute to 2 hours. As the base used, alkylamine (e.g., diisopropylethylamine) is exemplified. At this time, when a raw material compound has a substituent which is an obstacle of the present reaction, the substituent may be protected by the method described in Protective Groups in Organic Synthesis, Theodora W Green (John Wiley & Sons) or the like, and the protective group may be removed at a desired step.

Then, a Schiff base of an intermediate may be reduced or catalytic-reduced with metal hydride complex, preferably without isolation. As the metal hydride complex, metal borohydride such as sodium borohydride or sodium cyanoborohydride can be used. Catalytic reduction is performed using hydrogen, in the presence of homogeneous or heterogeneous catalyst such as Crabtree catalyst, Wilkinson catalyst, palladium charcoal, platinum charcoal or rhodium charcoal. The reducing reaction is performed at a temperature of about 0° C. to about 100° C. for about 1 minute to 24 hours. Preferably, the reaction is performed at about 20° C. to about 40° C. in the solvent using excessive amount (e.g., 3 to 5 mole equivalent) of sodium cyanoborohydride.

The reaction of forming Schiff base and the reducing reaction may be performed simultaneously, or it is also possible to obtain objective compound by performing the reaction of forming Schiff base in the presence of a reducing agent.

2) Modification of $R^B$ Part

Representatively, by amidating a carboxylic acid part which is the C-terminal, by a conventional method, using chloroorienticin B, vancomycin or the like as a raw material, the raw material can be converted into various amide derivatives which have $R^B=-NR^5R^{5'}$.

3) Modification of $R^C$ Part

Representatively, using chloroorienticin B, vancomycin or the like as a raw material, the resorcinol part is alkylated by a conventional method.

4) Modification of $R^D$ Part

Representatively, using chloroorienticin B, vancomycin or the like as a raw material, the methylamine part of the N-terminal part may be, example, N-alkylated by a conventional method.

5) Preparation of Aglycone

Representatively, using chloroorienticin B, vancomycin or the like as a raw material, the raw material may be de-glycosylated by the known method such as acid hydrolysis and the like. Specifically, the aglycone can be prepared by the method described in J. Med. Chem. (1965), 8, 18-22, J. Chem. Soc., Chem. Commun. (1988), 1306-1307, Biochemistry (2001), 40(15)4745-4755 or the like.

The present compound can be preferably synthesized by binding a monosaccharide to an OH part of an aromatic ring of the fourth amino acid residue of the glycopeptide skeleton of a starting material prepared by the aforementioned method, or a sugar residue which binds to it using glycosyltransferase or the like, elongating the sugar chain, oxidizing a hydroxymethyl group of the sugar residue at the terminal into an aldehyde group, reacting amine corresponding to $R^{41}$ in the presence of an acid or a base, if desired, to form a Schiff base which is an intermediated and, subsequently, N-alkylating the base by reduction, to form objective secondary amine. Specifically, the synthesis is as follows.

6) Elongation of Sugar Chain

A method of elongating a sugar chain is shown below, regarding representative compounds.

[Chemical formula 70]

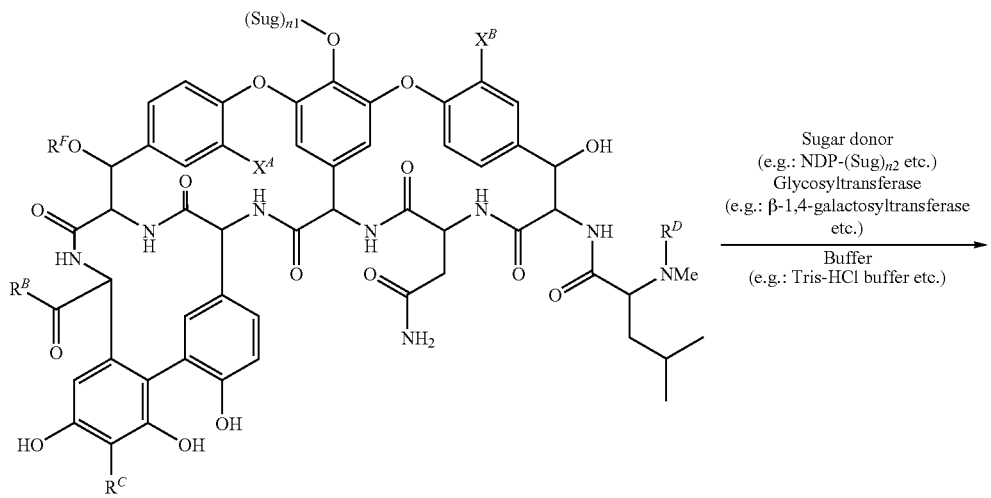

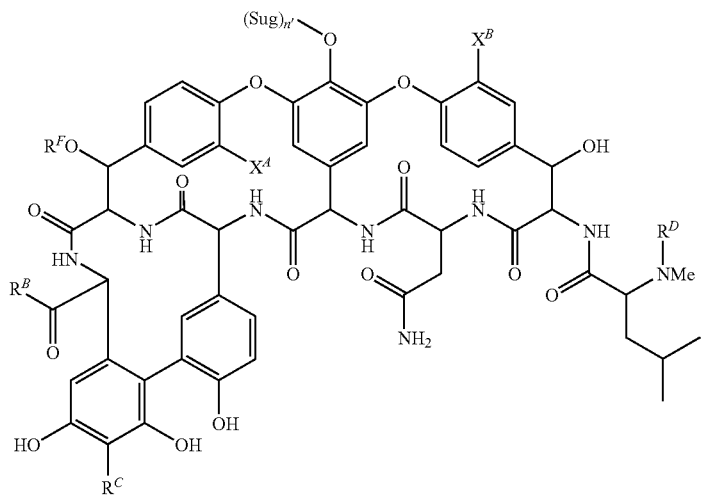

(wherein n1 is an integer of 0 to 5; n2 is an integer of 1 to 6;

n' is n1+n2 (wherein n' is 6 or less);

$R^B$, $R^C$, $R^D$, $R^F$, $X^A$, $X^B$, and Sug are as defined above; and

NDP is nucleotide-diphosphate; provided that, when n1 is 0, $(Sug)_{n1}$ represents H.)

Sugar chain modification may be performed on a starting material prepared by any method of 1) to 5), or a method of a combination thereof to form the sugar residue (I). The sugar chain modification is preferably performed by an enzymatic reaction. For example, for the enzymatic reaction, a sugar chain is elongated by reacting with a sugar donor in the presence of glycosyltransferase optionally in buffer. When a sugar chain is elongated by 2 or more monosaccharides, the reaction may be repeated plural times, or as described later, a sugar donor in which plurality of monosaccharides are connected in advance may be used.

As the buffer, buffers such as combination of a salt of an organic base such as Tris and the like, and an acid (e.g., Tris-HCl buffer, HEPES buffer, MES buffer etc); borate buffer; citrate buffer; acetate buffer; carbonate buffer and the like; are exemplified and preferable examples include Tris-HCl buffer, and MES buffer.

As the glycosyltransferase, β-1,4-galactosyltransferase, α-1,3-galactosyltransferase, β-1,3-galactosyltransferase, β-1,6-galactosyltransferase, α-2,6-sialyltransferase, α-1,4-galactosyltransferase, ceramidegalactosyltransferase, α-1,2- fucosyltransferase, α-1,3-fucosyltransferase, α-1,4-fucosyltransferase, α-1,6-fucosyltransferase, α-1,3-N-acetylgalactosaminyltransferase, α-1,6-N-acetylgalactosaminyltransferase, β-1,4-N-acetylgalactosaminyltransferase, polypeptide N-acetylgalactosaminyltransferase, β-1,4-N-acetylglucosaminyltransferase, β-1,2-N-acetylglucosaminyltransferase, β-1,3-N-acetylglucosaminyltransferase, β-1,6-N-acetylglucosaminyltransferase, α-1,4-N-acetylglucosaminyltransferase, β-1,4-mannosyltransferase, α-1,2-mannosyltransferase, α-1,3-mannosyltransferase, α-1,4-mannosyltransferase, α-1,6-mannosyltransferase, α-1,2-glucosyltransferase, α-1,3-glucosyltransferase, α-2,3-sialyltransferase, α-2,8-sialyltransferase, α-1,6-glucosaminyltransferase, α-1,6-xylosyltransferase, β-xylosyltransferase, (proteoglycan core structure synthesizing enzyme), β-1,3-glucuronosyltransferase, hyaluronic acid synthesizing enzyme, glycosyltransferase Gtf A to E described in J. Am. Chem. Soc. (2005), 127(30), 10747-10752, Proc. Natl. Acad. Sci. U.S.A. (2004), 101(13), 4390-4395, Chem. Asian. J. (2006), 1, 445-452 or the like, macrolide glycosyltransferase described in International Publication WO 2006/003456 pamphlet and the like are exemplified, and preferable is β-1, 4-galactosyltransferase.

As the sugar donor, compounds (NDP-Sugar) in which various nucleotide diphosphates such as uridine-diphosphate (UDP), thymidine-diphosphate (TDP) and like, and monosaccharides such as galactose, glucose, fructose, fucose, galactosamine, glucosamine, N-acetylgalactosamine, N-acetylglucosamine, vancosamine, epi-vancosamine, glucuronic acid, sialic acid and like, or sugar chains in which 2 to 5 same or different monosaccharides are connected linearly or branched are bound, in addition to oligosaccharides, and polysaccharides such as sucrose, starch and the like can be used. Preferable examples include UDP-galactose, UDP-N-acetylgalactosamine, and UDP-glucose. When a part which is to be the terminal of a sugar chain of an objective compound is elongated, a sugar donor in which the terminal is galactose is particularly preferable.

Optionally, a salt of a metal (e.g., Mg, Mn, Ca, Co, Zn, Cu etc.) and an inorganic acid (e.g., hydrochloric acid, hydrobromic acid, hydroiodic acid, sulfuric acid, nitric acid etc.) may be added. The metal salt is preferably $MnCl_2$ or the like.

Further, optionally, additive for enhancing reaction efficiency may be present together such as additive for enhancing the enzyme activity of lactoalbumin or the like; additive to decompose byproduct (e.g., alkaline phosphatase or the like); surfactant (e.g., Triton-X and the like).

The reaction temperature may be in conformity with an optimal temperature of glycosyltransferase. The temperature is 0 to 80° C., preferably 10 to 50° C., more preferably 20 to 40° C.

The reaction time is usually 1 to 100 hours, preferably 2 to 60 hours, more preferably 3 to 48 hours.

The pH of the buffer may be adjusted to an optimal pH of glycosyltransferase. Preferable pH is 2.0 to 12.0, more preferable is pH is 5.0 to 9.0, further preferable pH is 5.0 to 6.0.

In the sugar residue $(Sug)_{n'}$, the sugar on the root side is preferably glucose (e.g., β-D-glucose). On the other hand, the sugar on the terminal side is preferably galactose or N-acetylgalactosamine, more preferably galactose (e.g., β-D-galactose).

The sugar residue $(Sug)_{n'}$ is preferably a sugar residue represented by the formula:

[Chemical formula 71]

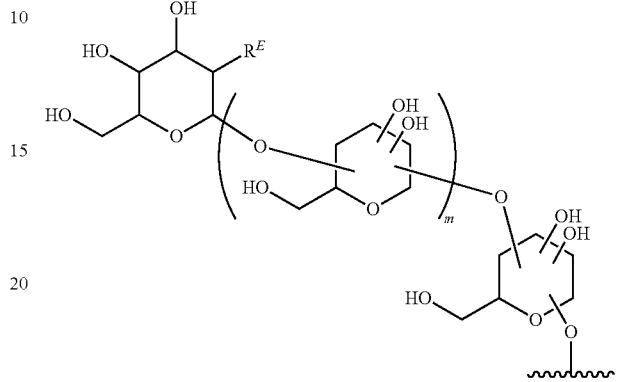

(wherein $R^E$ is —OH or —NHAc (Ac is acetyl)). More preferable is a sugar residue represented by the formula:

[Chemical formula 72]

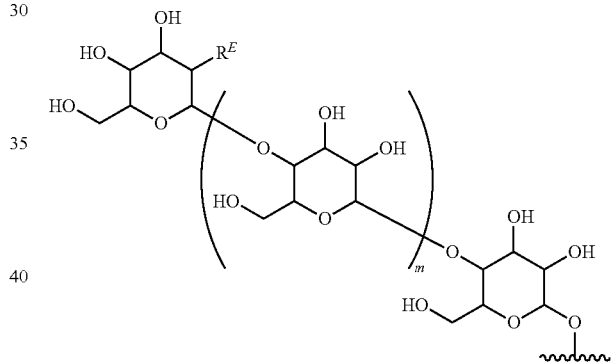

(wherein m is an integer of 0 to 4; and $R^E$ is as defined above). Further preferable is a sugar residue represented by the formula:

[Chemical formula 73]

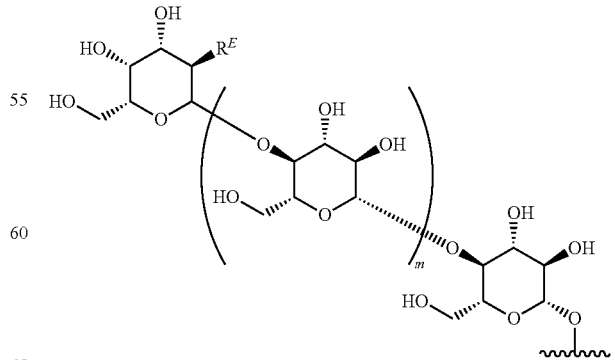

(wherein respective symbols are as defined above).

7) Oxidation of Hydroxymethyl Group

[Chemical formula 74]

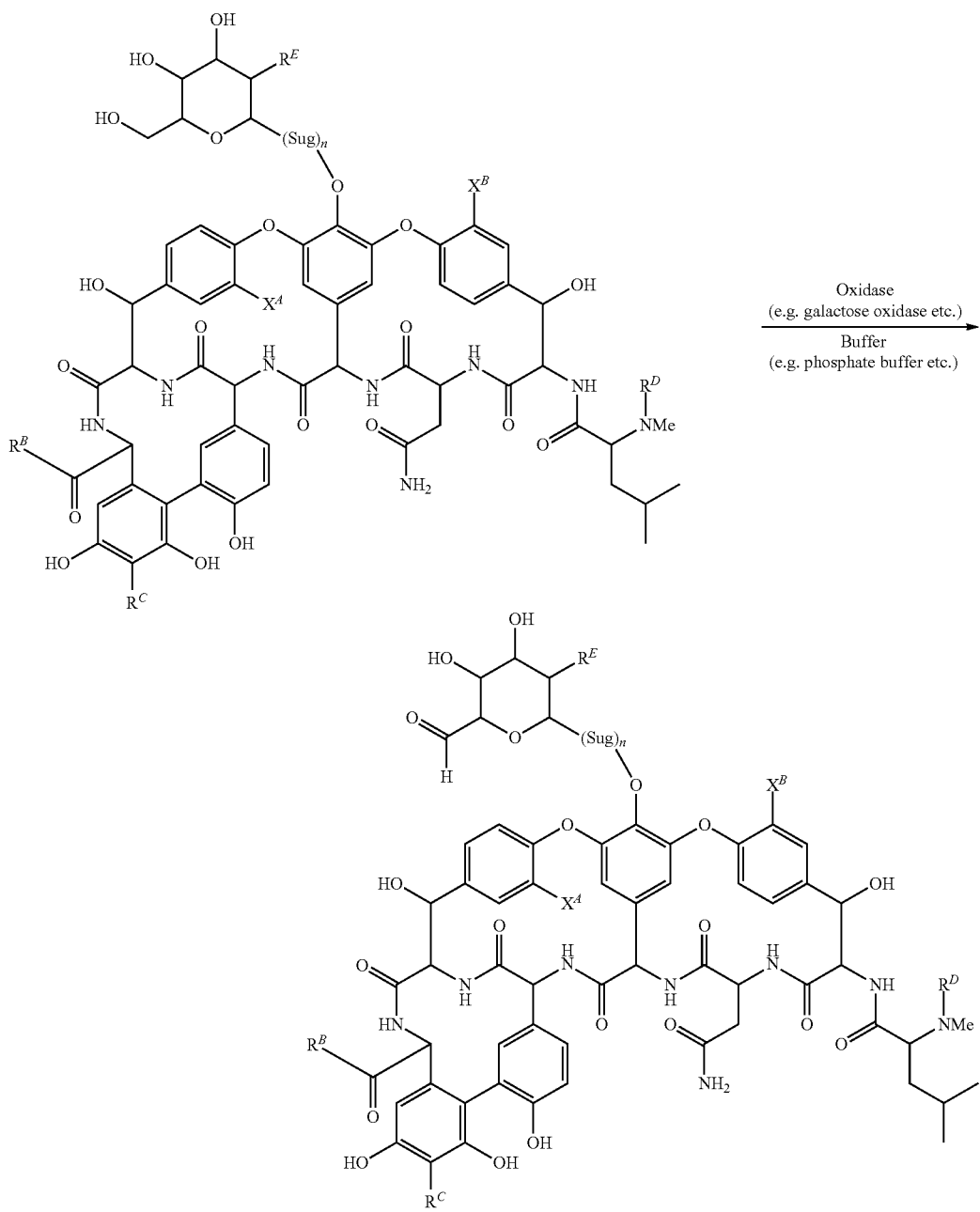

(wherein respective symbols are as defined above.)

A method of oxidizing the primary hydroxy group into aldehyde may be by oxidation with organic regent, or oxidation with enzyme, and is preferably the following method of oxidation with oxidase. According to the oxidation method, the objective hydroxy group can be selectively oxidized.

For the intermediate in which the sugar chain is elongated in above 6), the hydroxymethyl group is oxidized in the presence of oxidase optionally in buffer, to obtain the objective aldehyde intermediate.

As the buffer, phosphate buffer, borate buffer, citrate buffer, acetate buffer, carbonate buffer and the like are exemplified, and preferable is phosphate buffer.

As the oxidase, galactose oxidase and the like are exemplified.

Optionally, additive for improving the reaction efficiency to decompose byproduct (e.g., catalase and the like) may be present together.

The reaction temperature may be adjusted to an optimal temperature of the oxidase. Usually, the temperature is 0 to 80° C., preferably 10 to 50° C., more preferably 20 to 40° C.

The reaction time is usually 1 to 100 hours, preferably 2 to 96 hours, more preferably 2 to 30 hours.

The pH of the buffer may be adjusted to an optimal pH of the oxidase. Preferable pH is 2.0 to 12.0, more preferably pH is 5.0 to 9.0, further preferably pH is 5.0 to 7.0.

8) Modification of $R^{41}$ Part

[Chemical formula 75]

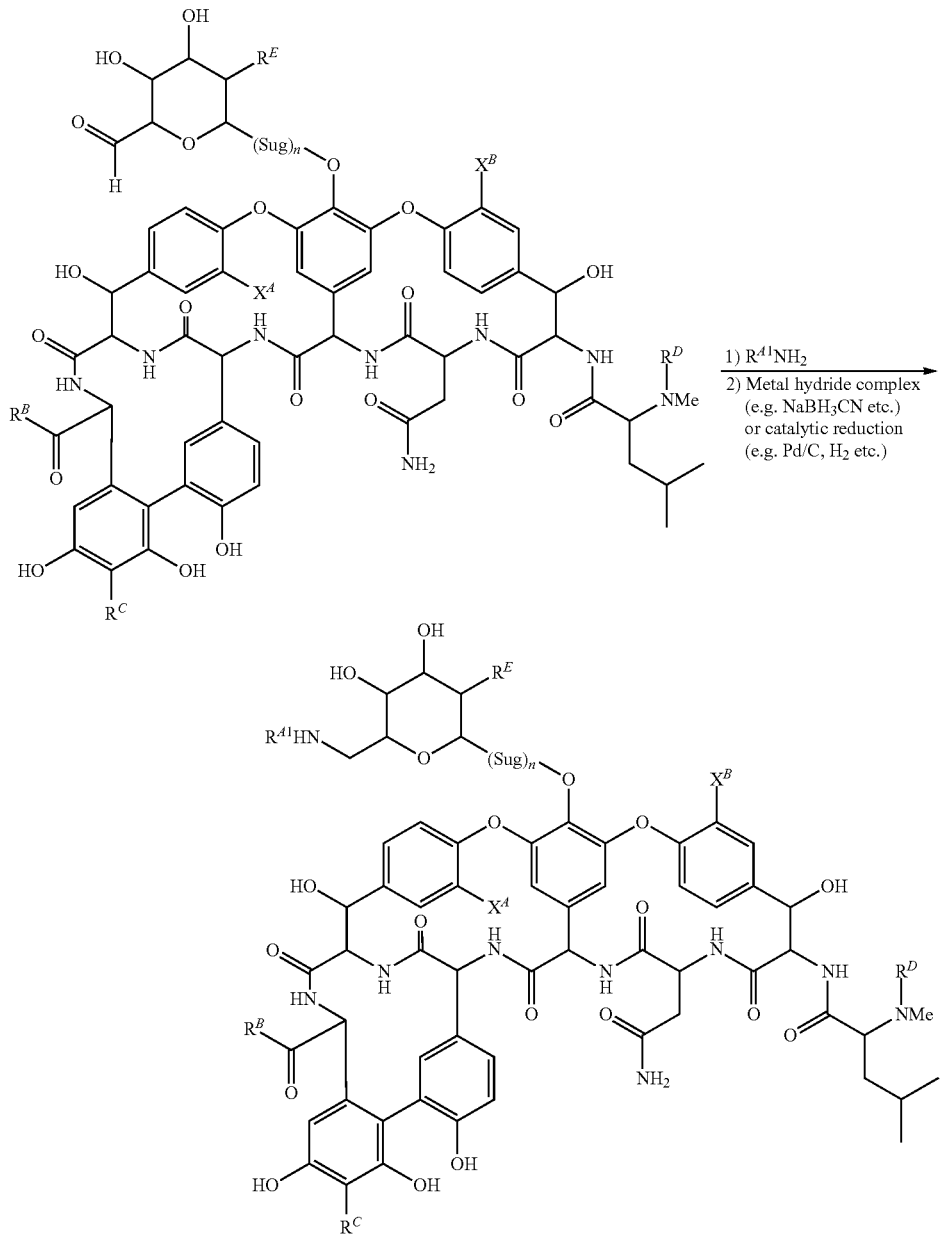

(wherein respective symbols are as defined above.)

The objective compound is obtained by reacting the aldehyde intermediate obtained in 7), and amine $R^{41}NH_2$ corresponding to objective $R^{41}$, preferably by the same method as that of modification of the $R^{42}$ part in 1). The amine reagent ($R^{41}NH_2$) is commercially available product, or can be synthesized according to the method described in International Publication WO 2006/057303.

According to the aforementioned method, the sugar residues (I-0), (I-1) and (I-2) are similarly formed.

In addition, the compound (X-1), (X-2) or (X-3) is present, as a byproduct, in admixture with the product obtained in 8) in some cases, and the compounds (IV-0) and (X-1), and compounds (IV-1) and (X-2) or the compounds (IV-2) and (X-3) can be each separated and isolated via a optional purification step (e.g., chromatography).

9) Production of Dehydrated Material

The compound (X-1), (X-2) or (X-3) can be also produced by the following method.

In the presence of water or organic solvent, or in the presence of mixed solvent thereof, the aldehyde compound (XI-1), (XI-2) or (XI-3) in which the sugar terminal is the dehydrated material is produced by adding a base to react the compound (IX-1), (IX-2) or (IX-3) in which the sugar terminal is aldehyde.

Examples of the base include diisopropylethylamine, triethylamine, 4-dimethylaminopyridine and the like.

The reaction temperature is 0° C. to 80° C., preferably 10° C. to 60° C., more preferably 15° C. to 40° C.

The reaction time is 1 to 100 hours, preferably 1 to 24 hours, more preferably 3 to 12 hours.

The produced aldehyde compound (XI-1), (XI-2) or (XI-3) in which the sugar terminal is dehydrated material can be subjected to modification of the $R^{41}$ part by the same method as that of above 8), and the objective compound (X-1), (X-2) or (X-3) can be obtained.

Pharmaceutical Composition

The present invention also includes a pharmaceutical composition containing the novel glycopeptide derivative of the present invention. Therefore, the glycopeptide compound in a form of a pharmaceutically acceptable salt can be preferably formulated for oral or parenteral administration for treating or preventing bacterial infection.

In the case of oral administration, the present compound can be also used as a conventional preparation, for example, as any dosage form of solid agents such as tablets, powders, granules, capsules; solutions; oily suspensions; or liquid agents such as syrups or elixirs. In the case of parenteral administration, the present compound can be used as aqueous or oily suspension injectables, or nose drops. Upon preparation thereof, conventional excipients, binders, lubricants, aqueous solvents, oily solvents, emulsifiers, suspending agents, preservatives, stabilizers and the like can be optionally used. As an antibacterial drug, particularly, oral agents, intravenous injectables or the like are preferable.

Preparations of the present invention are produced by combining (for example, mixing) a therapeutically effective amount of the present compound with a pharmaceutically acceptable carrier or diluent. A preparation of the present compound can be produced using well-known easily available ingredients by the known method.

Upon production of a pharmaceutically composition of the present invention, an active ingredients is mixed with a carrier, or diluted with a carrier, or is placed into a carrier in a form of capsules, sachets, papers or other containers. When a carrier works as a diluent, the carrier is a solid, semi-solid or liquid material which works as a medium, and they can be formulated into tablets, pills, powders, pastille, elixirs, suspending agents, emulsions, solutions, syrups, aerosols (solids in liquid medium), ointments, and contain an up to 10% active compound. It is preferable that the present compound is formulated into preparations prior to administration.

A person skilled in the art can use any of known suitable carriers for this formulation into preparations. In such preparations, a carrier is a solid, a liquid, or a mixture of a solid and a liquid. For example, for intravenous injection, the present compound is dissolved in a 4% dextrose/0.5% sodium citrate aqueous solution. A solid preparation includes powders, tablets and capsules. A solid carrier is one or more substances which serve also as a material for formulation into perfumes, lubricants, solubilizers, suspending agents, binders, tablets, disintegrating agents, or capsules. Tablets for oral administration contain suitable excipients such as calcium carbonate, sodium carbonate, lactose, and calcium phosphate together with disintegrating agents such as corn starch, and alginic acid and/or binders such as gelatin and acacia, and lubricants such as magnesium stearate, stearic acid, and talc.

In powders, a carrier is a finely divided solid, which is mixed with a finely divided active ingredient. In tablets, an active ingredient is mixed with a carrier having necessary binding property at a suitable ratio, and is solidified into a desired form and size. Powders and tablets contain about 1 to about 99% by weight of an active ingredient which is the novel compound of the present invention. A suitable solid carrier is magnesium carbonate, magnesium stearate, talc, sugar, lactose, pectin, dextrin, starch, gelatin, tragacanth gum, methylcellulose, sodium carboxymethylcellulose, low melting point wax, and cocoa butter.

Liquid preparations include suspending agents, emulsions, syrups and elixirs. An active ingredient can be dissolved or suspended in a pharmaceutically acceptable carrier such as sterile water, a sterile organic solvent, or a mixture of both of them. An active ingredient can be often dissolved in a suitable organic solvent, for example, an aqueous propylene glycol solution. Other compositions can be also produced by scattering a finely divided active ingredient in aqueous starch, a sodium carboxymethylcellulose solution, or a suitable oil.

A dose of the present compound is different depending on an administration method, an age, a weight and condition of a patient and a kind of a disease and, usually, in the case of oral administration, about 0.1 mg to 7000 mg, preferably about 0.5 mg to 2000 mg may be administered per adult a day, if necessary, by division. In addition, in the case of parenteral administration, about 0.1 mg to 1000 mg, preferably about 0.5 mg to 500 mg is administered per adult a day.

The following Examples and Test Examples illustrate the present invention in more detail below, but the present invention is not limited by them.

In Examples, the following abbreviations are used.

Me: Methyl,
Et: Ethyl,
Ph: Phenyl,
Ms: Methanesulfonyl,
DMF: Dimethylformamide,
DMSO: Dimethyl sulfoxide,
THF: Tetrahydrofuran
DIPEA: Diisopropylethylamine,
TFA: Trifluoroacetic acid,
EDCI: N-ethyl-N'-(3-dimethylaminopropyl)carbodiimide,
GalT: β-1,4-galactosyltransferase The compounds described in Table 11 to Table 51 were produced.

TABLE 11
| Example | Structure | Mass Spectrometry | Elementary analysis |
|---|---|---|---|
| 1 | 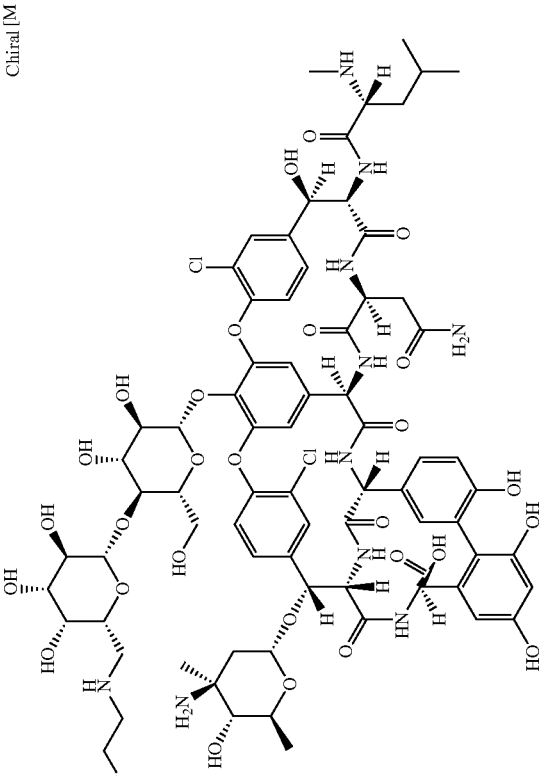 | Chiral [M + 1]⁺ = 1939 | Calculated value for C86H103Cl2F3N14O30·13.2H2O·4HCl<br>C: 44.44%,<br>H: 5.78%,<br>N: 8.44%,<br>Cl: 9.15%,<br>F: 2.45%<br>Measured value<br>C: 44.35%,<br>H: 5.59%,<br>N: 8.53%,<br>Cl: 9.17%,<br>F: 2.53% |

TABLE 11-continued

| Example | Structure | Mass Spectrometry | Elementary analysis |
|---|---|---|---|
| 2 | Chiral (structure) | [M + 1]⁺ = 1610 | Calculated value for C72H85Cl2N9O29•2.1HCl•13.8H2O<br>C: 44.65%,<br>H: 5.97%,<br>N: 6.51%,<br>Cl: 7.51%<br>Measured value<br>C: 44.60%,<br>H: 5.77%,<br>N: 6.68%,<br>Cl: 7.48% |

TABLE 11-continued
| Example | Structure | Mass Spectrometry | Elementary analysis |
|---|---|---|---|
| 3 | 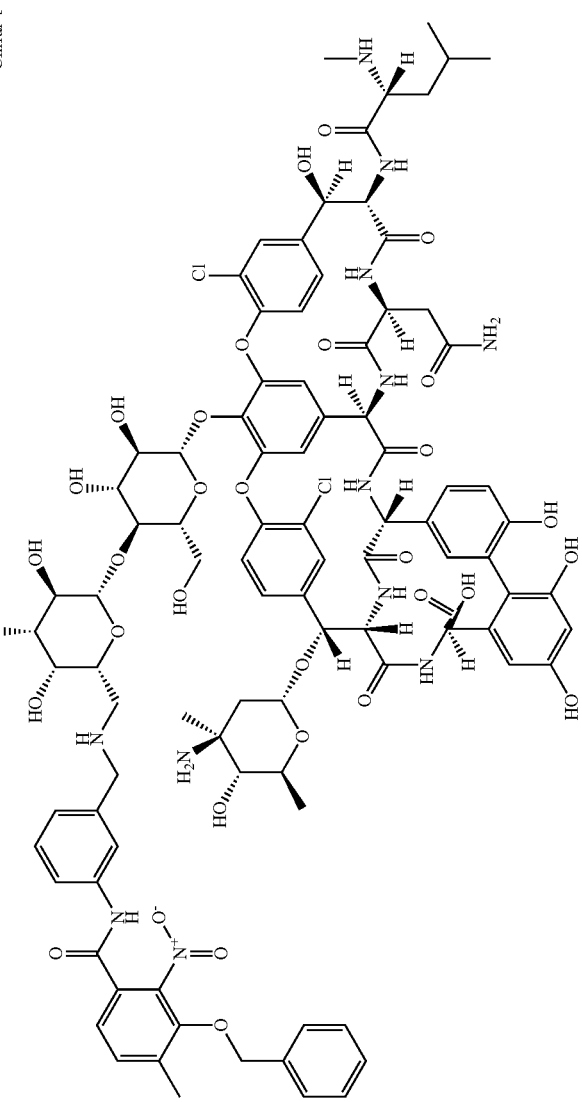 | Chiral [M + 1]$^+$ = 1983 | Calculated value for C94H104Cl2N12O32·3.5HCl·14.9H2O<br>C: 47.42%,<br>H: 5.81%,<br>N: 7.06%,<br>Cl: 8.19%<br>Measured value<br>C: 47.33%,<br>H: 5.57%,<br>N: 7.31%,<br>Cl: 8.20% |

TABLE 12
| Example | Structure | Mass Spectrometry | Elementary analysis |
|---|---|---|---|
| 4 | Chiral  | $[M + 1]^+ = 1938$ | Calculated value for $C_{94}H_{105}Cl_2N_{11}O_{30} \cdot 3.3HCl \cdot 14H_2O$<br>C: 48.83%,<br>H: 5.94%,<br>N: 6.66%,<br>Cl: 8.13%<br>Measured value<br>C: 48.59%,<br>H: 5.74%,<br>N: 6.90%,<br>Cl: 8.09% |

TABLE 12-continued
| Example | Structure | Mass Spectrometry | Elementary analysis |
|---|---|---|---|
| 5 | Chiral 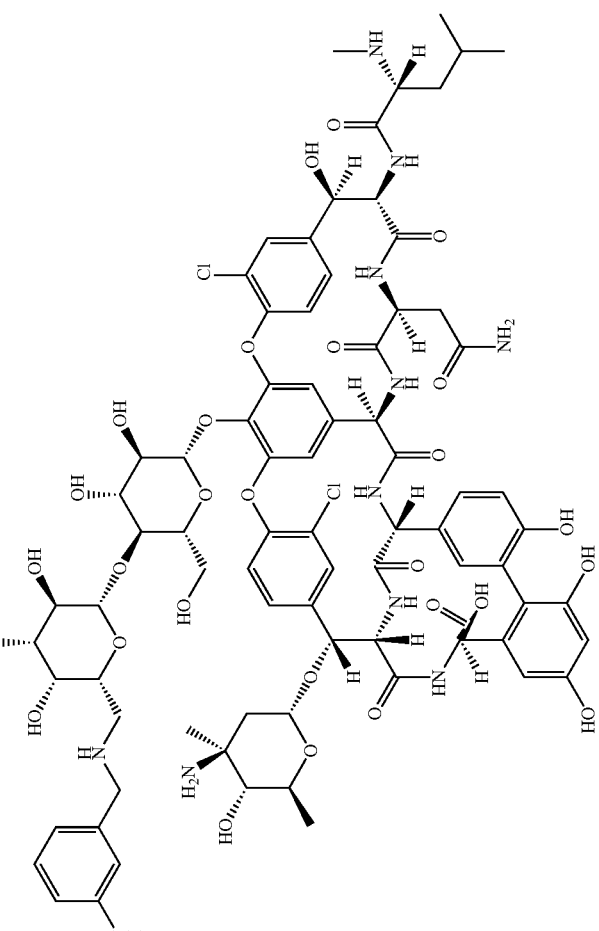 | [M + 1]$^+$ = 1886 | Calculated value for C86H95Cl4N11O29•3.4HCl•13.6H2O<br>C: 45.39%,<br>H: 5.65%,<br>N: 6.77%,<br>Cl: 11.53%<br>Measured value<br>C: 45.33%,<br>H: 5.24%,<br>N: 6.84%,<br>Cl: 11.45% |

TABLE 12-continued
| Example | Structure | Mass Spectrometry | Elementary analysis |
|---|---|---|---|
| 6 | 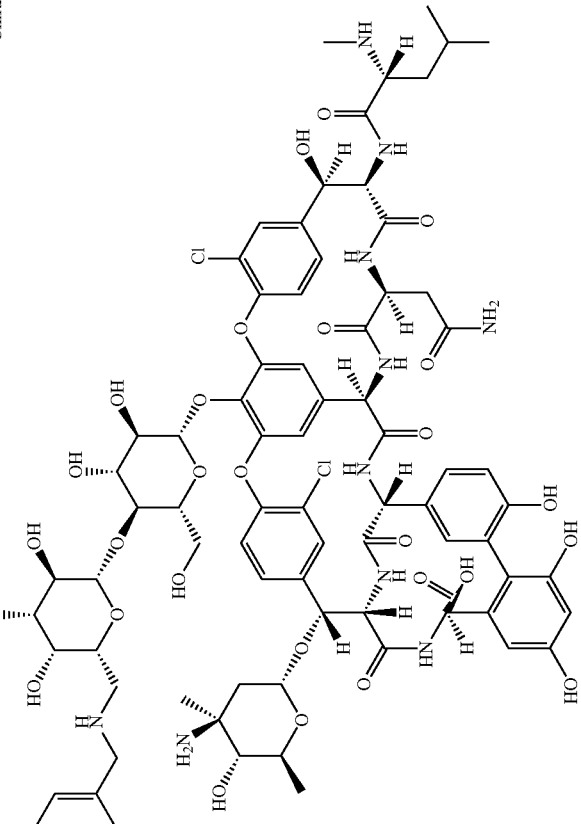 | Chiral [M + 1]$^+$ = 1902 | Calculated value for C87H96Cl2F3N11O30·3HCl·12.9H2O<br>C: 46.54%,<br>H: 5.60%,<br>N: 6.86%,<br>Cl: 7.89%,<br>F: 2.54%<br>Measured value<br>C: 46.45%,<br>H: 5.24%,<br>N: 6.96%,<br>Cl: 7.85%,<br>F: 2.48% |

TABLE 13

| Example | Structure | Mass Spectrometry analysis | Elementary analysis |
|---|---|---|---|
| 7 | Chiral (structure shown) | $[M+1]^+ = 1929$ | Calculated value for C89H101Cl2F3N12O29·3.4HCl·15.9H2O<br>C: 45.66%,<br>H: 5.86%,<br>N: 7.18%,<br>Cl: 8.18%,<br>F: 2.43%<br>Measured value<br>C: 45.69%,<br>H: 5.72%,<br>N: 7.27%,<br>Cl: 8.21%,<br>F: 2.26% |

TABLE 13-continued
| Example | Structure | Chiral | Mass Spectrometry | Elementary analysis |
|---|---|---|---|---|
| 8 | 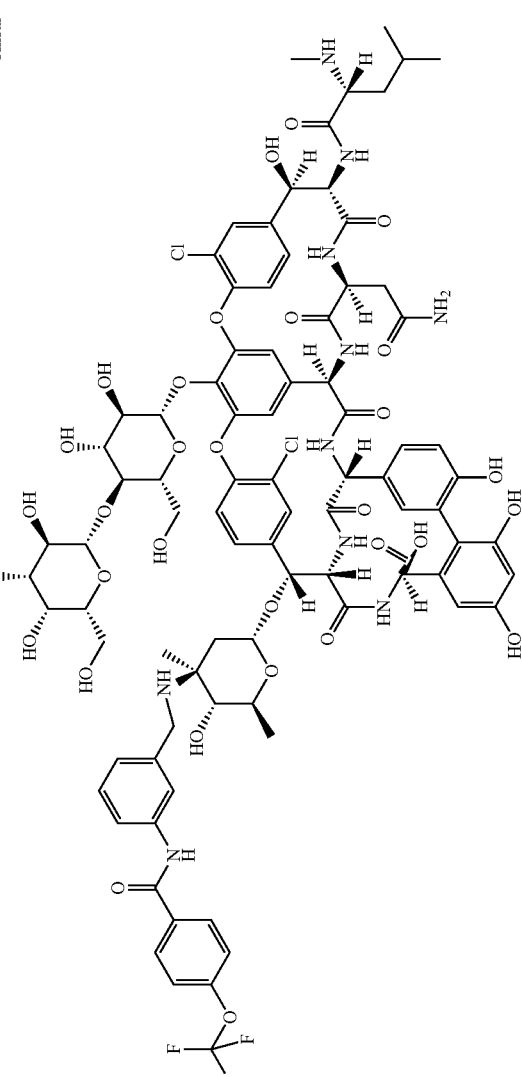 | Chiral | [M + 1]⁺ = 1903 | Calculated value for C87H95Cl2F3N10O31·2.4HCl·16H2O<br>C: 45.82%,<br>H: 5.72%,<br>N: 6.14%,<br>Cl: 6.84%,<br>F: 2.50%<br>Measured value<br>C: 45.85%,<br>H: 5.64%,<br>N: 6.00%,<br>Cl: 6.91%,<br>F: 2.48% |

TABLE 13-continued
| Example | Structure | Mass Spectrometry | Elementary analysis |
|---|---|---|---|
| 9 | 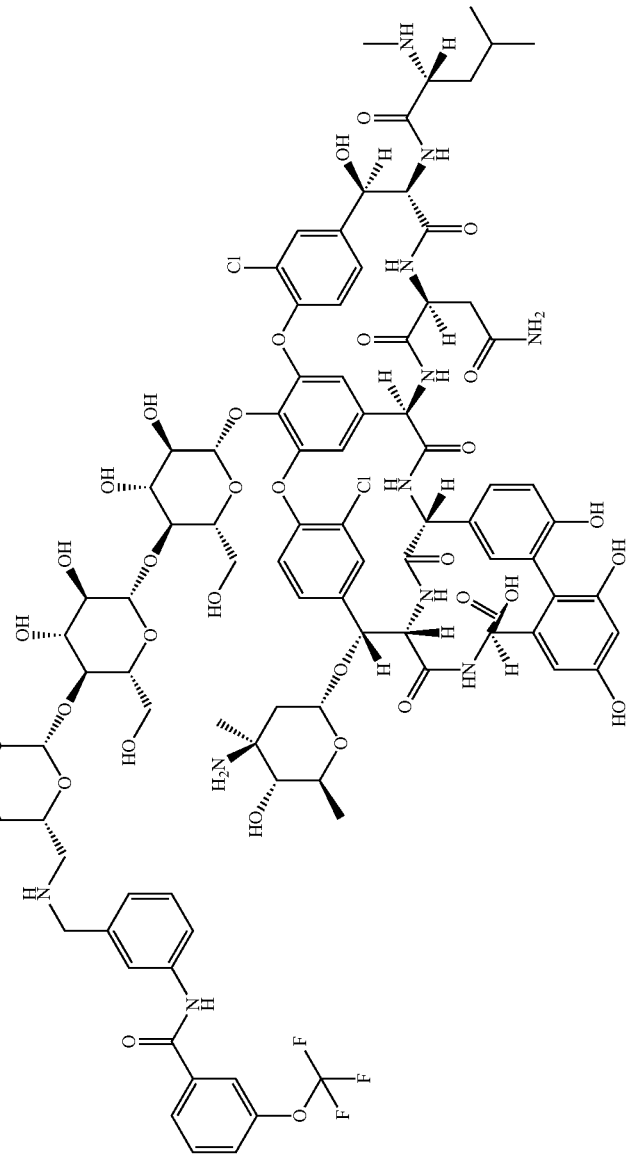 | [M + 1]⁺ = 2064 | Calculated value for C93H106Cl2F3N11O35·3.4HCl·18.4H2O<br>C: 44.30%,<br>H: 5.84%,<br>N: 6.11%,<br>Cl: 7.59%,<br>F: 2.26%<br>Measured value<br>C: 14.27%,<br>H: 5.72%,<br>N: 6.14%,<br>Cl: 7.53%,<br>F: 2.33% |

TABLE 14
| Example | Structure | Mass Spectrometry | Elementary analysis |
|---|---|---|---|
| 10 | Chiral 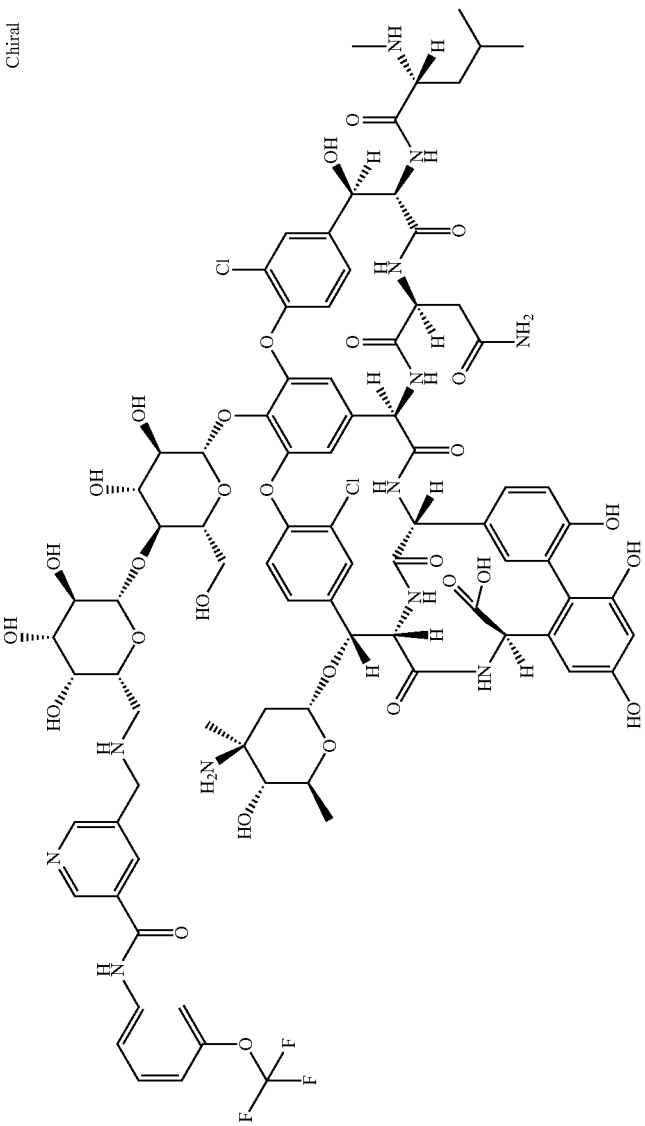 | [M + 1]+ = 1903 | Calculated value for C86H95Cl2F3N12O30•12.4H2O•4.1HCl<br>C: 45.35%,<br>H: 5.48%,<br>N: 7.38%,<br>Cl: 9.50%,<br>F: 2.50%<br>Measured value<br>C: 45.33%,<br>H: 5.45%,<br>N: 7.46%,<br>Cl: 9.57%,<br>F: 2.63% |

TABLE 14-continued
| Example | Structure | Mass Spectrometry | Elementary analysis |
|---|---|---|---|
| 11 | Chiral 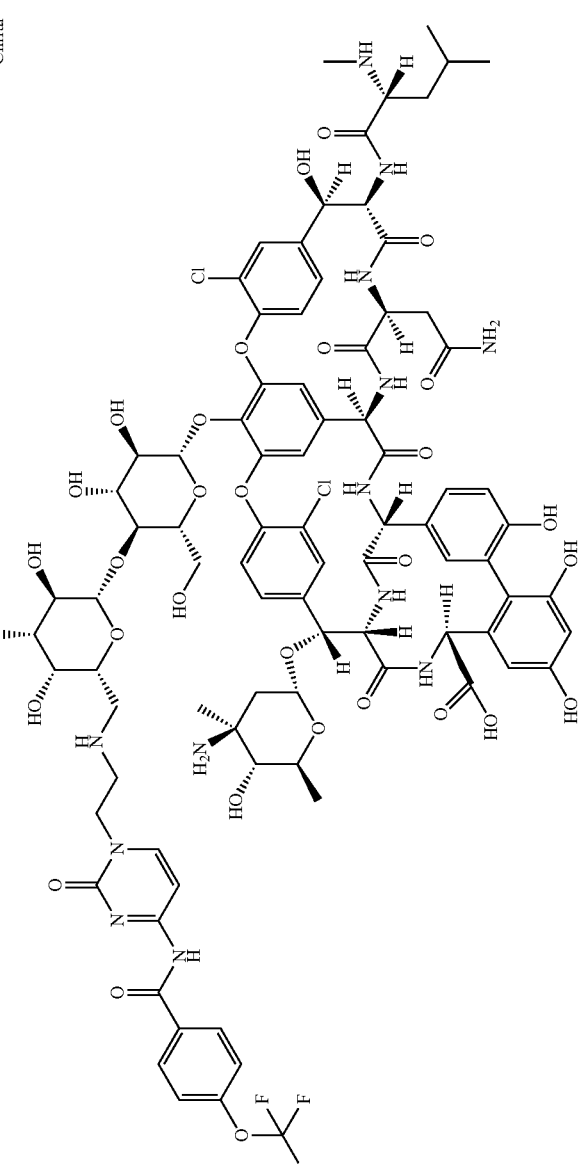 | [M + 1]+ = 1934 | Calculated value for C86H96Cl2F3N13O31•12.8H2O•3.6HCl<br>C: 44.96%,<br>H: 5.49%,<br>N: 7.93%,<br>Cl: 8.64%,<br>F: 2.48%<br>Measured value<br>C: 44.78%,<br>H: 5.33%,<br>N: 8.33%,<br>Cl: 8.67%,<br>F: 2.82% |

TABLE 14-continued

| Example | Structure | Mass Spectrometry | Elementary analysis |
|---|---|---|---|
| 12 | Chiral (structure) | [M + 1]⁺ = 1827 | Calculated value for C81H94Cl4N10O28S•11.2H2O•3.2HCl<br>C: 45.29%,<br>H: 5.61%,<br>N: 6.52%,<br>Cl: 11.88%,<br>S: 1.49%<br>Measured value<br>C: 45.29%,<br>H: 5.59%,<br>N: 6.65%,<br>Cl: 11.83%,<br>S: 1.51% |

TABLE 15

| Example | Structure | Mass Spectrometry | Elementary analysis |
|---|---|---|---|
| 13 | Chiral (structure shown) | [M + 1]⁺ = 1815 | Calculated value for C83H93Cl3N10O28S·11.1H2O·2.8HCl C: 47.04%, H: 5.61%, N: 6.61%, Cl: 9.70%, S: 1.51% Measured value C: 46.99%, H: 5.57%, N: 6.70%, Cl: 9.68%, S: 1.35% |

TABLE 15-continued

| Example | Structure | Mass Spectrometry | Elementary analysis |
|---|---|---|---|
| 14 | Chiral (structure shown) | [M + 1]$^+$ = 1789 | Calculated value for C86H98Cl2N10O28 C: 48.98%, H: 5.96%, N: 6.64%, Cl: 8.07%, Measured value C: 48.97%, H: 5.81%, N: 6.71%, Cl: 8.01% |

TABLE 15-continued

| Example | Structure | Chiral | Mass Spectrometry | Elementary analysis |
|---|---|---|---|---|
| 15 | 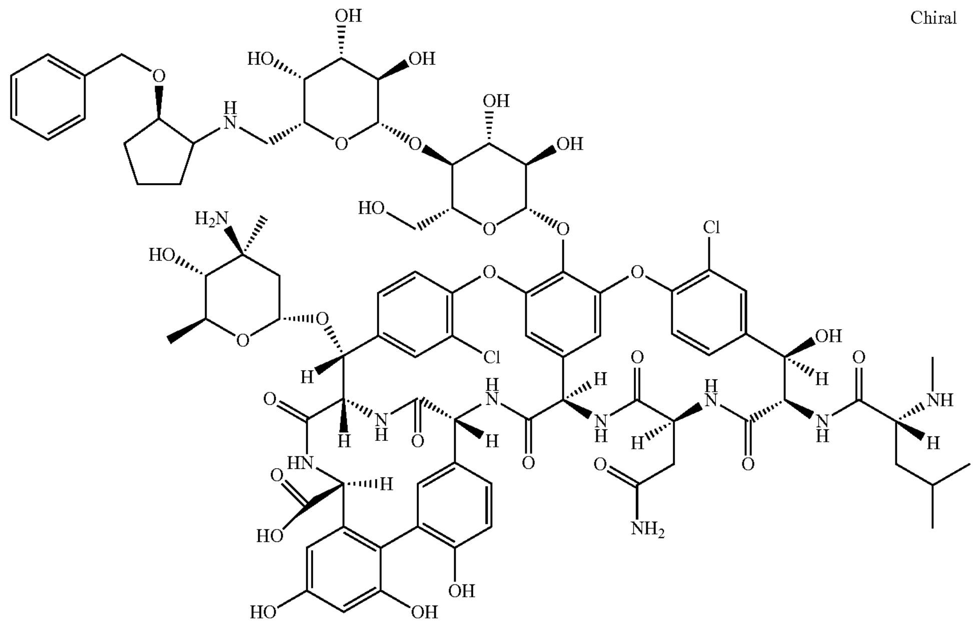 | Chiral | [M + 1]⁺ = 1783 | Calculated value for C84H100Cl2N10O29·10.7H2O·3.3HCl C: 48.09%, H: 5.99%, N: 6.68%, Cl: 8.96% Measured value C: 48.09%, H: 6.10%, N: 6.78%, Cl: 8.93% |

TABLE 16
| Example | Structure | Mass Spectrometry | Elementary analysis |
|---|---|---|---|
| 16 | Chiral 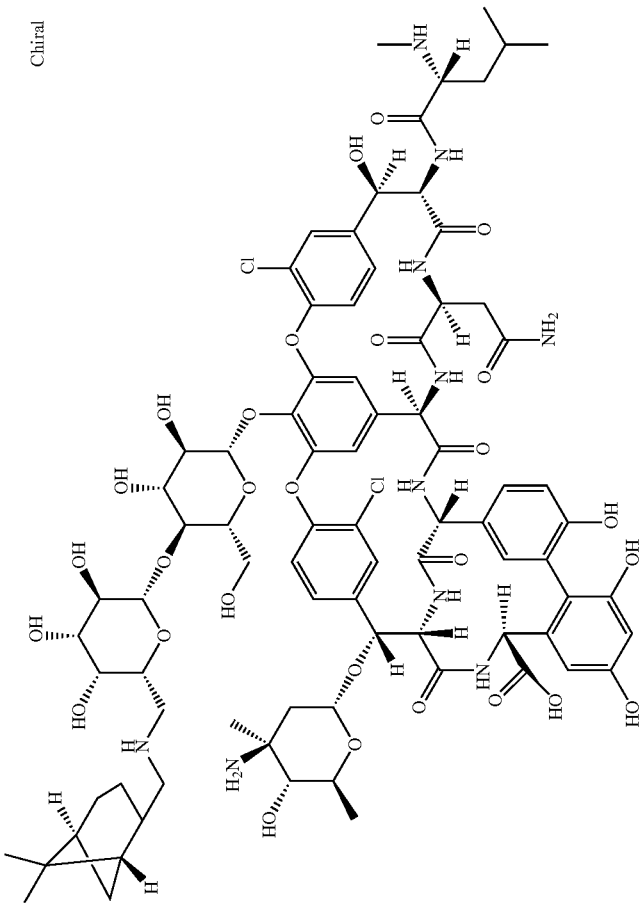 | [M + 1]$^+$ = 1745 | Calculated value for C82H102Cl2N10O28•12.1H2O•2.8HCl<br>C: 47.65%,<br>H: 6.29%,<br>N: 6.78%,<br>Cl: 8.23%<br>Measured value<br>C: 47.63%,<br>H: 6.17%,<br>N: 6.90%,<br>Cl: 8.21% |

TABLE 16-continued

| Example | Structure | Mass Spectrometry | Elementary analysis |
|---|---|---|---|
| 17 | Chiral | [M + 1]⁺ = 1723 | Calculated value for C79H100Cl2N10O29·11.9H2O··2.8HCl C: 46.49%, H: 6.25%, N: 6.86%, Cl: 8.34% Measured value C: 46.46%, H: 6.13%, N: 6.99%, Cl: 8.41% |

TABLE 16-continued
| Example | Structure | Mass Spectrometry | Elementary analysis |
|---|---|---|---|
| 18 | 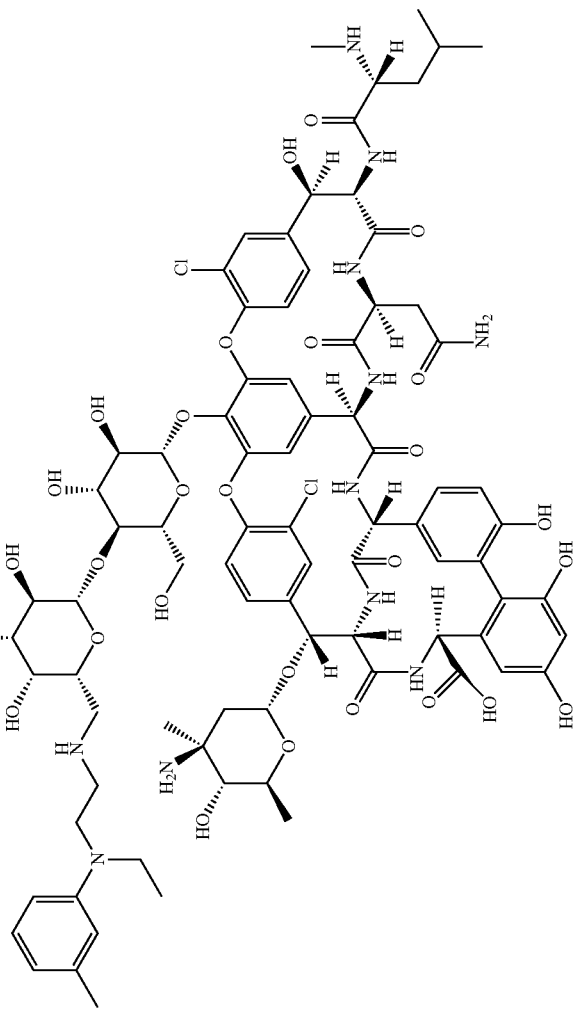 Chiral | [M + 1]⁺ = 1770 | Calculated value for C83H101Cl2N11O28•11.9H2O•3.4HCl C: 47.25%, H: 6.12%, N: 7.30%, Cl: 9.07% Measured value C: 47.22%, H: 6.07%, N: 7.44%, Cl: 9.03% |

TABLE 17
| Example | Structure | Mass Spectrometry | Elementary analysis |
|---|---|---|---|
| 19 | Chiral 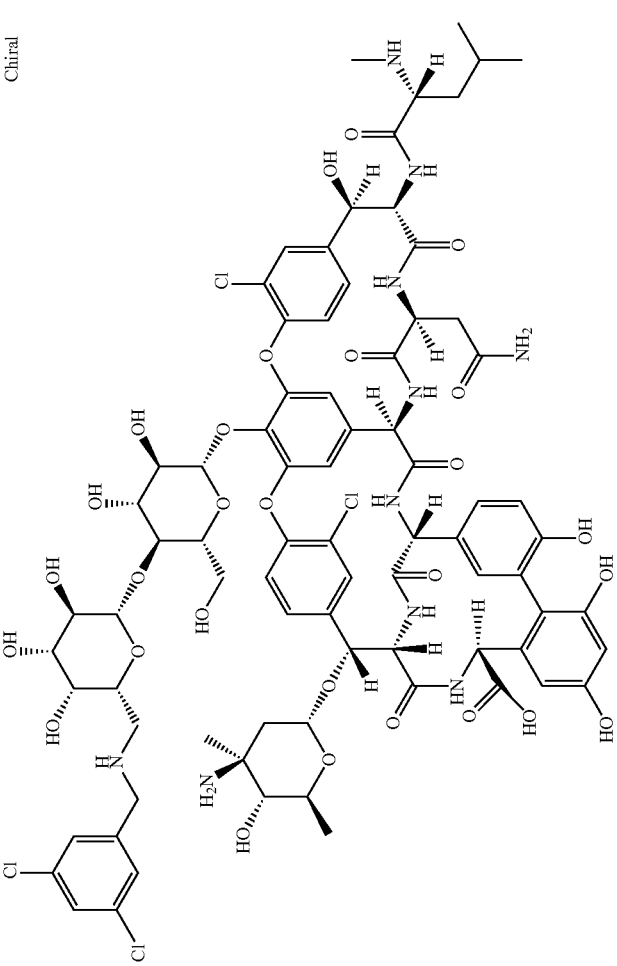 | [M + 1]+ = 1767 | Calculated value for C79H90Cl4N10O28·9.8H2O·3.9HCl<br>C: 45.44%,<br>H: 5.48%,<br>N: 6.71%,<br>Cl: 13.41%<br>Measured value<br>C: 45.42%,<br>H: 5.52%,<br>N: 6.89%,<br>Cl: 13.41% |

TABLE 17-continued

| Example | Structure | Mass Spectrometry | Elementary analysis |
|---|---|---|---|
| 20 | Chiral | [M + 1]⁺ = 1798 | Calculated value for $C_{84}H_{101}Cl_2N_{11}O_{29} \cdot 12.9H_2O \cdot 4.2HCl$<br>C: 46.17%,<br>H: 6.04%,<br>N: 7.05%,<br>Cl: 10.06%<br>Measured value<br>C: 46.15%,<br>H: 5.99%,<br>N: 7.15%,<br>Cl: 10.00% |

TABLE 17-continued
| Example | Structure | Mass Spectrometry | Elementary analysis |
|---|---|---|---|
| 21 | 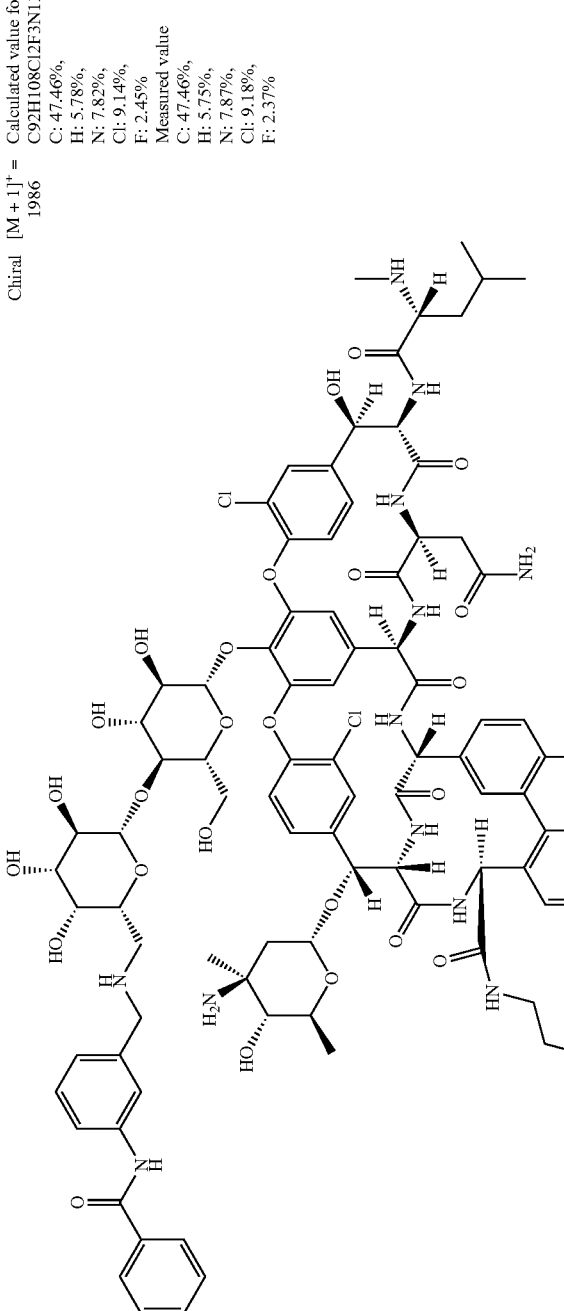 | Chiral [M + 1]+ = 1986 | Calculated value for C92H108Cl2F3N13O29•10.8H2O•4HCl<br>C: 47.46%,<br>H: 5.78%,<br>N: 7.82%,<br>Cl: 9.14%,<br>F: 2.45%<br>Measured value<br>C: 47.46%,<br>H: 5.75%,<br>N: 7.87%,<br>Cl: 9.18%,<br>F: 2.37% |

TABLE 18
| Example | Structure | Mass Spectrometry | Elementary analysis |
|---|---|---|---|
| 22 | 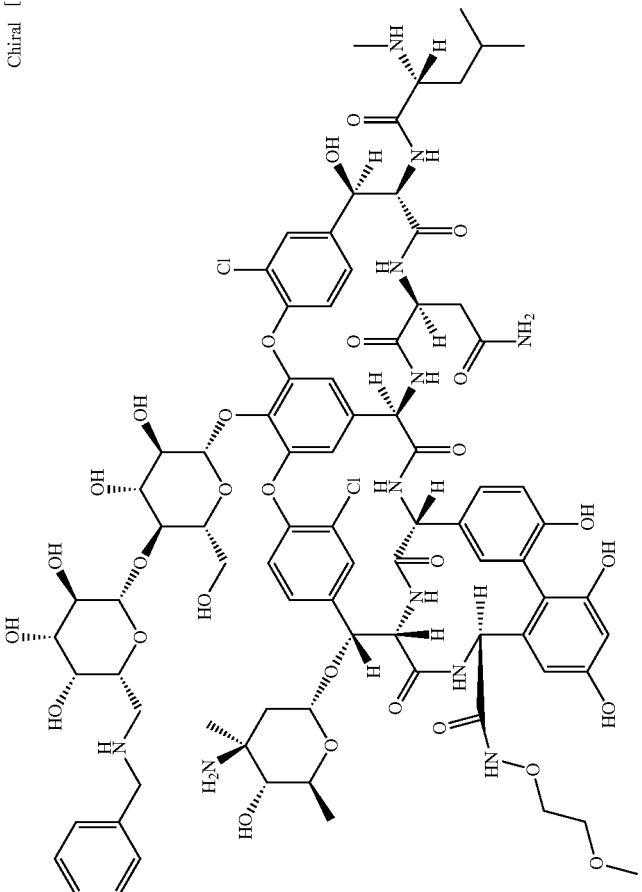 | Chiral [M + 1]+ = 1975 | Calculated value for C90H103Cl2F3N12O31•10.9H2O•3HCl<br>C: 47.36%,<br>H: 5.64%,<br>N: 7.36%,<br>Cl: 7.77%,<br>F: 2.50%<br>Measured value<br>C: 47.37%,<br>H: 5.58%,<br>N: 7.37%,<br>Cl: 7.80%,<br>F: 2.42% |

TABLE 18-continued
| Example | Structure | Mass Spectrometry analysis | Elementary analysis |
|---|---|---|---|
| 23 | 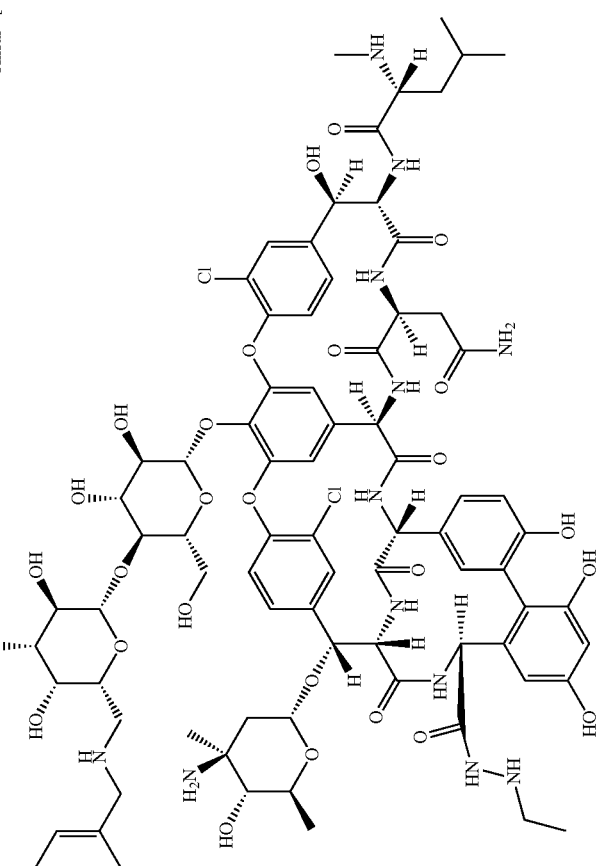 | Chiral [M + 1]⁺ = 1944 | Calculated value for C89H102Cl2F3N13O29•11.7H2O•3.3HCl C: 46.95%, H: 5.70%, N: 8.00%, Cl: 8.25%, F: 2.50% Measured value C: 46.93%, H: 5.54%, N: 8.03%, Cl: 8.31%, F: 2.45% |

TABLE 18-continued
| Example | Structure | Mass Spectrometry | Elementary analysis |
|---|---|---|---|
| 24 | 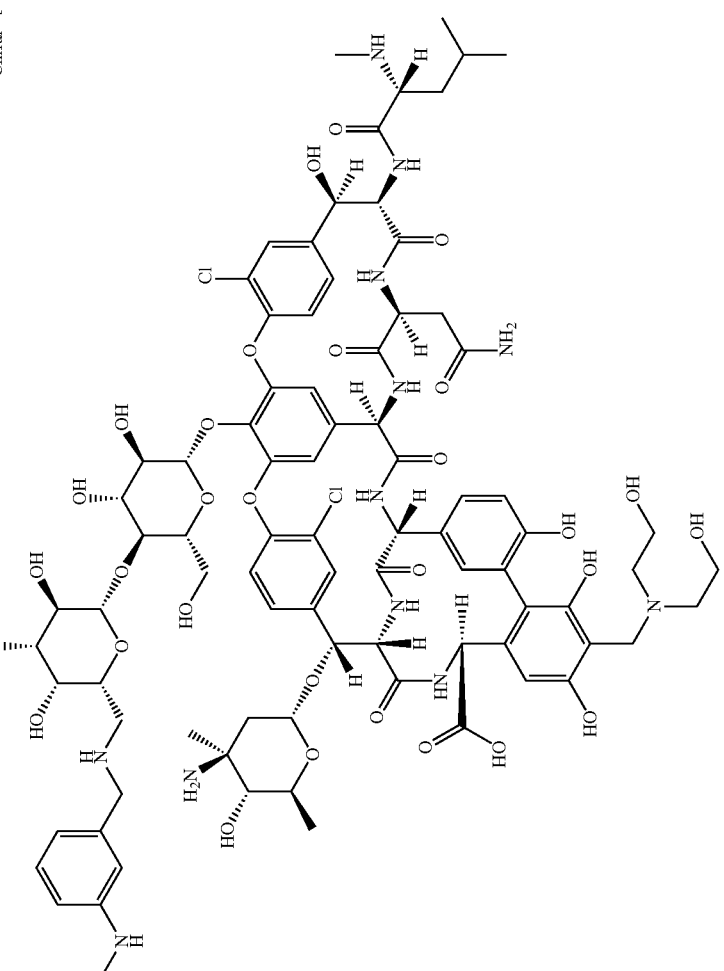 | Chiral [M + 1]⁺ = 2019 | Calculated value for C92H107Cl2F3N12O32·13.9H2O·3.5HCl<br>C: 46.06%,<br>H: 5.81%,<br>N: 7.01%,<br>Cl: 8.13%,<br>F: 2.38%<br>Measured value<br>C: 46.04%,<br>H: 5.73%,<br>N: 7.14%,<br>Cl: 8.08%,<br>F: 2.30% |

TABLE 19
| Example | Structure | Mass Spectrometry | Elementary analysis |
|---|---|---|---|
| 25 | 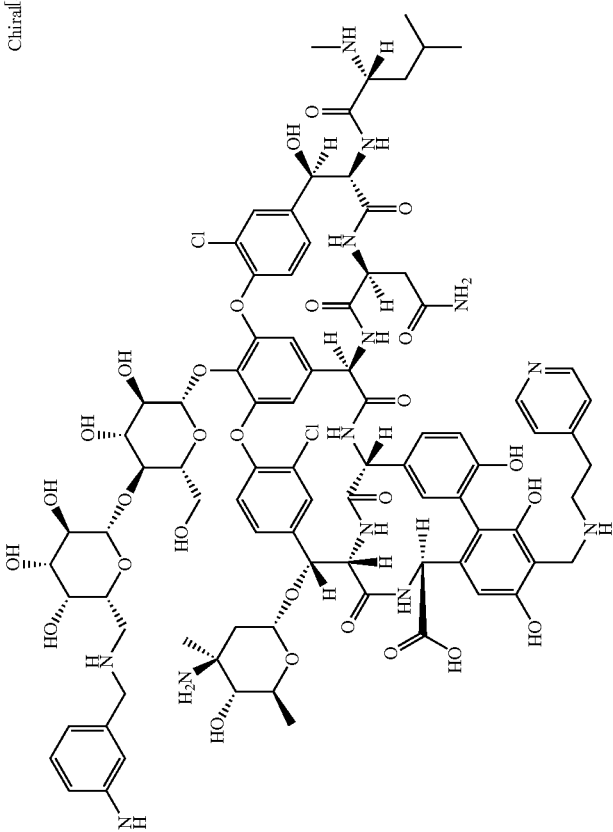 | Chiral[M + 1]⁺ = 2036 | Calculated value for C95H106Cl2F3N13O30•14.4H2O•4.3HCl<br>C: 46.5%,<br>H: 5.71%,<br>N: 7.42%,<br>Cl: 9.10%,<br>F: 2.32%<br>Measured value<br>C: 46.44%,<br>H: 5.55%,<br>N: 7.48%,<br>Cl: 9.06%,<br>F: 2.26% |

TABLE 19-continued
| Example | Structure | Mass Spectrometry | Elementary analysis |
|---|---|---|---|
| 26 | 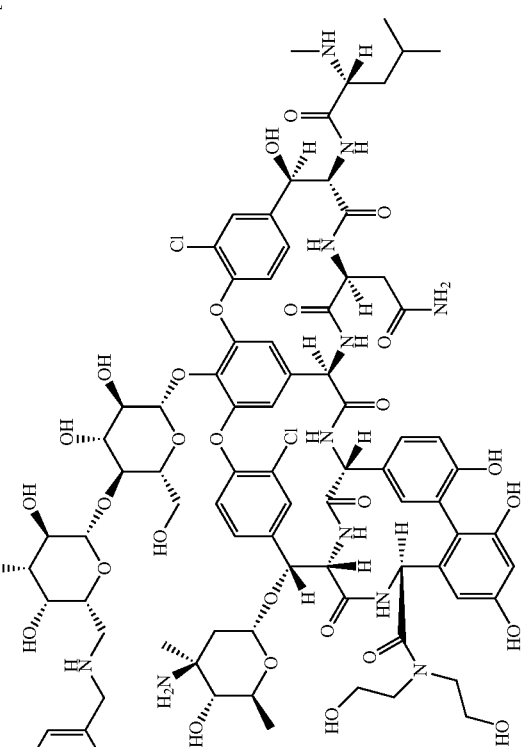 | Chiral[M + 1]$^+$ = 1989 | Calculated value for C91H105Cl2F3N12O31•11.9H2O•2.7HCl<br>C: 47.45%,<br>H: 5.75%,<br>N: 7.30%,<br>Cl: 7.23%,<br>F: 2.47%<br>Measured value<br>C: 47.14%,<br>H: 5.74%,<br>N: 7.44%,<br>Cl: 7.25%,<br>F: 2.28% |

TABLE 19-continued
| Example | Structure | Mass Spectrometry | Elementary analysis |
|---|---|---|---|
| 27 | 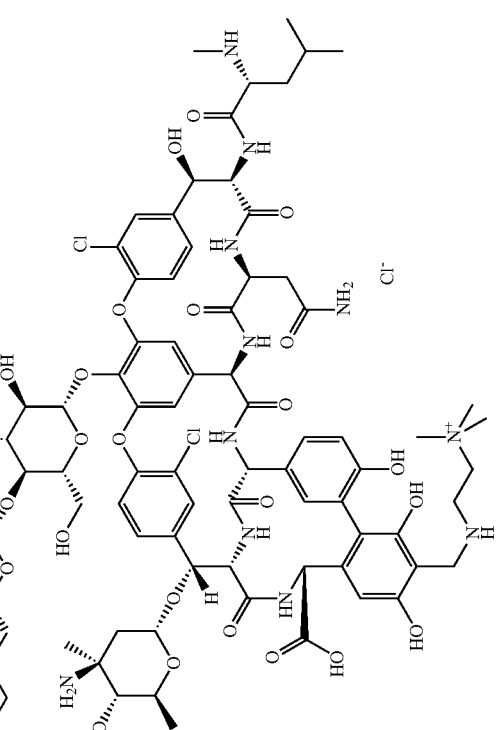 | Chiral[M + 1]+ = 2017 | Calculated value for C93H111Cl2F3N13O30•CH•13.9H2O•3.6HCl<br>C: 45.85%,<br>H: 5.89%,<br>N: 7.17%,<br>Cl: 9.61%,<br>F: 2.34%<br>Measured value<br>C: 45.84%,<br>H: 5.58%,<br>N: 7.13%,<br>Cl: 9.55%,<br>F: 2.77% |

TABLE 20

| Example | Structure | Mass Spectrometry | Elementary analysis |
|---|---|---|---|
| 28 | Chiral (structure shown) | [M + 1]$^+$ = 2039 | Calculated value for C90H103Cl2F3N12O33S·13.5H2O·2.7HCl<br>C: 45.37%,<br>H: 5.61%,<br>N: 7.05%,<br>Cl: 6.99%,<br>F: 2.39%,<br>S: 1.35%<br>Measured value<br>C: 45.33%,<br>H: 5.47%,<br>N: 7.02%,<br>Cl: 6.99%,<br>F: 2.37%,<br>S: 1.36% |

TABLE 20-continued
| Example | Structure | Mass Spectrometry | Elementary analysis |
|---|---|---|---|
| 29 | 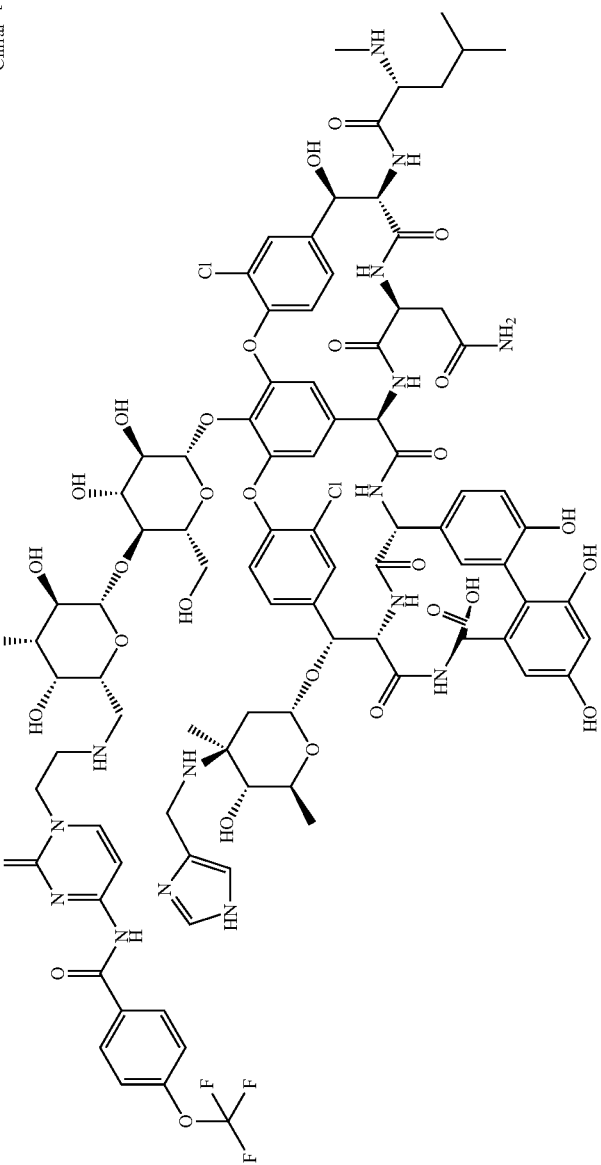 Chiral | [M + 1]⁺ = 2014 | Calculated value for C90H100Cl2F3N15O31•13.7H2O•4.2HCl C: 44.75%, H: 5.49%, N: 8.70%, Cl: 9.10%, F: 2.36% Measured value C: 44.70%, H: 5.55%, N: 8.89%, Cl: 9.10%, F: 2.25% |

TABLE 20-continued

| Example | Structure | Mass Spectrometry | Elementary analysis |
|---|---|---|---|
| 30 | Chiral (structure) | $[M+1]^+$ = 1982 | Calculated value for $C_{91}H_{100}Cl_2F_3N_{13}O_{30} \cdot 13.1H_2O \cdot 3.7HCl$<br>C: 46.42%,<br>H: 5.56%,<br>N: 7.73%,<br>Cl: 8.58%,<br>F: 2.42%<br>Measured value<br>C: 46.41%,<br>H: 5.58%,<br>N: 7.81%,<br>Cl: 8.54%,<br>F: 2.29% |

TABLE 21
| Example | Structure | Mass Spectrometry | Elementary analysis |
|---|---|---|---|
| 31 | Chiral 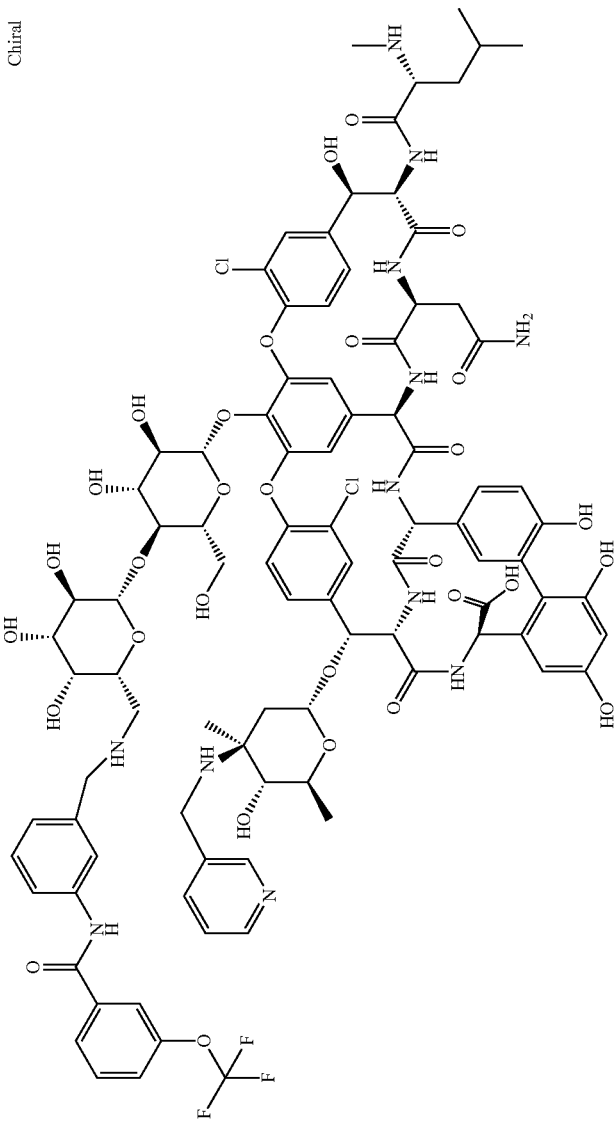 | [M + 1]⁺ = 1993 | Calculated value for C93H101Cl2F3N12O30•12.2H2O•3.2HCl C: 47.91%, H: 5.56%, N: 7.21%, Cl: 7.91%, F: 2.44% Measured value C: 47.92%, H: 5.54%, N: 7.33%, Cl: 7.95%, F: 2.31% |

TABLE 21-continued
| Example | Structure | Mass Spectrometry | Elementary analysis |
|---|---|---|---|
| 32 | Chiral 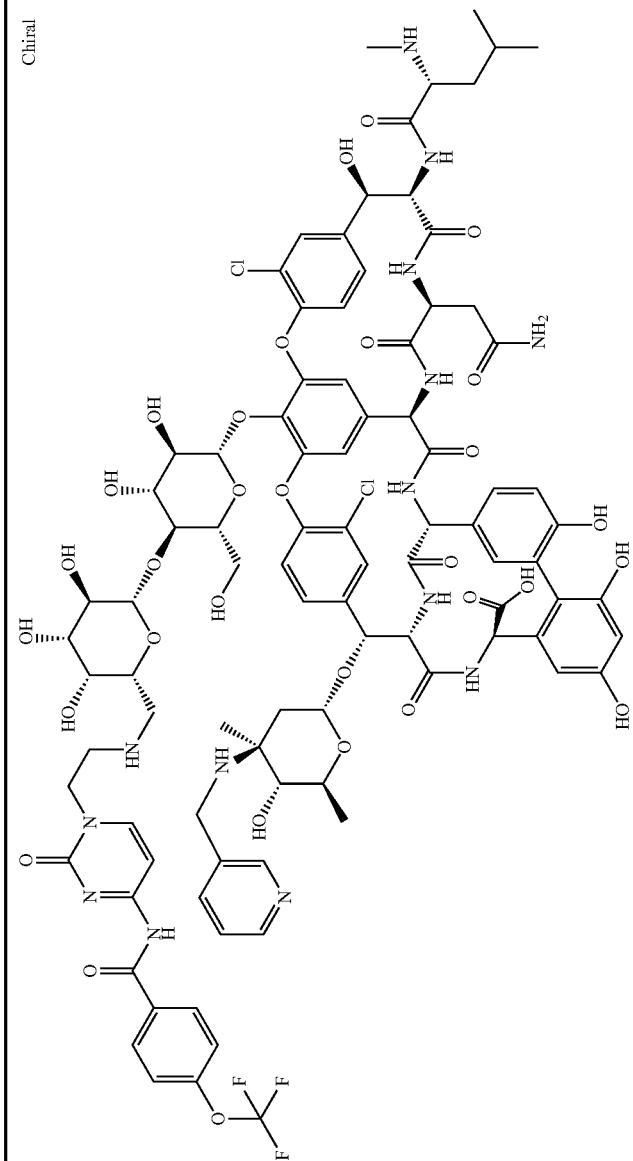 | [M + 1]⁺ = 2025 | Calculated value for C92H101Cl2F3N14O31•13.2H2O•3.5HCl C: 46.19%, H: 5.52%, N: 8.20%, Cl: 8.15%, F: 2.38% Measured value C: 46.15%, H: 5.53%, N: 8.47%, Cl: 8.15%, F: 2.40% |

TABLE 21-continued
| Example | Structure | Mass Spectrometry | Elementary analysis |
|---|---|---|---|
| 33 | Chiral 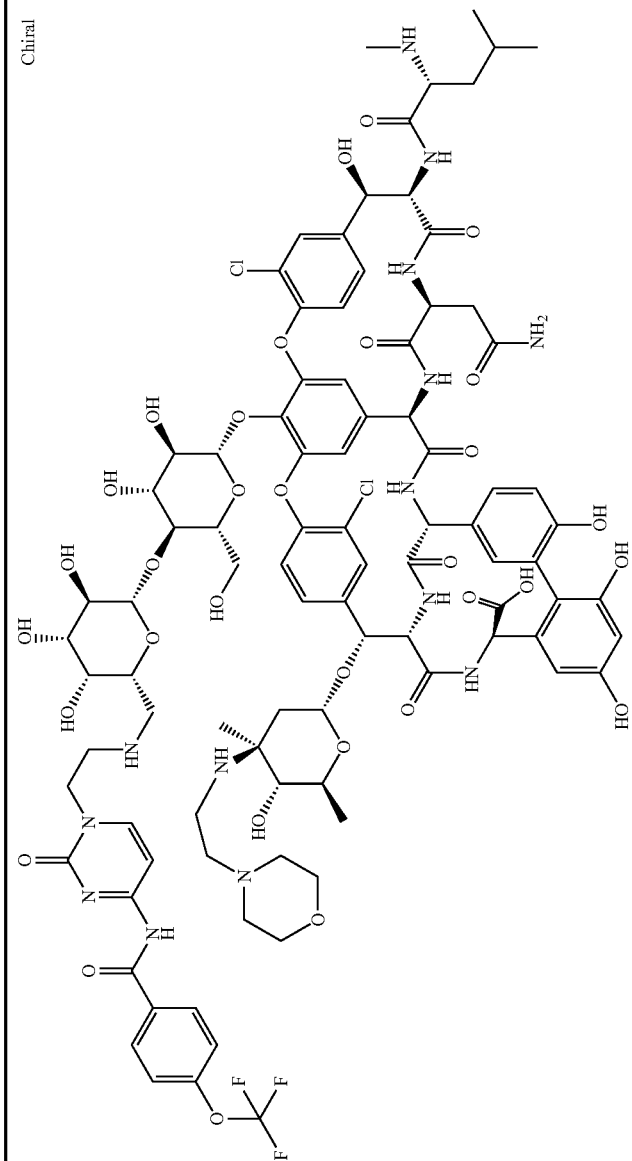 | $[M+1]^+ = 2047$ | Calculated value for $C_{92}H_{107}Cl_2F_3N_{14}O_{32} \cdot 12.7H_2O \cdot 3.7HCl$<br>C: 45.80%,<br>H: 5.69%,<br>N: 8.13%,<br>Cl: 8.38%,<br>F: 2.36%<br>Measured value<br>C: 45.77%,<br>H: 5.72%,<br>N: 8.27%,<br>Cl: 8.36%,<br>F: 2.33% |

TABLE 22
| Example | Structure | Mass Spectrometry | Elementary analysis |
|---|---|---|---|
| 34 | Chiral 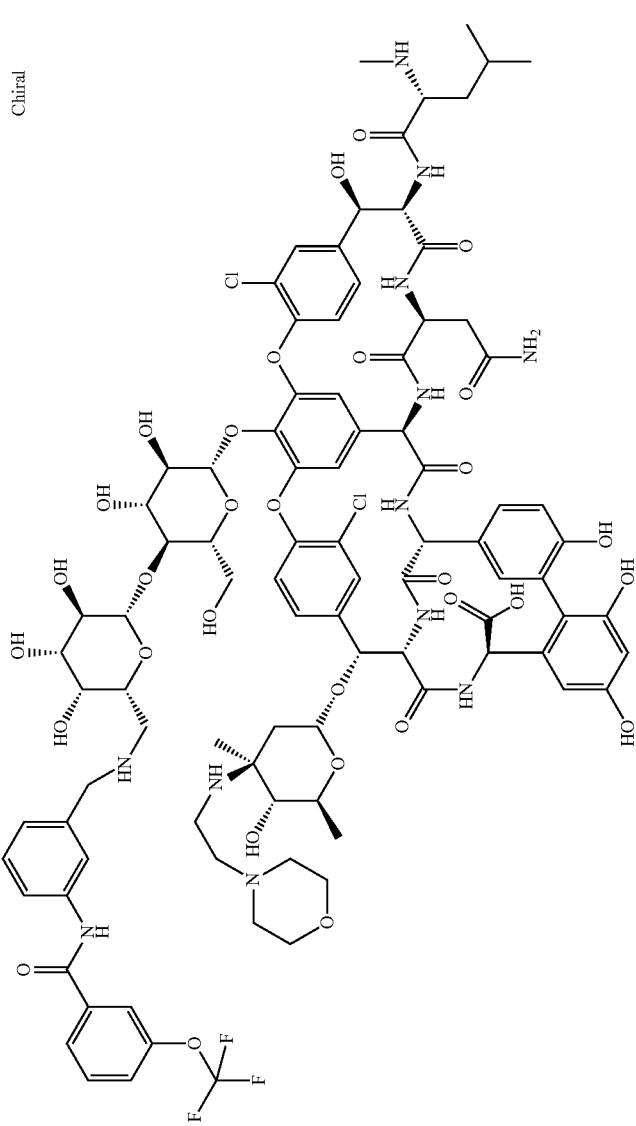 | $[M+1]^+ = 2015$ | Calculated value for $C_{93}H_{107}Cl_2F_3N_{12}O_{31} \cdot 11H_2O \cdot 3.3HCl$<br>C: 47.83%,<br>H: 5.71%,<br>N: 7.20%,<br>Cl: 8.05%,<br>F: 2.44%<br>Measured value<br>C: 47.83%,<br>H: 5.84%,<br>N: 7.24%,<br>Cl: 8.04%,<br>F: 2.29% |

TABLE 22-continued

| Example | Structure | | Mass Spectrometry | Elementary analysis |
|---|---|---|---|---|
| 35 | Chiral (structure) | | [M + 1]⁺ = 2052 | Calculated value for C91H106Cl2F3N43O34•11.8H2O•2.9HCl<br>C: 46.08%,<br>H: 5.63%,<br>N: 7.68%,<br>Cl: 7.32%,<br>F: 2.40%<br>Measured value<br>C: 45.91%,<br>H: 5.58%,<br>N: 8.58%,<br>Cl: 7.30%,<br>F: 2.50% |

TABLE 22-continued

| Example | Structure | Mass Spectrometry | Elementary analysis |
|---|---|---|---|
| 36 | Chiral | $[M + 1]^+ = 2020$ | Calculated value for $C_{92}H_{106}Cl_2F_3N_{11}O_{33} \cdot 11.8H_2O \cdot 3.2HCl$<br>C: 47.00%,<br>H: 5.69%,<br>N: 6.55%,<br>Cl: 7.84%,<br>F: 2.42%<br>Measured value<br>C: 46.99%,<br>H: 5.63%,<br>N: 6.62%,<br>Cl: 7.84%,<br>F: 2.28% |

TABLE 23

| Example | Structure | Chiral | Mass Spectrometry | Elementary analysis |
|---|---|---|---|---|
| 37 | 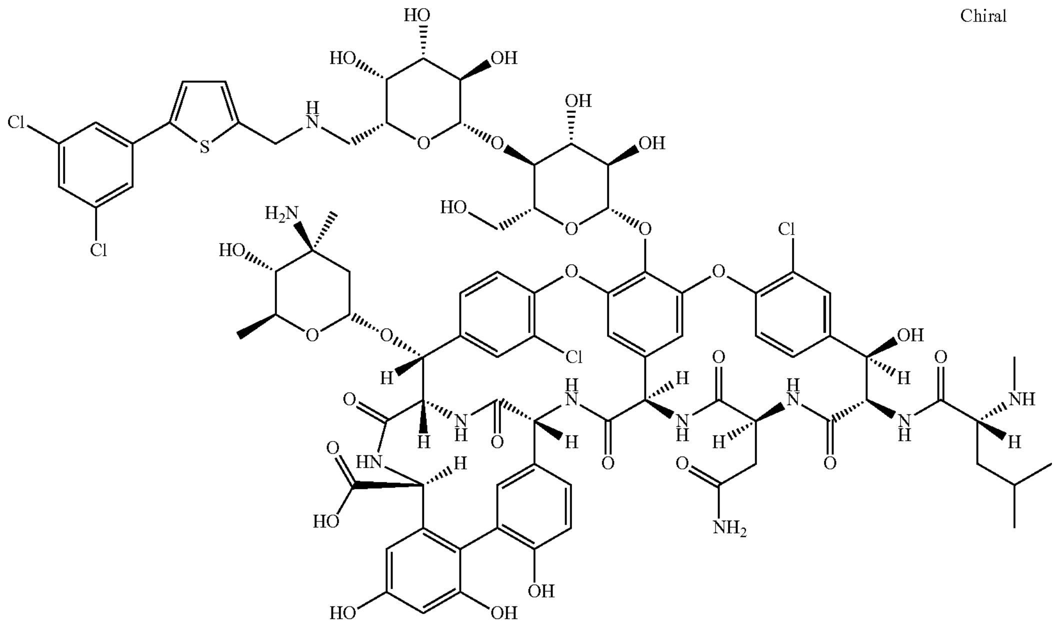 | | [M + 1]⁺ = 1849 | Calculated value for C83H92Cl4N10O28S•19.4H2O•4.1HCl<br>C: 42.41%,<br>H: 5.78%,<br>N: 5.96%,<br>Cl: 12.22%,<br>S: 1.36%<br>Measured value<br>C: 42.38%,<br>H: 5.35%,<br>N: 6.15%,<br>Cl: 12.24%,<br>S: 1.30% |

TABLE 23-continued

| Example | Structure | | Mass Spectrometry | Elementary analysis |
|---|---|---|---|---|
| 38 | 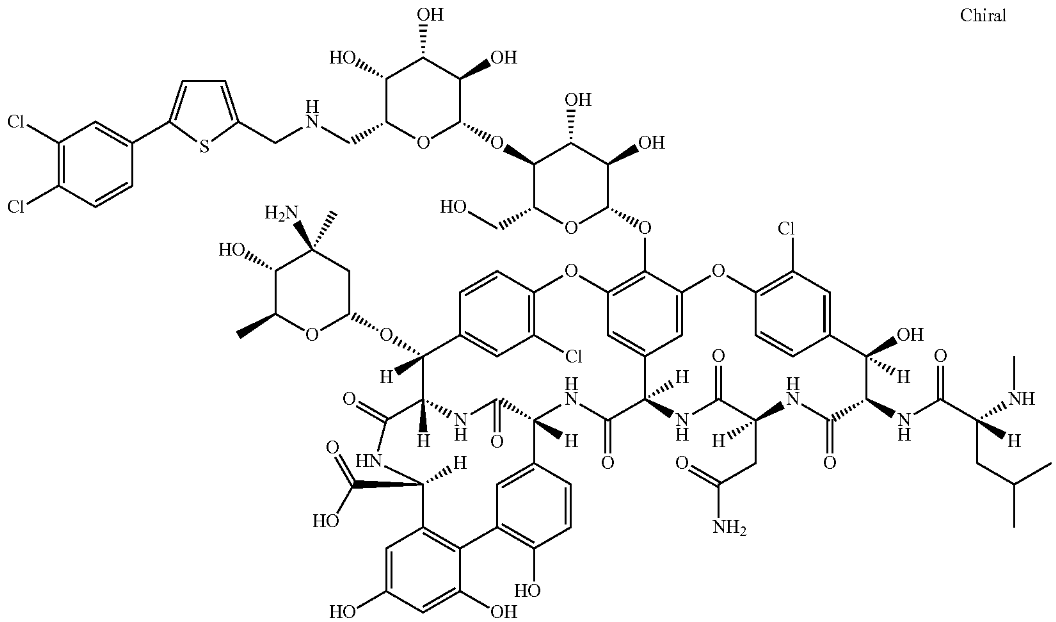 | Chiral | [M + 1]⁺ = 1849 | Calculated value for C83H92Cl4N10O28S•20.9H2O•4.4HCl C: 41.74%, H: 5.83%, N: 5.86%, Cl: 12.47%, S: 1.34% Measured value C: 41.68%, H: 5.26%, N: 6.04%, Cl: 12.36%, S: 1.23% |

TABLE 23-continued
| Example | Structure | Mass Spectrometry | Elementary analysis |
|---|---|---|---|
| 39 | Chiral 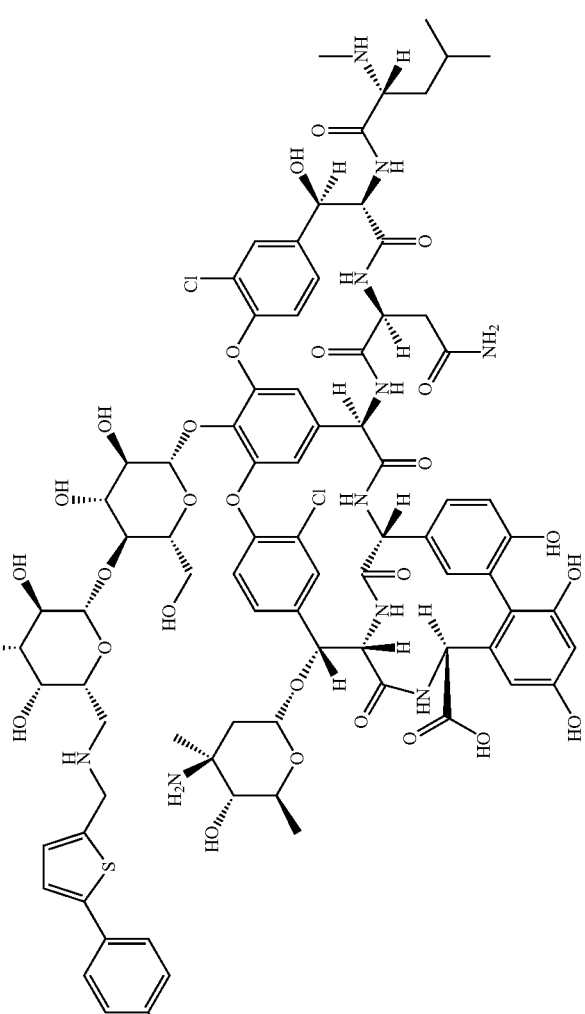 | [M + 1]+ = 1799 | Calculated value for C83H93Cl2FN10O28S•14.1H2O•3.6HCl<br>C: 45.60%,<br>H: 5.75%,<br>N: 6.41%,<br>Cl: 9.08,<br>F: 0.87%,<br>S: 1.47%<br>Measured value<br>C: 45.61%,<br>H: 5.82%,<br>N: 6.49%,<br>Cl: 9.06%,<br>F: 0.94%,<br>S: 1.44% |

TABLE 24

| Example | Structure | Mass Spectrometry | Elementary analysis |
|---|---|---|---|
| 40 | Chiral | $[M+1]^+ = 1849$ | Calculated value for $C_{84}H_{93}Cl_2F_3N_{10}O_{28}S \cdot 20.4H_2O \cdot 4.5HCl$<br>C: 42.35%,<br>H: 5.85%,<br>N: 5.88%,<br>Cl: 9.67,<br>F: 2.39%,<br>S: 1.35%<br>Measured value<br>C: 42.31%,<br>H: 5.58%,<br>N: 5.99%,<br>Cl: 9.63%,<br>F: 2.23%,<br>S: 1.26% |

TABLE 24-continued
| Example | Structure | Mass Spectrometry | Elementary analysis |
|---|---|---|---|
| 41 | Chiral 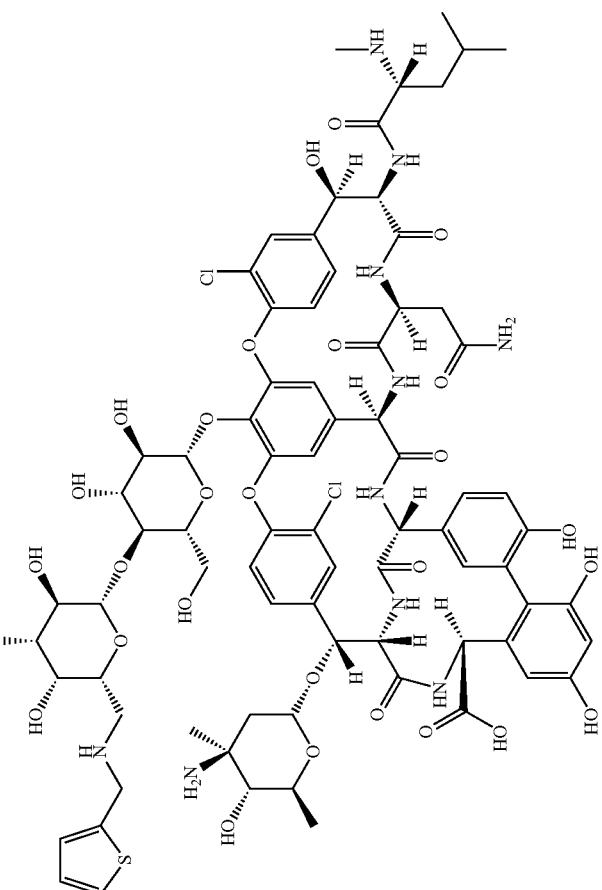 | [M + 1]⁺ = 1865 | Calculated value for C84H93Cl2F3N10O29S•13.7H2O•4.2HCl<br>C: 44.51%,<br>H: 5.54%,<br>N: 6.18%,<br>Cl: 9.70,<br>F: 2.51%,<br>S: 1.41%<br>Measured value<br>C: 44.55%,<br>H: 5.47%,<br>N: 6.27%,<br>Cl: 9.63%,<br>F: 2.23%,<br>S: 1.26% |

TABLE 24-continued
| Example | Structure | Mass Spectrometry | Elementary analysis |
|---|---|---|---|
| 42 | 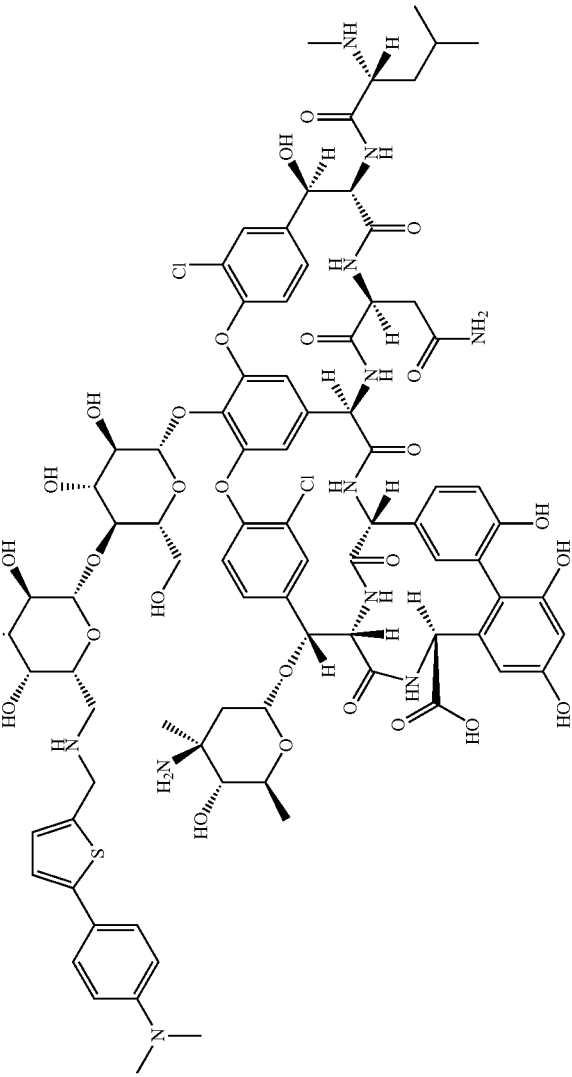 Chiral | $[M+1]^+ = 1824$ | Calculated value for $C85H99Cl2N11O28S\cdot15.2H2O\cdot5.1HCl$<br>C: 44.67%,<br>H: 5.93%,<br>N: 6.74%,<br>Cl: 11.01,<br>S: 1.40%<br>Measured value<br>C: 44.58%,<br>H: 5.43%,<br>N: 6.90%,<br>Cl: 11.00%,<br>S: 1.30% |

TABLE 25

| Example | Structure | Mass Spectrometry | Elementary analysis |
|---|---|---|---|
| 43 | Chiral (structure shown) | $[M+1]^+ = 1799$ | Calculated value for C83H93Cl2FN10O28S•10.7H2O•3.1HCl<br>C: 47.33%,<br>H: 5.62%,<br>N: 6.65%,<br>Cl: 8.58,<br>F: 0.90%,<br>S: 1.52%<br>Measured value<br>C: 47.26%,<br>H: 5.12%,<br>N: 6.63%,<br>Cl: 8.58%,<br>F: 0.96%,<br>S: 1.49% |

TABLE 25-continued
| Example | Structure | Chiral | Mass Spectrometry | Elementary analysis |
|---|---|---|---|---|
| 44 | 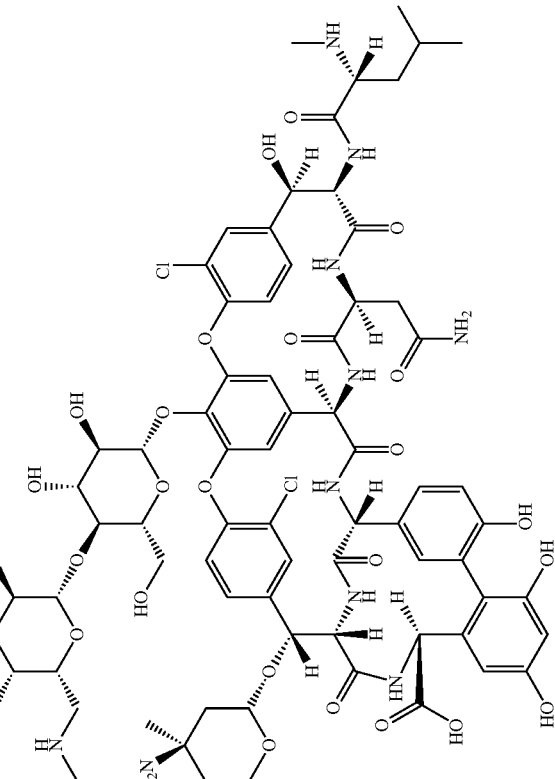 | | [M + 1]$^+$ = 1825 | Calculated value for C88H98Cl2N10O29S·10H2O··3.2HCl<br>C: 48.08%,<br>H: 5.75%,<br>N: 6.60%,<br>Cl: 8.68%,<br>S: 1.51%<br>Measured value<br>C: 48.03%,<br>H: 5.68%,<br>N: 6.81%,<br>Cl: 8.64%,<br>S: 1.42% |

TABLE 25-continued
| Example | Structure | Mass Spectrometry | Elementary analysis |
|---|---|---|---|
| 45 | 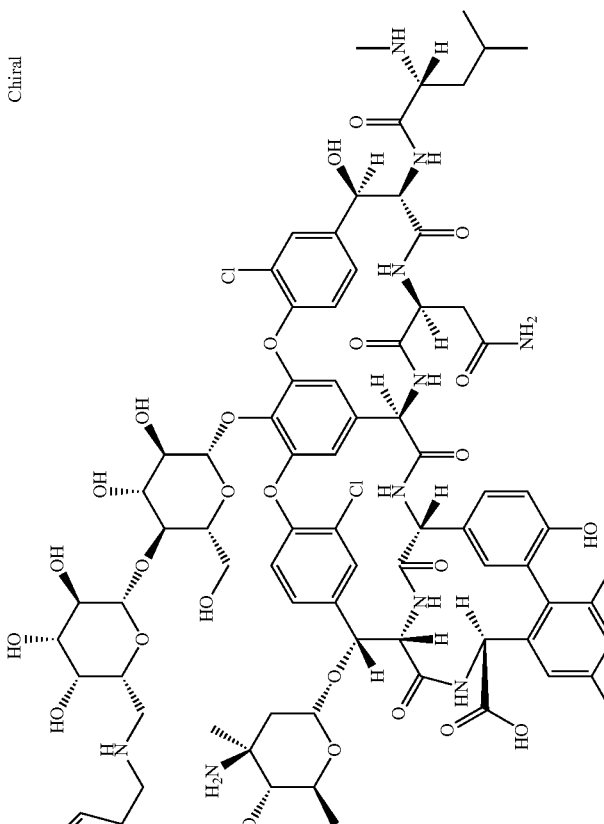 | [M + 1]$^+$ = 1825 | Calculated value for C84H94Cl3N11O28•13.3H2O•2.6HCl C: 47.00%, H: 5.79%, N: 7.18%, Cl: 9.25% Measured value C: 46.95%, H: 5.54%, N: 7.31%, Cl: 9.23% |

TABLE 26
| Example | Structure | Mass Spectrometry | Elementary analysis |
|---|---|---|---|
| 46 | 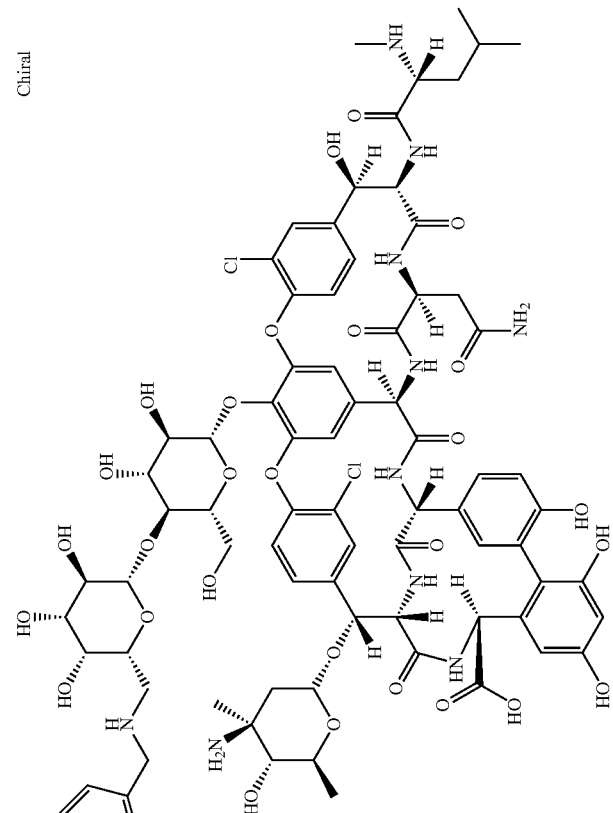 Chiral | [M + 1]+ = 1825 | Calculated value for C85H95Cl3N10O28•12.4H2O•2.6HCl<br>C: 47.95%,<br>H: 5.79%,<br>N: 6.58%,<br>Cl: 9.32%<br>Measured value<br>C: 47.89%,<br>H: 5.62%,<br>N: 6.73%,<br>Cl: 9.33% |

TABLE 26-continued
| Example | Structure | Mass Spectrometry | Elementary analysis |
|---|---|---|---|
| 47 | Chiral 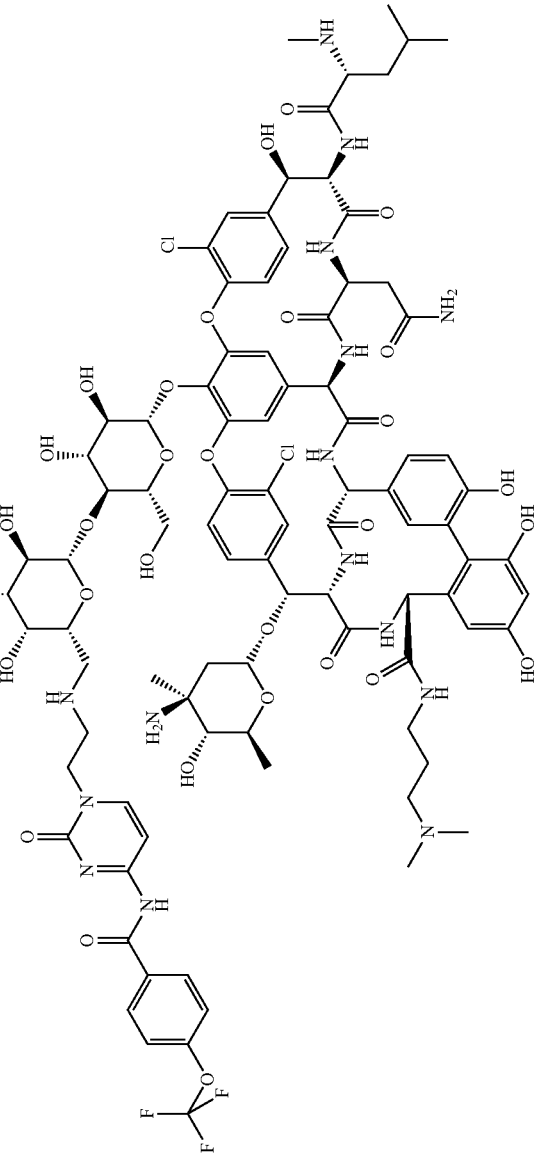 | [M + 1]+ = 2018 | Calculated value for C91H108Cl2F3N15O30•12.7H2O•4.3HCl<br>C: 45.44%,<br>H: 5.77%,<br>N: 8.73%,<br>Cl: 9.29%,<br>F: 2.37%<br>Measured value<br>C: 45.42%,<br>H: 5.55%,<br>N: 8.77%,<br>Cl: 9.32%,<br>F: 2.30% |

TABLE 26-continued

| Example | Structure | Chiral | Mass Spectrometry | Elementary analysis |
|---|---|---|---|---|
| 48 | 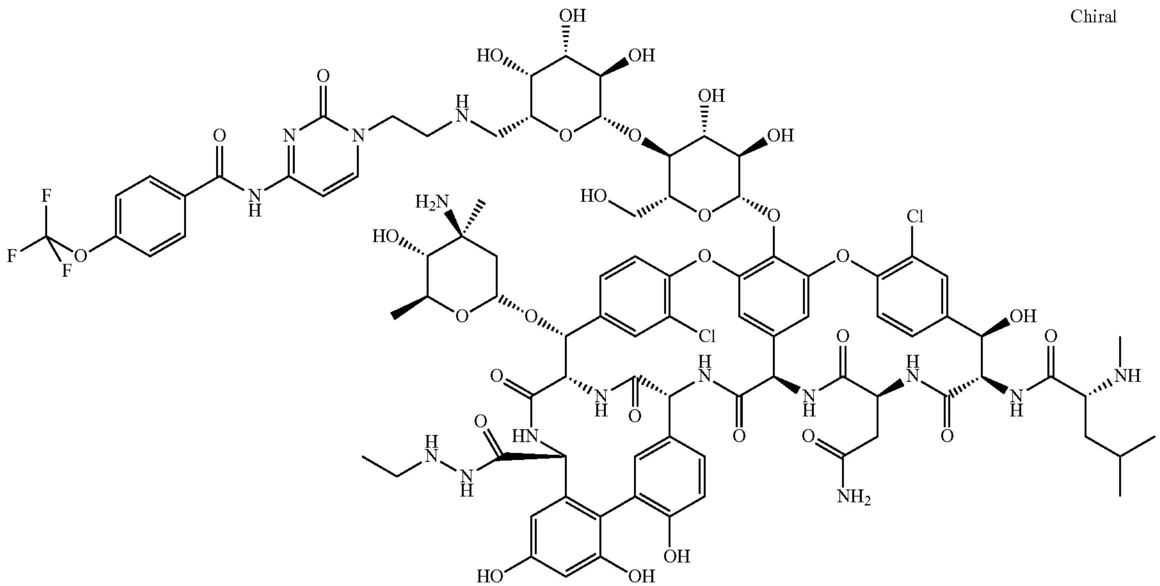 | Chiral | [M + 1]$^+$ = 1976 | Calculated value for C88H102Cl2F3N15O30•10.2H2O•3.3HCl<br>C: 46.32%,<br>H: 5.55%,<br>N: 9.21%,<br>Cl: 8.23%,<br>F: 2.50%<br>Measured value<br>C: 46.32%,<br>H: 5.48%,<br>N: 9.32%,<br>Cl: 8.22%,<br>F: 2.10% |

TABLE 27
| Example | Structure | Mass Spectrometry | Elementary analysis |
|---|---|---|---|
| 49 | 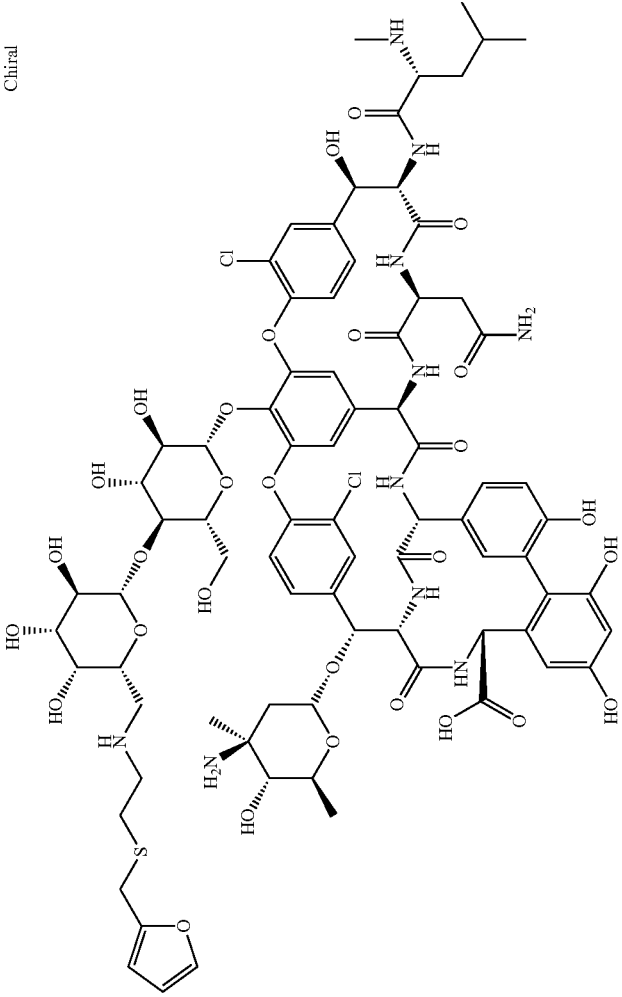 Chiral | [M + 1]⁺ = 1749 | Calculated value for C79H94Cl2N10O29S•14.0H2O•3.1HCl<br>C: 44.84%,<br>H: 5.96%,<br>N: 6.62%,<br>Cl: 8.55%,<br>S: 1.52%<br>Measured value<br>C: 44.81%,<br>H: 5.91%,<br>N: 6.77%,<br>Cl: 8.59%,<br>S: 1.45% |

TABLE 27-continued
| Example | Structure | Mass Spectrometry | Elementary analysis |
|---|---|---|---|
| 50 | Chiral 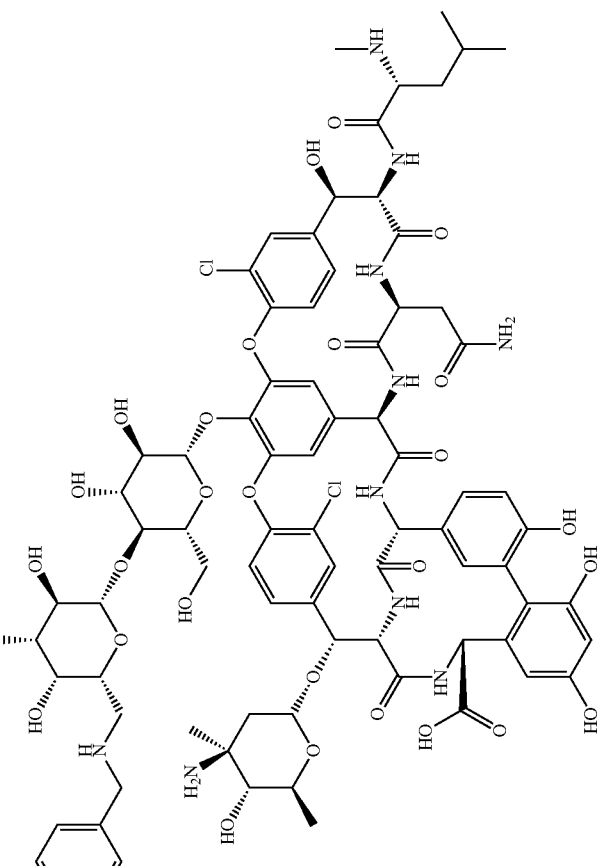 | [M + 1]⁺ = 2068 | Calculated value for C85H95Cl2F10O29•12.3H2O•3.1HCl<br>C: 47.59%,<br>H: 5.77%,<br>N: 6.53%,<br>Cl: 8.43%,<br>F: 0.89%<br>Measured value<br>C: 47.58%,<br>H: 5.78%,<br>N: 6.72%,<br>Cl: 8.43%,<br>F: 0.98% |

TABLE 27-continued
| Example | Structure | Mass Spectrometry | Elementary analysis |
|---|---|---|---|
| 51 | Chiral 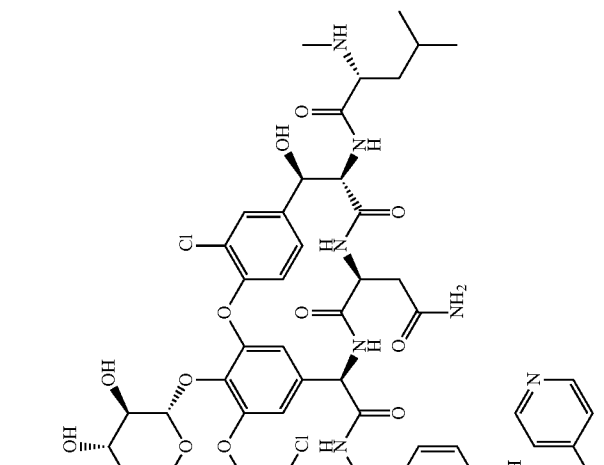 | [M + 1]⁺ = 1809 | Calculated value for C94H106Cl2F3N15O31•16.2H2O•5.6HCl C: 44.00%, H: 5.66%, N: 8.19%, Cl: 10.50%, F: 2.22% Measured value C: 43.97%, H: 5.67%, N: 8.32%, Cl: 10.45%, F: 2.13% |

TABLE 28
| Example | Structure | Mass Spectrometry | Elementary analysis |
|---|---|---|---|
| 52 | Chiral 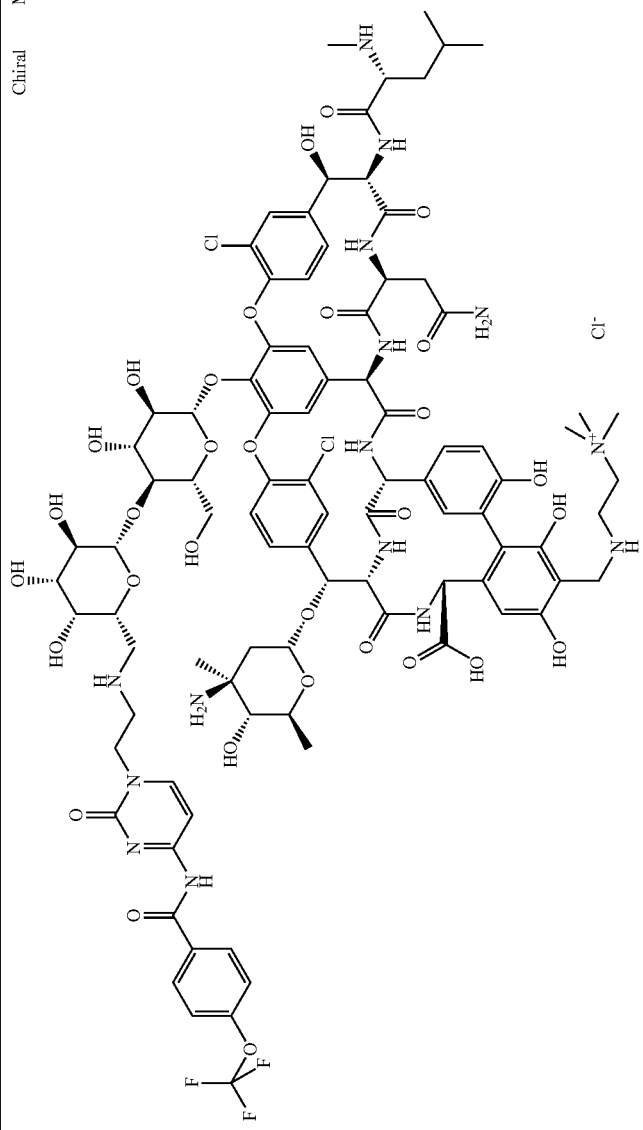 | M + Cl⁻ + Cl⁻ [Cl]⁻ = 2048 | Calculated value for C92H111Cl2F3N15O31·Cl·15.3H2O·5.2HCl C: 43.90%, H: 5.92%, N: 8.35%, Cl: 10.14%, F: 2.26% Measured value C: 43.88%, H: 5.86%, N: 8.42%, Cl: 10.11%, F: 2.16% |

TABLE 28-continued
| Example | Structure | | Mass Spectrometry | Elementary analysis |
|---|---|---|---|---|
| 53 | 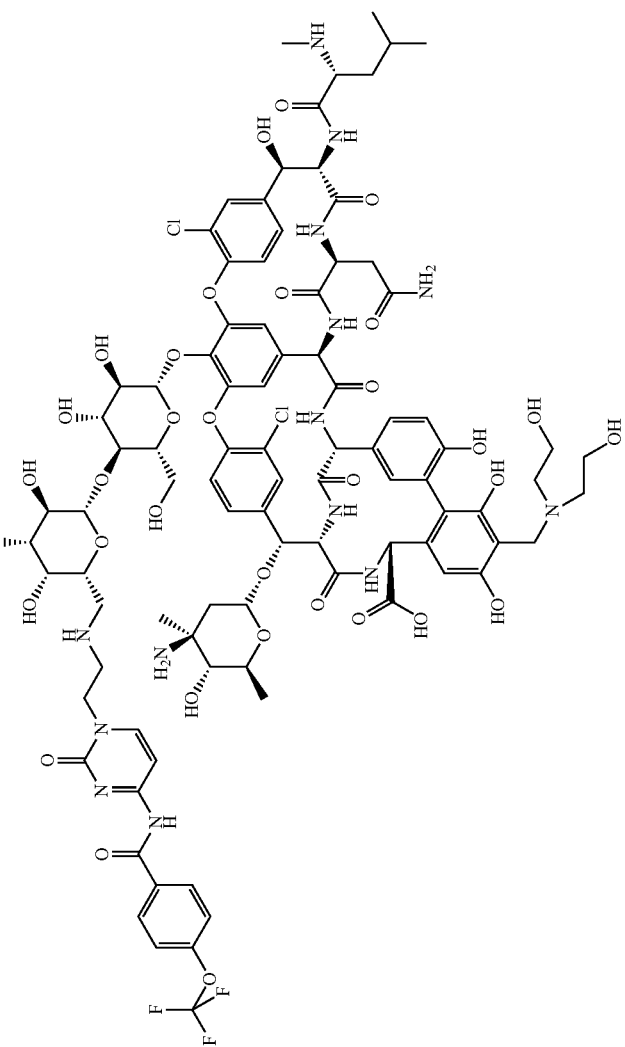 | Chiral | [M + 1]⁺ = 2051 | Calculated value for C91H107Cl2F3N14O3·16.0H2O·4.0HCl C: 43.95%, H: 5.80%, N: 7.89%, Cl: 8.55%, F: 2.29% Measured value C: 43.79%, H: 5.49%, N: 8.52%, Cl: 8.61%, F: 2.10% |

TABLE 28-continued
| Example | Structure | Mass Spectrometry | Elementary analysis |
|---|---|---|---|
| 54 | Chiral 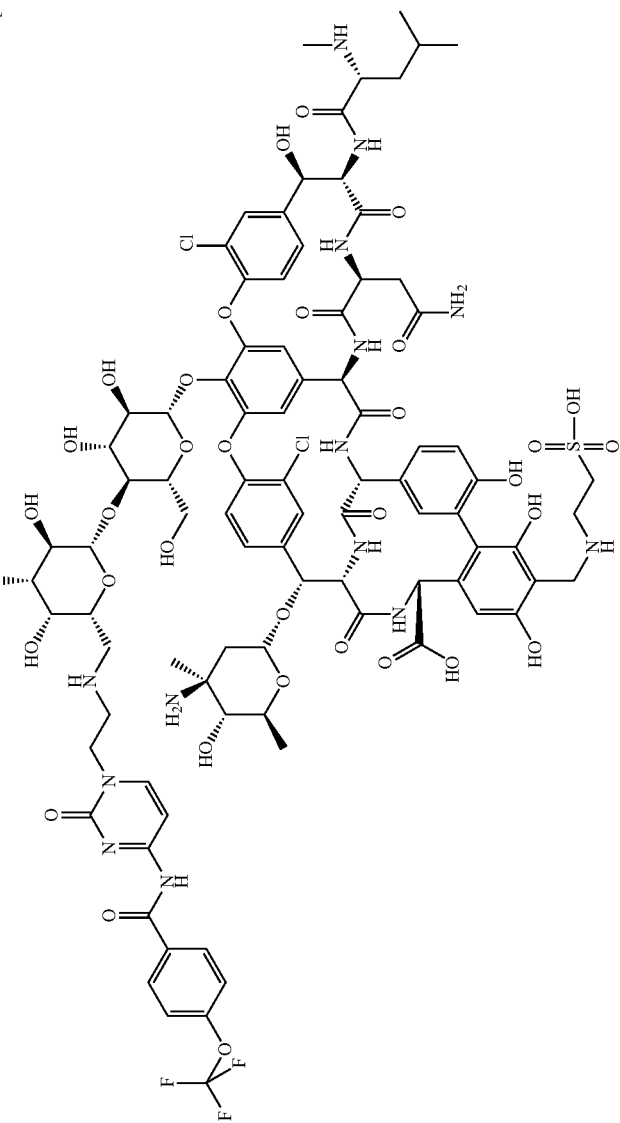 | [M + 1]+ = 2071 | Calculated value for C89H103Cl2F3N14O34S•17.8H2O•2.8HCl C: 42.83%, H: 5.71%, N: 7.86%, Cl: 6.82%, F: 2.28%, S: 1.28% Measured value C: 42.77%, H: 5.59%, N: 8.45%, Cl: 6.75%, F: 2.24%, S: 1.23% |

TABLE 29

| Example | Structure | Mass Spectrometry | Elementary analysis |
|---|---|---|---|
| 55 | Chiral (structure) | [M + 1]⁺ = 1783 | Calculated value for C80H91Cl2F3N10O29•16.0H2O•2.9HCl<br>C: 44.11%,<br>H: 5.83%,<br>N: 6.43%,<br>Cl: 7.97%,<br>F: 2.62%<br>Measured value<br>C: 44.08%,<br>H: 5.66%,<br>N: 6.51%,<br>Cl: 7.93%,<br>F: 2.70% |

TABLE 29-continued
| Example | Structure | Chiral | Mass Spectrometry | Elementary analysis |
|---|---|---|---|---|
| 56 | 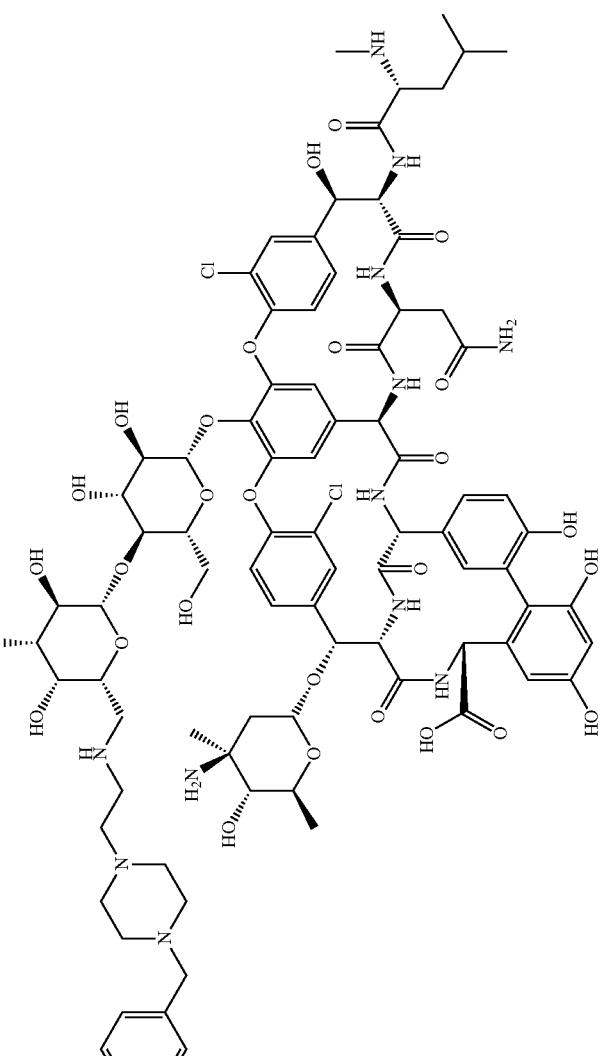 | | [M + 1]$^+$ = 1811 | Calculated value for C85H101Cl2N12O28•17.8H2O•4.5HCl<br>C: 44.44%,<br>H: 6.32%,<br>N: 7.32%,<br>Cl: 10.03%<br>Measured value<br>C: 44.43%,<br>H: 6.23%,<br>N: 7.43%,<br>Cl: 9.98% |

TABLE 29-continued
| Example | Structure | | Mass Spectrometry | Elementary analysis |
|---|---|---|---|---|
| 57 | 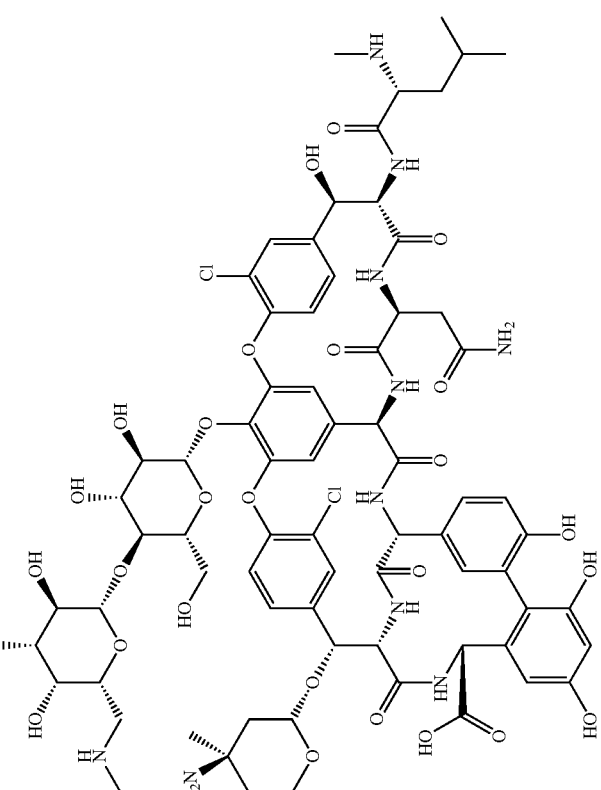 | Chiral | [M + 1]+ = 1806 | Calculated value for C82H101Cl2N11O29S•15.0H2O•4.3HCl<br>C: 44.07%,<br>H: 6.10%,<br>N: 6.89%,<br>Cl: 9.99%,<br>S: 1.43%<br>Measured value<br>C: 44.09%,<br>H: 6.00%,<br>N: 6.99%,<br>Cl: 9.96%,<br>S: 1.32% |

TABLE 30

| Example | Structure | Mass Spectrometry | Elementary analysis |
|---|---|---|---|
| 58 | Chiral | [M + 1]⁺ = 1792 | Calculated value for C84H95Cl2N11O29•14.1H2O•3.3HCl<br>C: 46.54%,<br>H: 5.88%,<br>N: 7.11%,<br>Cl: 8.67%<br>Measured value<br>C: 46.49%,<br>H: 5.78%,<br>N: 7.23%,<br>Cl: 8.65% |

TABLE 30-continued

| Example | Structure | Mass Spectrometry | Elementary analysis |
|---|---|---|---|
| 59 | Chiral (structure shown) | $[M+1]^+ = 1764$ | Calculated value for C83H95Cl2N11O28•15.1H2O•3.4HCl<br>C: 46.12%,<br>H: 6.00%,<br>N: 7.13%,<br>Cl: 8.86%<br>Measured value<br>C: 46.13%,<br>H: 6.00%,<br>N: 7.28%,<br>Cl: 8.86% |

TABLE 30-continued

| Example | Structure | Mass Spectrometry | Elementary analysis |
|---|---|---|---|
| 60 | Chiral | $[M+1]^+ = 1825$ | Calculated value for C85H95Cl3N10O29·14.0H2O·3.4HCl<br>C: 46.34%,<br>H: 5.78%,<br>N: 6.36%,<br>Cl: 10.30%<br>Measured value<br>C: 46.35%,<br>H: 5.67%,<br>N: 6.45%,<br>Cl: 10.29% |

TABLE 31

| Example | Structure | Chiral | Mass Spectrometry | Elementary analysis |
|---|---|---|---|---|
| 61 | 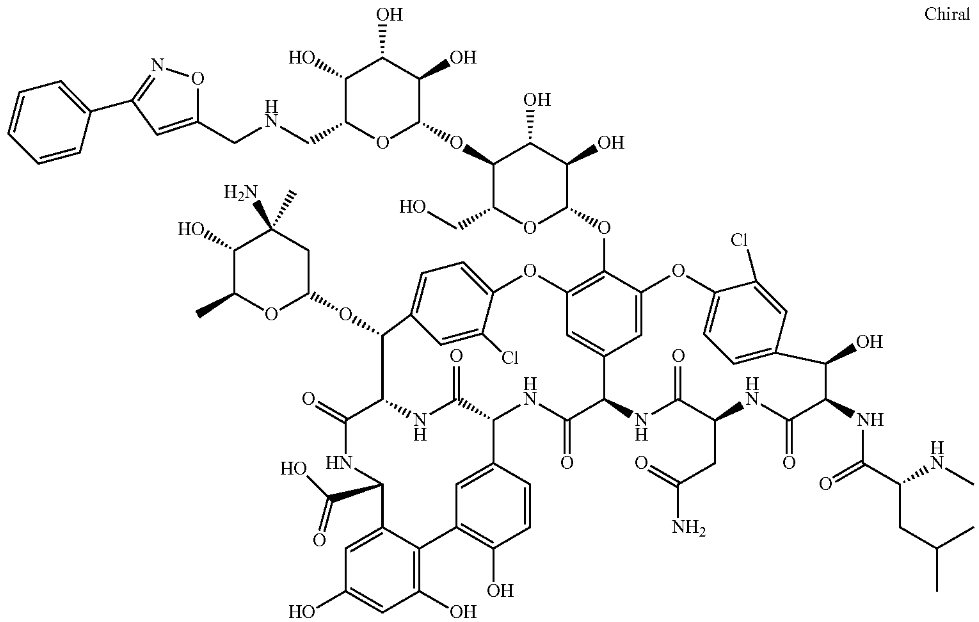 | | $[M+1]^+ = 1766$ | Calculated value for C82H93Cl2N11O29•3.2HCl•10.9H2O<br>C: 47.34%,<br>H: 5.72%,<br>N: 7.41%,<br>Cl: 8.86%<br>Measured value<br>C: 47.32%,<br>H: 5.62%,<br>N: 7.60%,<br>Cl: 8.81% |

TABLE 31-continued
| Example | Structure | | Mass Spectrometry | Elementary analysis |
|---|---|---|---|---|
| 62 | 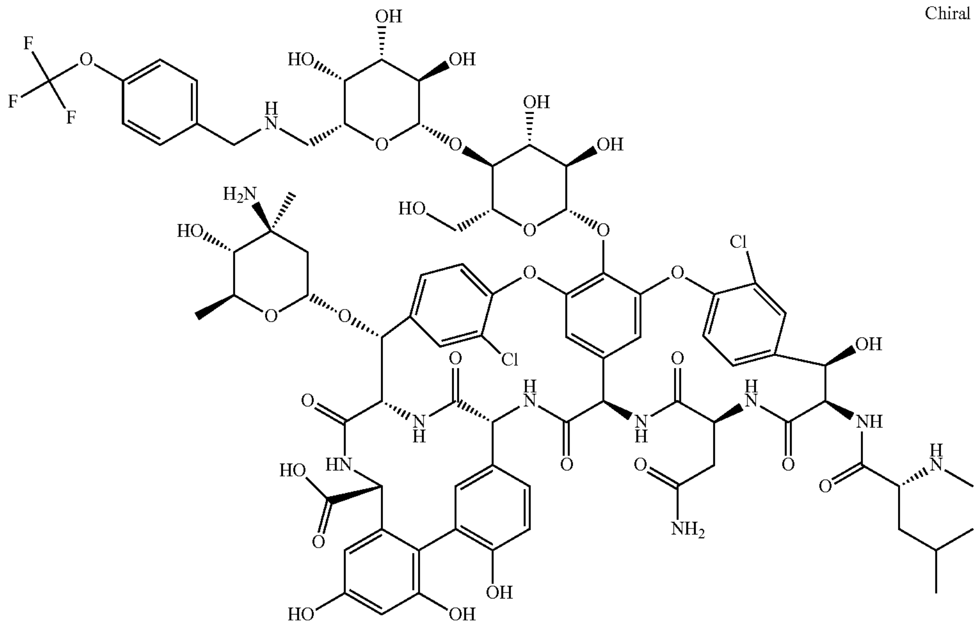 | Chiral | [M + 1]⁺ = 1783 | Calculated value for C80H91Cl2F3N10O29•3.1HCl•10.6H2O C: 46.01%, H: 5.56%, N: 6.71%, Cl: 8.66%, F: 2.73% Measured value C: 45.94%, H: 5.44%, N: 6.87%, Cl: 8.60%, F: 3.35% |

TABLE 31-continued

| Example | Structure | | Mass Spectrometry | Elementary analysis |
|---|---|---|---|---|
| 63 | 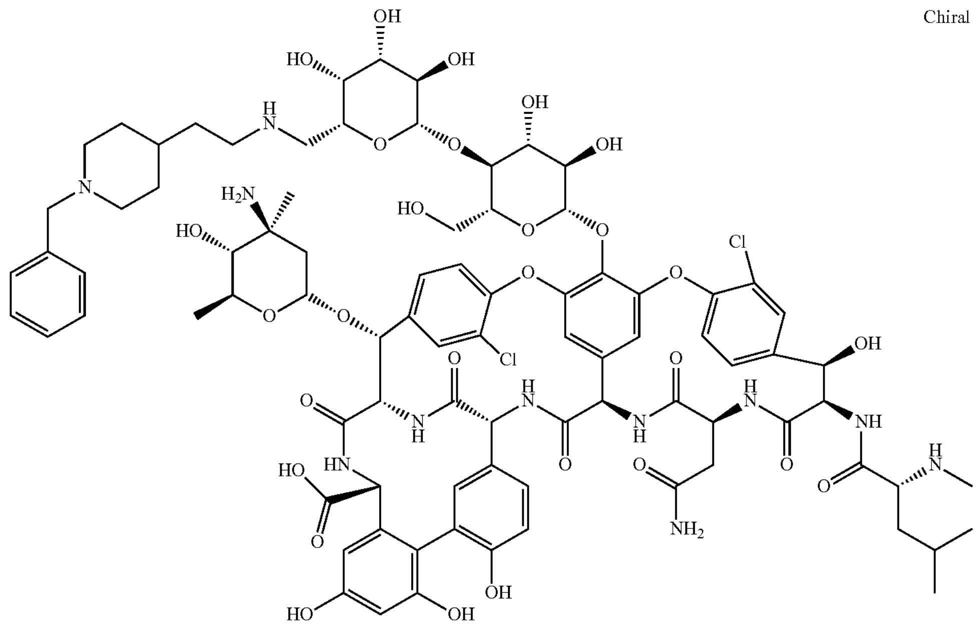 | Chiral | [M + 1]+ = 1810 | Calculated value for C86H105Cl2N11O28•3.8HCl•12.6H2O<br>C: 47.44%,<br>H: 6.20%,<br>N: 7.08%,<br>Cl: 9.44%<br>Measured value<br>C: 47.39%,<br>H: 6.03%,<br>N: 7.21%,<br>Cl: 9.34% |

TABLE 32
| Example | Structure | Mass Spectrometry | Elementary analysis |
|---|---|---|---|
| 64 | Chiral 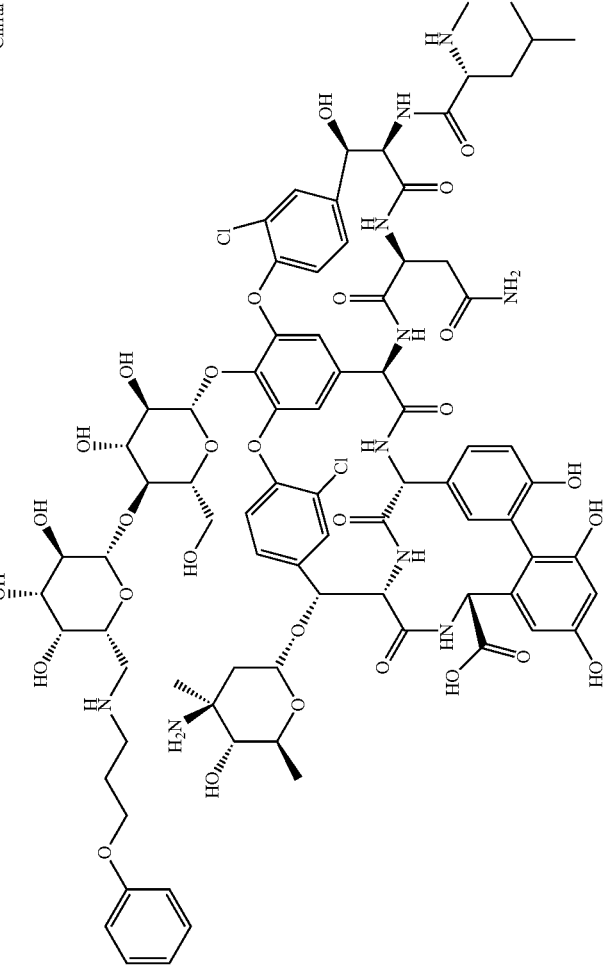 | [M + 1]⁺ = 1743 | Calculated value for C81H96Cl2N10O29·2.8HCl·10.5H2O<br>C: 47.79%,<br>H: 5.93%,<br>N: 6.88%,<br>Cl: 8.36%<br>Measured value<br>C: 47.82%,<br>H: 5.83%,<br>N: 6.74%,<br>Cl: 8.30% |

TABLE 32-continued

| Example | Structure | Mass Spectrometry | Elementary analysis |
|---|---|---|---|
| 65 | Chiral | $[M+1]^+ = 1764$ | Calculated value for $C_{83}H_{95}Cl_2N_{11}O_{28} \cdot 3.1HCl \cdot 11.2H_2O$<br>C: 47.92%,<br>H: 5.84%,<br>N: 7.41%,<br>Cl: 8.69%<br>Measured value<br>C: 47.94%,<br>H: 5.85%,<br>N: 7.64%,<br>Cl: 8.66% |

TABLE 32-continued

| Example | Structure | Mass Spectrometry | Elementary analysis |
|---|---|---|---|
| 66 | Chiral | [M + 1]+ = 1732 | Calculated value for C79H95Cl2N11O29•2.6HCl•11.8H2O<br>C: 46.49%,<br>H: 5.99%,<br>N: 7.55%,<br>Cl: 7.99%<br>Measured value<br>C: 46.48%,<br>H: 5.93%,<br>N: 7.60%,<br>Cl: 7.99% |

TABLE 33
| Example | Structure | Mass Spectrometry | Elementary analysis |
|---|---|---|---|
| 67 | 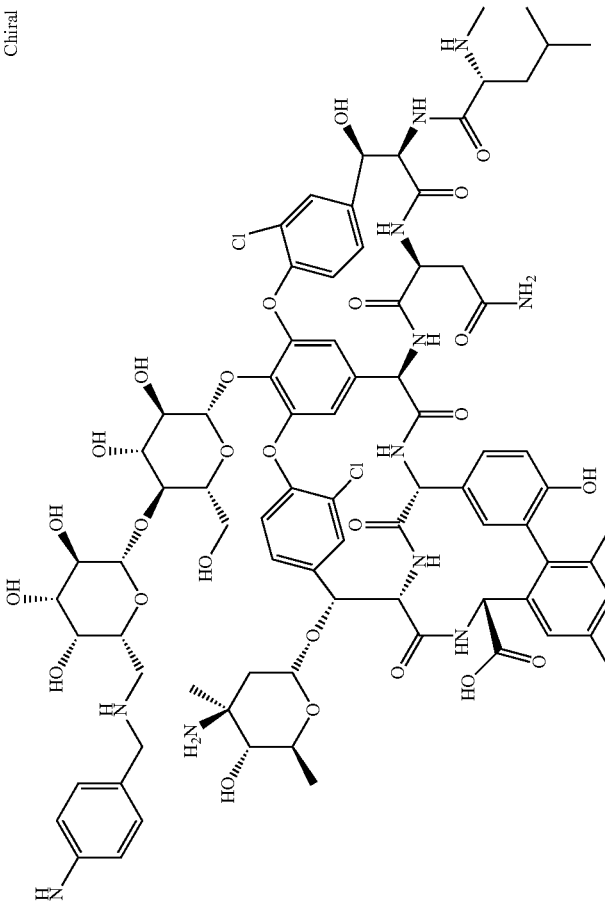 | Chiral [M + 1]+ = 1900 | Calculated value for C87H97Cl4N11O29•2.8HCl•12.0H2O C: 47.05%, H: 5.62%, N: 6.94%, Cl: 10.86% Measured value C: 47.03%, H: 5.57%, N: 7.22%, Cl: 10.79% |

TABLE 33-continued
| Example | Structure | Mass Spectrometry | Elementary analysis |
|---|---|---|---|
| 68 | Chiral 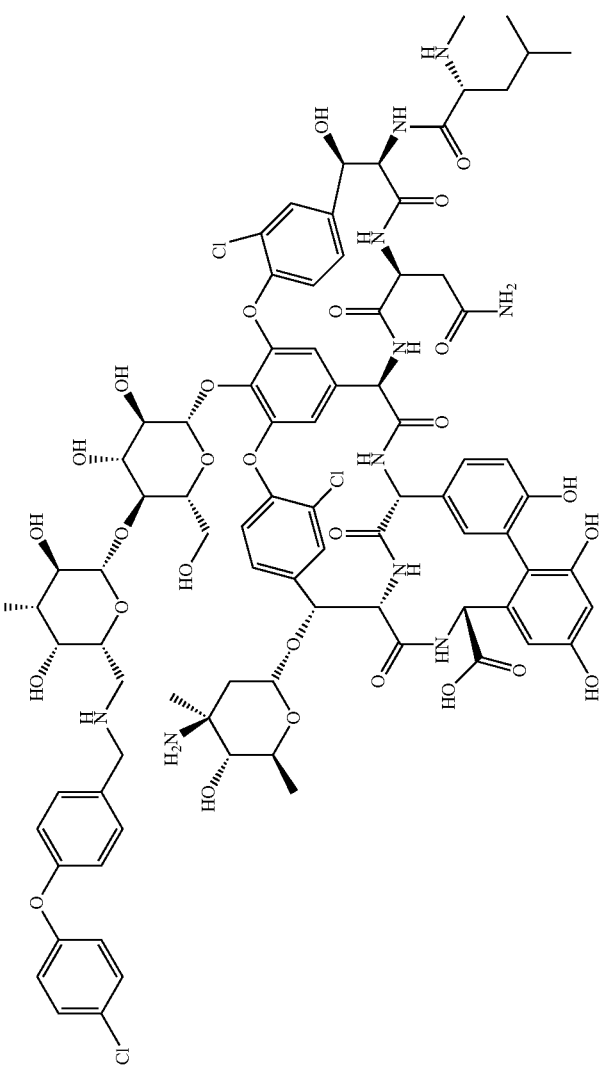 | [M + 1]⁺ = 1825 | Calculated value for C85H95Cl3N10O29•2.7HCl•12.3H2O<br>C: 47.55%,<br>H: 5.74%,<br>N: 6.52%,<br>Cl: 9.41%<br>Measured value<br>C: 47.51%,<br>H: 5.65%,<br>N: 6.59%,<br>Cl: 9.44% |

TABLE 33-continued
| Example | Structure | Mass Spectrometry | Elementary analysis |
|---|---|---|---|
| 69 | 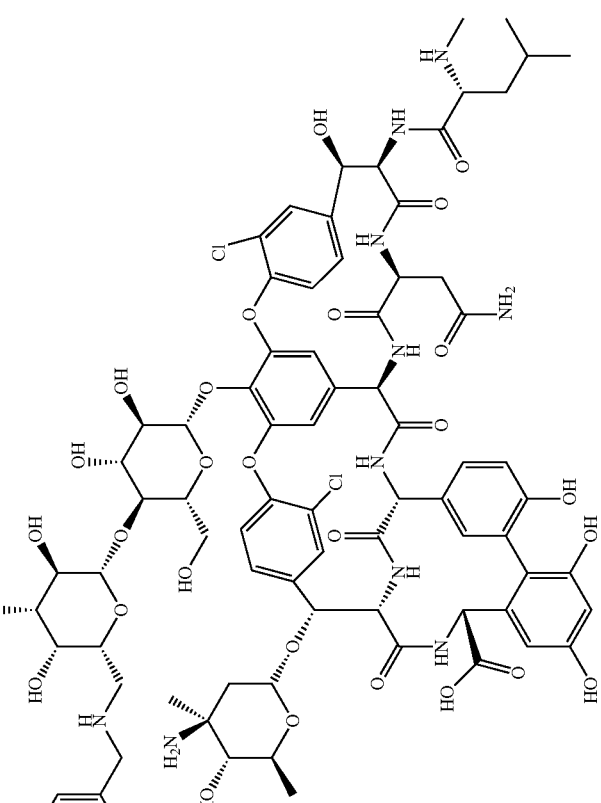 | Chiral [M + 1]⁺ = 1900 | Calculated value for $C_{87}H_{97}Cl_4N_{11}O_{29} \cdot 3.1HCl \cdot 11.7H_2O$<br>C: 46.93%,<br>H: 5.59%,<br>N: 6.92%,<br>Cl: 11.31%<br>Measured value<br>C: 46.91%,<br>H: 5.51%,<br>N: 6.99%,<br>Cl: 11.28% |

TABLE 34
| Example | Structure | Chiral | Mass Spectrometry | Elementary analysis |
|---------|-----------|--------|-------------------|---------------------|
| 70 | 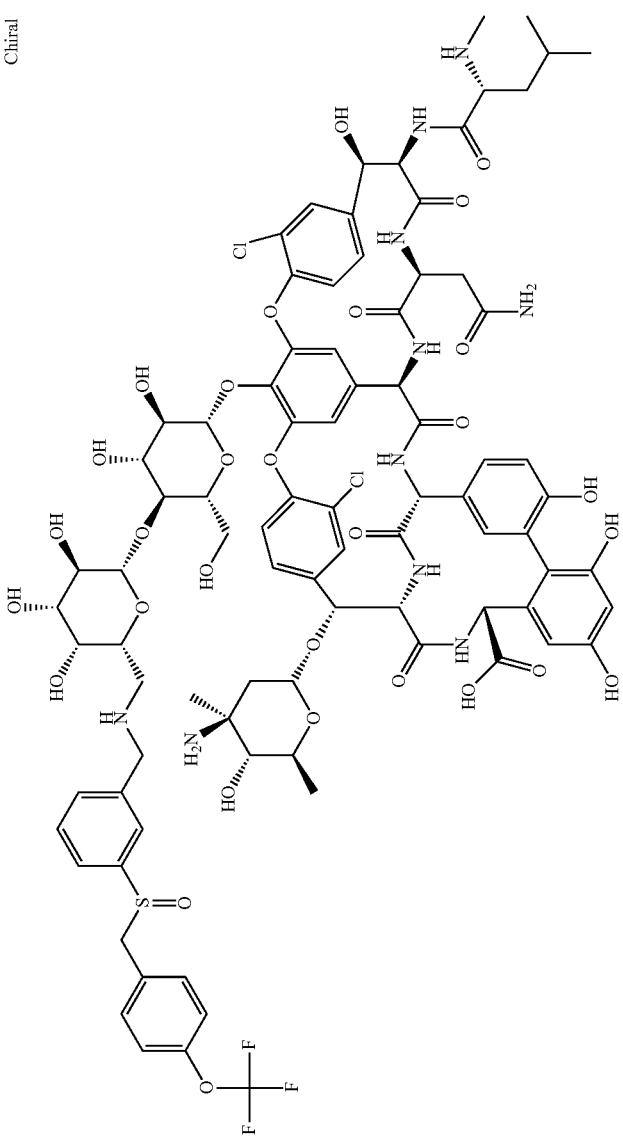 | Chiral | $[M+1]^+ = 1921$ | Calculated value for $C_{87}H_{97}Cl_2F_3N_{10}O_{30}S \cdot 3.1HCl \cdot 12.2H_2O$<br>C: 46.33%,<br>H: 5.56%,<br>N: 6.21%,<br>Cl: 8.02%,<br>F: 2.53%,<br>S: 1.42%<br>Measured value<br>C: 46.34%,<br>H: 5.47%,<br>N: 6.29%,<br>Cl: 7.96%,<br>F: 2.39%,<br>S: 1.38% |

TABLE 34-continued
| Example | Structure | Mass Spectrometry | Elementary analysis |
|---|---|---|---|
| 71 | Chiral 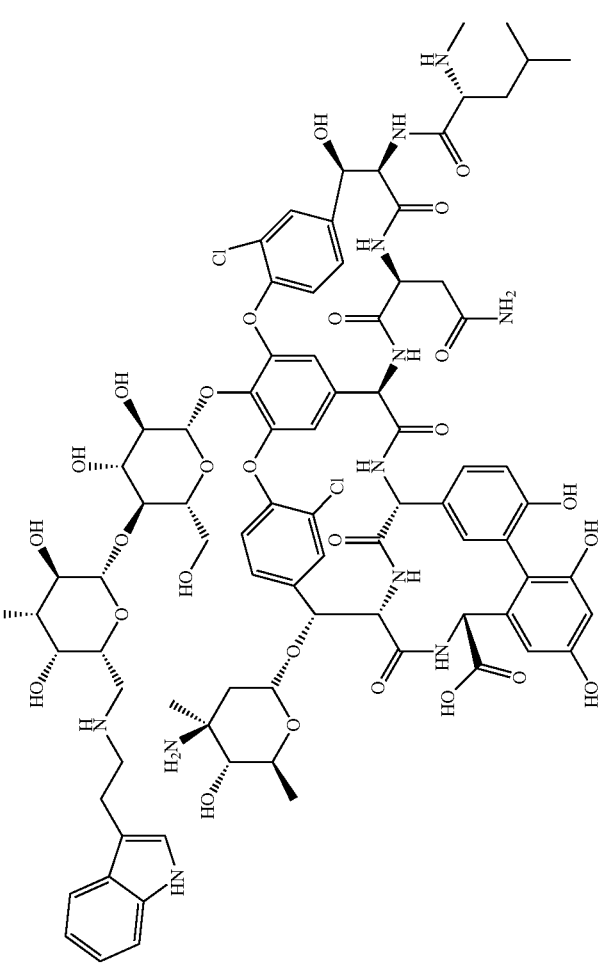 | [M + 1]⁺ = 1752 | Calculated value for C82H95Cl2N11O28•3.2HCl•11.2H2O<br>C: 47.53%,<br>H: 5.87%,<br>N: 7.44%,<br>Cl: 8.90%<br>Measured value<br>C: 47.50%,<br>H: 5.95%,<br>N: 7.56%,<br>Cl: 8.84% |

TABLE 34-continued
| Example | Structure | Mass Spectrometry | Elementary analysis |
|---|---|---|---|
| 72 | 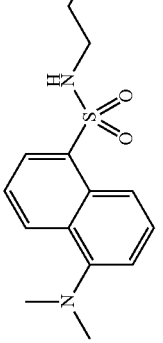 | Chiral [M + 1]+ = 1927 | Calculated value for C89H108Cl2N12O30S·4.4HCl·11.2H2O<br>C: 46.66%,<br>H: 5.93%,<br>N: 7.34%,<br>Cl: 9.90%,<br>S: 1.40%<br>Measured value<br>C: 46.61%,<br>H: 6.00%,<br>N: 7.59%,<br>Cl: 9.98%,<br>S: 2.07% |

TABLE 35

| Example | Structure | Mass Spectrometry | Elementary analysis |
|---|---|---|---|
| 73 | Chiral (structure shown) | [M + 1]⁺ = 1725 | Calculated value for C81H94Cl2N10O28•3.1HCl•12.8H2O<br>C: 46.99%,<br>H: 5.97%,<br>N: 6.77%,<br>Cl: 8.73%<br>Measured value<br>C: 46.97%,<br>H: 5.90%,<br>N: 6.88%,<br>Cl: 8.79% |

TABLE 35-continued
| Example | Structure | Mass Spectrometry | Elementary analysis |
|---|---|---|---|
| 74 | Chiral 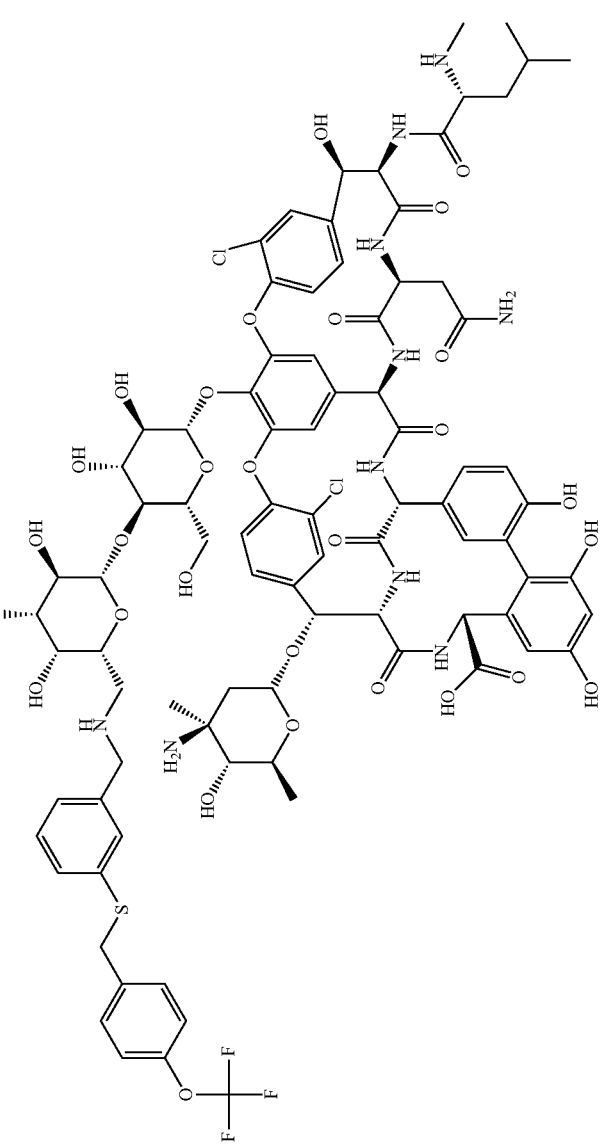 | [M + 1]+ = 1905 | Calculated value for $C_{87}H_{97}Cl_2F_3N_{10}O_{29} \cdot 3.1HCl \cdot 11.3H_2O$<br>C: 47.00%,<br>H: 5.56%,<br>N: 6.30%,<br>Cl: 8.13%,<br>F: 2.56%,<br>S: 1.44%<br>Measured value<br>C: 47.05%,<br>H: 5.49%,<br>N: 6.33%,<br>Cl: 8.06%,<br>F: 2.46%,<br>S: 1.37% |

TABLE 35-continued
| Example | Structure | | Mass Spectrometry | Elementary analysis |
|---|---|---|---|---|
| 75 | Chiral 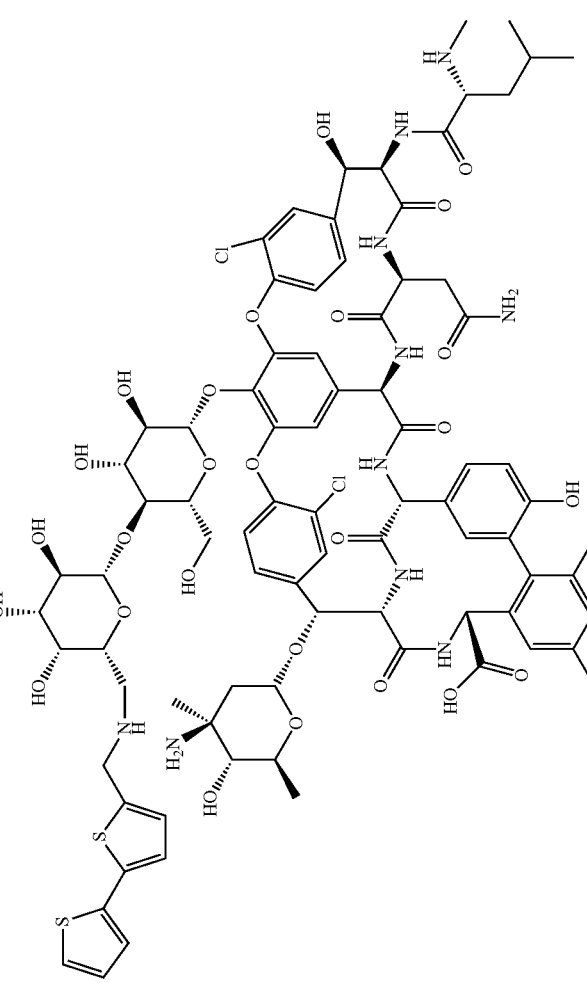 | | [M + 1]⁺ = 1787 | Calculated value for C81H92Cl2N10O28S2•12.8H2O•2.6HCl C: 46.02%, H: 5.73%, N: 6.63%, Cl: 7.71%, S: 3.03% Measured value C: 46.02%, H: 5.58%, N: 6.76%, Cl: 7.71%, S: 2.94% |

TABLE 36
| Example | Structure | Mass Spectrometry | Elementary analysis |
|---|---|---|---|
| 76 | Chiral 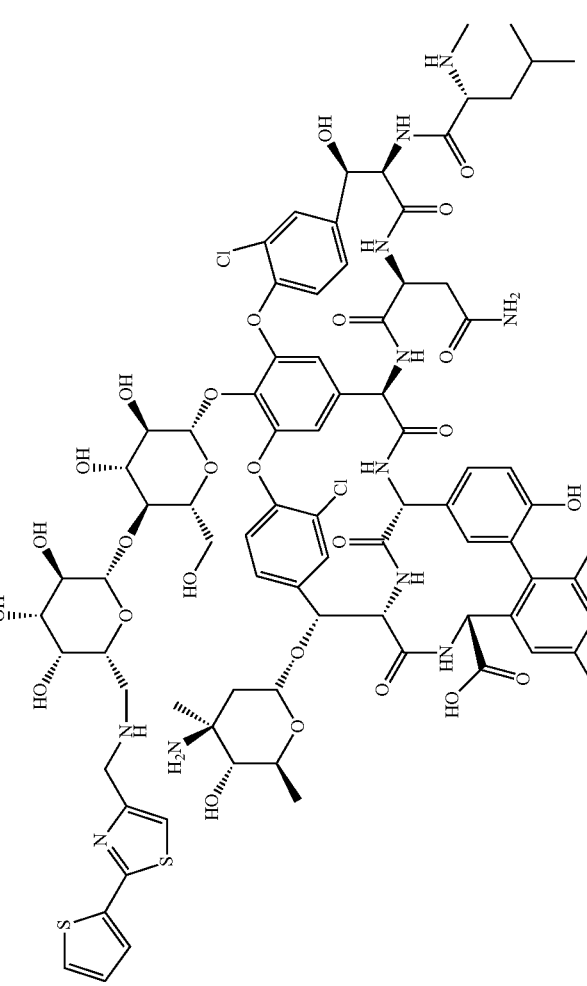 | $[M+1]^+ = 1788$ | Calculated value for C80H91Cl2N11O28S2·12.1H2O·3.1HCl<br>C: 45.31%,<br>H: 5.62%,<br>N: 7.27%,<br>Cl: 8.53%,<br>S: 3.02%<br>Measured value<br>C: 45.27%,<br>H: 5.35%,<br>N: 7.39%,<br>Cl: 8.47%,<br>S: 3.16% |

TABLE 36-continued

| Example | Structure | Mass Spectrometry | Elementary analysis |
|---|---|---|---|
| 77 | Chiral [structure] | $[M+1]^+ = 1782$ | Calculated value for $C_{82}H_{93}Cl_2N_{11}O_{28}S \cdot 12.9H_2O \cdot 2.8HCl$<br>C: 46.50%,<br>H: 5.79%,<br>N: 7.27%,<br>Cl: 8.03%,<br>S: 1.51%<br>Measured value<br>C: 45.48%,<br>H: 5.70%,<br>N: 7.40%,<br>Cl: 8.03%,<br>S: 1.48% |

TABLE 36-continued
| Example | Structure | Mass Spectrometry | Elementary analysis |
|---|---|---|---|
| 78 | Chiral 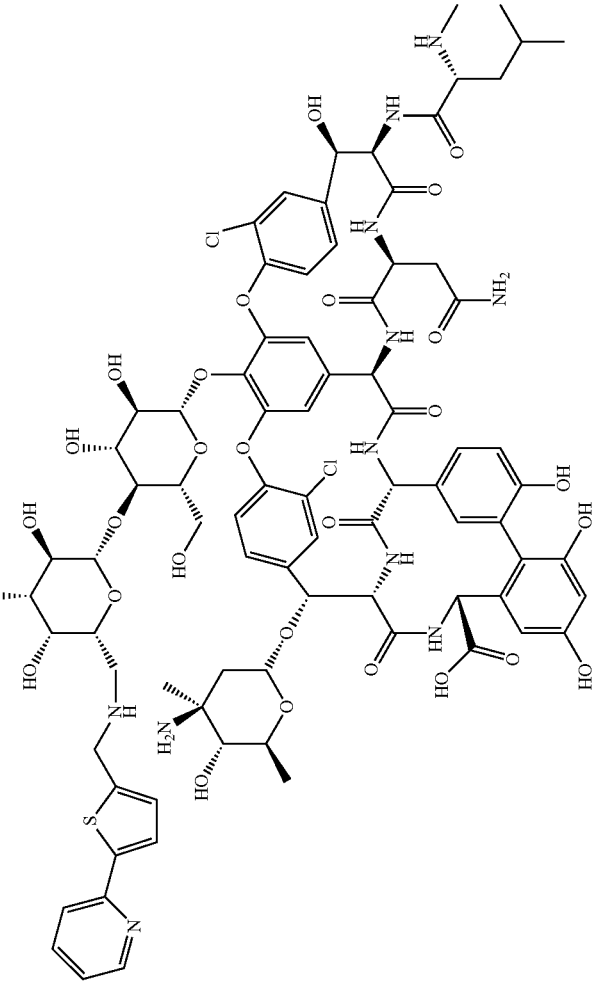 | [M + 1]⁺ = 1782 | Calculated value for C82H93Cl2N11O28S•14.3H2O•3.5HCl C: 45.41%, H: 5.81%, N: 7.10%, Cl: 8.99%, S: 1.48% Measured value C: 45.33%, H: 5.60%, N: 7.19%, Cl: 9.01%, S: 1.43% |

TABLE 37
| Example | Structure | | Mass Spectrometry | Elementary analysis |
|---|---|---|---|---|
| 79 | 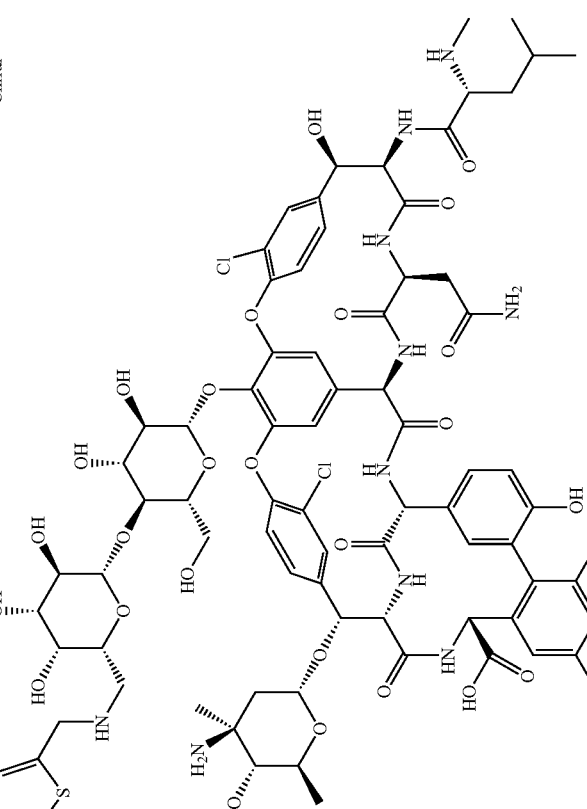 | Chiral | [M + H]+ = 1806 | Calculated value for C84H94C12N11O28S•(H2O)12.4•(HCl)2.3 C: 47.70%, H: 5.72%, N: 7.29%, Cl: 7.21%, S: 1.52% Measured value C: 47.71%, H: 5.59%, N: 7.35%, Cl: 7.23%, S: 1.37% |

TABLE 37-continued
| Example | Structure | Mass Spectrometry | Elementary analysis |
|---|---|---|---|
| 80 | 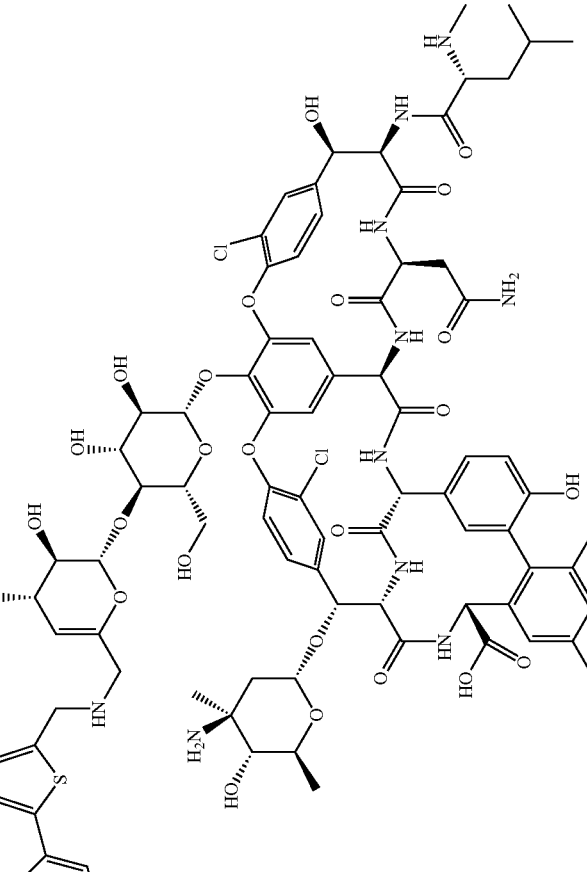 | Chiral [M + H]+ = 1797 | Calculated value for C83H91Cl3N10O27S•(H2O)10•(HCl)3.2 C: 47.56%, H: 5.49%, N: 6.68%, Cl: 10.49%, S: 1.53% Measured value C: 47.55%, H: 5.40%, N: 6.81%, Cl: 10.51%, S: 1.39% |

TABLE 37-continued

| Example | Structure | Mass Spectrometry | Elementary analysis |
|---|---|---|---|
| 81 | (chiral structure) | [M + 1]$^+$ = 1817 | Calculated value for C83H92Cl2F2N10O28S•(H2O)12•(HCl)3.2<br>C: 46.33%,<br>H: 5.58%,<br>N: 6.51%,<br>Cl: 8.57%,<br>F: 1.77%,<br>S: 1.49%<br>Measured value<br>C: 46.30%,<br>H: 5.43%,<br>N: 6.62%,<br>Cl: 8.50%,<br>F: 1.74%,<br>S: 1.42% |

TABLE 38
| Example | Structure | Mass Spectrometry | Elementary analysis |
|---|---|---|---|
| 82 | Chiral 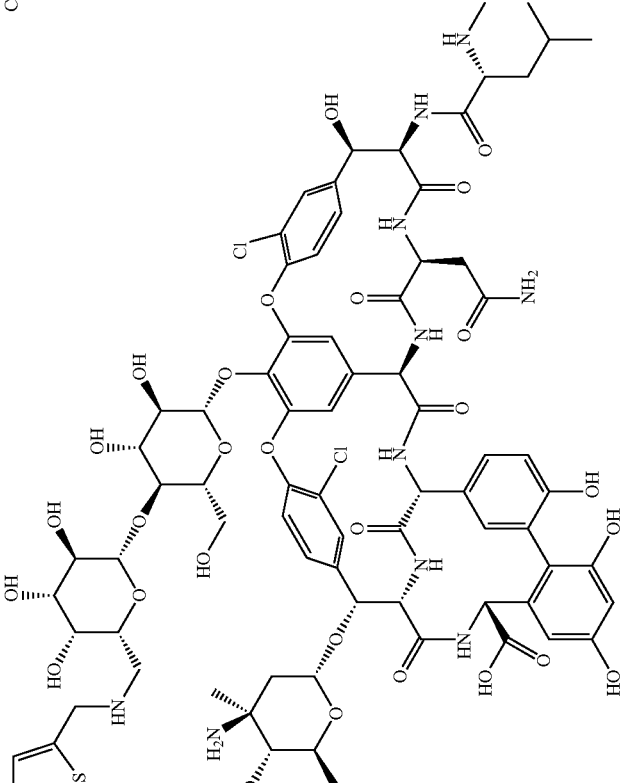 | $[M+1]^+ = 1817$ | Calculated value for C83H92Cl2F2N10O28S•(H2O)9.9•(HCl)3.3 C: 47.08%, H: 5.48%, N: 6.62%, Cl: 8.87%, F: 1.79%, S: 1.51% Measured value C: 47.12%, H: 5.49%, N: 6.85%, Cl: 8.82%, F: 1.79%, S: 1.42% |

TABLE 38-continued
| Example | Structure | Mass Spectrometry | Elementary analysis |
|---|---|---|---|
| 83 | 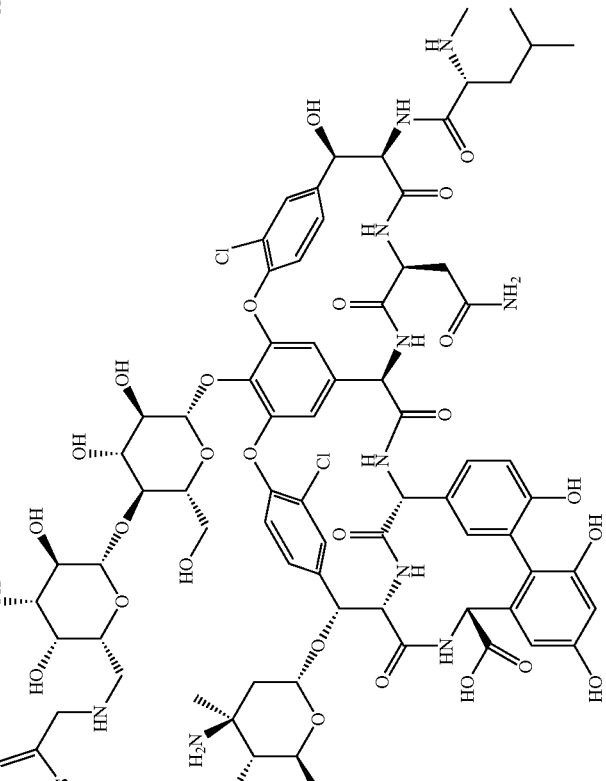 | Chiral [M + 1]+ = 1811 | Calculated value for C84H96Cl2N10O29S•(H2O)11.2•(HCl)3.0 C: 47.50%, H: 5.76%, N: 6.60%, Cl: 8.35%, S: 1.51% Measured value C: 47.49%, H: 5.67%, N: 6.61%, Cl: 8.35%, S: 1.44% |

TABLE 38-continued
| Example | Structure | Mass Spectrometry | Elementary analysis |
|---|---|---|---|
| 84 | 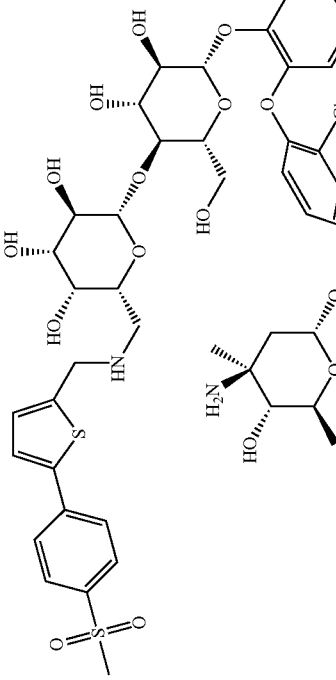 Chiral | $[M+1]^+ = 1859$ | Calculated value for $C_{84}H_{96}Cl_2N_{10}O_{30}S_2 \cdot (H_2O)12.4 \cdot (HCl)3.2$<br>C: 15.84%,<br>H: 5.68%,<br>N: 6.36%,<br>Cl: 8.38%,<br>S: 2.91%<br>Measured value<br>C: 45.82%,<br>H: 5.57%,<br>N: 6.53%,<br>Cl: 8.40%,<br>S: 2.70% |

TABLE 39

| Example | Structure | Mass Spectrometry | Elementary analysis |
|---|---|---|---|
| 85 | Chiral | [M + 1]⁺ = 1826 | Calculated value for C83H93Cl2N10O30S·(H2O)11.3·(HCl)2.4 C: 47.05%, H: 5.61%, N: 7.27%, Cl: 7.36%, S: 1.51% Measured value C: 47.03%, H: 5.53%, N: 7.42%, Cl: 7.34%, S: 1.40% |

TABLE 39-continued

| Example | Structure | Mass Spectrometry | Elementary analysis |
|---|---|---|---|
| 86 | (chemical structure) | Chiral [M + 1]⁺ = 1795 | Calculated value for C84H96Cl2N10O28S•(H2O)12.4•(HCl)2.8 C: 47.54%, H: 5.87%, N: 6.60%, Cl: 8.02%, S: 1.51% Measured value C: 47.51%, H: 5.62%, N: 6.65%, Cl: 7.98%, S: 1.42% |

TABLE 39-continued
| Example | Structure | Mass Spectrometry | Elementary analysis |
|---|---|---|---|
| 87 | Chiral 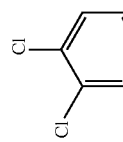 | [M + 1]⁺ = 1844 | Calculated value for C84H93Cl4N10O28•(H2O)17•(HCl)2.9 C: 44.67%, H: 5.80%, N: 6.82%, Cl: 10.83% Measured value C: 14.69%, H: 5.87%, N: 6.89%, Cl: 10.82% |

TABLE 40
| Example | Structure | Mass Spectrometry | Elementary analysis |
|---|---|---|---|
| 88 | Chiral 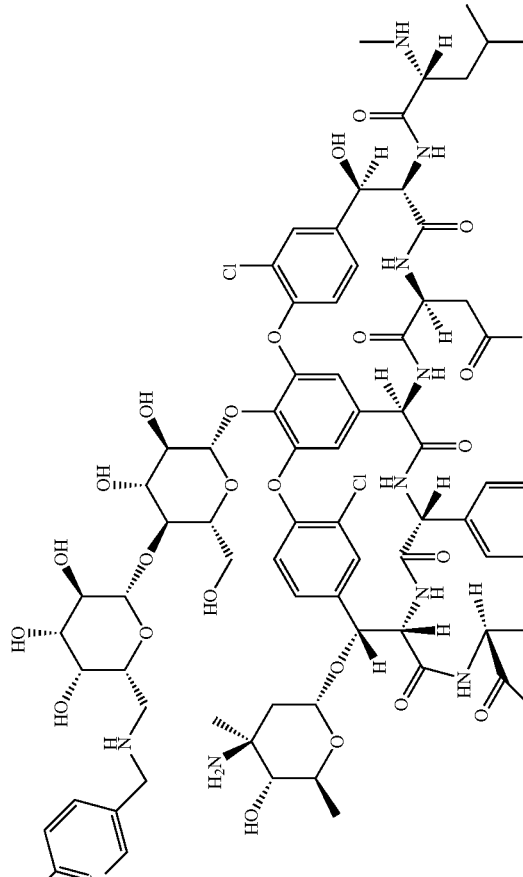 | [M + 1]+ = 1812 | Calculated value for C84H93Cl2F2N11O28•(H2O)16.5•(HCl)2.6 C: 45.74%, H: 5.88%, N: 6.99%, Cl: 7.39%, F: 1.72% Measured value C: 45.73%, H: 5.82%, N: 7.05%, Cl: 7.36%, F: 1.62% |

TABLE 40-continued
| Example | Structure | Mass Spectrometry | Elementary analysis |
|---|---|---|---|
| 89 | 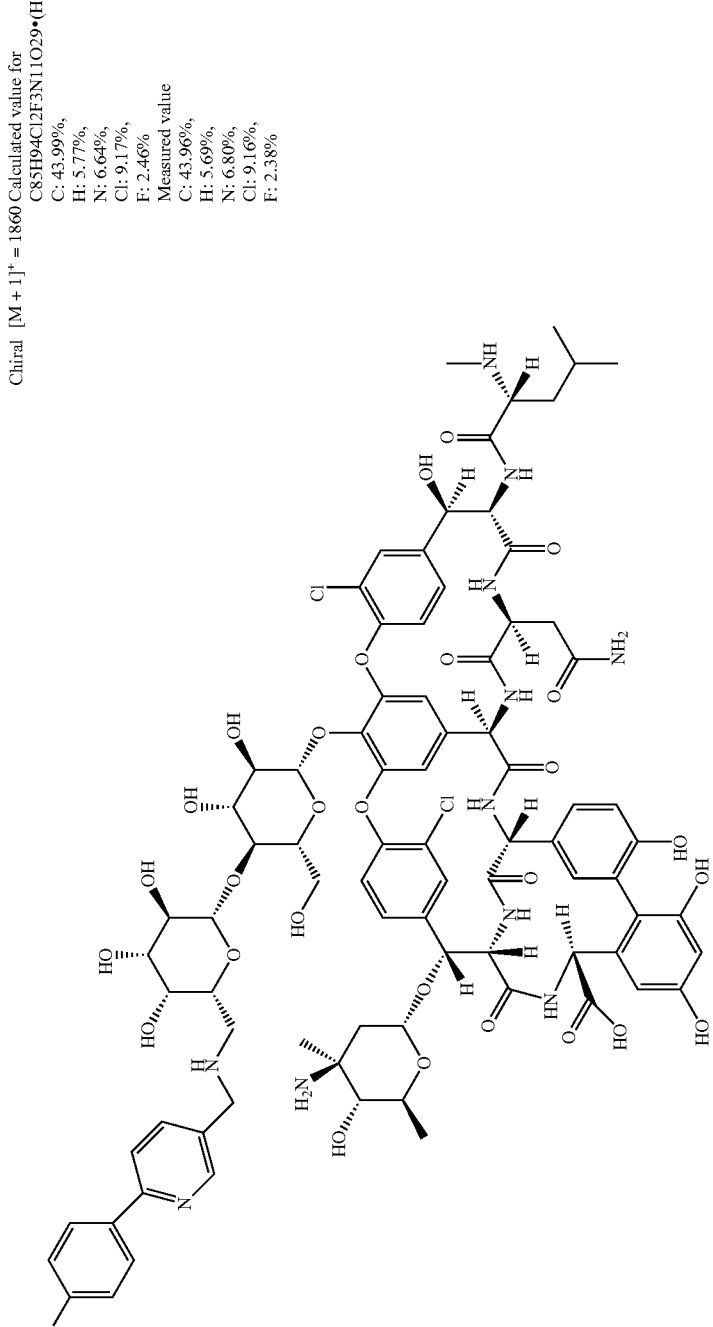 | Chiral [M + 1]$^+$ = 1860 | Calculated value for C85H94Cl2F3N11O29•(H2O)17.4•(HCl)4<br>C: 43.99%,<br>H: 5.77%,<br>N: 6.64%,<br>Cl: 9.17%,<br>F: 2.46%<br>Measured value<br>C: 43.96%,<br>H: 5.69%,<br>N: 6.80%,<br>Cl: 9.16%,<br>F: 2.38% |

TABLE 40-continued
| Example | Structure | Mass Spectrometry | Elementary analysis |
|---|---|---|---|
| 90 | Chiral 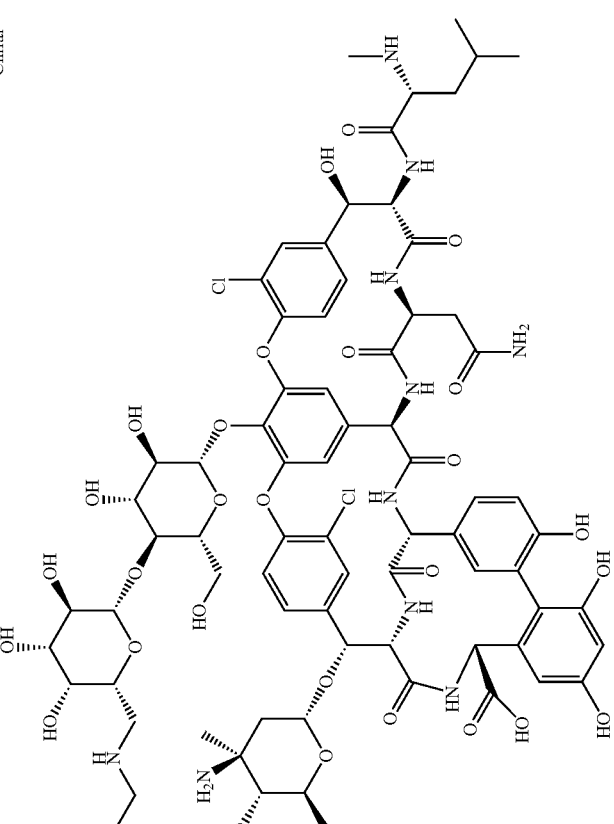 | [M + 1]⁺ = 1804 | Calculated value for C86H99Cl2N11O28•(H2O)15.4•(HCl)4.2 C: 46.19%, H: 6.04%, N: 6.89%, Cl: 9.83% Measured value C: 46.20%, H: 5.83%, N: 6.98%, Cl: 9.76% |

TABLE 41
| Example | Structure | Mass Spectrometry | Elementary analysis |
|---|---|---|---|
| 91 | Chiral 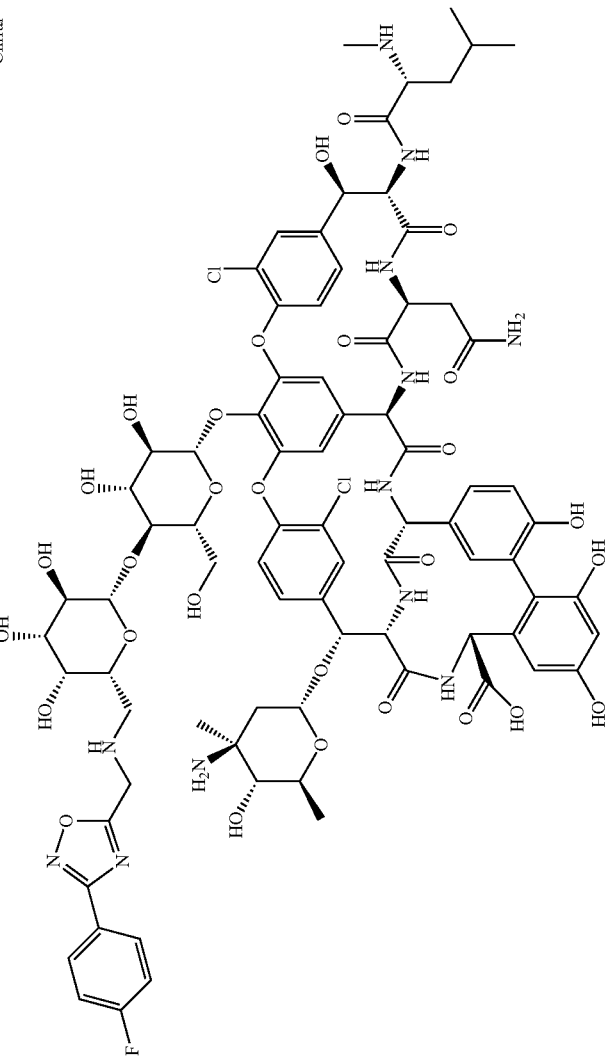 | [M + 1]⁺ = 1785 | Calculated value for C81H91Cl2FN12O29•(H2O)15•(HCl)2.6 C: 45.22%, H: 5.79%, N: 7.81%, Cl: 7.58%, F: 0.88% Measured value C: 45.23%, H: 5.87%, N: 7.80%, Cl: 7.61%, F: 0.87% |

TABLE 41-continued
| Example | Structure | Mass Spectrometry | Elementary analysis |
|---|---|---|---|
| 92 | 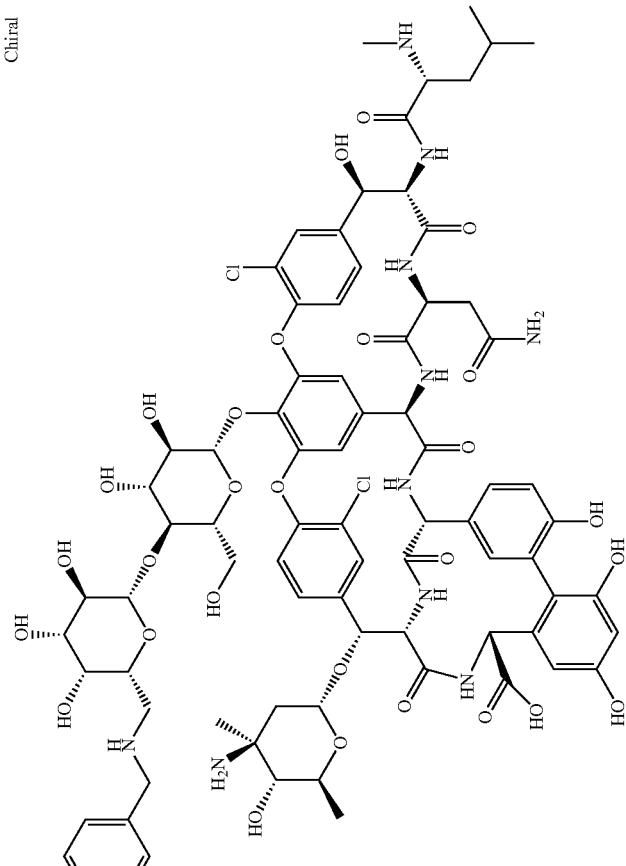 Chiral | [M + 1]$^+$ = 1828 | Calculated value for C84H93Cl3FN11O28•(H2O)13.3•(HCl)3 C: 46.30%, H: 5.67%, N: 7.07%, Cl: 9.76%, F: 0.87% Measured value C: 46.27%, H: 5.63%, N: 7.21%, Cl: 9.69%, F: 0.77% |

TABLE 41-continued
| Example | Structure | Mass Spectrometry | Elementary analysis |
|---|---|---|---|
| 93 | 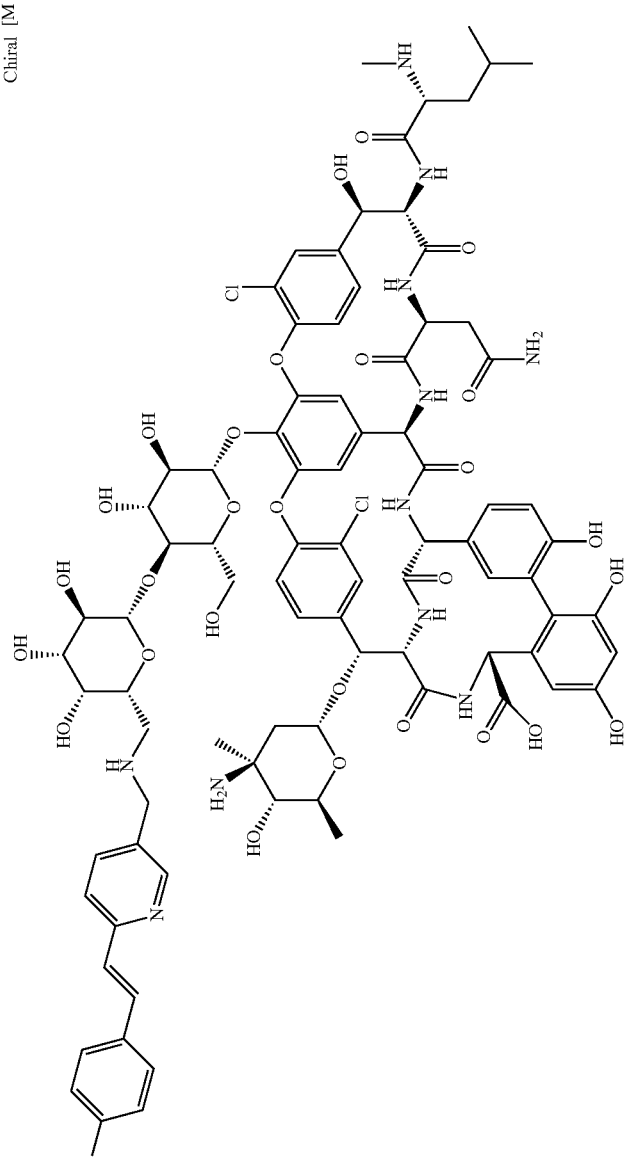 | Chiral [M + 1]⁺ = 1820 | Calculated value for C86H96Cl2FN11O28•(H2O)14.6•(HCl)2.7 C: 47.31%, H: 5.91%, N: 7.06%, Cl: 7.63%, F: 0.87% Measured value C: 47.26%, H: 5.83%, N: 7.17%, Cl: 7.69%, F: 0.77% |

TABLE 42

| Example | Structure | Mass Spectrometry | Elementary analysis |
|---|---|---|---|
| 94 | Chiral | [M + 1]⁺ = 1842 | Calculated value for C84H94Cl3N11O28S·(H2O)14.4·(HCl)2.6 C: 45.89%, H: 5.75%, N: 7.01%, Cl: 9.03%, S: 1.46% Measured value C: 45.84%, H: 5.63%, N: 7.14%, Cl: 9.05%, S: 1.51% |

TABLE 42-continued
| Example | Structure | Mass Spectrometry | Elementary analysis |
|---|---|---|---|
| 95 | 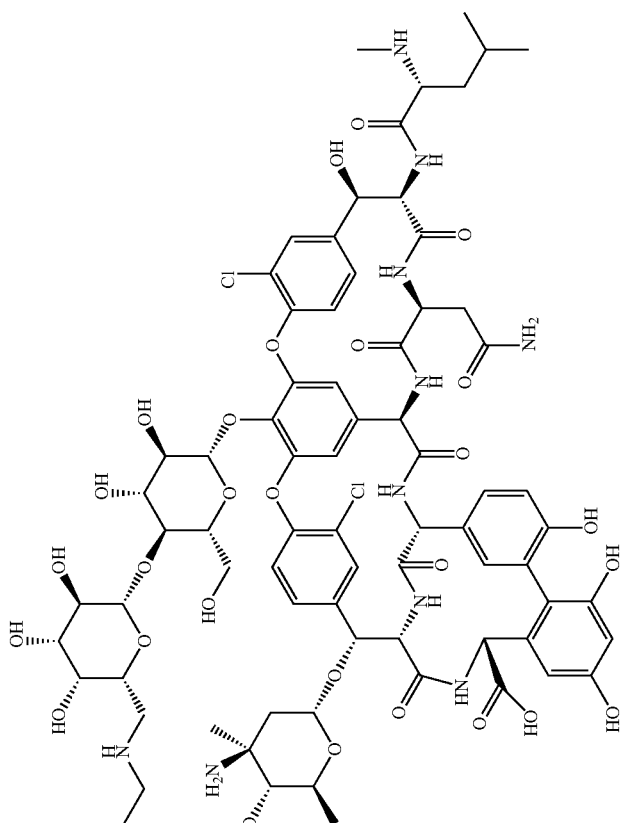 Chiral | [M + 1]$^+$ = 1874 | Calculated value for C84H94Cl3N11O30S•(H2O)14.5•(HCl)3.2 C: 44.76%, H: 5.64%, N: 6.84%, Cl: 9.75%, S: 1.42% Measured value C: 44.69%, H: 5.51%, N: 6.97%, Cl: 9.69%, S: 1.43% |

TABLE 42-continued

| Example | Structure | Mass Spectrometry | Elementary analysis |
|---|---|---|---|
| 96 | Chiral (structure shown) | [M + 1]⁺ = 1860 | Calculated value for C84H93Cl4N11O29·(H2O)13.5·(HCl)3 C: 45.55%, H: 5.60%, N: 6.96%, Cl: 11.20% Measured value C: 45.53%, H: 5.50%, N: 7.15%, Cl: 11.14% |

TABLE 43

| Example | Structure | Mass Spectrometry | Elementary analysis |
|---|---|---|---|
| 97 | Chiral | [M + 1]⁺ = 1835 | Calculated value for C82H91Cl2F3N12O29•(H2O)13.7•(HCl)2.9 C: 44.99%, H: 5.59%, N: 7.68%, Cl: 7.94%, F: 2.60% Measured value C: 45.13%, H: 5.69%, N: 7.71%, Cl: 7.99%, F: 2.30% |

TABLE 43-continued
| Example | Structure | Mass Spectrometry | Elementary analysis |
|---|---|---|---|
| 98 | 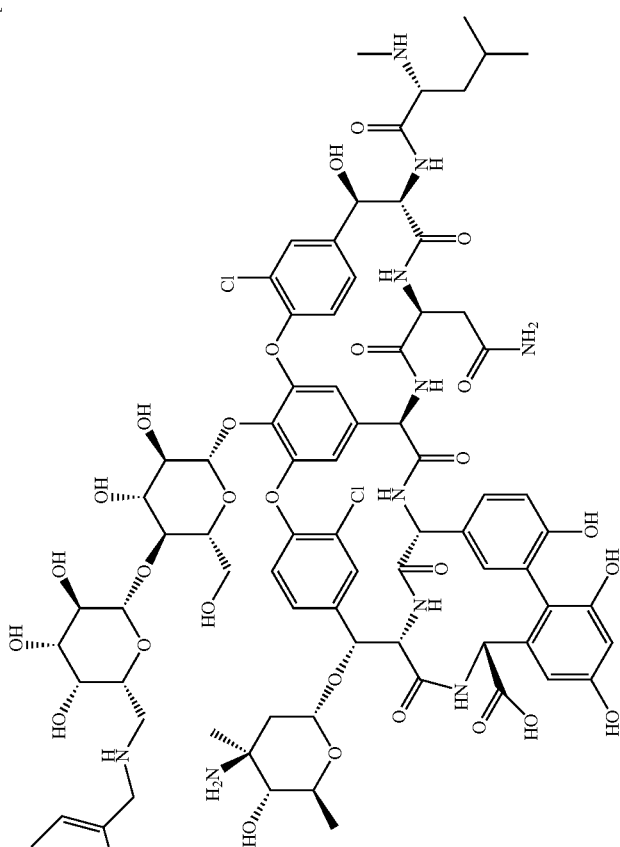 | Chiral [M + 1]$^+$ = 1826 | Calculated value for C84H94Cl3N11O29•(H2O)14.3•(HCl)3.7 C: 45.43%, H: 5.73%, N: 6.94%, Cl: 10.70% Measured value C: 45.34%, H: 5.68%, N: 7.15%, Cl: 10.75% |

TABLE 43-continued
| Example | Structure | Mass Spectrometry | Elementary analysis |
|---|---|---|---|
| 99 | 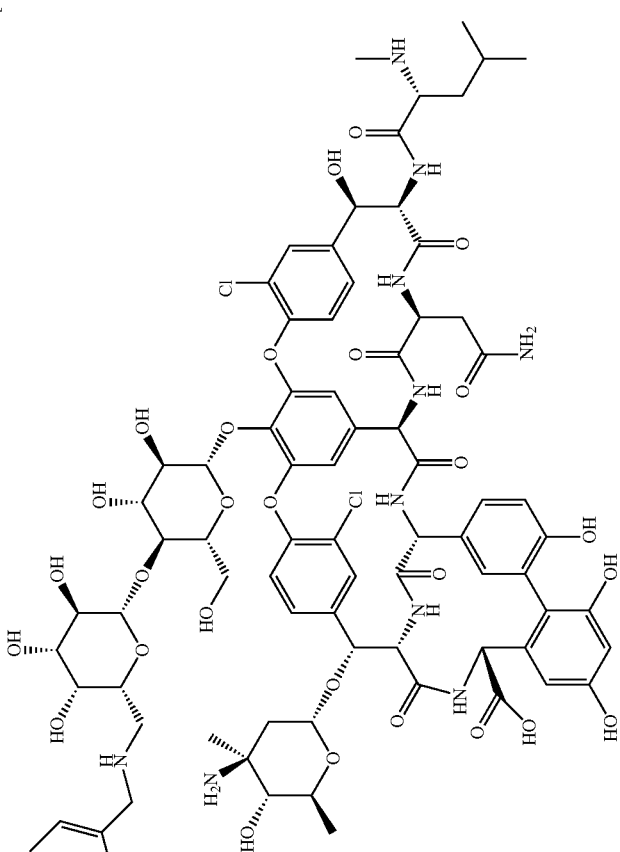 | Chiral [M + 1]+ = 1828 | Calculated value for C84H93Cl2F2N11O29•(H2)13.5•(HCl)3.3 C: 46.00%, H: 5.67%, N: 7.03%, Cl: 8.57%, F: 1.73% Measured value C: 45.98%, H: 5.62%, N: 7.13%, Cl: 8.59%, F: 1.49% |

TABLE 44
| Example | Structure | Mass Spectrometry | Elementary analysis |
|---|---|---|---|
| 100 | Chiral 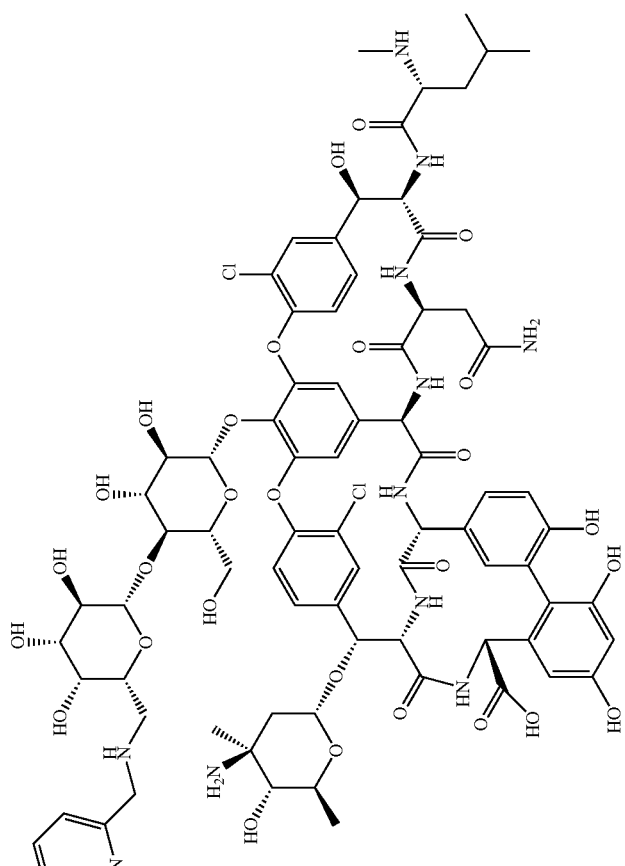 | [M + 1]$^+$ = 1810 | Calculated value for C84H94Cl3N11O28•(H2O)14•(HCl)3.5 C: 46.03%, H: 5.77%, N: 7.03%, Cl: 10.51% Measured value C: 45.96%, H: 5.53%, N: 7.12%, Cl: 10.47% |

TABLE 44-continued
| Example | Structure | Mass Spectrometry | Elementary analysis |
|---------|-----------|-------------------|---------------------|
| 101 | 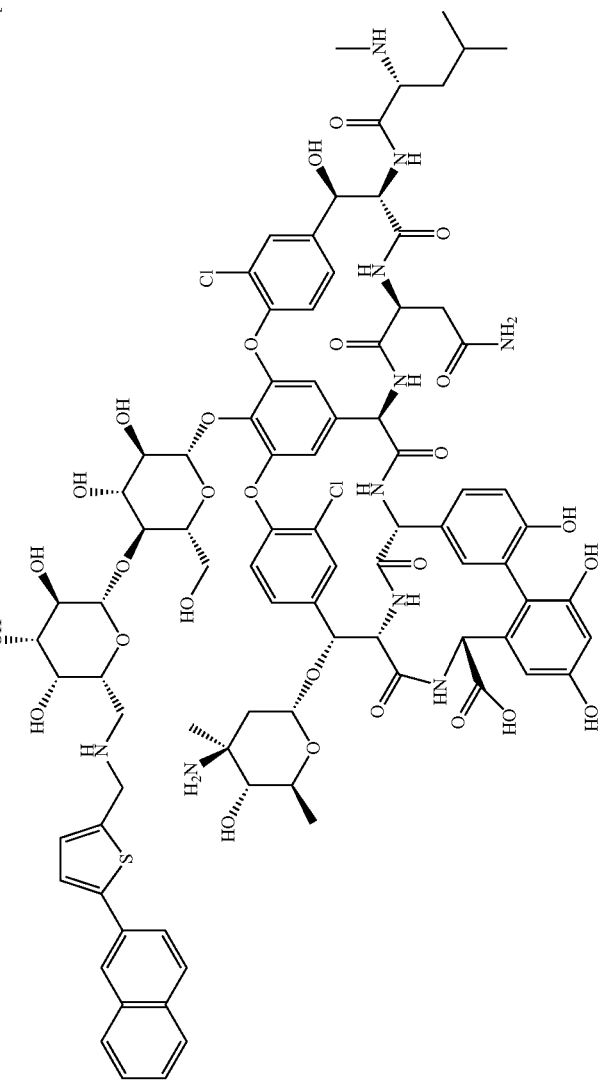 | Chiral [M + 1]$^+$ = 1831 | Calculated value for C87H96Cl2N10O28S•21.7(H2O)•3.5(HCl) C: 44.50%, H: 6.15%, N: 5.70%, Cl: 8.30%, S: 1.30% Measured value C: 44.44%, H: 6.13%, N: 5.96%, Cl: 8.29%, S: 1.36% |

TABLE 44-continued
| Example | Structure | Mass Spectrometry | Elementary analysis |
|---|---|---|---|
| 102 | 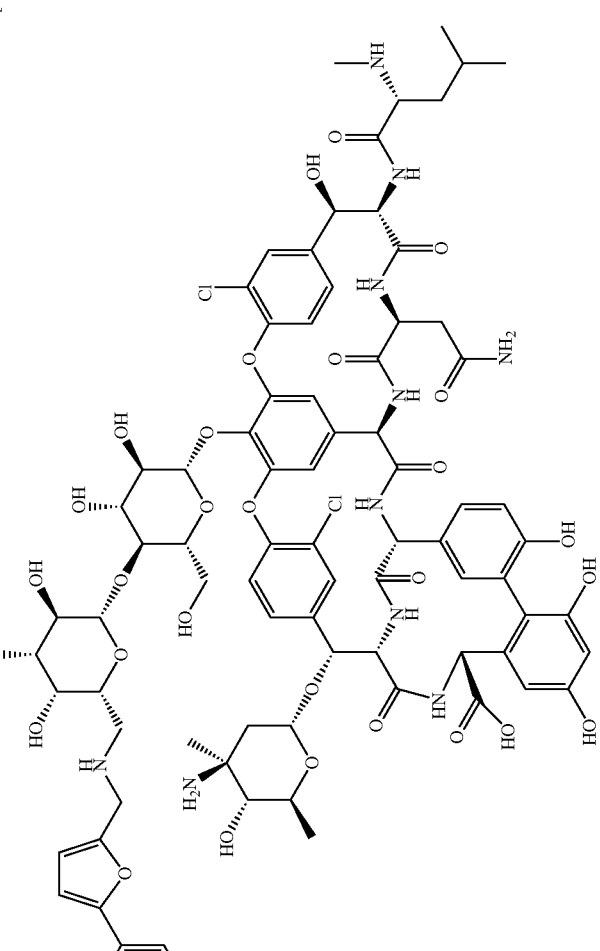 | Chiral [M + 1]⁺ = 1799 | Calculated value for C83H93Cl3N10O29•48.4(H2O)•3.4(HCl) C: 44.37%, H: 5.87%, N: 5.91%, Cl: 10.1% Measured value C: 44.18%, H: 5.95%, N: 6.21%, Cl: 10.06% |

TABLE 45

| Example | Structure | Mass Spectrometry | Elementary analysis |
|---|---|---|---|
| 103 | (chiral structure) | [M + 1]⁺ = 1811 | Calculated value for C83H93Cl3N12O28•19.0(H2O)•2.8(HCl)<br>C: 44.26%,<br>H: 5.98%,<br>N: 7.16%,<br>Cl: 9.15%<br>Measured value<br>C: 44.16%,<br>H: 5.97%,<br>N: 7.45%,<br>Cl: 9.11% |

TABLE 45-continued
| Example | Structure | | Mass Spectrometry | Elementary analysis |
|---|---|---|---|---|
| 104 | 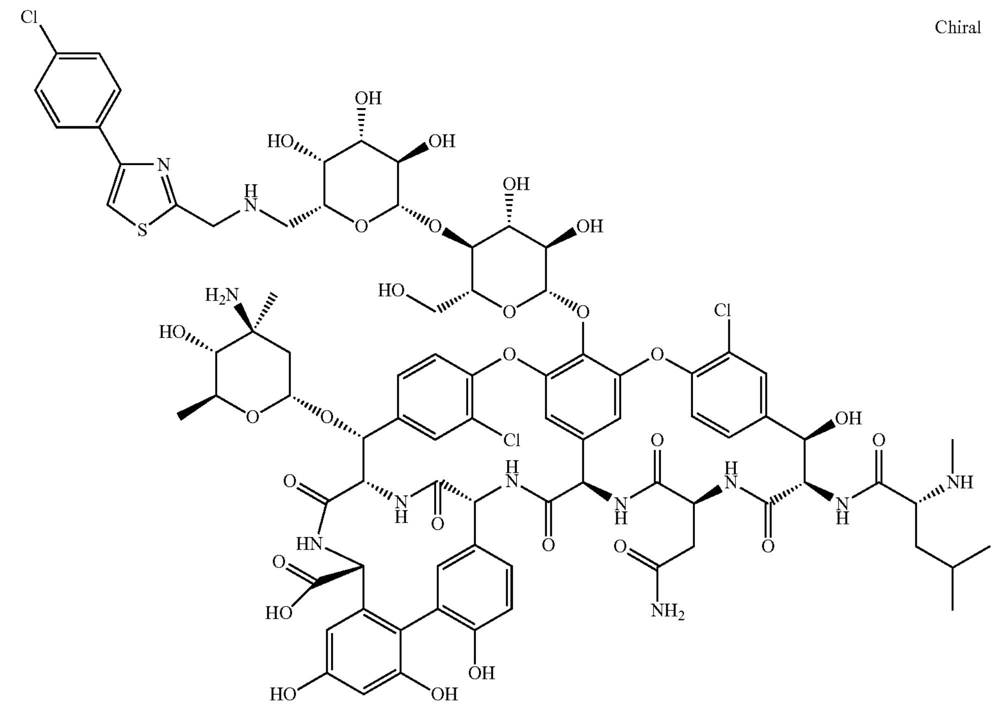 | Chiral | [M + 1]⁺ = 1816 | Calculated value for C82H92Cl3N11O28S·19.6(H2O)·3.4(HCl) C: 42.96%, H: 6.06%, N: 6.56%, Cl: 9.88%, S: 1.49% Measured value C: 42.91%, H: 5.91%, N: 6.71%, Cl: 9.89%, S: 1.40% |

TABLE 45-continued
| Example | Structure | | Mass Spectrometry | Elementary analysis |
|---|---|---|---|---|
| | | Chiral | | |
| 105 | 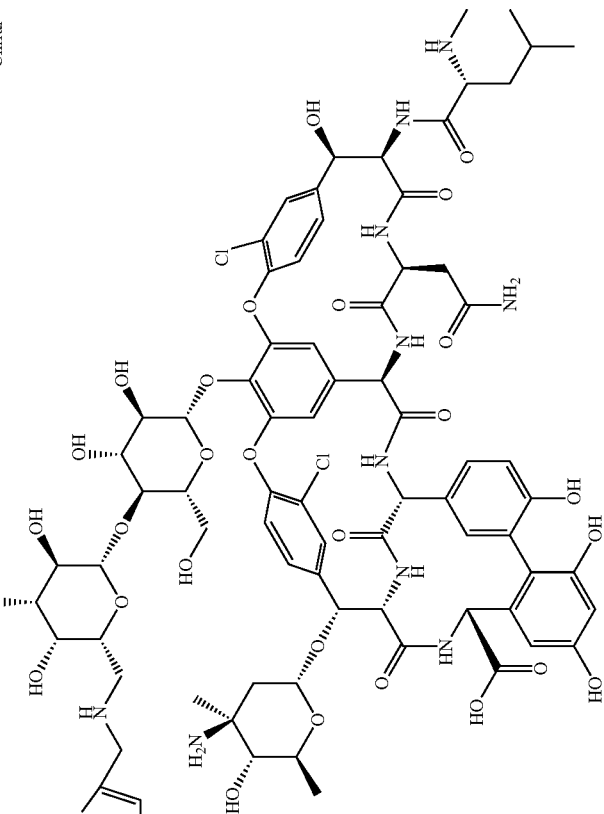 | | [M + 1]+ = 1800 | |

TABLE 46
| Example | Structure | Mass Spectrometry | Elementary analysis |
|---|---|---|---|
| 106 | 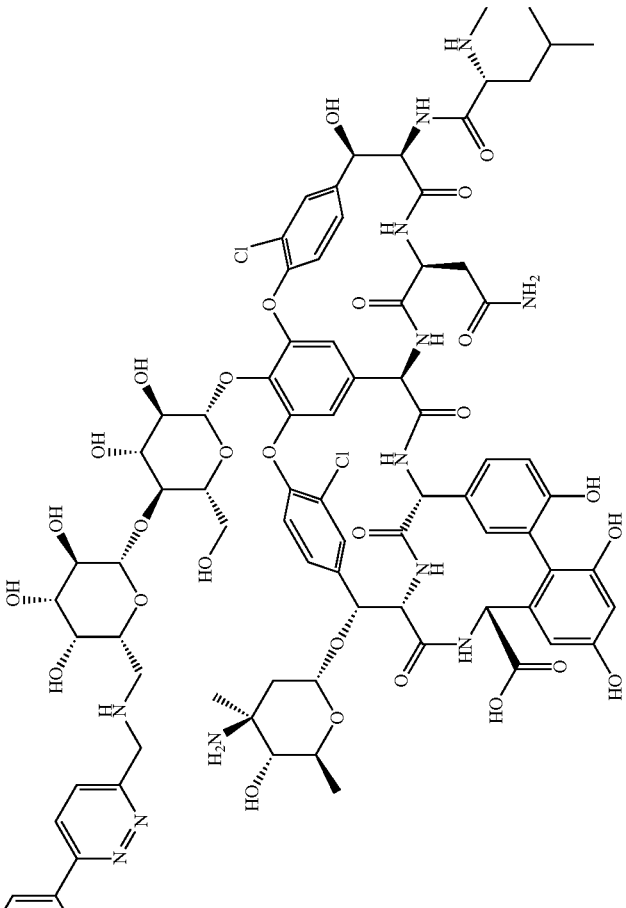 Chiral | [M + 1]⁺ = 1811 | |

TABLE 46-continued
| Example | Structure | Mass Spectrometry | Elementary analysis |
|---|---|---|---|
| 107 | 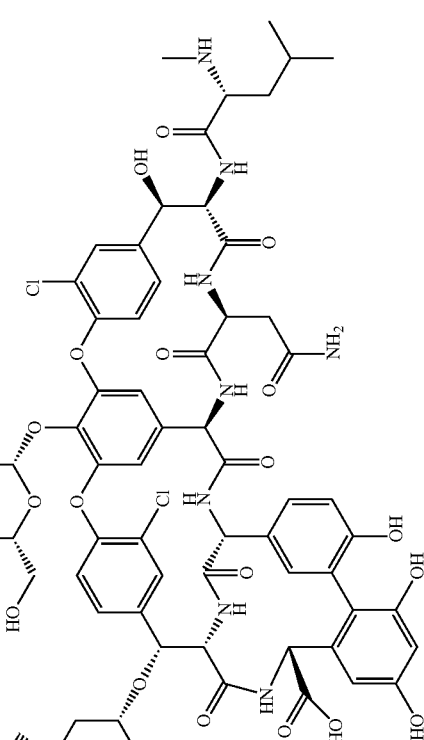 | Chiral [M + 1]+ = 1815 | Calculated value for C83H93Cl3N10O28S•(H2O)13.1•(HCl)3.0 C: 46.10%, H: 5.70%, N: 6.48%, Cl: 9.84%, S: 1.48% Measured value C: 46.06%, H: 5.70%, N: 6.56%, Cl: 9.88%, S: 1.41% |

TABLE 46-continued
| Example | Structure | Mass Spectrometry | Elementary analysis |
|---|---|---|---|
| 108 | Chiral 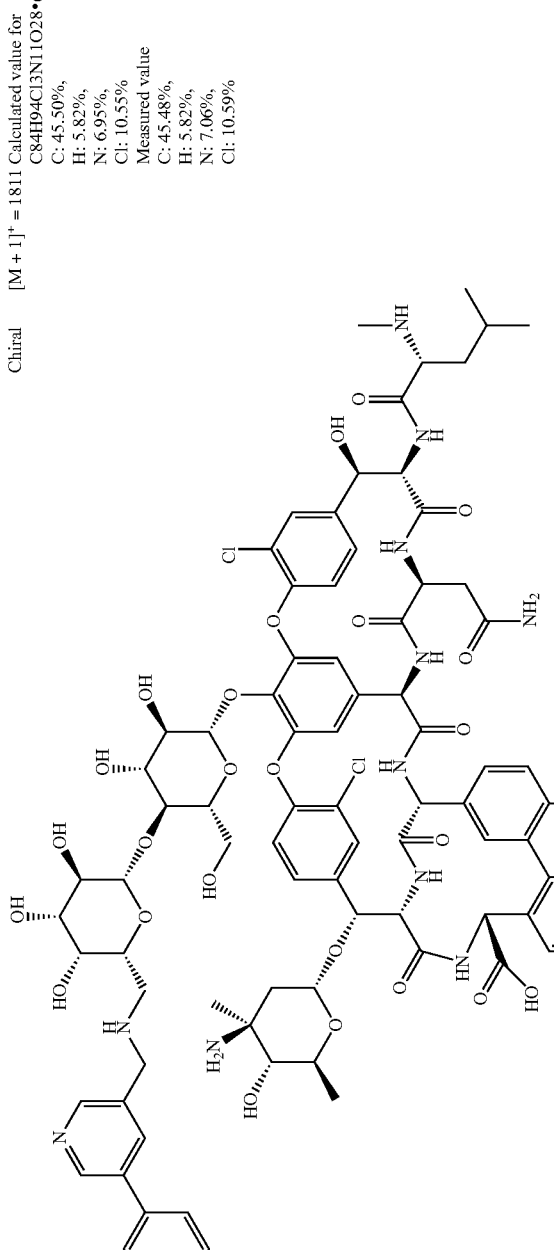 | [M + 1]⁺ = 1811 | Calculated value for C84H94Cl3N11O28•(H2O)15.2•(HCl)3.6 C: 45.50%, H: 5.82%, N: 6.95%, Cl: 10.55% Measured value C: 45.48%, H: 5.82%, N: 7.06%, Cl: 10.59% |

TABLE 47
| Example | Structure | Mass Spectrometry | Elementary analysis |
|---|---|---|---|
| 109 | 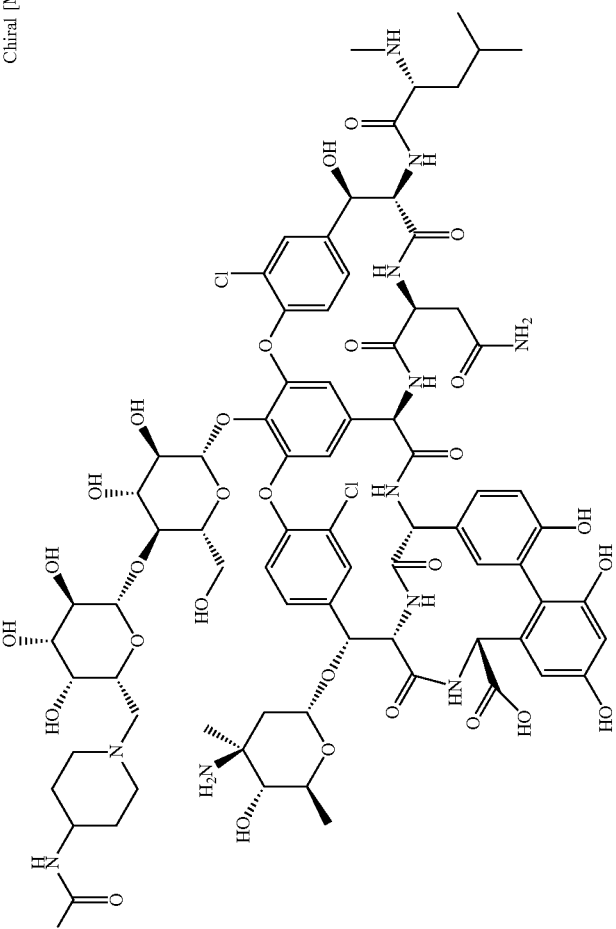 | Chiral [M + 1]⁺ = 1896 | Calculated value for C85H99Cl2F3N12O30•(H2O)13.6•(HCl)2.9<br>C: 45.43%,<br>H: 5.79%,<br>N: 7.48%,<br>Cl: 7.73%,<br>F: 2.54%<br>Measured value<br>C: 45.38%,<br>H: 5.72%,<br>N: 7.92%,<br>Cl: 7.76%,<br>F: 2.96% |

TABLE 48
| Example | Structure | Chiral | Mass Spectrometry | Elementary analysis |
|---|---|---|---|---|
| 110 | 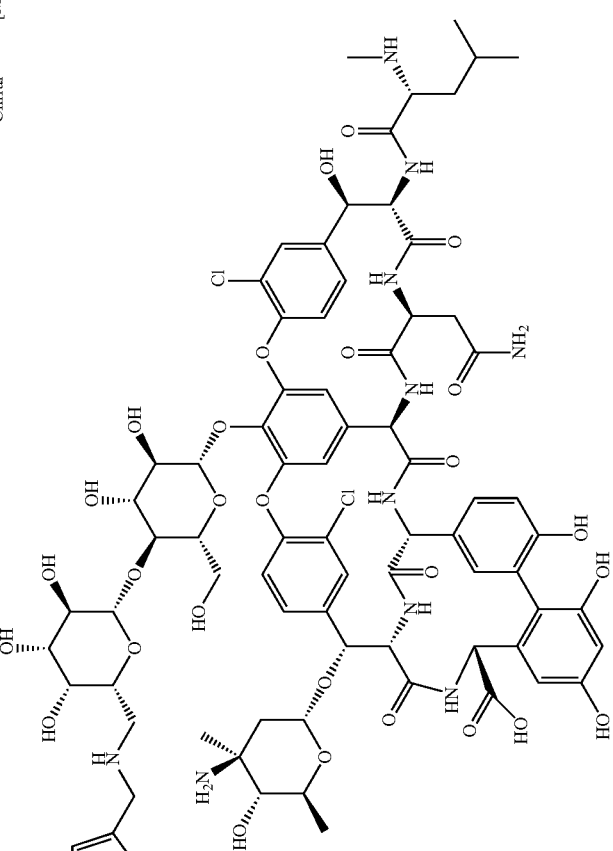 | Chiral | [M + 1]+ = 1847 | Calculated value for C83H93Cl3N10O28S2•(H2O)15.4•(HCl)2.6•(CH3CN)0.7<br>C: 45.05%,<br>H: 5.76%,<br>N: 6.66%,<br>Cl: 8.82%,<br>S: 2.85%<br>Measured value<br>C: 45.08%,<br>H: 5.54%,<br>N: 6.80%,<br>Cl: 8.80%,<br>S: 2.57% |

TABLE 48-continued
| Example | Structure | Mass Spectrometry | Elementary analysis |
|---|---|---|---|
| 111 | Chiral 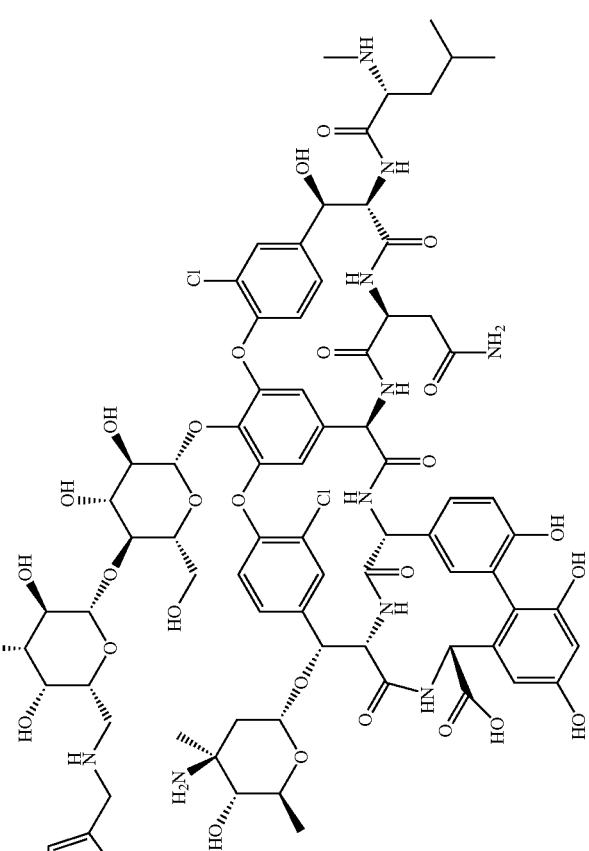 | $[M+1]^+ = 1831$ | Calculated value for C83H93Cl3N10O29S•(H2O)14.1•(HCl)2.7<br>C: 45.61%,<br>H: 5.71%,<br>N: 6.41%,<br>Cl: 9.25%,<br>S: 1.47%<br>Measured value<br>C: 45.61%,<br>H: 5.52%,<br>N: 6.52%,<br>Cl: 9.18%,<br>S: 1.26% |

TABLE 48-continued
| Example | Structure | Mass Spectrometry | Elementary analysis |
|---|---|---|---|
| 112* | Chiral 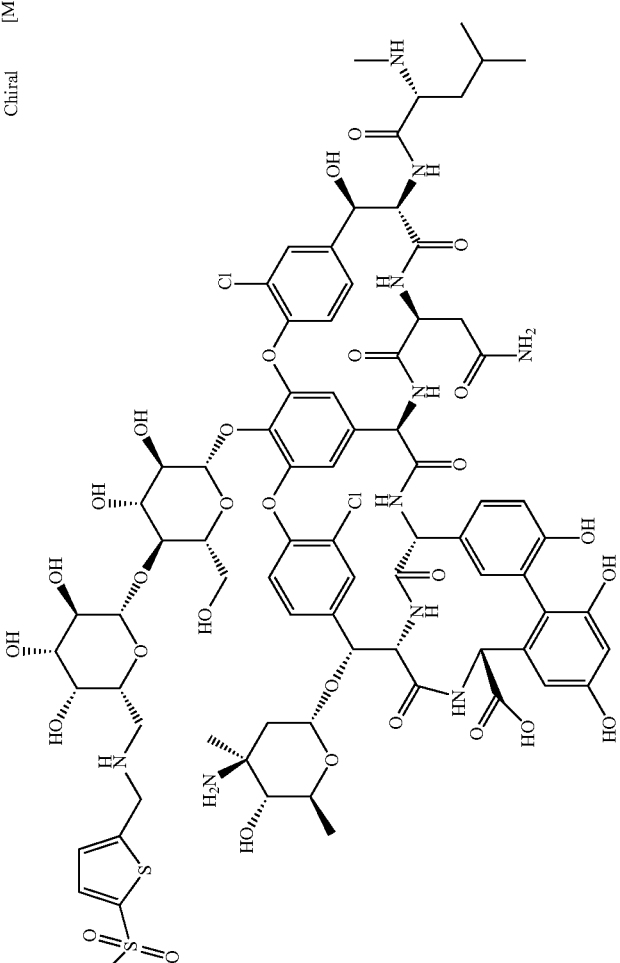 | [M + 1]+ = 1879 | Calculated value for C83H93Cl3N10O30S2•(H2O)15.8•(HCl)2.8 C: 43.96%, H: 5.66%, N: 6.18%, Cl: 9.07%, S: 2.83% Measured value C: 43.95%, H: 5.37%, N: 6.14%, Cl: 9.09%, S: 2.61% |

TABLE 49
| Example | Structure | Mass Spectrometry | Elementary analysis |
|---|---|---|---|
| 113 | 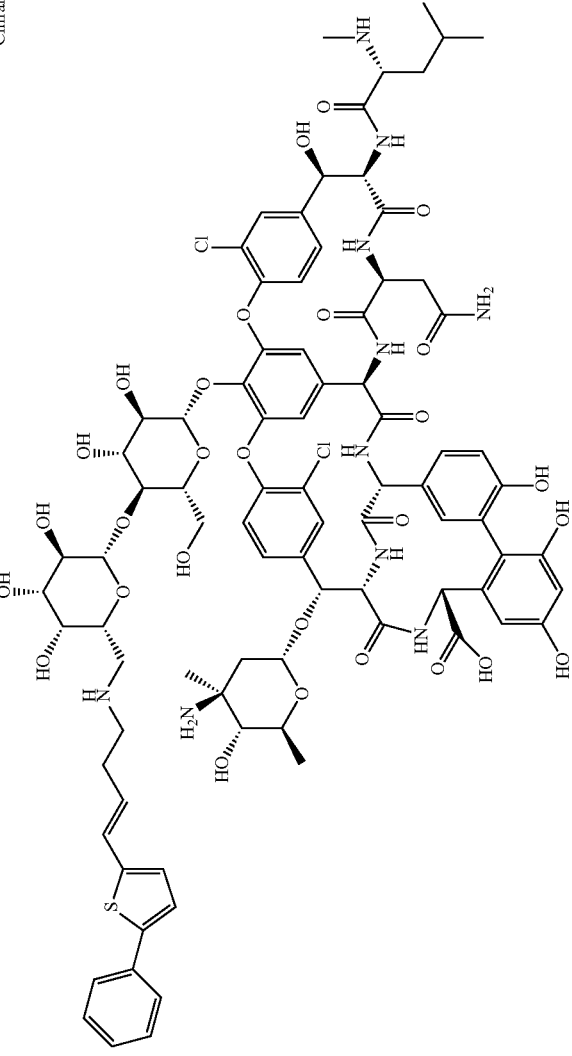 | Chiral [M + 1]+ = 1821 | Calculated value for C86H98Cl2N10O28S•(H2O)15.5•(HCl)2.9<br>C: 46.79%,<br>H: 6.02%,<br>N: 6.34%,<br>Cl: 7.87%,<br>S: 1.45%<br>Measured value<br>C: 46.74%,<br>H: 5.75%,<br>N: 6.27%,<br>Cl: 7.80%,<br>S: 1.37% |

TABLE 49-continued
| Example | Structure | Mass Spectrometry | Elementary analysis |
|---|---|---|---|
| 114 | 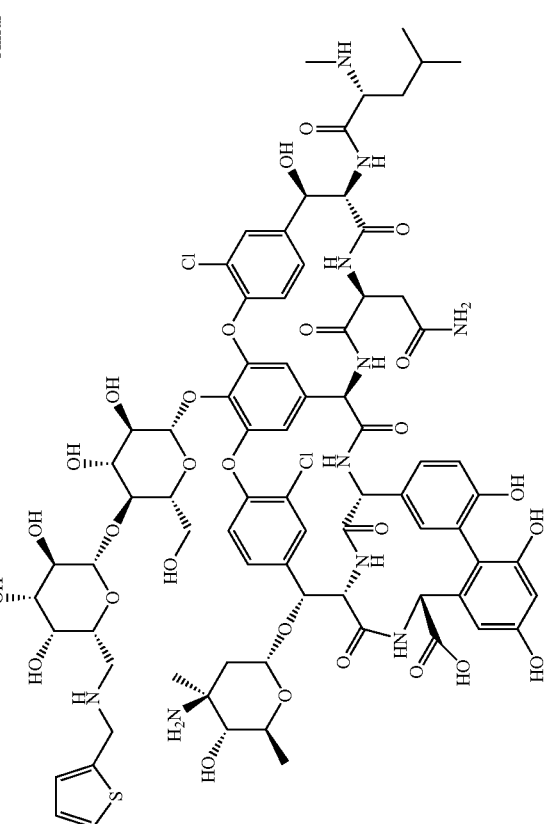 | Chiral [M + 1]⁺ = 1858 | Calculated value for C84H94Cl3N11O29S•(H2O)18.3•(HCl)3.3•(CH3CN)0.6 C: 43.83%, H: 5.86%, N: 6.96%, Cl: 9.57%, S: 1.37% Measured value C: 43.76%, H: 5.59%, N: 7.03%, Cl: 9.59%, S: 1.32% |

TABLE 49-continued
| Example | Structure | Mass Spectrometry | Elementary analysis |
|---|---|---|---|
| 115 | 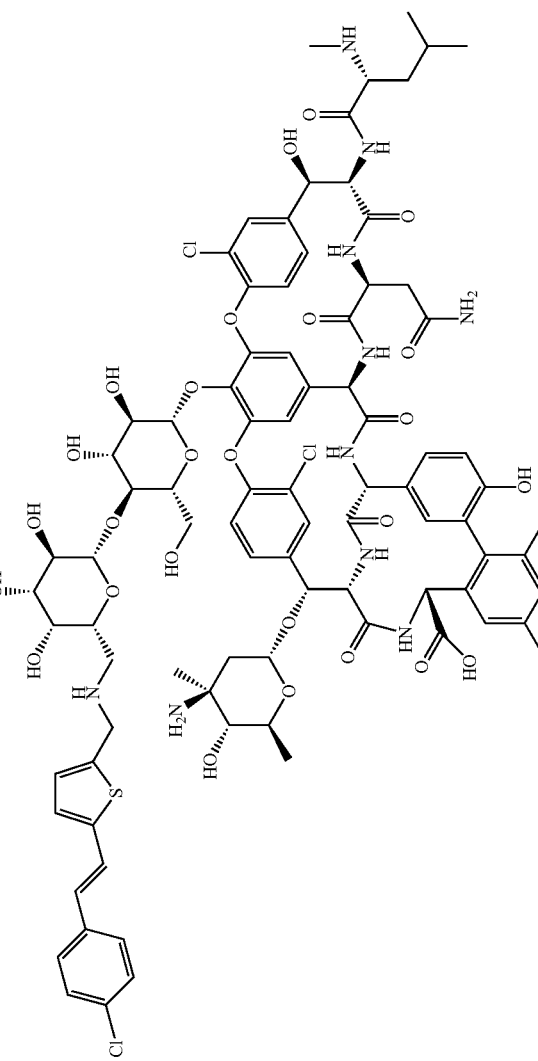 | Chiral [M + 1]+ = 1841 | Calculated value for C85H95Cl3N10O28S•(H2O)20.1•(HCl)4.8•(CH3CN)0.6<br>C: 43.05%,<br>H: 5.94%,<br>N: 6.17%,<br>Cl: 11.50%,<br>S: 1.33%<br>Measured value<br>C: 42.76%,<br>H: 5.64%,<br>N: 6.33%,<br>Cl: 11.49%,<br>S: 1.31% |

TABLE 50
| Example | Structure | Mass Spectrometry | Elementary analysis |
|---|---|---|---|
| 116 | Chiral 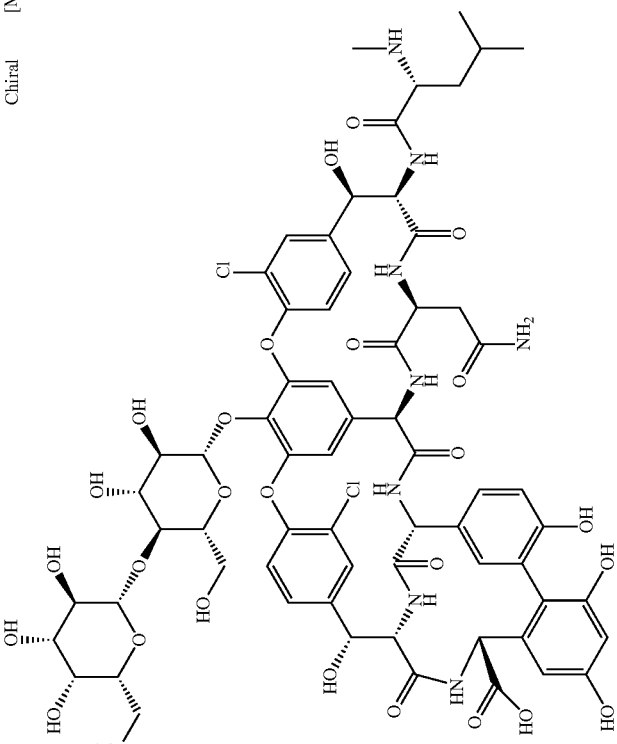 | [M + 1]+ = 1688 | Calculated value for C80H83Cl2N9O26S•(H2O)13.6•(HCl)2.1 C: 47.78%, H: 5.63%, N: 6.27%, Cl: 7.23%, S: 1.59% Measured value C: 47.77%, H: 5.58%, N: 6.39%, Cl: 7.18%, S: 1.53% |

TABLE 50-continued
| Example | Structure | Mass Spectrometry | Elementary analysis |
|---|---|---|---|
| 117 | Chiral 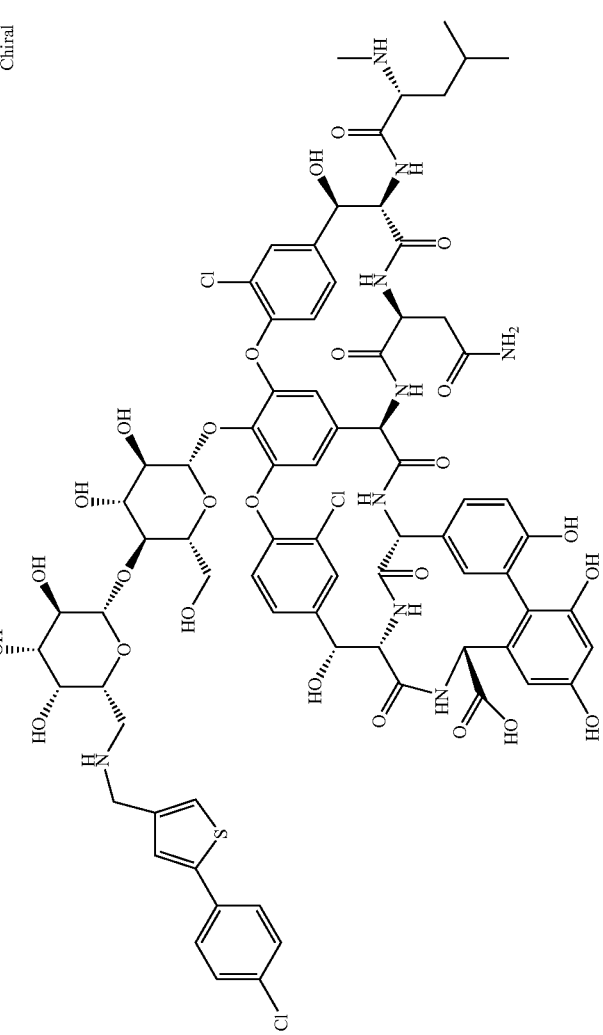 | $[M+1]^+ = 1672$ | Calculated value for $C_{76}H_{80}Cl_3N_9O_{26}S \cdot (H_2O)_{11.6} \cdot (HCl)_{1.4}$<br>C: 47.20%,<br>H: 5.45%,<br>N: 6.52%,<br>Cl: 8.07%,<br>S: 1.66%<br>Measured value<br>C: 47.13%,<br>H: 5.36%,<br>N: 6.59%,<br>Cl: 8.13%,<br>S: 1.62% |

TABLE 50-continued

| Example | Structure | Mass Spectrometry | Elementary analysis |
|---|---|---|---|
| 118 | Chiral | [M + 1]+ = 1673 | Calculated value for C75H79Cl3N10O26S·(H2O)11.2·(HCl)1.9 C: 46.29%, H: 5.35%, N: 7.2%, Cl: 8.93%, S: 1.65% Measured value C: 46.07%, H: 5.20%, N: 7.27%, Cl: 8.84%, S: 1.46% |

TABLE 51
| Example | Structure | Mass Spectrometry | Elementary analysis |
|---|---|---|---|
| 119 | 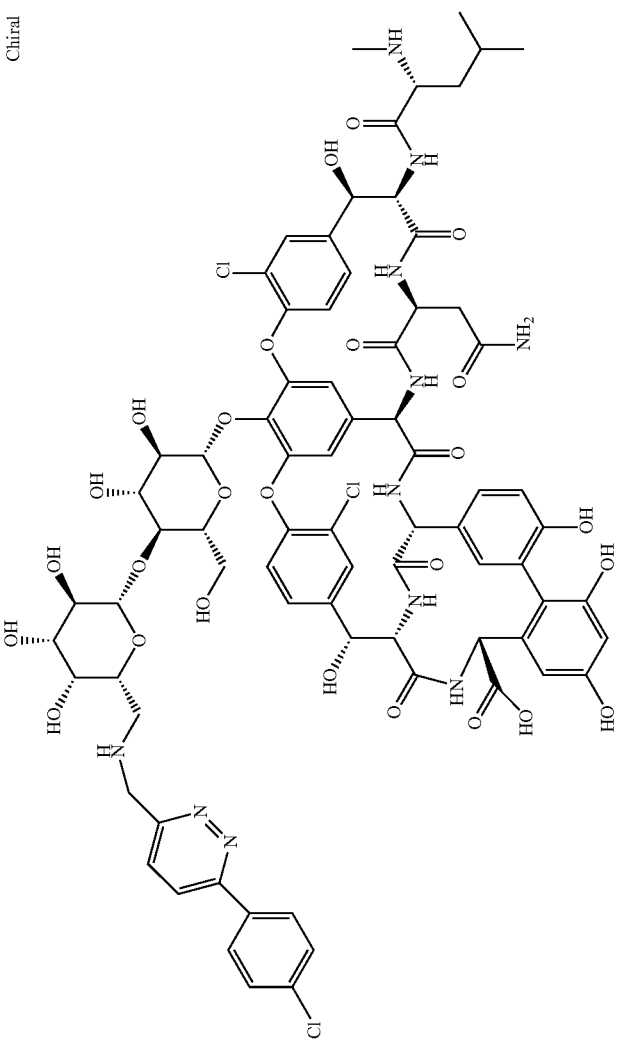 | Chiral [M + 1]⁺ = 1668 | Calculated value for C76H80Cl3N11O26•(H2O)10.2•(HCl)2.6 C: 46.85%, H: 5.33%, N: 7.91%, Cl: 10.19% Measured value C: 46.81%, H: 5.33%, N: 8.27%, Cl: 10.16% |

TABLE 51-continued

| Example | Structure | Mass Spectrometry | Elementary analysis |
|---|---|---|---|
| 120 | Chiral | [M + 1]⁺ = 1668 | Calculated value for C76H80Cl3N11O26•(H2O)13.1•(HCl)1.8 C: 46.30%, H: 5.52%, N: 7.82%, Cl: 8.63% Measured value C: 46.27%, H: 5.41%, N: 7.88%, Cl: 8.66% |

TABLE 51-continued
| Example | Structure | Chiral | Mass Spectrometry | Elementary analysis |
|---|---|---|---|---|
| 121 | 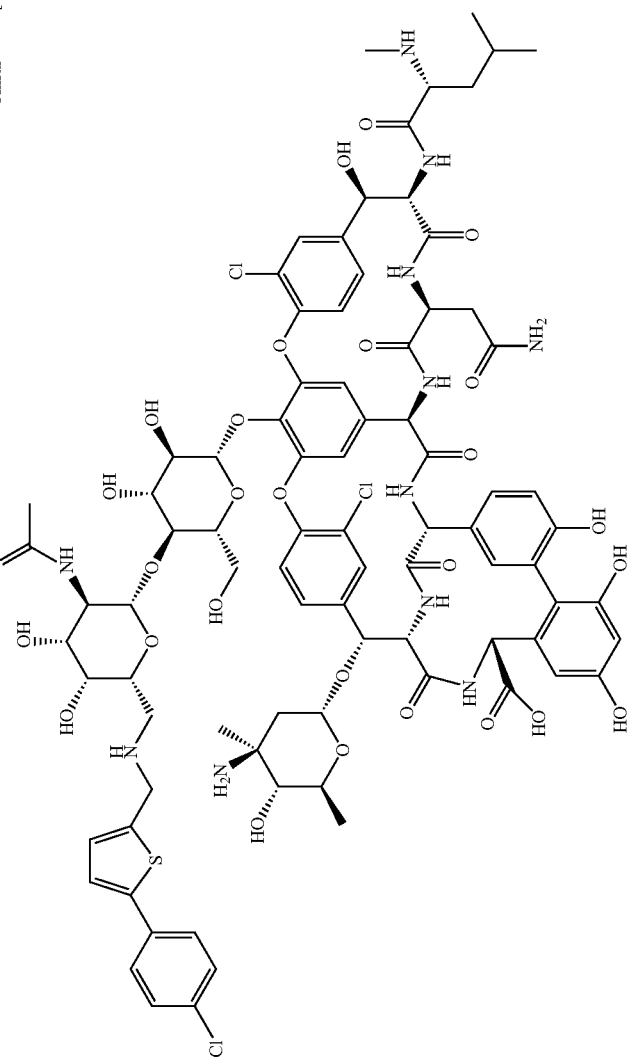 | Chiral | [M + 1]+ = 1856 | Calculated value for C85H96Cl3N11O28S·(H2O)18.7·(HCl)3.1<br>C: 44.23%,<br>H: 5.96%,<br>N: 6.68%,<br>Cl: 9.37%,<br>S: 1.39%<br>Measured value<br>C: 44.22%,<br>H: 5.76%,<br>N: 6.59%,<br>Cl: 9.32%,<br>S: 1.34% |

As a typical example of processes for producing these compounds, processes for producing compounds of Example 13, Example 30, Example 80, Example 117 and Example 121 will be exemplified below.

Other Example compounds can be produced by the same methods as follows.

Example 13

First Step

Production of Intermediate Compound 2

[Chemical formula 76]

Chloroorienticin B (compound 1) (100 mg, 0.069 mmol) was dissolved in 5 mL of 50 mM Tris-HCl buffer (pH 7.4) containing 25 mM $MnCl_2$. 30 U of alkaline phosphatase (P6774 manufactured by Sigma), 3 mg of α-lactoalubumin, 63 mg (0.1 mmol) of UDP-galactose, and 3 U of cow milk-derived β1,4 galactosyltransferase (G5507 manufactured by Sigma) were sequentially added, and the mixture was stirred at 30° C. for 15 hours. The reaction mixture was purified by reverse phase column chromatography to obtain 90 mg (yield 81%) of compound 2 as a colorless solid.

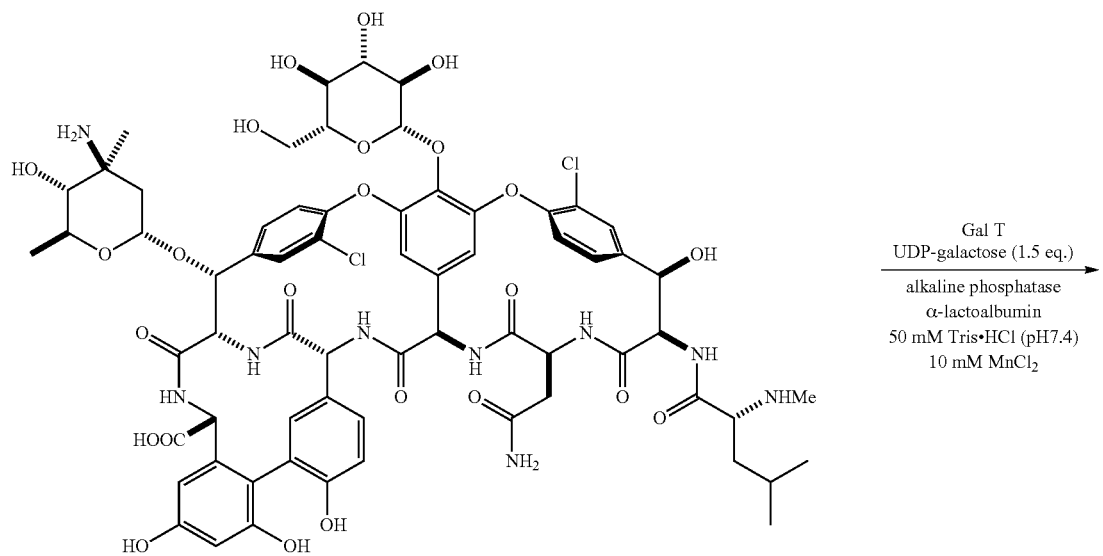

1; Chloroorienticin B

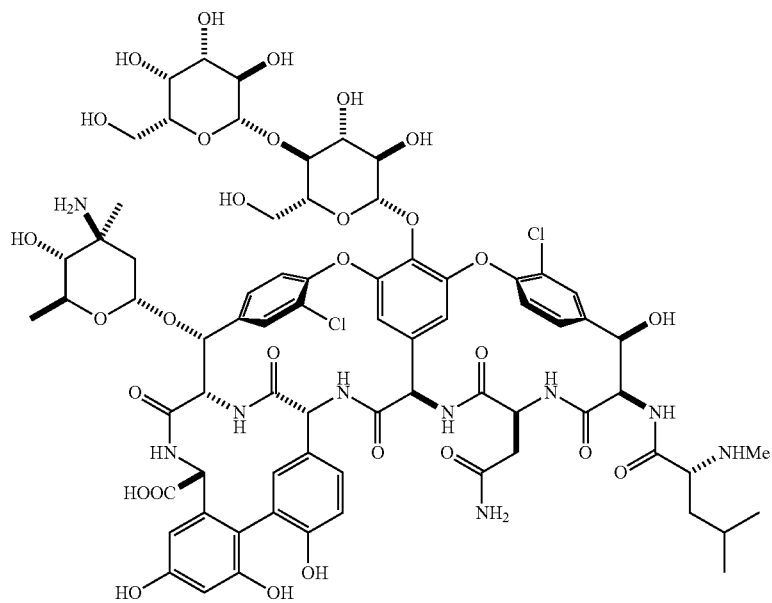

2

Second Step

Production of Intermediate Compound 3

[Chemical formula 77]

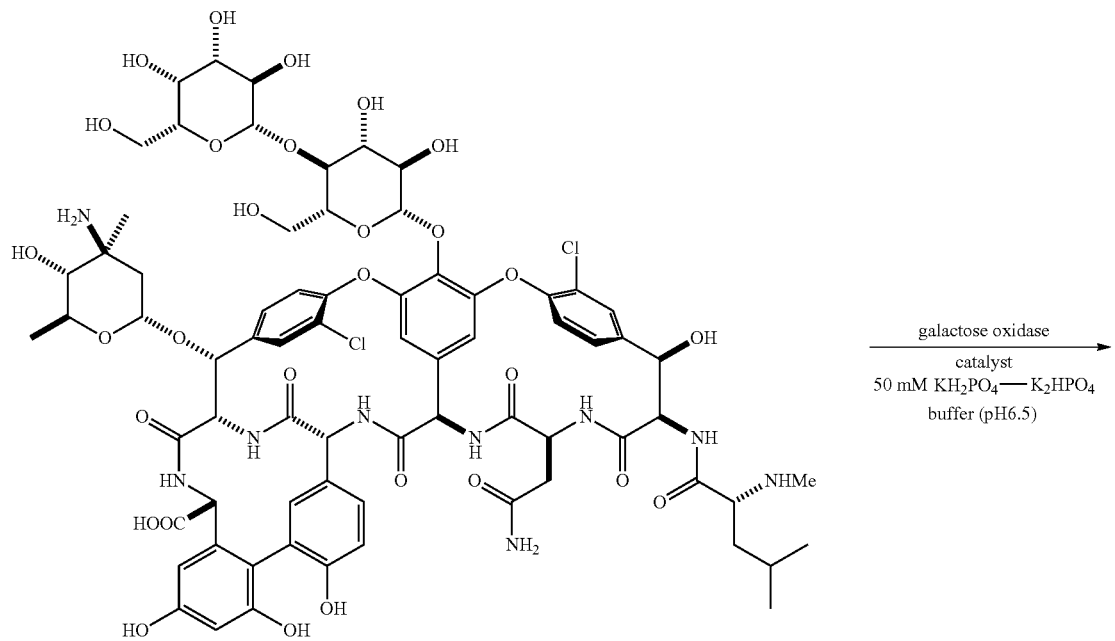

2

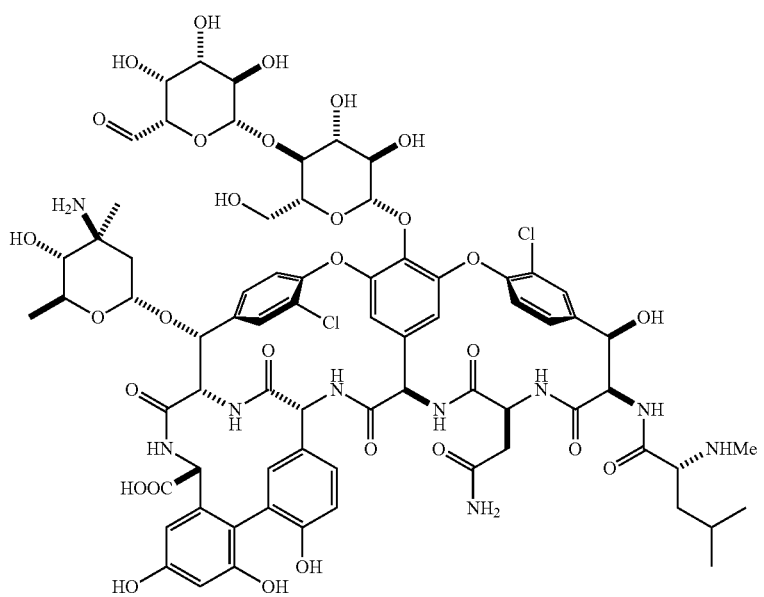

3

The compound 2 obtained in the first step (30 mg, 0.019 mmol) was dissolved in 3 mL of a 50 mM $KH_2PO_4$—$K_2HPO_4$ buffer (pH 6.5). 3000 U of catalase (C30 manufactured by Sigma), and 300 U of Dactylium dendroides-derived galactose oxidase (15996 manufactured by MP Biomedicals) were sequentially added and the mixture was stirred at 30° C. for 24 hours. The reaction mixture was purified by reverse phase column chromatography to obtain 25 mg (yield 83%) of compound 3 as a white powder.

Third Step

Production of Objective Compound 4

[Chemical formula 78]

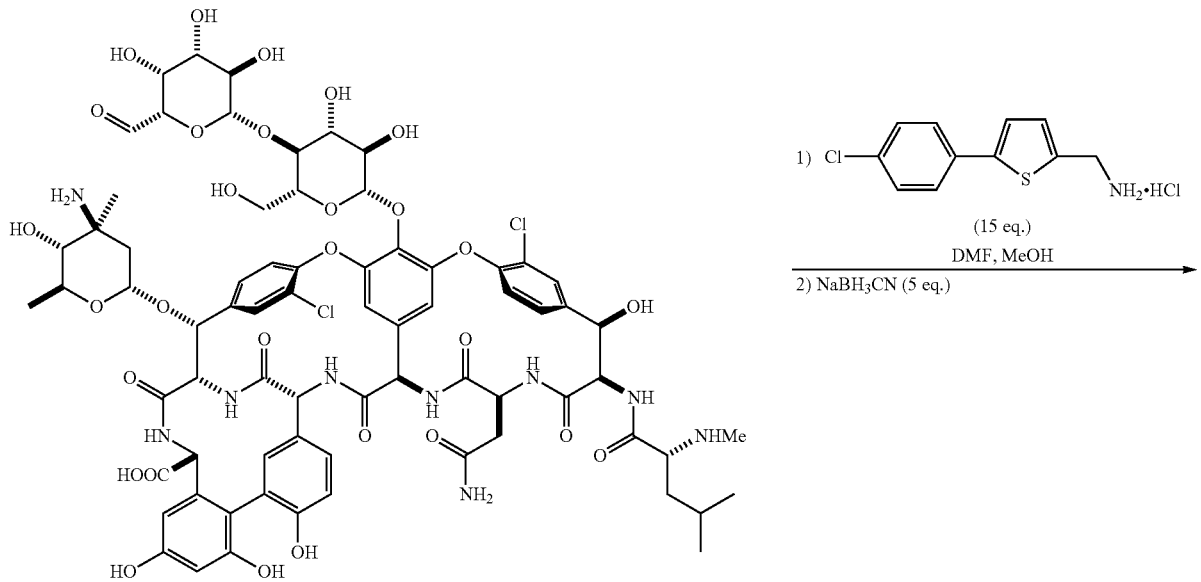

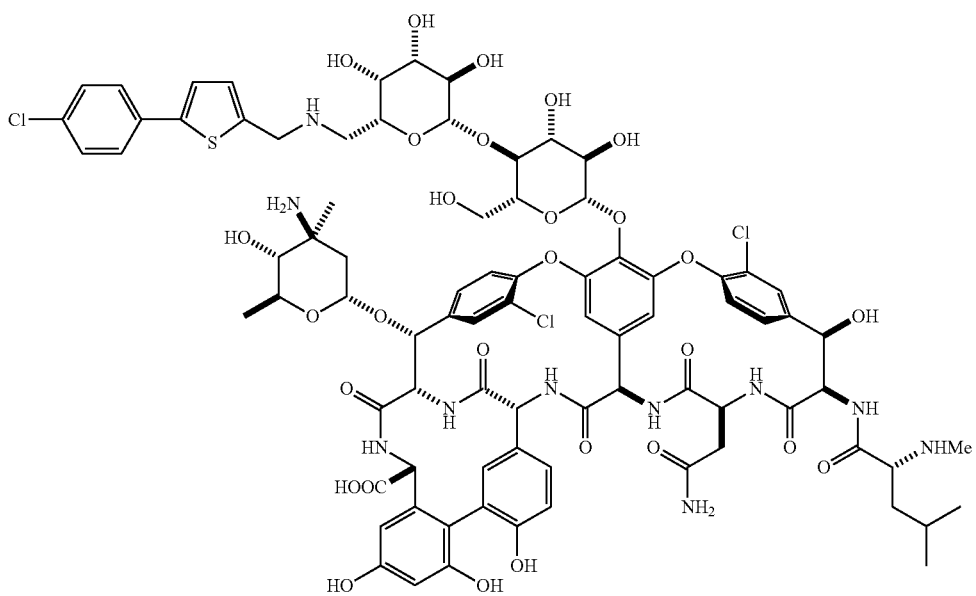

(5-(4-Chlorophenyl)thiophen-2-yl)methaneamine hydrochloride (359 mg, 1.4 mmol) was dissolved in a mixed solvent of 30 mL of dimethylformamide and 30 mL of methanol. The compound 3 obtained in the second step (150 mg, 0.093 mmol) was added, and the mixture was stirred at room temperature for 2 hours. Sodium cyanoborohydride (29 mg, 0.46 mmol) was added, and the mixtures was stirred at 70° C. for 2 hours. The reaction solution was poured into diethyl ether, the produced precipitate was collected by filtration, and the resulting crude solid was washed with 5% aqueous sodium chloride solution to remove unreacted sodium cyanoborohydrate. The resulting crude solid was purified by reverse phase column chromatography to obtain 78 mg (yield 46%) of compound 4 as a colorless solid.

Example 30

First Step

Production of Intermediate Compound 5

[Chemical formula 79]

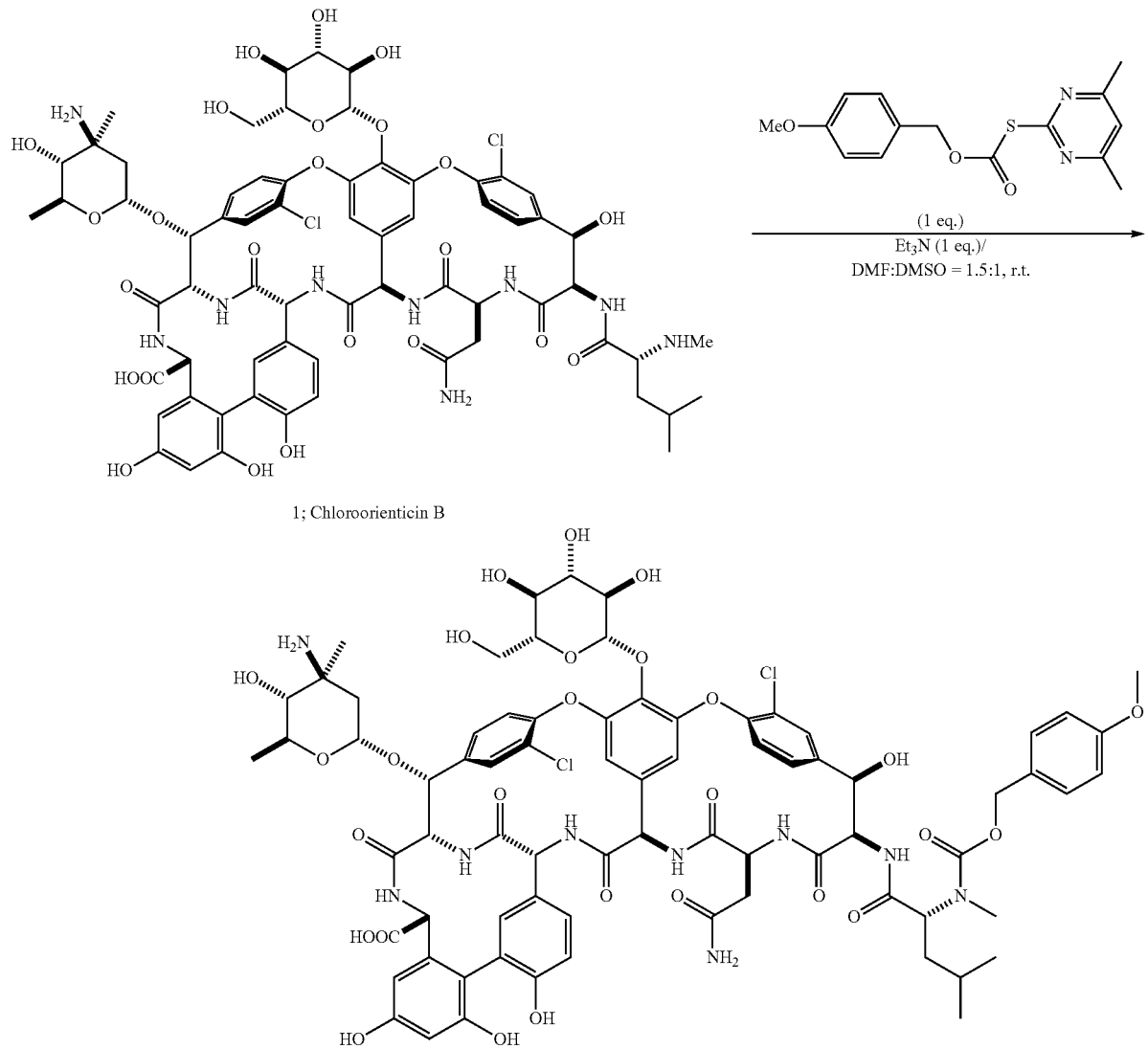

1; Chlooorienticin B

5

Under nitrogen gas stream, 20 g (12.4 mmol) of chloroorienticin B (compound 1) was dissolved in a mixed solvent of 150 mL of dimethylformamide and 1000 mL of dimethyl sulfoxide. Triethylamine (1.8 mL, 12.9 mmol) was added dropwise at room temperature, 3.93 g (12.9 mmol) of thiocarbonic acid (4,6-dimethyl-pyrimidin-2-yl)ester (4-methoxybenzyl) ester was added, and the mixture was stirred at room temperature for 45 hours. The reaction solution was concentrated under reduced pressure, and the remaining solution was poured into 1 L of cooled 5% aqueous sodium chloride solution. 1N hydrochloric acid was added to adjust to pH=3, and the mixture was stirred for 1 hour under ice-cooling. The produced precipitate was collected by filtration, dried, dissolved again in 100 mL of dimethyl sulfoxide, and poured into 1 L of cooled 5% aqueous sodium chloride solution. 1N hydrochloric acid was added to adjust to pH=3, and the mixture was stirred for 1 hour under ice-cooling. The produced precipitate was collected by filtration, washed with distilled water, and dried at room temperature for 3 days. The resulting crude solid was suspended in 400 mL of ethyl acetate, and stirred at room temperature for 2 hours, and the precipitate was collected by filtration, and dried to obtain 22.8 g (HPLC purity 89%) of compound 5 as a pale flesh-colored solid.

Second Step

Production of Intermediate Compound 6

[Chemical formula 80]

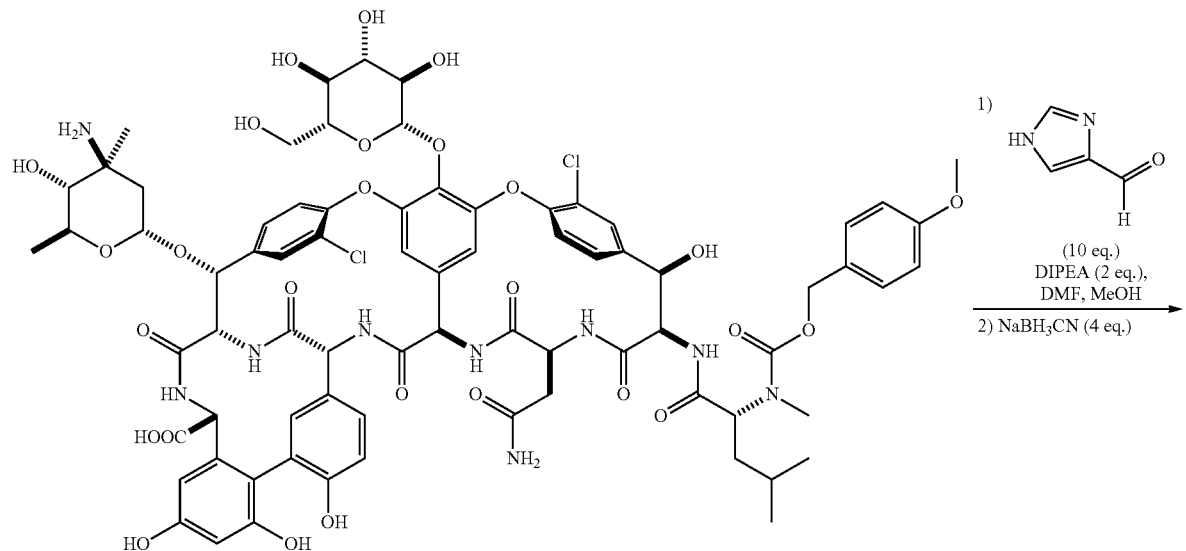

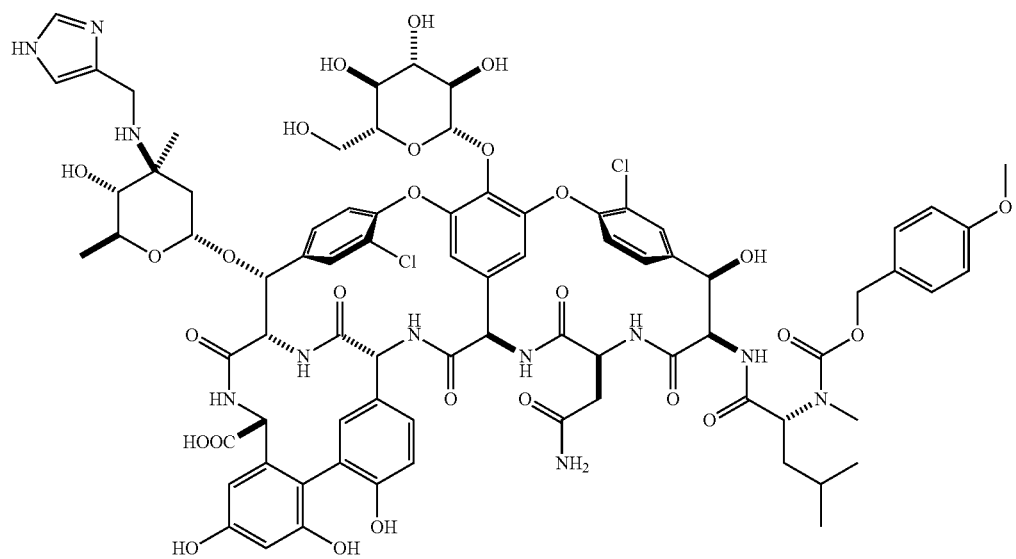

The compound 5 obtained in the first step (1 g, 0.62 mmol) was dissolved in a mixed solvent of 31 mL of dimethylformamide and 31 mL of methanol. 4-Formylimidazole (596 mg, 6.2 mmol), and 0.22 mL (1.24 mmol) of diisopropylethylamine were added sequentially, and the mixture was stirred at 70° C. for 2 hours. After the reaction mixture was cooled to room temperature, 156 mg (2.5 mmol) of sodium cyanoborohydride was added, and the mixture was stirred at 70° C. for 3 hours. Methanol in the reaction solution was distilled under reduced pressure, and the remaining solution was poured into cooled 10% aqueous sodium chloride solution. The produced precipitate was collected by filtration, and the resulting crude solid was washed with 5% aqueous sodium chloride solution to remove unreacted sodium cyanoborohydride. The washed solid was dried to obtain 869 mg (HPLC purity 73%, yield 60%) as a crude solid of compound 6.

Third Step

Production of Intermediate Compound 7

[Chemical formula 81]

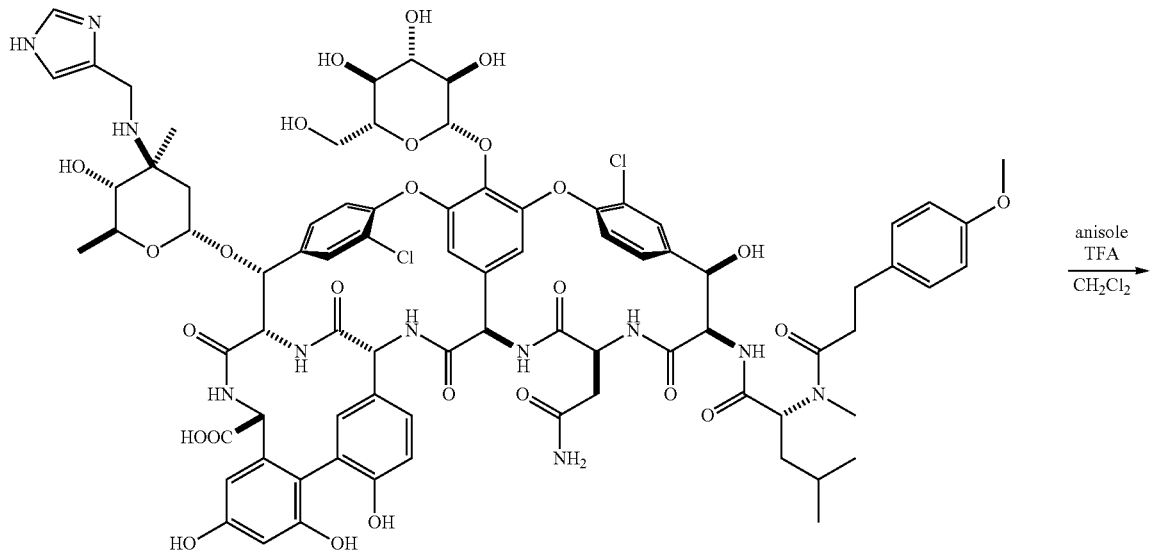

6

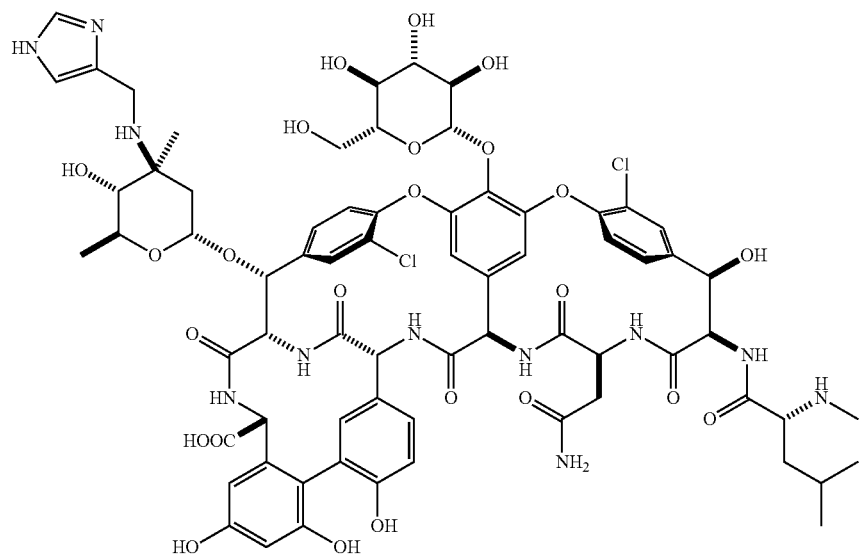

7

The crude solid of compound 6 obtained in the second step (869 mg, HPLC purity 73%, 0.375 mmol) was dissolved in 26 mL of dichloromethane, and the solution was cooled under ice-cooling. Anisole (1.4 mL) and 1.26 mL of trifluoroacetic acid were sequentially added dropwise, and the mixture was stirred for 2 hours under ice-cooling. The reaction solution was poured into ethyl acetate, the produced precipitate was collected by filtration, and the resulting crude solid was further washed with ethyl acetate. The washed solid was purified by reverse phase column chromatography to obtain 556 mg (yield 97%) of compound 7 as a colorless solid.

Fourth Step

Production of Intermediate Compound 8

[Chemical formula 82]

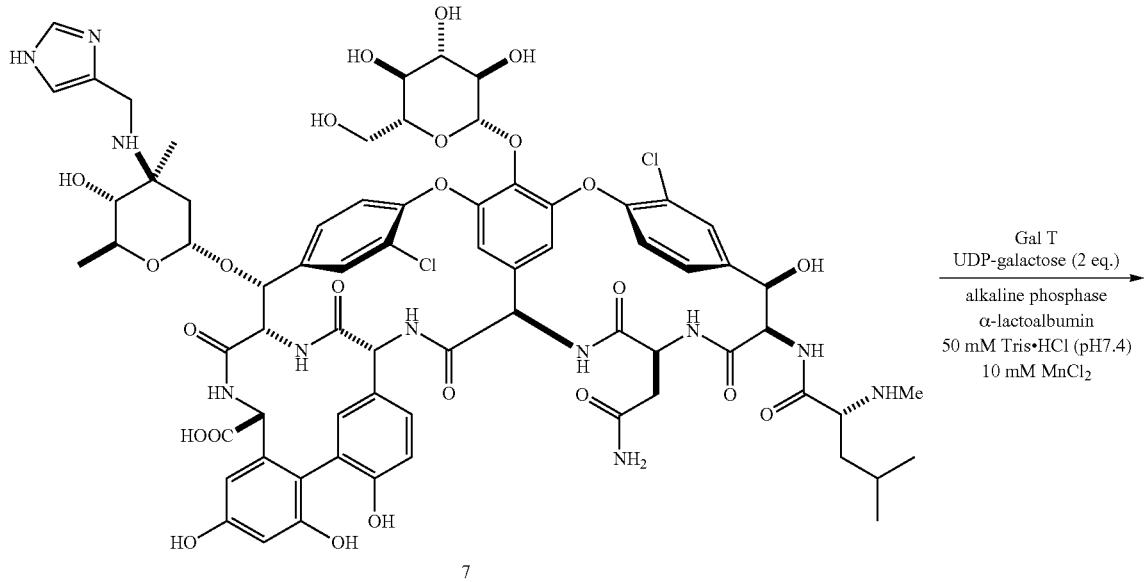

7

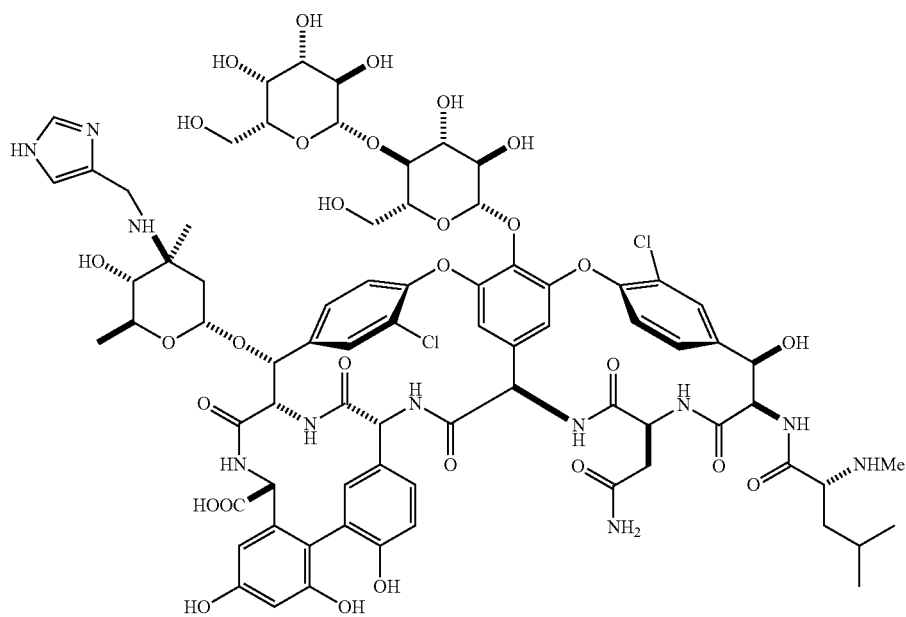

8

The compound 7 obtained in the third step (556 mg, 0.363 mmol) was dissolved in 37 mL of 50 mM Tris-HCl buffer (pH 7.4) containing 10 mM $MnCl_2$. 180 U of alkaline phosphatase (P6774 manufactured by Sigma), 18 mg of α-lactoalubumin, 443 mg (0.73 mmol) of UDP-galactose, and 18 U of human-derived β 1,4 galactosyltransferase (BGT401 manufactured by TOYOBO CO., LTD.) were sequentially added, and the mixture was stirred at 30° C. for 24 hours. The reaction mixture was loaded on a column filled with Diaion HP-20, and the column was washed with distilled water, and eluted with 50% aqueous acetonitrile solution containing 0.1% trifluoroacetic acid. The eluate was concentrated under reduced pressure, and the remaining aqueous solution was lyophilized to obtain 541 mg (yield 88%) of compound 8 as a colorless solid.

Fifth Step

Production of Intermediate Compound 9

[Chemical formula 83]

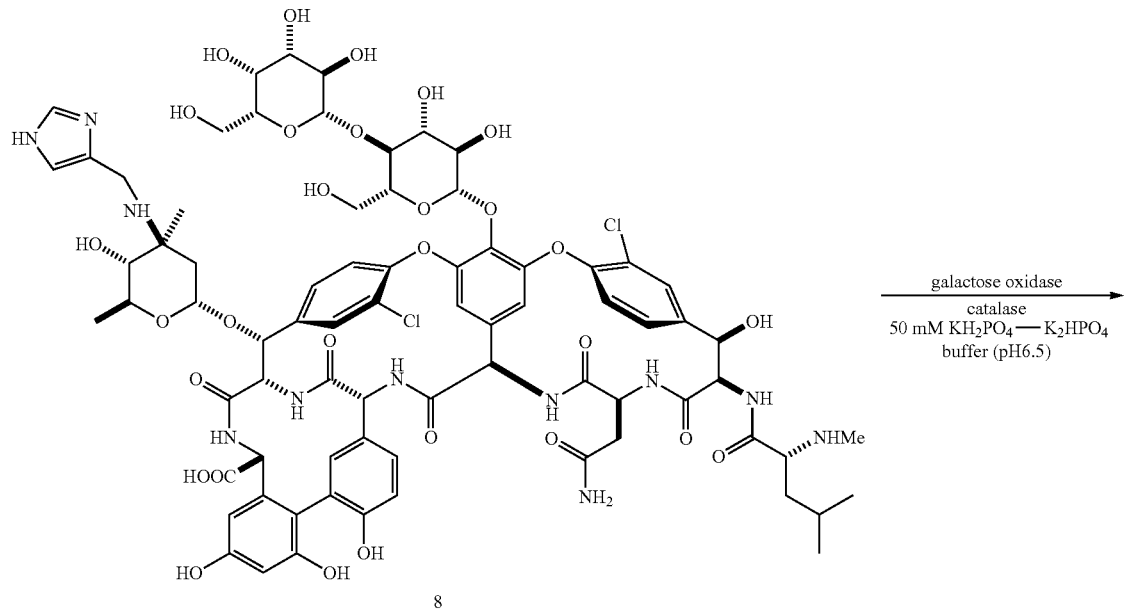

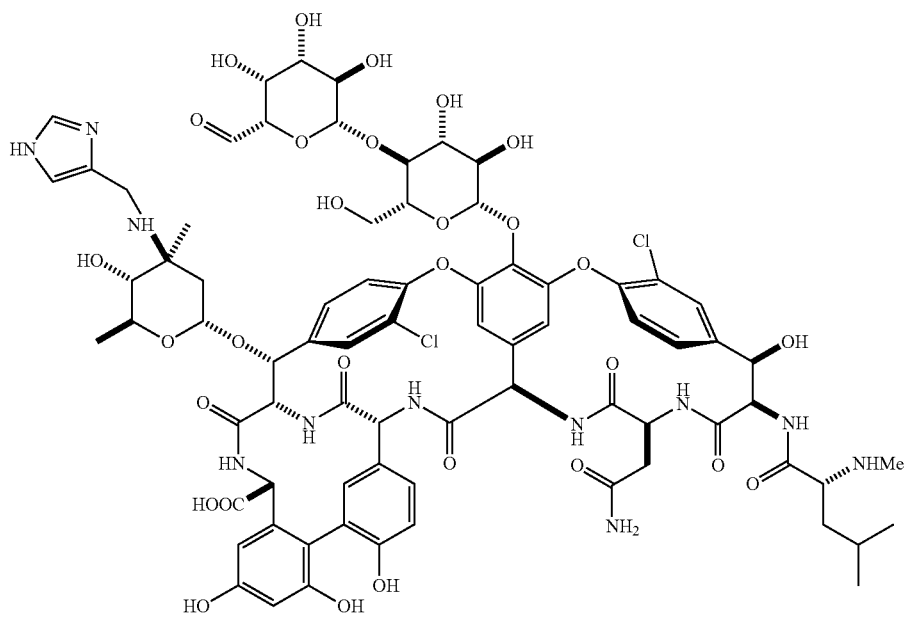

The compound 8 obtained by the fourth step (541 mg, 0.32 mmol) was dissolved in 95 mL of 50 mM $KH_2PO_4$—$K_2HPO_4$ buffer (pH 6.5). 500 KU of catalase (C30 manufactured by Sigma), and 5 KU of Dactylium dendroides-derived galactose oxidase (15996 manufactured by MP Biomedicals) were sequentially added, and the mixture was stirred for 25° C. for 48 hours. The reaction mixture was loaded on column filled with Diaion HP-20, and the column was washed with distilled water, and eluted with 30% aqueous acetonitrile solution containing 0.1% trifluoroacetic acid. The eluate was concentrated under reduced pressure, and the remaining aqueous solution was lyophilized to obtain 470 mg (yield 87%) of compound 9 as a colorless solid.

Sixth Step

Production of Intermediate Compound 11

[Chemical formula 84]

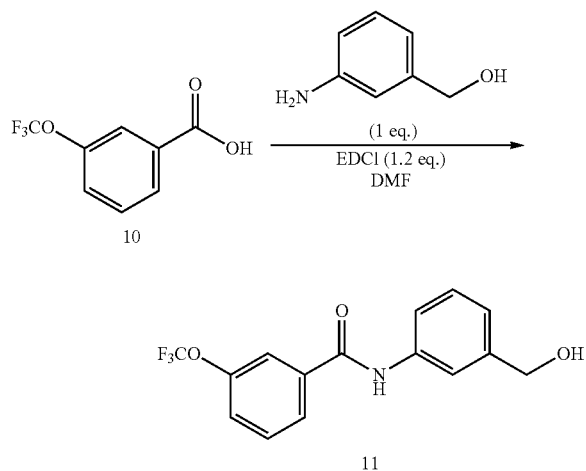

3-Trifluoromethoxybenzoic acid (compound 10) (3.58 g, 17.4 mmol), and 2.14 g (17.4 mmol) of 3-aminobenzyl alcohol were dissolved in 87 mL of dimethylformamide. N-ethyl-N'-(3-dimethylaminopropyl)carbodiimide hydrochloride (4 g, 20.9 mmol) was added, and the mixture was stirred at room temperature for 3 hours. The reaction mixture was poured into distilled water, this was extracted with ethyl acetate, and the extract was washed sequentially with 2N hydrochloric acid, aqueous saturated sodium bicarbonate solution, and aqueous saturated sodium chloride solution, and dried with anhydrous magnesium sulfate. After the desiccant was filtered, the filtrate was distilled under reduced pressure to obtain 3.94 g (yield 73%) of compound 11 as a colorless solid.

Seventh Step

Production of Intermediate Compound 12

[Chemical formula 85]

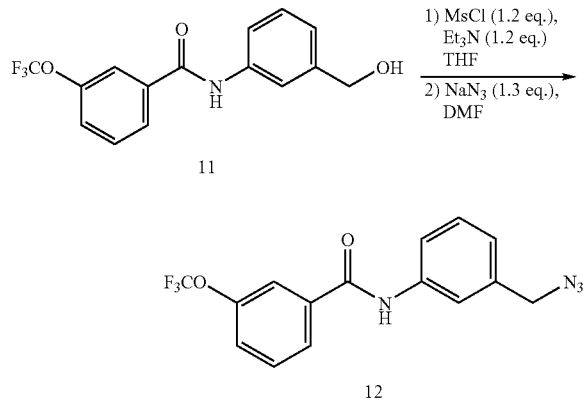

The compound 11 obtained in the sixth step (3.94 g, 12.7 mmol) was dissolved in 64 mL of tetrahydrofuran. Triethylamine (2.13 mL, 15.2 mmol), and 1.18 mL (15.2 mmol) of methanesulfonyl chloride were sequentially added dropwise, and the mixture was stirred at room temperature for 2 hours. The reaction mixture was poured into distilled water, and extracted with ethyl acetate, and the extract was washed with an aqueous saturated sodium chloride solution, and dried with anhydrous magnesium sulfate. After the desiccant was filtered, the filtrate was distilled under reduced pressure to obtain solid, which was dissolved in 64 mL of dimethylformamide. Sodium azide (1.07 g, 16.5 mmol) was added, and the mixture was stirred at 40° C. for 4 hours. The reaction mixture was poured into purified water, extracted with ethyl acetate, washed with aqueous saturated sodium chloride solution, and dried with anhydrous magnesium sulfate. The desiccant was filtered, and the filtrate was distilled under reduced pressure to obtain 4.1 g (yield 96%) of compound 12 as a colorless solid.

Eighth Step

Production of Intermediate Compound 13

[Chemical formula 86]

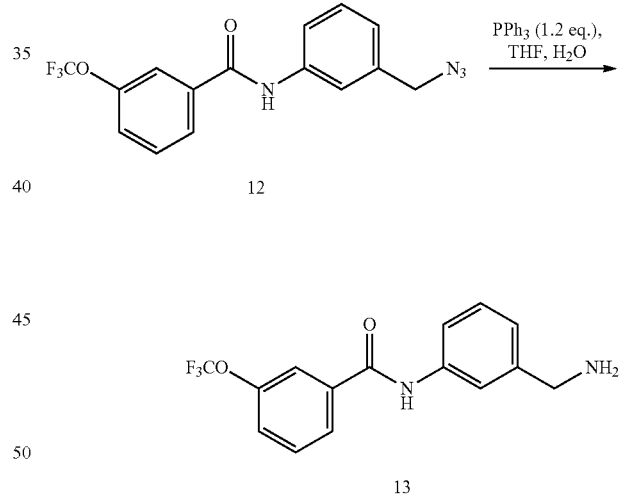

The compound 12 obtained in the seventh step (4.1 g, 12.2 mmol) was dissolved in mixed solvent of 45 mL of tetrahydrofuran and 15 mL of purified water. Triphenylphosphine (3.85 g, 14.6 mmol) was added, and the mixture was stirred at room temperature for 5 hours. The reaction mixture was poured into 4N hydrochloric acid, and the aqueous solution was washed with ethyl acetate, and adjusted with a 2N sodium hydroxide aqueous solution to pH=12. The aqueous solution was extracted with ethyl acetate, and the extract was dried with anhydrous magnesium sulfate. After the desiccant was filtered, the filtrate was distilled under reduced pressure to obtain 2.89 g (yield 76%) of compound 13 as a colorless solid.

Ninth Step

Production of Intermediate Compound 14

[Chemical formula 87]

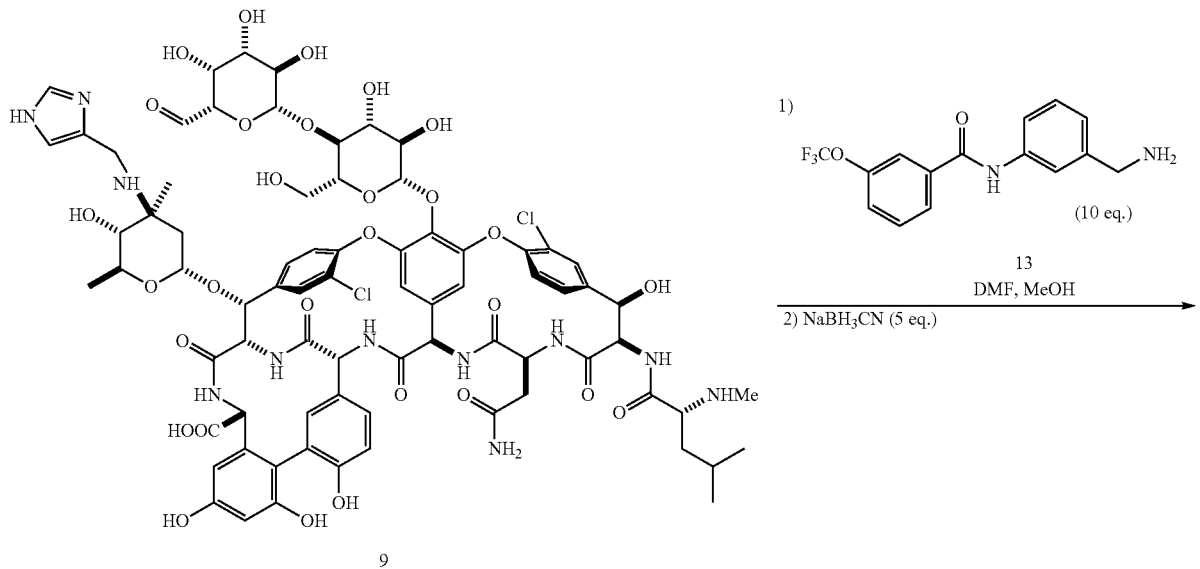

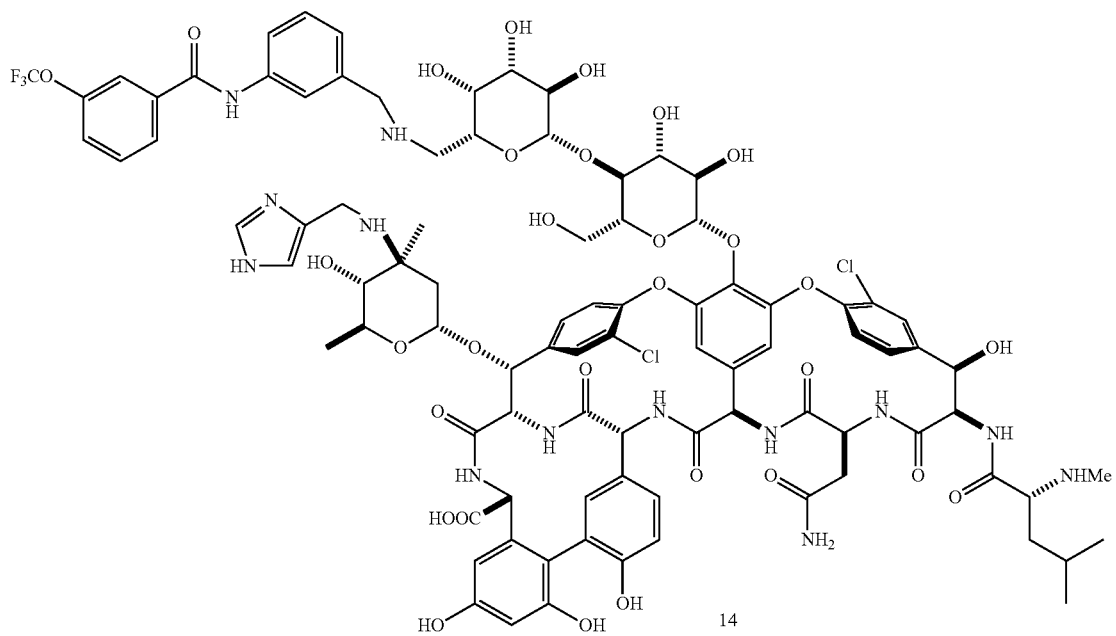

The compound 13 obtained in the eighth step (435 mg 1.4 mmol) was dissolved in mixed solvent of 20 mL of dimethylformamide and 60 mL of methanol. The compound 9 obtained in the fifth step (241 mg, 0.14 mmol) was added, and the mixture was stirred at room temperature for 3 hours. Sodium cyanoborohydride (45 mg, 0.72 mmol) was added, and the mixture was stirred at 70° C. for 3 hours. The reaction solutions was poured into diethyl ether, the produced precipitate was collected by filtration, and the resulting crude solid was washed with 5% aqueous sodium chloride solution to remove unreacted sodium cyanoborohydride. The resulting crude solid was purified by reveres phase column chromatography to obtain 52 mg (yield 18%) of compound 14 as a colorless solid.

Example 80

First Step

Production of Intermediate Compound 15

[Chemical formula 88]

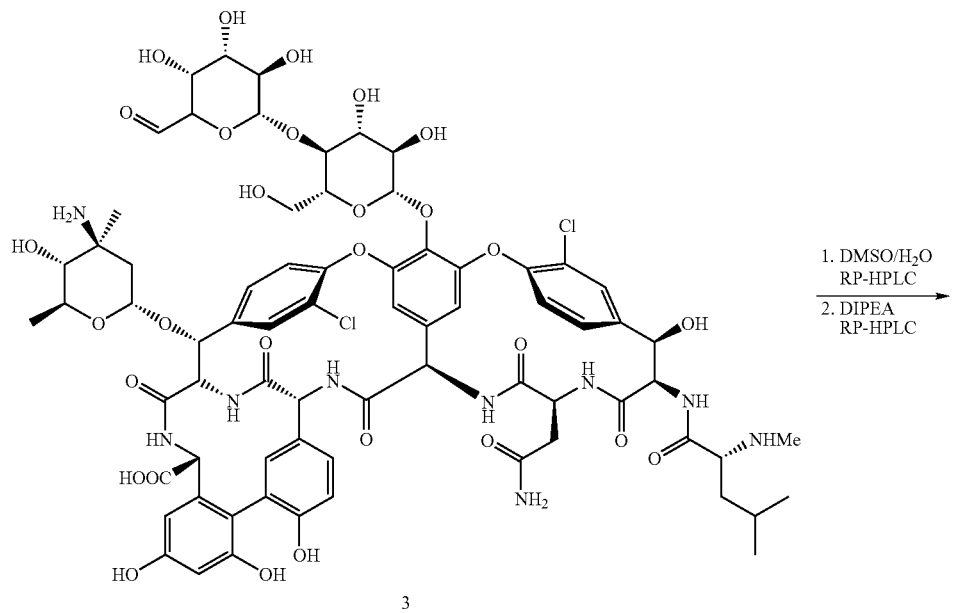

3

1. DMSO/H₂O
   RP-HPLC
2. DIPEA
   RP-HPLC

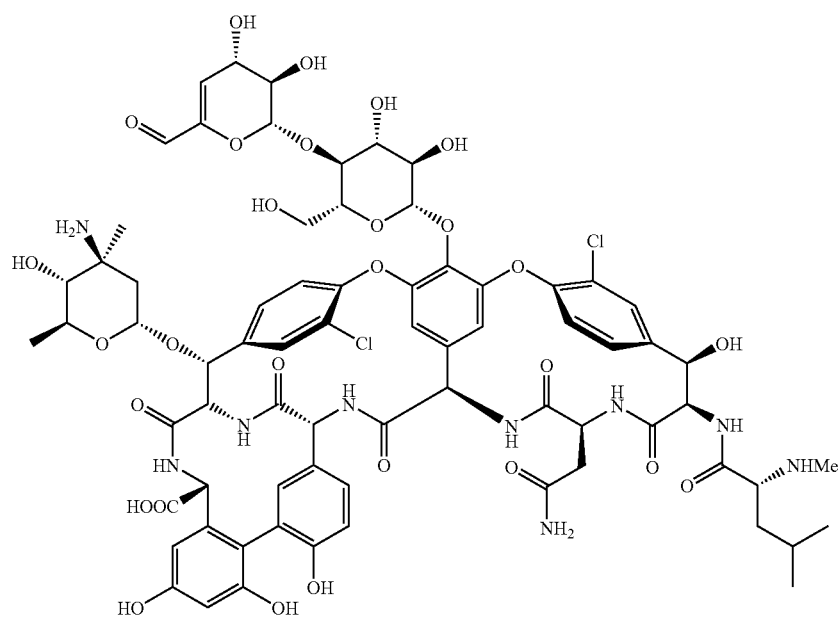

15

A compound 3 (547 mg, 0.34 mmol) which can be synthesized by the same procedure as that of Example 13 was dissolved in mixed solvent of 3 mL of dimethyl sulfoxide and 1 mL of water, and the solution was allowed to stand for 48 hours, and purified by reverse phase column chromatography to obtain crude purified compound 15 and unreacted compound 3.

Subsequently, the unreacted compound 3 was dissolved in 3 mL of water, 0.3 mL of diisopropylethylamine was added and this was allowed to stand for 8 hours, and purified by reverse phase column chromatography to obtain crude purified compound 15. The resulting crude purified compounds 15 were combined, and purified again by reverse phase column chromatography to obtain 189 mg (yield 35%) of compound 15 as a white powder.

Second Step

Production of Objective Compound 16

[Chemical formula 89]

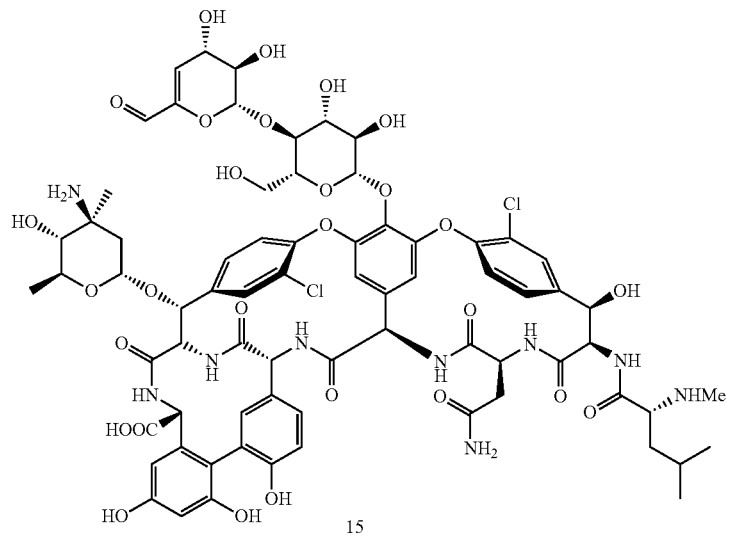

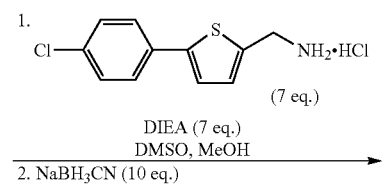

DIEA (7 eq.)
DMSO, MeOH
2. NaBH₃CN (10 eq.)

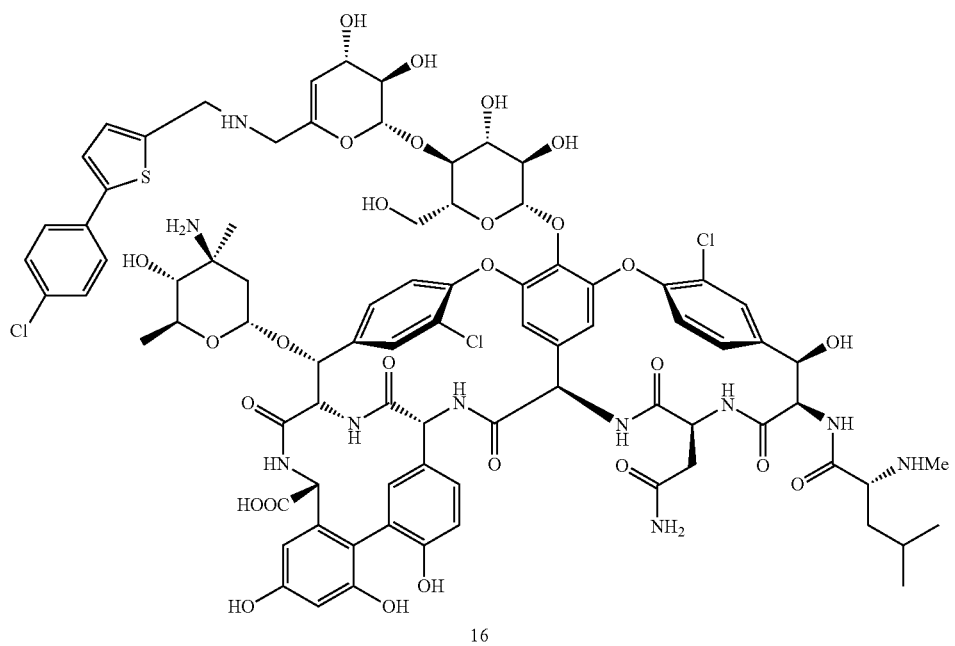

The compound 15 (248 mg, 0.156 mmol) was dissolved in mixed solvent of 7.2 mL of dimethyl sulfoxide and 7.2 mL of methanol, 273 mg (1.05 mmol) of (5-(4-chlorophenyl)thiophen-2-yl)methaneamine hydrochloride and diisopropylamine (1.05 mmol) were added, and mixture was stirred at room temperature for 1.5 hours. Then, 94 mg (1.50 mmol) of sodium cyanoborohydride was added, and the mixture was stirred at 70° C. for 2 hours. The reaction solution poured into ethyl acetate at room temperature. The produced precipitate was collected by filtration, and the resulting crude solid was washed with aqueous saturated sodium chloride solution. The resulting crude solid was purified by reverse phase column chromatography to obtain 13 mg (yield 5%) of compound 16 as a white powder.

Example 117

First Step

Production of Intermediate Compound 17

[Chemical formula 90]

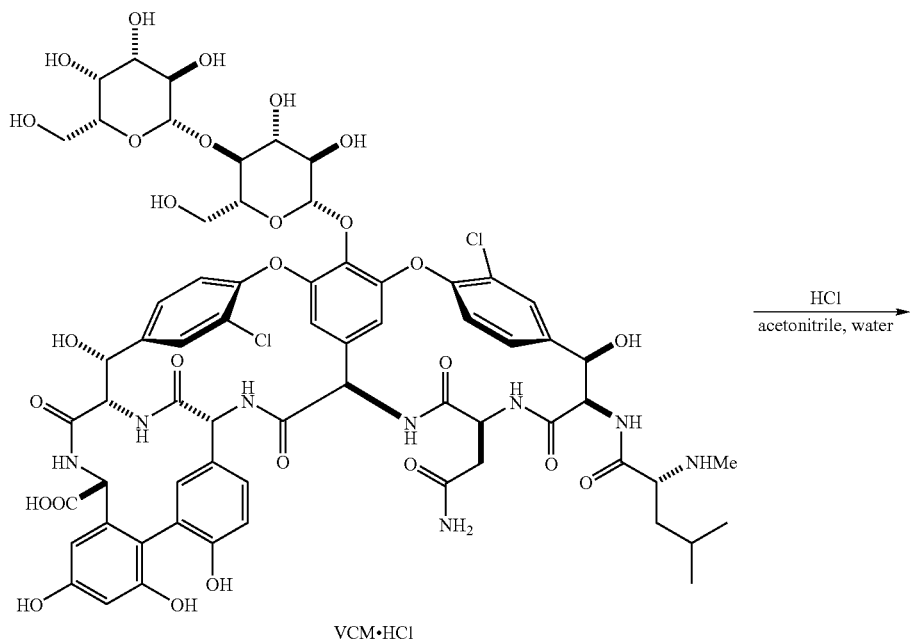

VCM·HCl

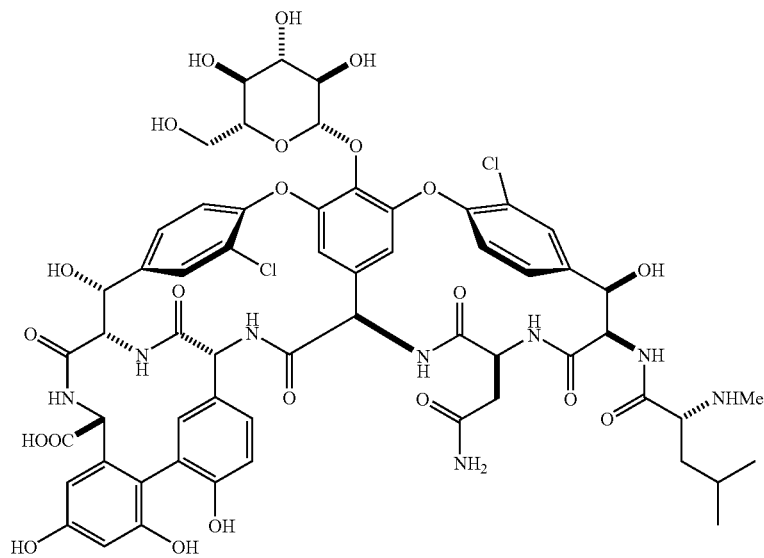

17

Vancomycin hydrochloride (50 g, 33.7 mmol) was dissolved in mixed solvent of 100 mL of acetonitrile and 750 mL of distilled water. Concentrated hydrochloric acid 250 mL was added, and the mixture was stirred at 45° C. for 1 hour. The precipitated solid was purified by HP20SS reverse phase column chromatography to obtain 16.5 g (yield 37.5%) of compound 17 as a colorless solid.

Second Step
Production of Intermediate Compound 18
[Chemical formula 91]
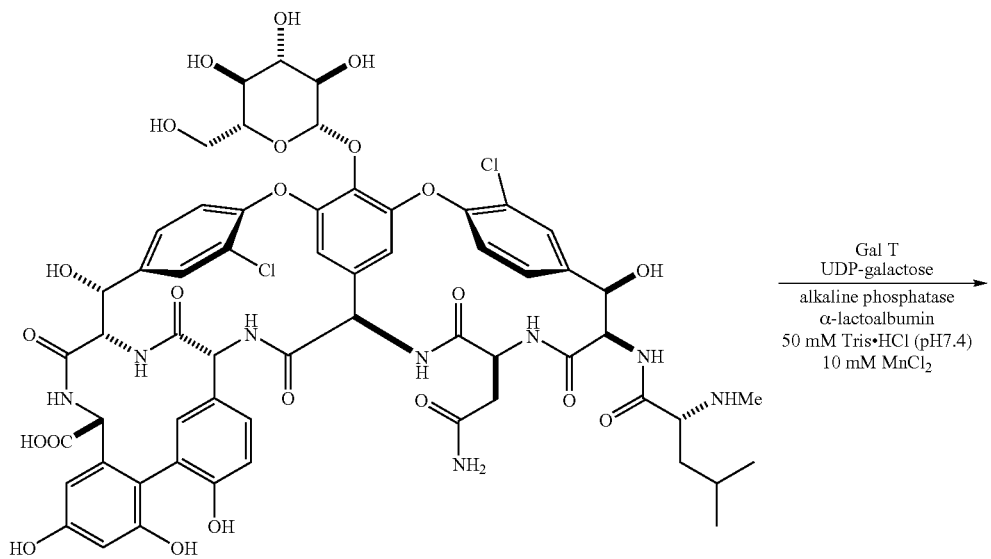
17
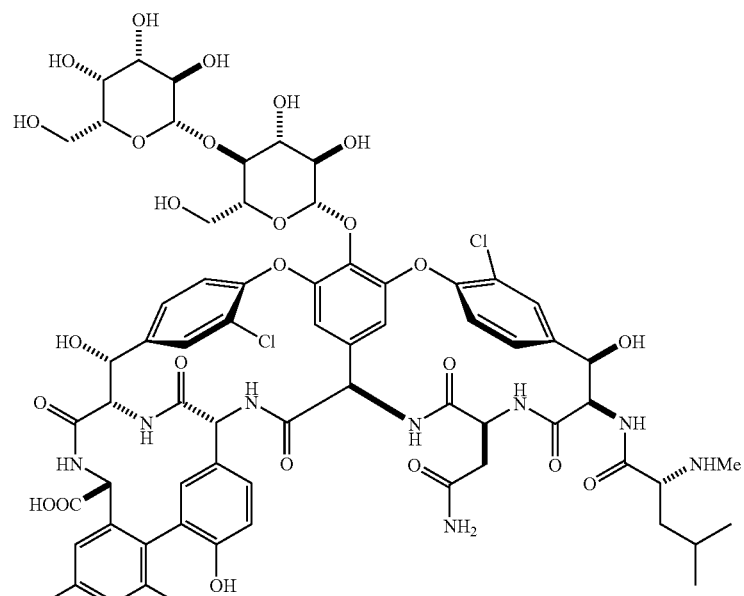
18
The compound 17 (40 mg, 0.031 mmol) was reacted by the same procedure as that of Example 13 to obtain 25 mg (yield 55.6%) of compound 18 as a colorless solid.

Third Step

Production of Intermediate Compound 19

[Chemical formula 92]

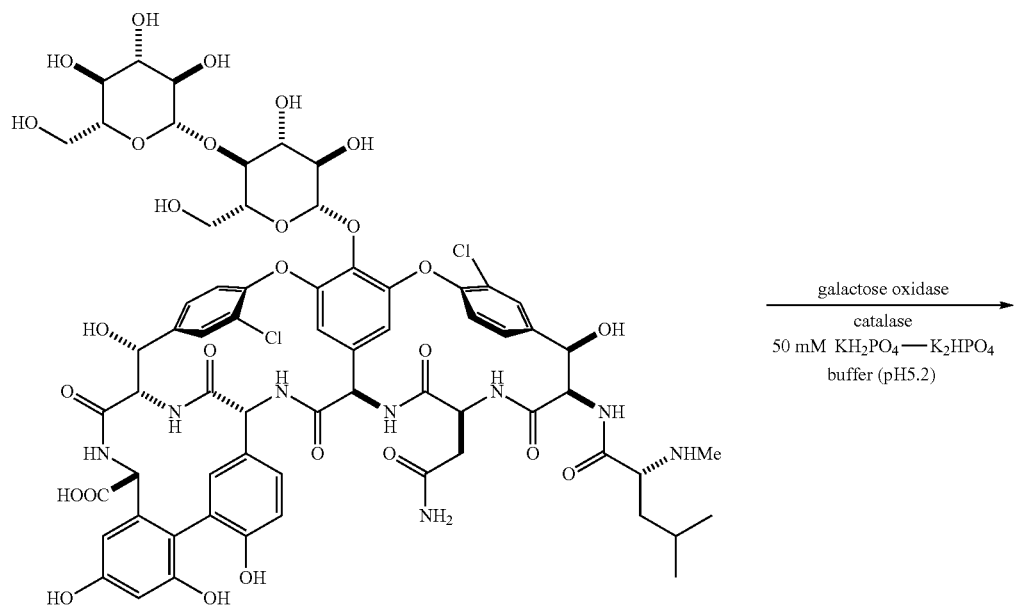

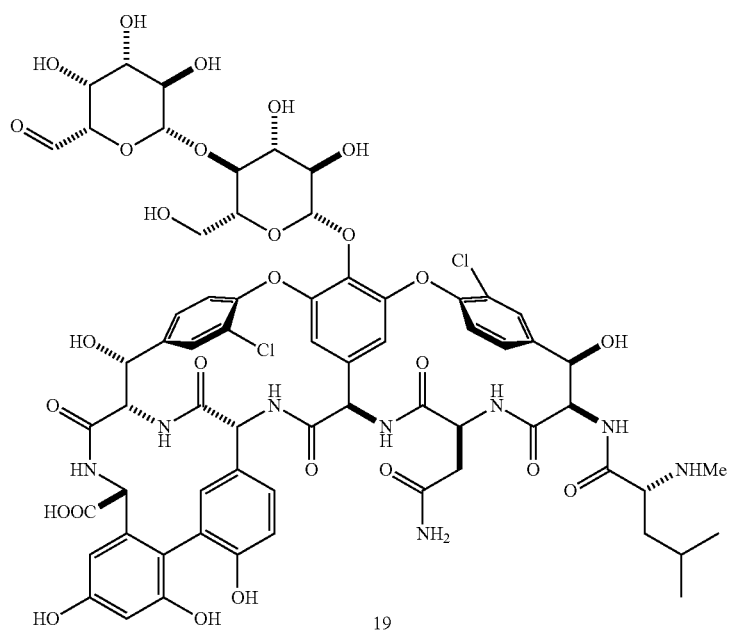

The compound 18 (300 mg, 0.204 mmol) was dissolved in 90 mL of 50 mM $KH_2PO_4$—$K_2HPO_4$ buffer (pH 5.2). Catalase, and Dactylium dendroides-derived galactose oxidase were sequentially added, and the mixture was stirred at 30° C. for 24 hours. The reaction mixture was purified by HP20SS reverse phase column chromatography to obtain 262 mg (yield 87%) of compound 19 as a white powder.

Fourth Step

Production of Objective Compound 20

[Chemical formula 93]

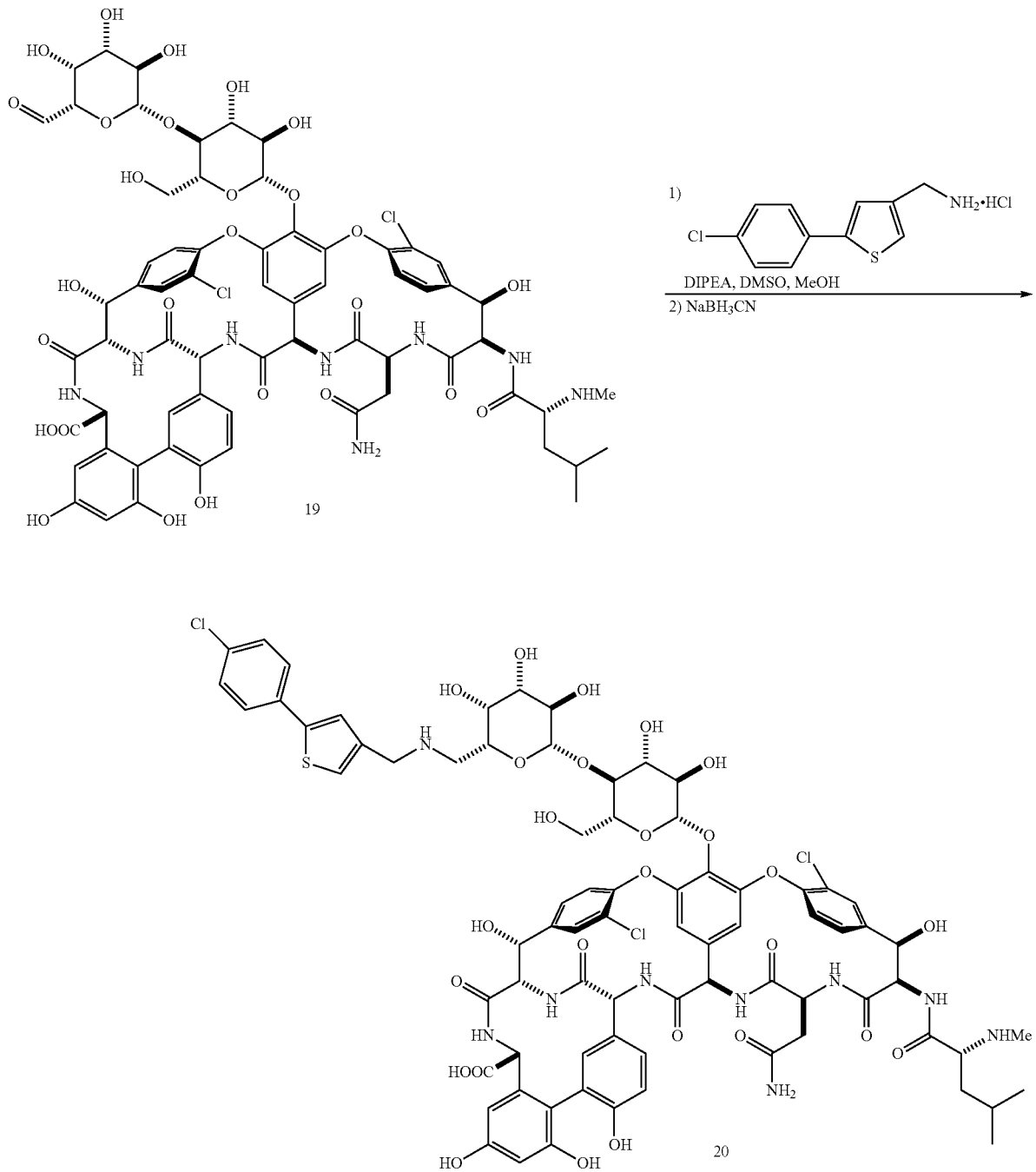

The compound 19 (350 mg, 0.24 mmol) was dissolved in mixed solvent of 10 mL of dimethyl sulfoxide and 10 mL of methanol. To this solution were added 435 mg (1.7 mmol) of (5-(4-chlorophenyl)thiophen-3-yl)methaneamine hydrochloride, and 0.29 mL (1.7 mmol) of diisopropylethylamine, and the mixture was stirred at room temperature for 2 hours. Sodium cyanoborohydride (167 mg, 2.4 mmol) was added, and the mixture was stirred at 70° C. for 1 hour. After methanol in the reaction solution was distilled off under reduced pressure, the remaining solution was poured into ethyl acetate, then the produced precipitate was collected by filtration, and the resulting crude solid was rinsed with 10% aqueous sodium chloride solution. The resulting crude solid was purified by reverse phase column chromatography to obtain 115 mg (yield 29%) of compound 20 as a colorless solid.

Synthesis Example 121
First Step
Production of Intermediate Compound 21
[Chemical formula 94]
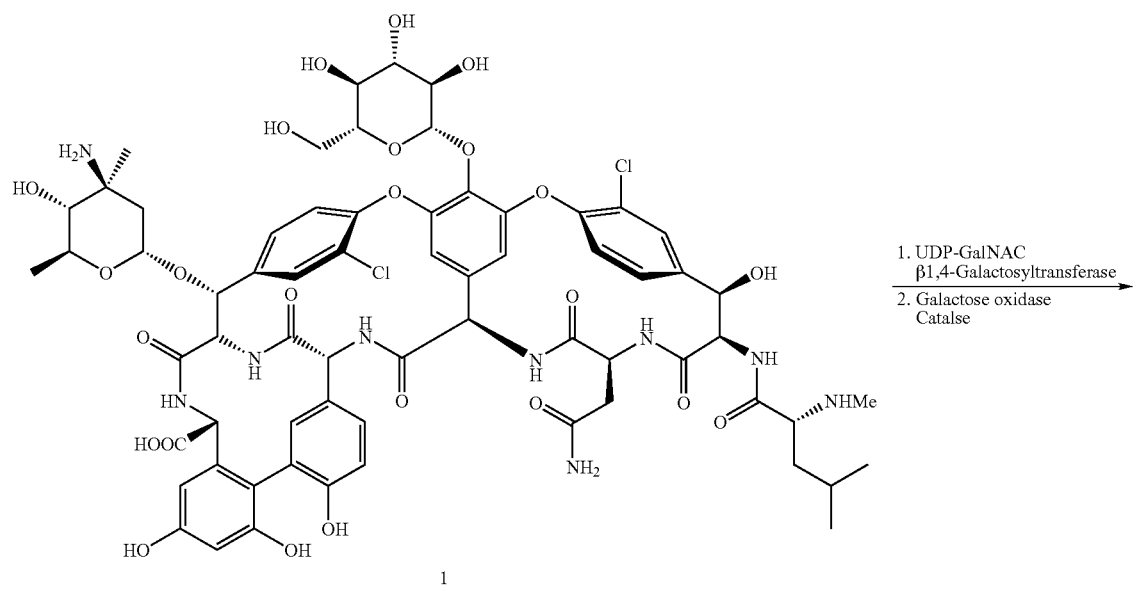
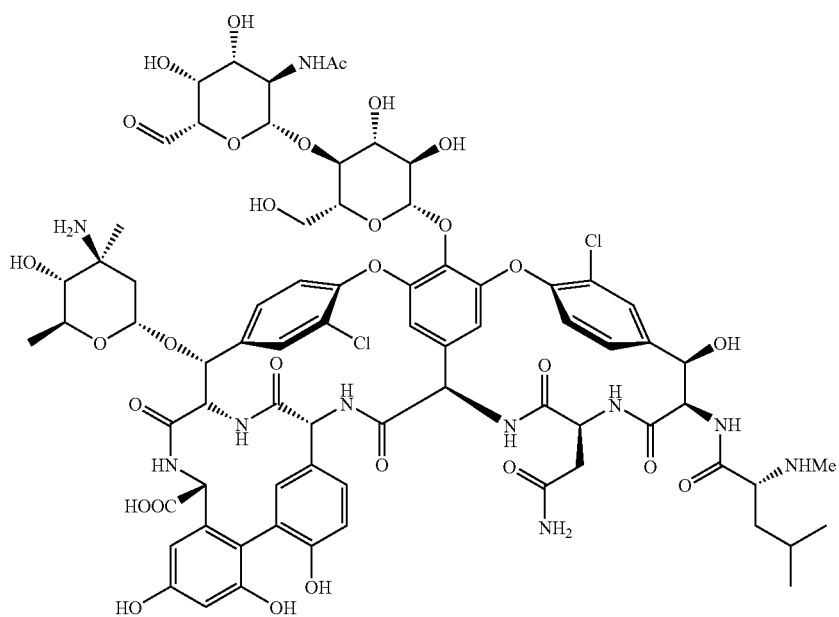
Synthesis was performed according to the same procedure like Example 13, and 592 mg (HPLC purity 65%, yield 56%) of mixture containing compound 21 and unreacted compound 1 was obtained from 600 mg (0.41 mmol) of compound 1 as a raw material.

Second Step

Synthesis of Objective Compound 22

[Chemical formula 95]

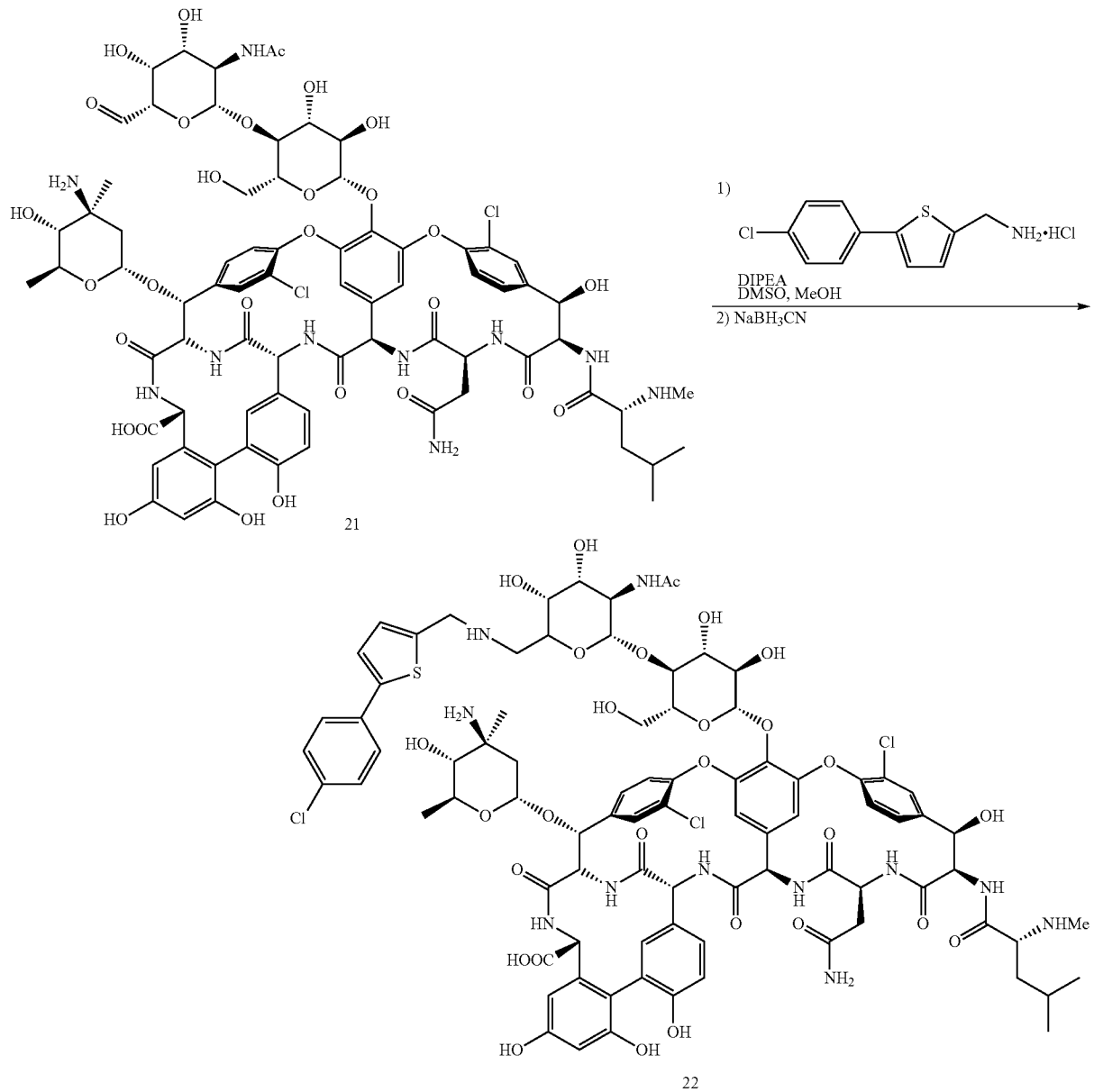

Synthesis was performed according to the same procedure like Example 13, and 80.2 mg (0.043 mmol, yield 36%) of compound 22 as a white powder was obtained from 300 mg (HPLC purity 65%, 0.118 mmol) of mixture containing compound 21 as a raw material.

Test Example 1

In Vitro Measurement of Antibacterial Activity (Test Method)
Some of the present compounds were measured for a minimum growth inhibition concentration (MIC) by a small amount of liquid dilution method using a cation-adjusted Muller Hinton liquid medium well-known to a person skilled in the art.

(Result)
The present compounds exhibited the high antibacterial activity against various bacterium including vancomycin-resistant bacterium. Particularly, compounds of Examples 1, 5, 6, 10, 11, 13, 30, 31, 43, 45, 50, 65, 69, 75, 82, 83, 85 and 88 had MIC: 2 to 4 µg/ml against E. faecalis SR7914 which is vancomycin-resistant Enterococcus (VRE VanA), and MIC: 1 to 4 µg/ml (vancomycin is >64 µg/ml) against E. faecium SR7940, and exhibited the remarkably higher activity than the existing drugs.

PREPARATION EXAMPLE

Following Preparation Examples 1 to 8 are illustrative, and are not meant to limit the scope of the invention at all. The term "active ingredient" means the present compound, a tautomer thereof, a prodrug thereof, a pharmaceutically acceptable salt thereof, or a solvate thereof.

Preparation Example 1

A hard gelatin capsule is produced using the following ingredients

|  | Dose (mg/capsule) |
| --- | --- |
| Active ingredient | 250 |
| Starch (dry) | 200 |
| Magnesium stearate | 10 |
| Total | 460 mg |

Preparation Example 2

A tablet is produced using the following ingredients:

|  | Dose (mg/tablet) |
| --- | --- |
| Active ingredient | 250 |
| Cellulose (microcrystalline) | 400 |
| Silicon dioxide (fumed) | 10 |
| Stearic acid | 5 |
| Total | 665 mg |

Ingredients are mixed, and compressed into a tablet of a weight of 665 mg.

Preparation Example 3

An aerosol solution containing the following ingredients is produced:

|  | Weight |
| --- | --- |
| Active ingredient | 0.25 |
| Ethanol | 25.75 |
| Propellant 22 (chlorodifluoromethane) | 74.00 |
| Total | 100.00 |

An active ingredient and ethanol are mixed, this mixture is added to a part of a propellant 22, and this is cooled to −30° C., and then is transferred to a filling apparatus. Then, a required amount is supplied to a stainless steel container, and this is diluted with a remaining propellant. A valve unit is attached to a container.

Preparation Example 4

A tablet containing 60 mg of an active ingredient is produced as follows:

| Active ingredient | 60 mg |
| --- | --- |
| Starch | 45 mg |
| Microcrystalline cellulose | 35 mg |
| Polyvinylpyrrolidone (10% solution in water) | 4 mg |
| Sodium carboxymethylstarch | 4.5 mg |
| Magnesium stearate | 0.5 mg |
| Talc | 1 mg |
| Total | 150 mg |

An active ingredient, starch and cellulose are applied to a sieve of No. 45 mesh U.S., and are mixed well. An aqueous solution containing polyvinylpyrrolidone is mixed with the resulting powder and, then, the mixture is passed through a No. 14 mesh U.S. sieve. The thus obtained granule is dried at 50° C., and passed through a No. 18 mesh U.S. sieve. Sodium carboxymethylstarch, magnesium stearate and talc which have been passed through a No. 60 mesh U.S. sieve in advance are added to this granule, and these are mixed, and compressed with a tabletting machine to obtain a tablet of a weight of 150 mg.

Preparation Example 5

A capsule containing 80 mg of an active ingredient is produced as follows:

| Active ingredient: | 80 mg |
| --- | --- |
| Starch | 59 mg |
| Microcrystalline cellulose | 59 mg |
| Magnesium stearate | 2 mg |
| Total | 200 mg |

An active ingredient, starch, cellulose and magnesium stearate are mixed, and passed through a No. 45 mesh U.S. sieve, and each 200 mg is filled into hard gelatin capsule.

Preparation Example 6

A suppository containing 225 mg of an active ingredient is produced as follows:

| Active ingredient | 225 mg |
| --- | --- |
| Saturated fatty acid glyceride | 2000 mg |
| Total | 2225 mg |

An active ingredient is passed through a No. 60 mesh U.S. sieve, and is suspended in saturated fatty acid glyceride which has been heated requisition-minimally and melted in advance. Then, this mixture is placed into a mold of apparently 2 g, and is cooled.

Preparation Example 7

A suspension containing 50 mg of an active ingredient is produced as follows:

| Active ingredient | 50 mg |
| --- | --- |
| Sodium carboxymethylcellulose | 50 mg |
| Syrup | 1.25 ml |

-continued

| | |
|---|---|
| Benzoic acid solution | 0.10 ml |
| Perfume | q.v. |
| Pigment | q.v. |
| Purified water ad. | 5 ml |

An active ingredient is applied to a sieve of No. 45 mesh U.S., and is mixed with sodium carboxymethylcellulose and a syrup to obtain a smooth paste. A benzoic acid solution and a perfume are diluted with a part or water and the mixture is stirred. Then, water is added at a sufficient amount to a required volume.

Preparation Example 8

A preparation for intravenous injection is produced as follows:

| | |
|---|---|
| Active ingredient | 100 mg |
| Saturated fatty acid glyceride | 1000 ml |

A solution of the ingredients is usually intravenously administered to a patient at a rate of 1 ml per 1 minute.

INDUSTRIAL APPLICABILITY

The glycopeptide derivative of the present invention, a pharmaceutically acceptable salt thereof and a solvate thereof are useful in medical treatment and exhibit the pharmacological activity including the antibacterial activity. The compound of the present invention is useful in treating infection caused by, particularly, meticillin-resistant *Staphylococcus aureus*. In addition, this compound is useful for treating infection with *Enterococcus* including vancomycin-resistant *Enterococcus* (VRE). As an example of such a disease, there is serious *staphylococcus* infection, for example, *staphylococcus* endocarditis and *staphylococcus* sepsis.

The invention claimed is:

1. A glycopeptide compound, or pharmaceutically acceptable salt thereof which is characterized in that a sugar residue (I) represented by the formula

[Chemical Formula 1]

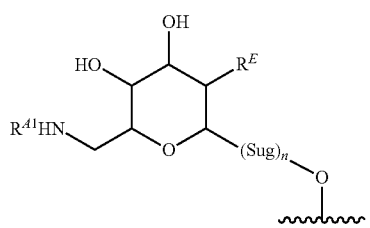

(I)

wherein n is an integer of t to 5;
Sugs are each independently a monosaccharide, $(Sug)_n$ is a divalent sugar residue formed by binding same or different i to 5 monosaccharides; $R^{41}$ is optionally substituted lower alkyl, optionally substituted lower alkenyl or optionally substituted cycloalkyl; and
$R^E$ is OH or NHAc (Ac is acetyl);
is bound to an aromatic ring of the fourth amino acid residue in a glycopeptide skeleton.

2. The glycopeptide compound, or pharmaceutically acceptable salt thereof according to claim 1, wherein the monosaccharide is selected from the group consisting of glucose, galactose, fructose, fucose, mannose, rhamnose, galactosamine, glucosamine, N-acetylgalactosamine, N-acetylglucosamine, vancosamine, epi-vancosamine, glucuronic acid, sialic acid, deoxyglucose, and deoxygalactose.

3. The glycopeptide compound, or pharmaceutically acceptable salt thereof according to claim 1, wherein the monosaccharide is glucose.

4. The glycopeptide compound, or pharmaceutically acceptable salt thereof according to any one of claims 1 to 3, wherein n is 1 or 2.

5. The glycopeptide compound, or pharmaceutically acceptable salt thereof according to claim 1, wherein the monosaccharide is glucose; and n is 1 or 2.

6. The glycopeptide compound, or pharmaceutically acceptable salt thereof according to claim 1, wherein the sugar residue (I) is a sugar residue (I-0) represented by the formula:

[Chemical Formula 2]

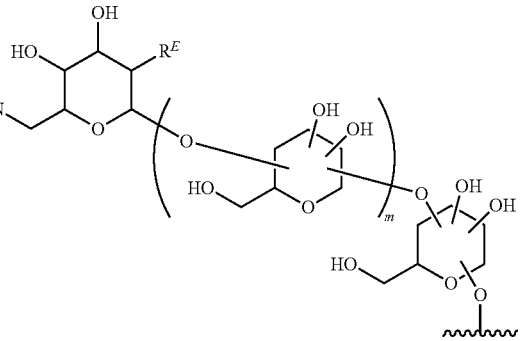

(I-0)

wherein
m is an integer of 0 to 4;
and Rm and RE are each as defined in claim 1.

7. The glycopeptide compound, or pharmaceutically acceptable salt thereof according to claim 1, wherein the sugar residue (I) is a sugar residue (I-1) represented by the formula:

[Chemical formula 3]

(I-1)

wherein
m is an integer of 0 to 4; and
$R^{41}$ and $R^E$ are each as defined in claim 1.

8. The glycopeptide compound, or pharmaceutically acceptable salt thereof according to claim 1, wherein the sugar residue (I) is a sugar residue (I-2) represented by the formula:

[Chemical formula 4]

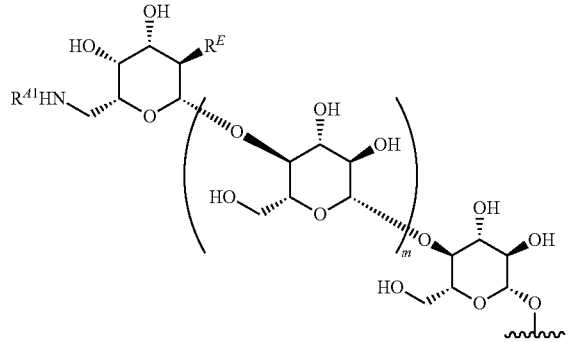

(I-2)

wherein
m is an integer of 0 to 4;
$R^{A1}$ and $R^E$ are each as defined in claim 1.

9. The glycopeptide compound, or pharmaceutically acceptable salt thereof according to any one of claims 1 to 3 or 5 to 8, wherein the compound has a partial structure (II) represented by the formula:

[Chemical formula 5]

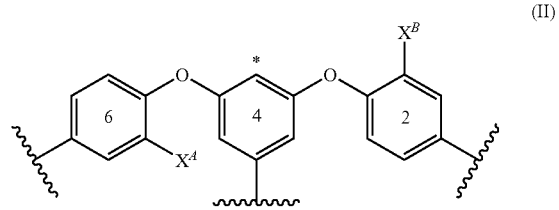

(II)

wherein the ring 2, the ring 4 and the ring 6 represent aromatic rings of the second, fourth and sixth amino acid residues of a glycopeptide antibiotic, respectively;

$X^A$ and $X^B$ each represent independently hydrogen or halogen; and

* represents a binding position with a sugar residue.

10. The glycopeptide compound, or pharmaceutically acceptable salt thereof according to claim 1, wherein the compound has a partial structure (III) represented by the formula;

[Chemical formula 6]

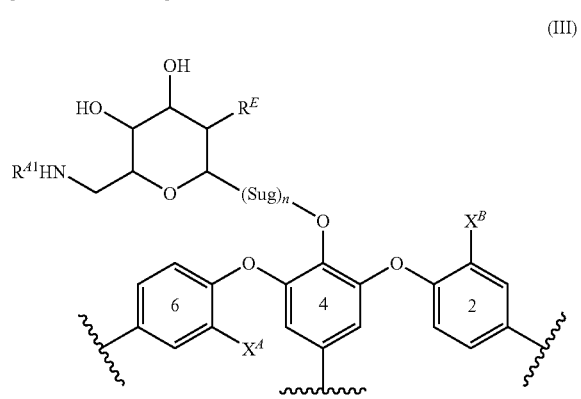

(III)

wherein
the ring 2, the ring 4 and the ring 6 represent aromatic rings of the second, fourth and sixth amino acid residues of a glycopeptide antibiotic, respectively;

$X^A$ and $X^B$ each represent independently hydrogen or halogen; and other symbols are each as defined in claim 1.

11. The glycopeptide compound, or pharmaceutically acceptable salt thereof according to claim 10, wherein the partial structure (III) is a partial structure (III-0) represented by the formula:

[Chemical formula 7]

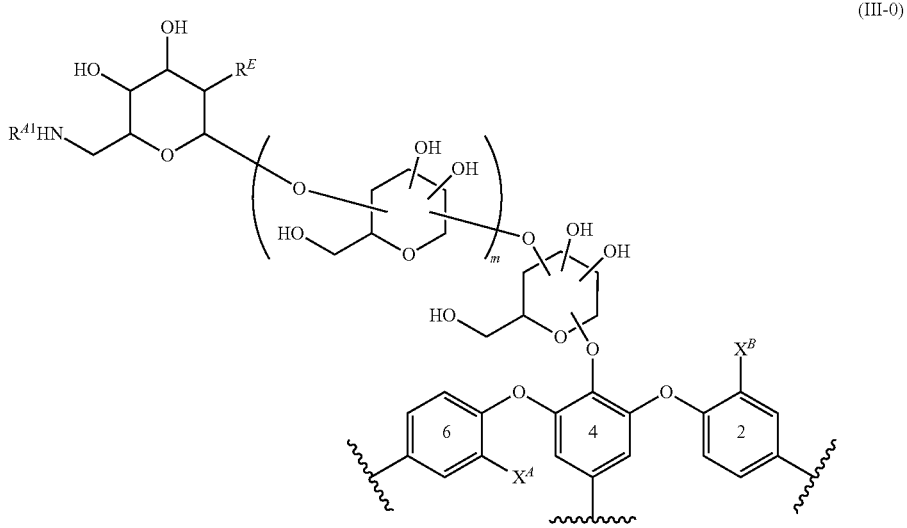

(III-0)

wherein the ring 2, the ring 4 and the ring 6 represent aromatic rings of the second, fourth and sixth amino acid residues of a glycopeptide antibiotic;

$X^A$ and $X^B$ each represent independently hydrogen or halogen;

m is an integer of 0 to 4.

12. The glycopeptide compound, or pharmaceutically acceptable salt thereof according to claim 10, wherein the partial structure (III) is a partial structure (III-1) represented by the formula:

[Chemical formula 8]

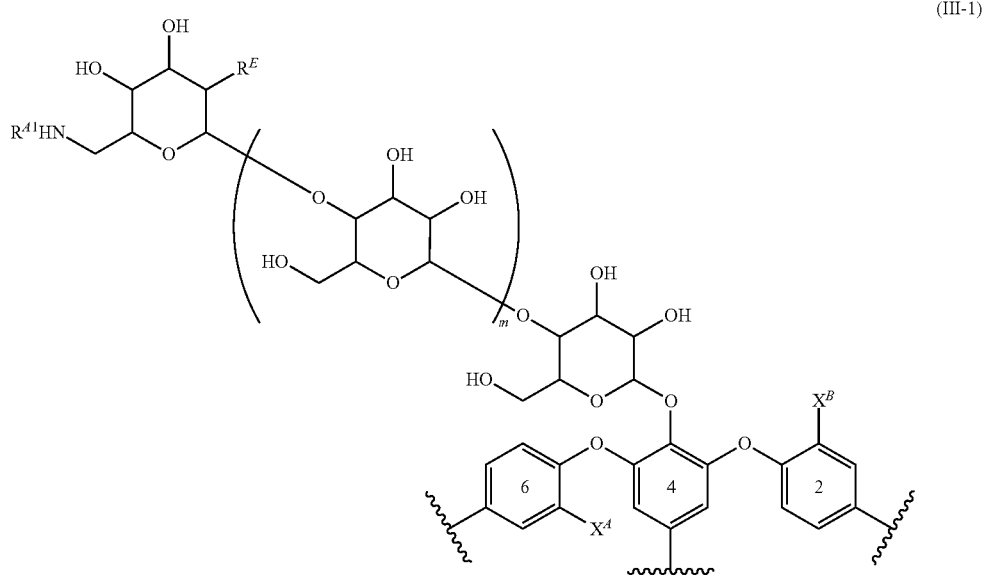

(III-1)

wherein
the ring 2, the ring 4 and the ring 6 represent aromatic rings of the second, fourth and sixth amino acid residue of a glycopeptides antibiotic, respectively;
$X^A$ and $X^B$ each represents independently hydrogen or halogen;
m is an integer of 0 to 4.

13. The glycopeptide compound, or pharmaceutically acceptable salt thereof according to claim 10, wherein the partial structure (III) is a partial structure (III-2) represented by the formula:

[Chemical formula 9]

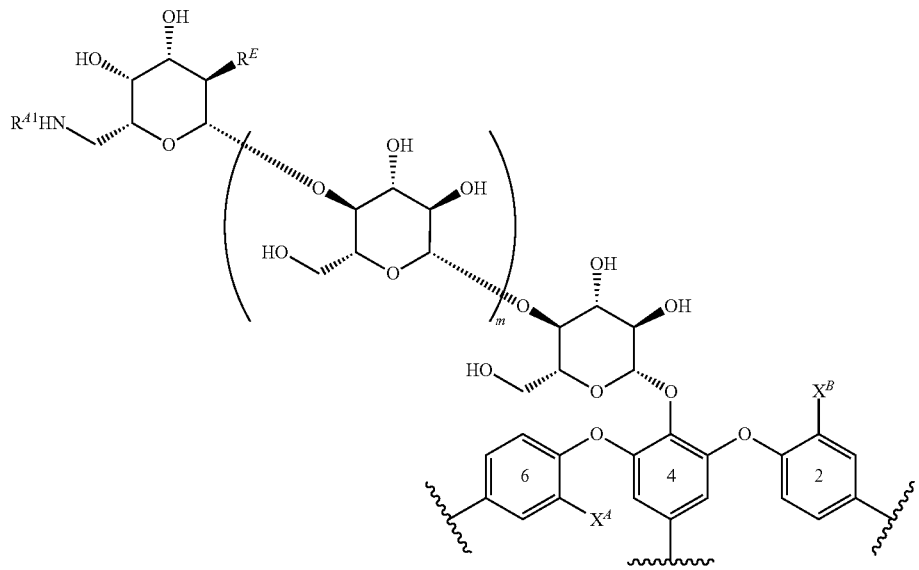

(III-2)

wherein the ring 2, the ring 4 and the ring 6 represent aromatic rings of the second, fourth and sixth amino acid residues of a glycopeptide antibiotic, respectively;

$X^A$ and $X^B$ each represent independently hydrogen or halogen;

m is an integer of 0 to 4.

14. The compound, or pharmaceutically acceptable salt thereof according to claim 1, wherein the compound is represented by the formula:

[Chemical formula 10]

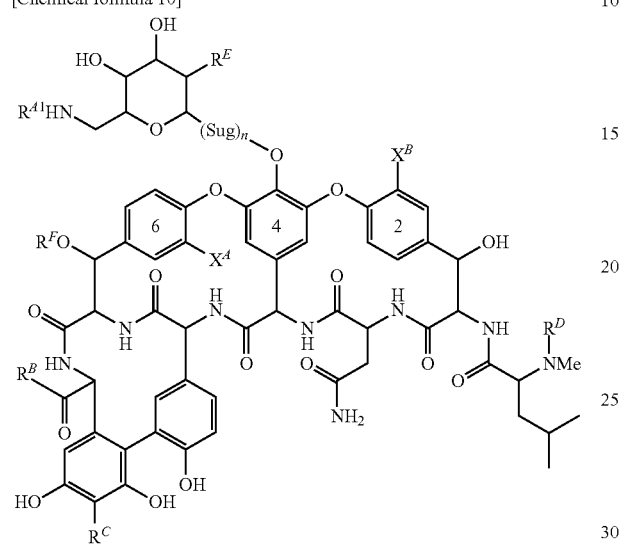

(IV)

wherein $R^F$ is hydrogen or a sugar residue;

$R^B$ is —OH, —NR$^5$R$^{5'}$ (wherein R$^5$ and R$^{5'}$ each are independently hydrogen, optionally substituted lower alkyl, optionally substituted lower alkyloxy, or optionally substituted amino or amino acid residue) or —OR$^6$ (wherein R$^6$ is optionally substituted lower alkyl (a hetero atom group may intervene in the lower alkyl part));

$R^C$ is hydrogen or optionally substituted alkyl (a hetero atom group may intervene in the lower alkyl part);

$R^D$ is hydrogen or lower alkyl; and other symbols are each as defined in claim 1.

15. The compound, or pharmaceutically acceptable salt thereof according to claim 14, wherein the compound is represented by the formula

[Chemical formula 11]

(IV-0)

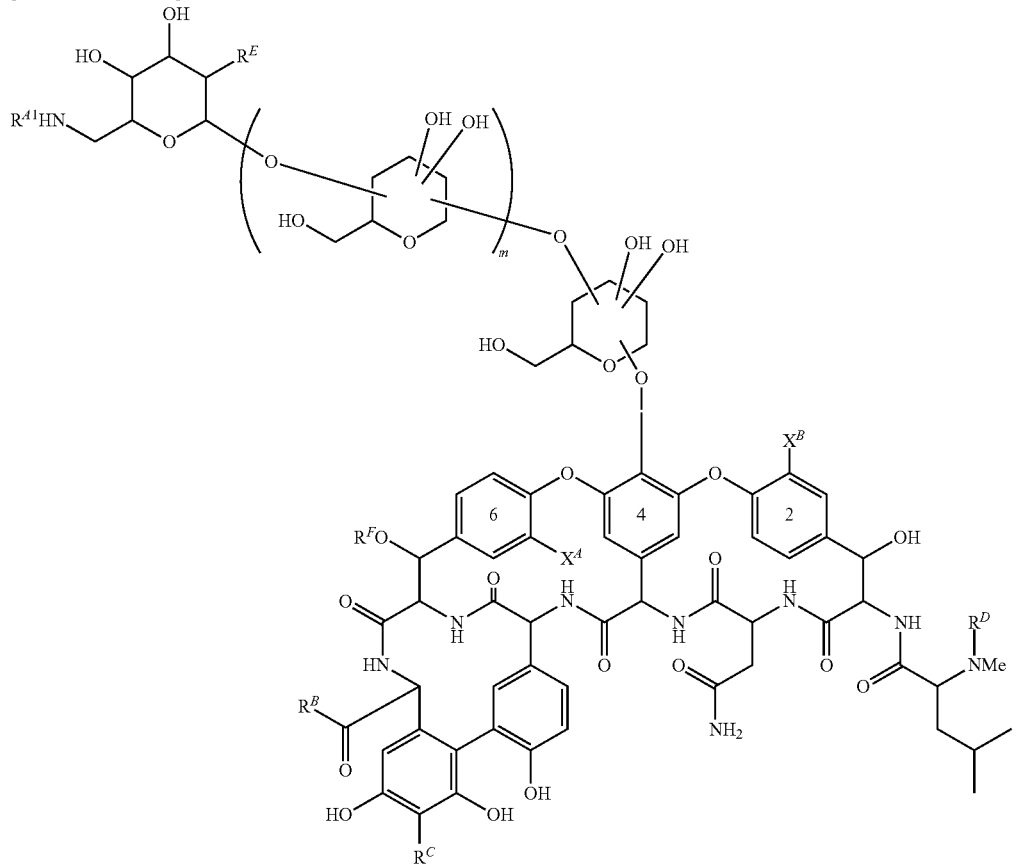

wherein
m is an integer of 0 to 4;
other symbols are each as defined in claim 14.

16. The compound, or pharmaceutically acceptable salt thereof according to claim 15, wherein the compound is represented by the formula:

[Chemical formula 12]

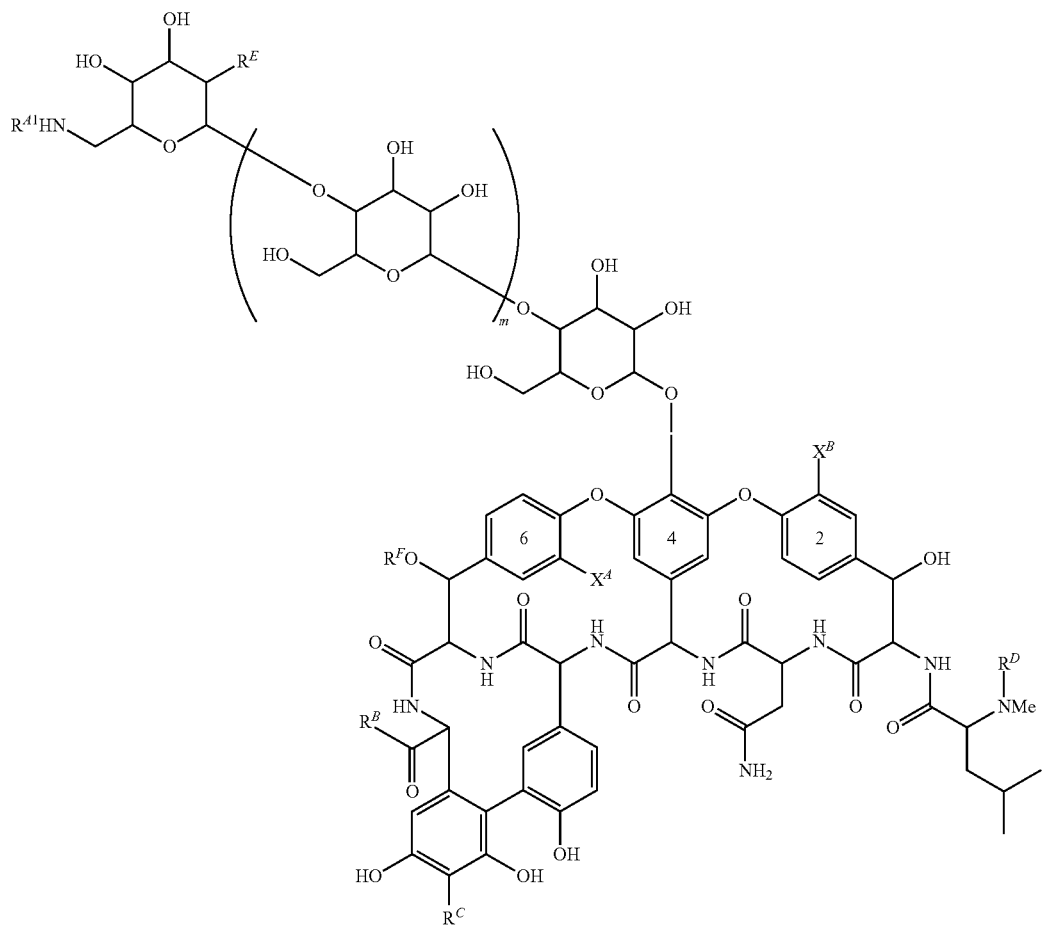

(IV-1)

wherein respective symbols are each as defined in claim 15.

17. The compound, or pharmaceutically acceptable salt thereof according to claim 15, wherein the compound is represented by the formula:

[Chemical formula 13]

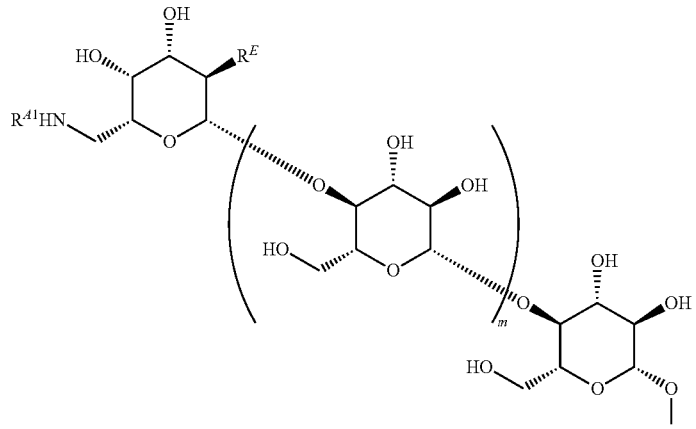

(IV-2)

-continued

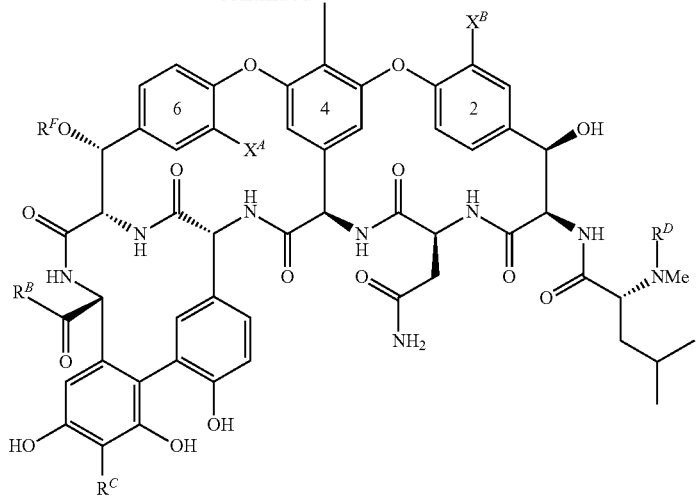

wherein
respective symbols are each as defined in claim 15.

18. The compound, or pharmaceutically acceptable salt thereof according to claim 1, wherein the compound is represented by the formula:

[Chemical formula 14]

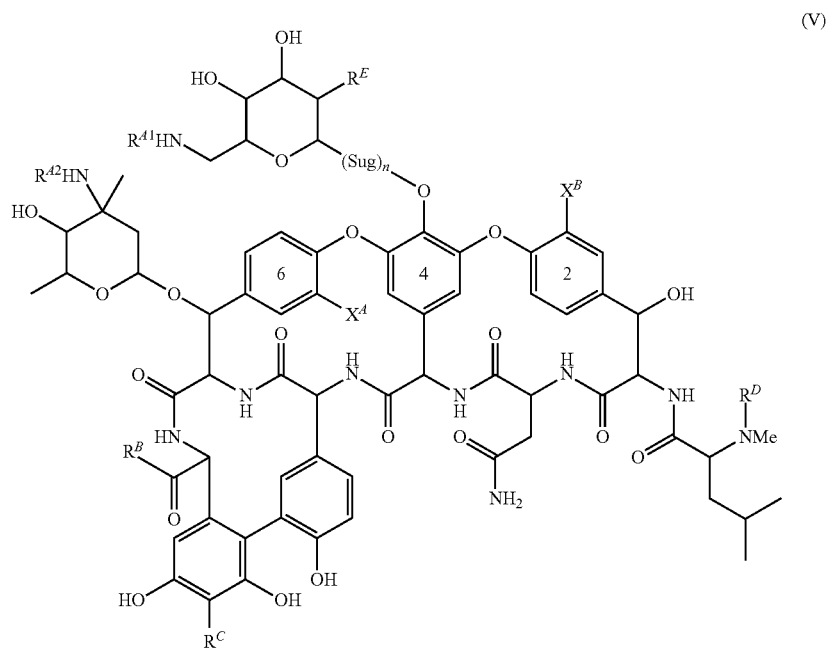

(V)

wherein $R^{42}$ is hydrogen or optionally substituted lower alkyl;

$R^B$ is —OH, —NR$^5$R$^{5'}$ (wherein R$^5$ and R$^{5'}$ each are independently hydrogen, optionally substituted lower alkyl, optionally substituted lower alkyloxy, optionally substituted amino or amino sugar residue) or —OR$^6$ (wherein R$^6$ is optionally substituted lower alkyl (a hetero atom group may intervene in the lower alkyl part));

$R^c$ is hydrogen or optionally substituted lower alkyl (a hetero atom group may intervene in the lower alkyl part);

$R^D$ is hydrogen or lower alkyl;

$X^A$ and $X^B$ each are independently hydrogen or halogen; and other symbols are each as defined in claim 1.

19. The compound, or pharmaceutically acceptable salt thereof according to claim 18, wherein the compound is represented by the formula:

[Chemical formula 15]
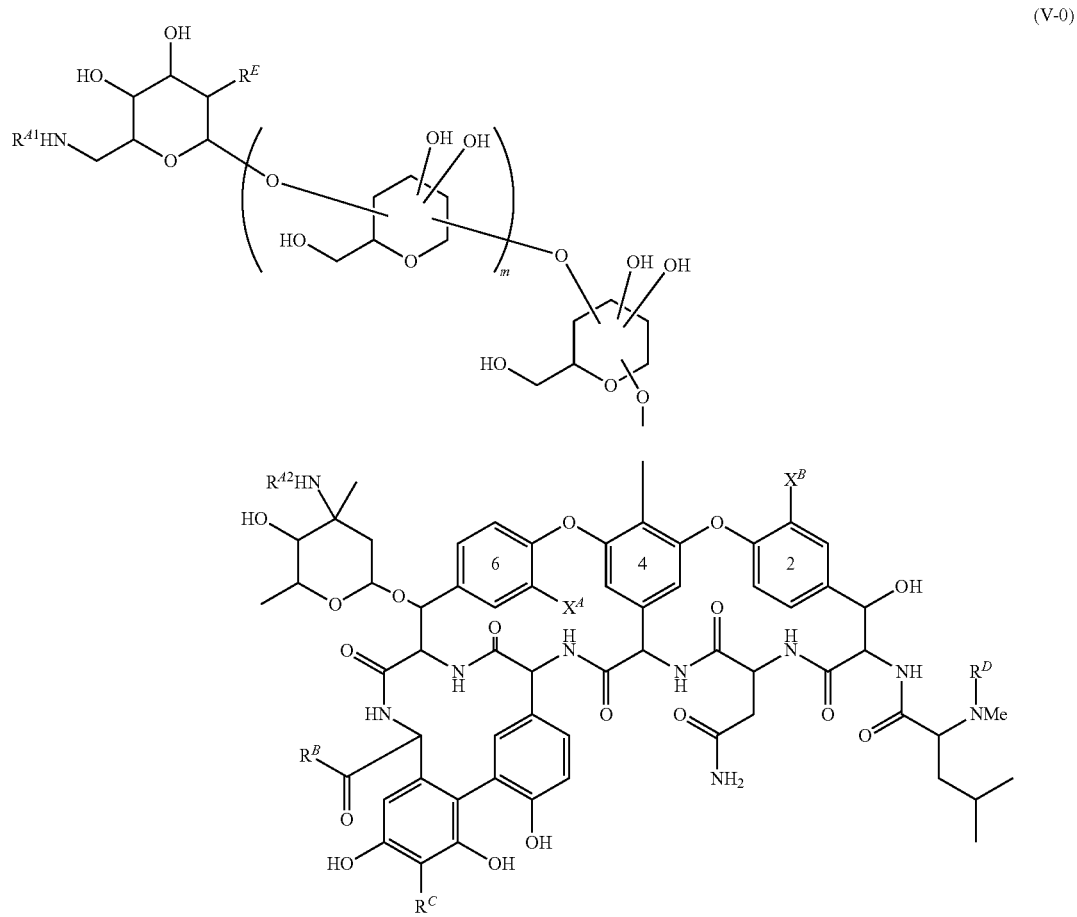
(V-0)
wherein
m is an integer of 0 to 4; and other symbols are each as defined in claim 18.
[Chemical formula 16]
20. The compound, or pharmaceutically acceptable salt thereof according to claim 19, wherein the compound is represented by the formula:
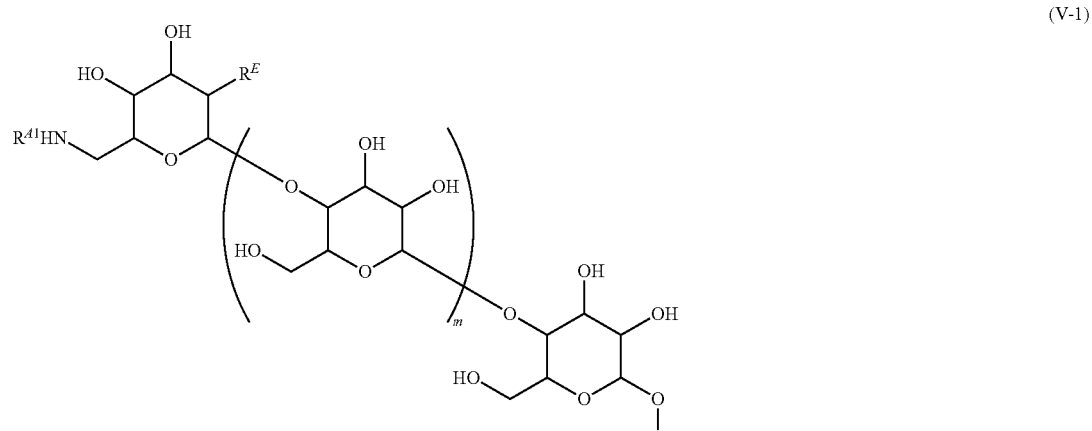
(V-1)

-continued

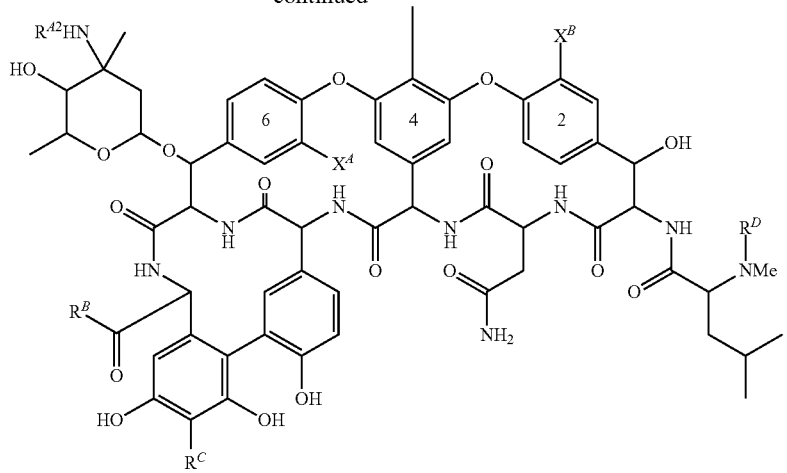

wherein respective symbols are each as defined in claim 19.

21. The compound, or pharmaceutically acceptable salt thereof according to claim 19, wherein the compound is represented by the formula:

[Chemical formula 17]

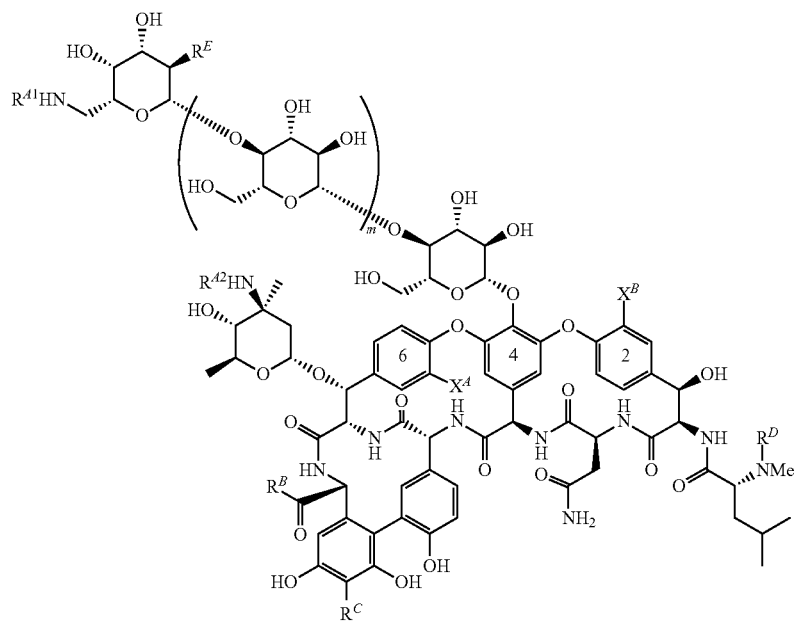

(V-2)

wherein respective symbols are each as defined in claim 19.

22. The compound, or pharmaceutically acceptable salt thereof according to claim 1, wherein the compound is represented by the formula:

[Chemical formula 18]

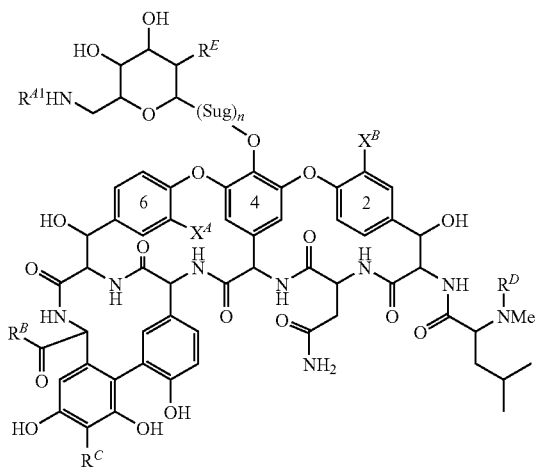

(VI)

wherein $R^B$ is —OH, —NR$^5$R$^{5'}$ (wherein $R^5$ and $R^{5'}$ each are independently hydrogen, optionally substituted alkyl, optionally substituted alkyloxy, or optionally substituted amino or amino sugar residue) or —OR$^6$ (wherein $R^6$ is optionally substituted alkyl (a hetero atom group may intervene in the alkyl part));

$R^c$ is hydrogen or optionally substituted alkyl (a hetero atom group may intervene in the alkyl part);

$R^D$ is hydrogen or lower alkyl;

$X^A$ and $X^B$ each are independently hydrogen or halogen; and other symbols are each as defined in claim 1.

23. The compound, or pharmaceutically acceptable salt thereof according to claim 22, wherein the compound is represented by the formula

[Chemical formula 19]

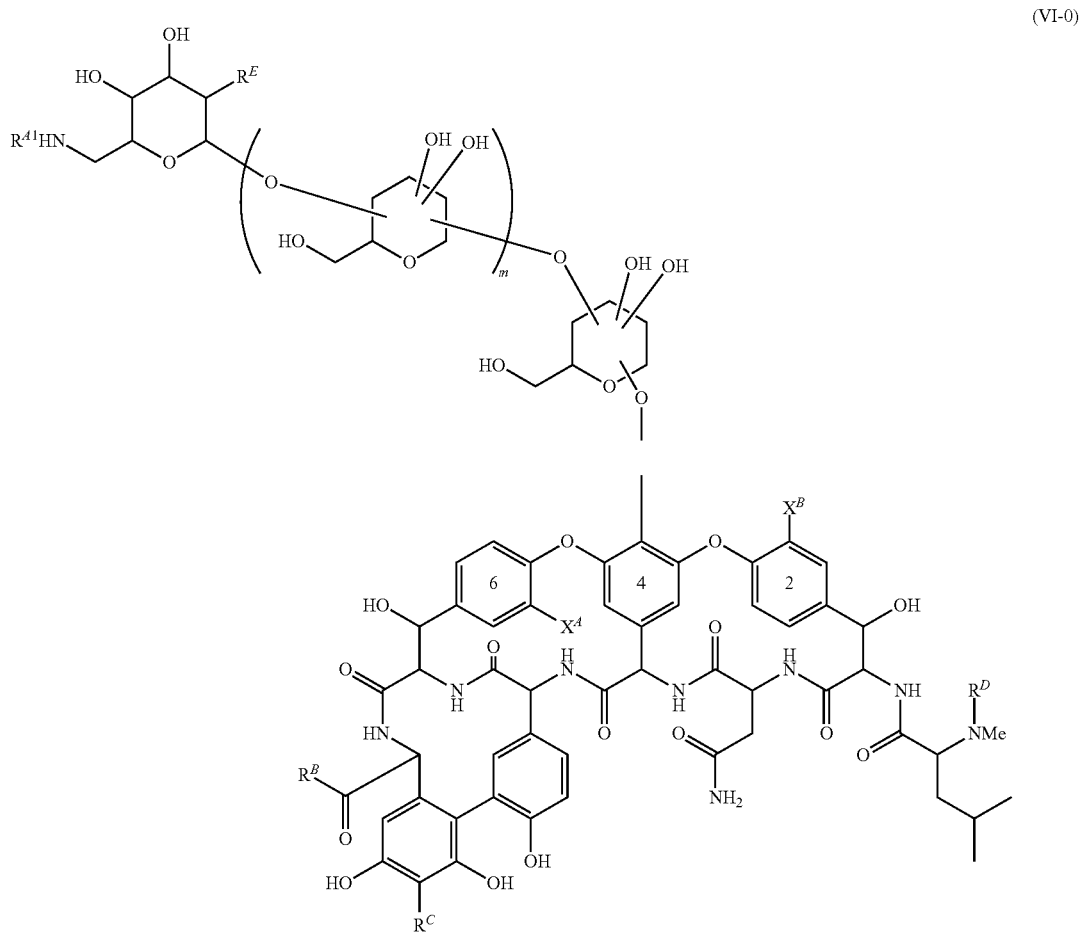

(VI-0)

wherein m is an integer of 0 to 4; and other symbols are each as defined in claim 22.

24. The compound, or pharmaceutically acceptable salt thereof according to claim 23, wherein the compound is represented by the formula:

[Chemical formula 20]

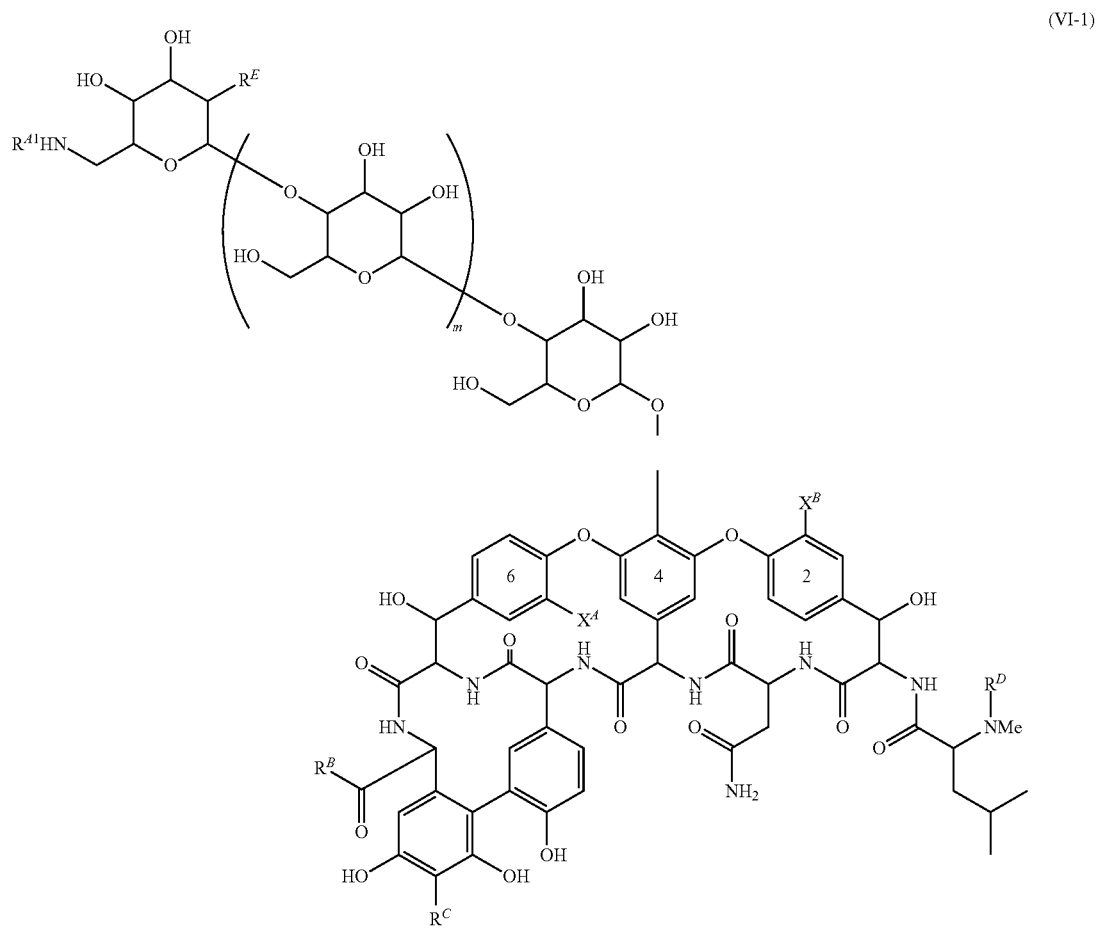

(VI-1)

wherein respective symbols are each as defined in claim 23.

25. The compound, or pharmaceutically acceptable salt thereof according to claim 23, wherein the compound is represented by the formula:

[Chemical formula 21]

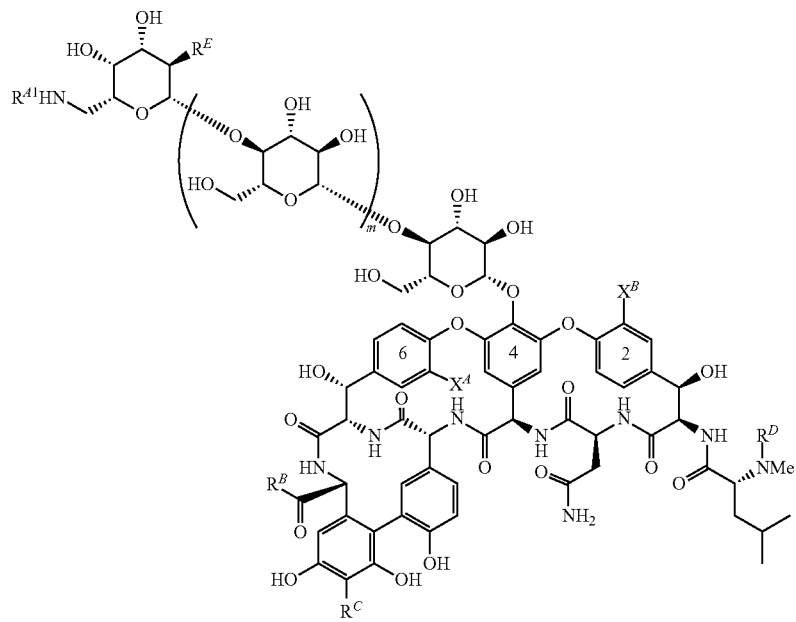

(VI-2)

wherein
respective symbols are each as defined in claim 23.

26. The compound, or pharmaceutically acceptable salt thereof according to any one of claims 6 to 8, 11 to 13, 15 to 17, 19 to 21, and 23 to 25, wherein m is 0 or 1.

27. The compound, or pharmaceutically acceptable salt thereof according to claim 1, wherein $R^E$ is OH.

28. The compound, or pharmaceutically acceptable salt thereof according to claim 1, wherein each substituents is an optionally substituted lower alkyl, optionally substituted lower alkenyl, or optionally substituted cycloalkyl of $R^{41}$ are selected from the following Substituent group A: optionally substituted aryl, optionally substituted heteroaryl, optionally substituted heterocycle, optionally substituted aralkylthio, optionally substituted heteroaralkylthio, optionally substituted cycloalkyl, optionally substituted lower alkyloxy, optionally substituted aralkyloxy, optionally substituted aryloxy, optionally substituted arylsulfonylamino, and optionally substituted amino.

29. The compound, or pharmaceutically acceptable salt thereof according to claim 28, wherein each of the substituents of "optionally substituted" groups in Substituent group A of claim 28 are selected from the following Substituent group B:
optionally substituted arylaminocarbonylamino, optionally substituted arylaminocarbonyl, optionally substituted arylcarbonyl, optionally substituted arylcarbonylamino, optionally substituted arylcarbonylaminoalkyl, oxo, halogen, optionally substituted aryl, optionally substituted aryloxy, optionally substituted arylthio, optionally substituted arylamino, optionally substituted arylaminoalkyl, optionally substituted arylaminocarbonylalkyl, optionally substituted arylsulfonyl, optionally substituted lower alkyl, optionally substituted aralkyl, optionally substituted amino, optionally substituted aralkylcarbonylamino, optionally substituted aralkylamino, optionally substituted aralkylaminocarbonyl, optionally substituted aralkylsulfinyl, optionally substituted arylsulfonylamino, optionally substituted arylaminosulfonyl, optionally substituted aralkylthio, halo lower alkyl, lower alkyloxy, lower alkylamino, halo lower alkyloxy, optionally substituted heteroaryl, optionally substituted heteroarylalkyl, optionally substituted heteroarylcarbonyl, optionally substituted heteroaryloxy, optionally substituted heteroarylthio, optionally substituted aryl lower alkenyl, optionally substituted heteroaryl lower alkenyl, optionally substituted cycloalkyl, optionally substituted cycloalkyloxy, optionally substituted cycloalkylthio, optionally substituted cycloalkylaminocarbonyl, optionally substituted cycloalkyl lower alkenyl, optionally substituted cycloalkylsulfonyl, optionally substituted cycloalkylaminocarbonylamino, optionally substituted cycloalkylaminoalkyl, optionally substituted cycloalkyl lower alkylamino, optionally substituted cycloalkylamino, optionally substituted cycloalkyl lower alkyl, optionally substituted cycloalkylcarbonyl, optionally substituted cycloalkyl lower alkylcarbonylamino, optionally substituted cycloalkylcarbonylamino, optionally substituted cycloalkylcarbonylaminoalkyl, optionally substituted cycloalkyl lower alkylaminocarbonyl, optionally substituted cycloalkylsulfonylamino, optionally substituted cycloalkylaminocarbonylalkyl, and optionally substituted cycloalkylaminosulfonyl.

30. The compound, or pharmaceutically acceptable salt thereof according to claim 29, wherein each of the substituents of "optionally substituted" groups in Substituent group B of claim 30 are selected from the following Substituent group C:
lower alkyl, lower alkyloxy, lower alkylsulfonyl, nitro, aralkyloxy, halogen, cyano, halo lower alkyl, halo lower alkyloxy, and di-lower alkylamino.

31. The compound, or pharmaceutically acceptable salt thereof according to any one of claims 14 to 25 or 27 to 30, wherein $R^B$ is OH; $R^C$ is H; and $R^D$ is H.

32. A process for producing the glycopeptide compound, or pharmaceutically acceptable salt thereof as defined in claim 6, comprising the following steps:

(step 1)
a step converting a sugar residue (VI) represented by the formula:

[Chemical formula 22]

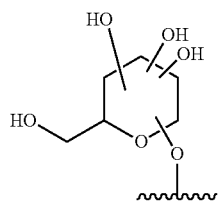
(VI)

into a group (VII) represented by the formula:

[Chemical formula 23]

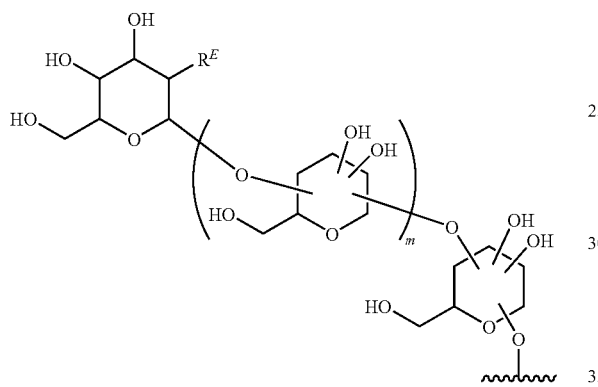
(VII)

wherein $R^E$ is OH or NHAc; and m is an integer of 0 to 2;
by performing 1+m (m is an integer of 0 to 2) times of glycosylating reaction in the presence of glycosyltransferase and a sugar donor using a glycopeptide compound or a salt thereof as a raw material,
wherein an aromatic ring of a fourth amino acid residue is substituted with the sugar residue (VI);

(step 2)
a step converting the hydroxymethylene part in the sugar at the end of the group (VII) into a group (VIII) represented by the formula:

[Chemical formula 24]

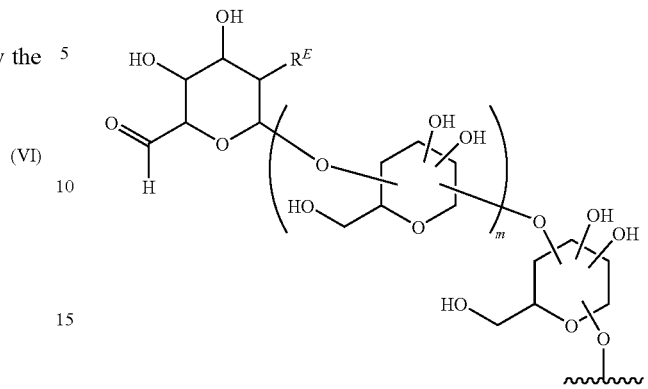
(VIII)

wherein respective symbols are as defined above;
by an oxidation reaction; and (step 3)
a step converting the group (VIII) into a sugar residue (I-0) represented by the formula:

[Chemical formula 25]

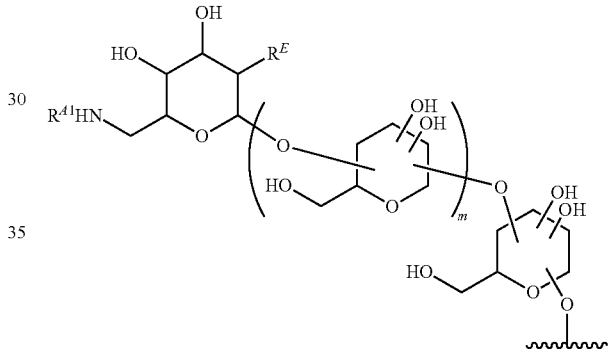
(I-0)

wherein respective symbols are as defined above;
by reductive amination reaction of the aldehyde group of the group (VIII) with a compound (A) represented by the formula $R^{41}NH_2$.

33. A process for producing the compound (IV-0), or pharmaceutically acceptable salt thereof as defined in claim 15 represented by the formula:

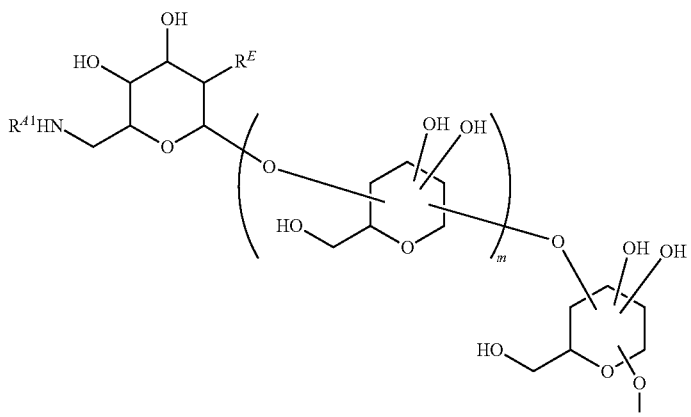
(IV-0)

-continued

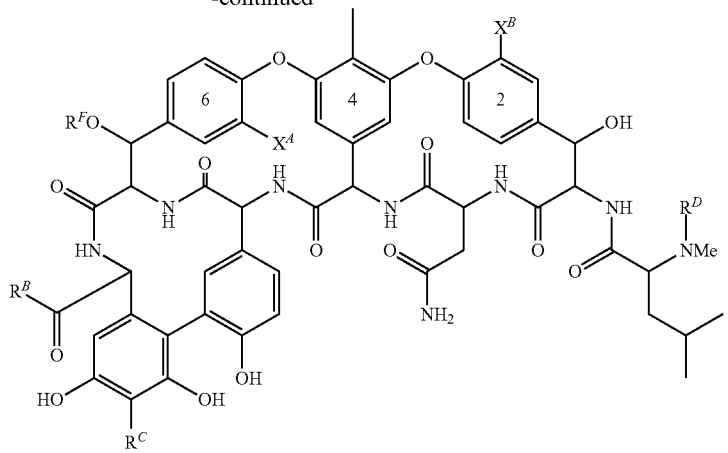

wherein respective symbols are as defined below, comprising the following steps:

(step 1)

a step of reacting 1+m (m is an integer of 0 to 2) times of glycosylating reaction in the presence of glycosyltransferase and a sugar donor using a compound (VII-I) as a raw material, represented by the formula:

[Chemical formula 26]

(VII-1)

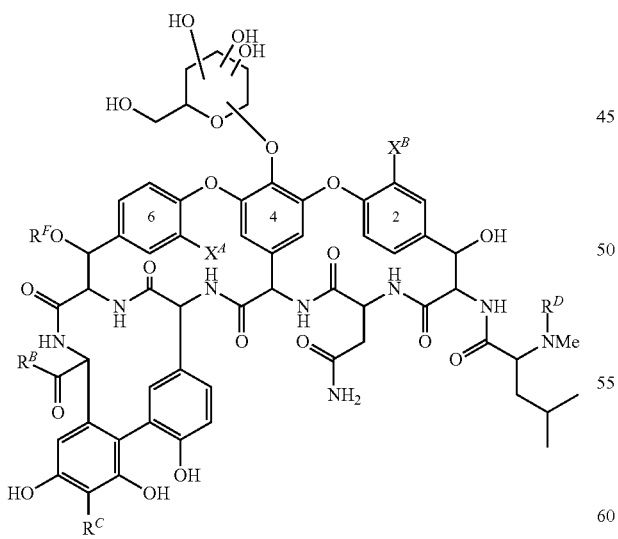

to obtain a compound (VIII-1), or salt thereof represented by the formula:

[Chemical formula 27]

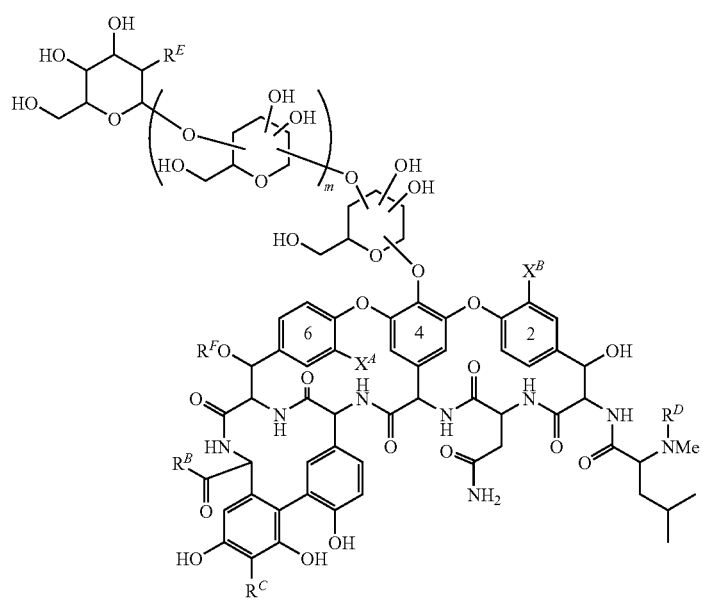

(VIII-1)

wherein $R^E$ is OH or NHAc; and other symbols are as defined above, (step 2)
a step of subjecting the compound (VIII-I) or salt thereof to an oxidation reaction to obtain a compound (IX-1) or salt thereof represented by the formula:

[Chemical formula 28]

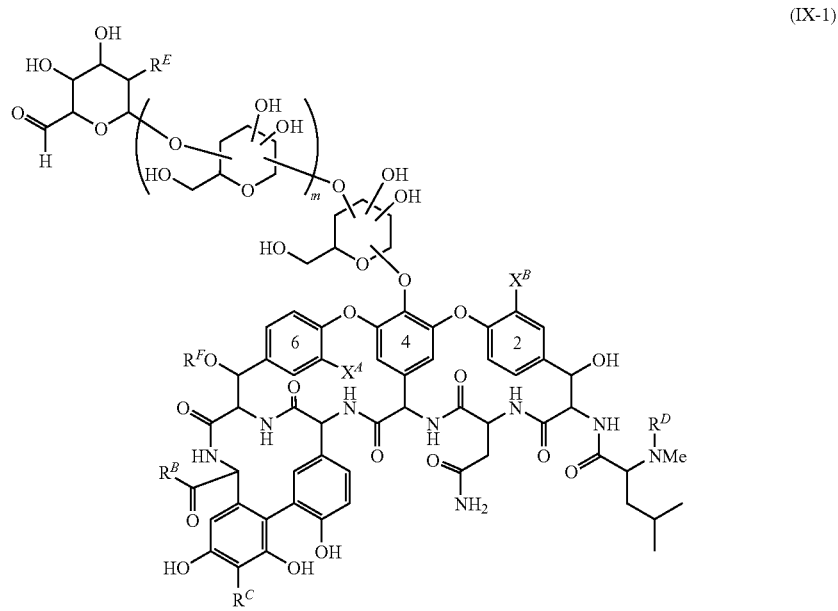

(IX-1)

wherein respective symbols are as defined above, and
(step 3)
a step of subjecting the compound (IX-1) or salt thereof to a reductive animation reaction with a compound (A) represented by the formula: $R^{A1}NH_2$.

34. A process for producing the compound (IV1) or a pharmaceutically acceptable salt thereof as defined in claim 16 represented by the formula:

[Chemical formula 33]

(IV-1)

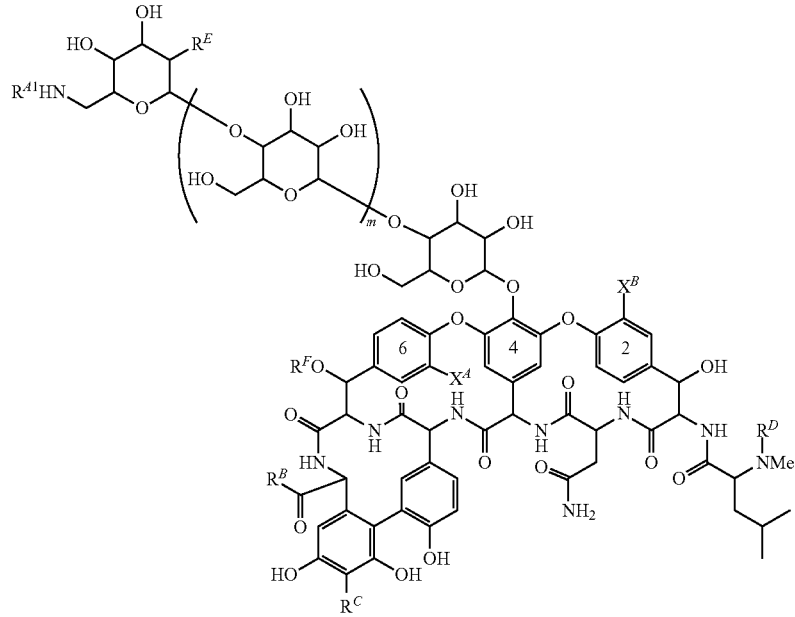

wherein respective symbols are as defined below, comprising the following steps:

(step 1)

a step of reacting 1+m (m is an integer of 0 to 2) times of glycosylating reaction in the presence of glycosyltransferase and a sugar donor using a compound (VII-1) as a raw material represented by the formula:

[Chemical formula 30]

(VII-1)

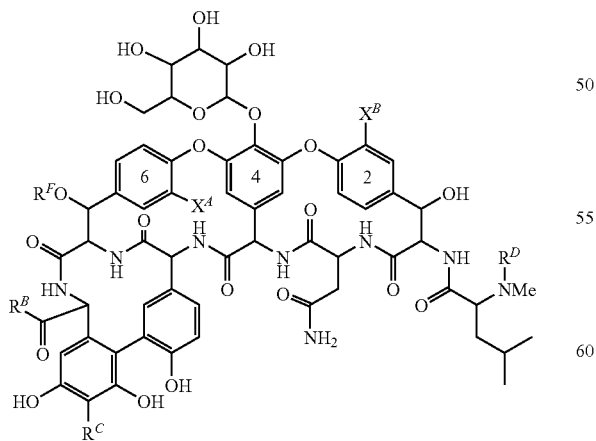

to obtain a compound (VIII-2) or a salt thereof represented by the formula:

[Chemical formula 31]
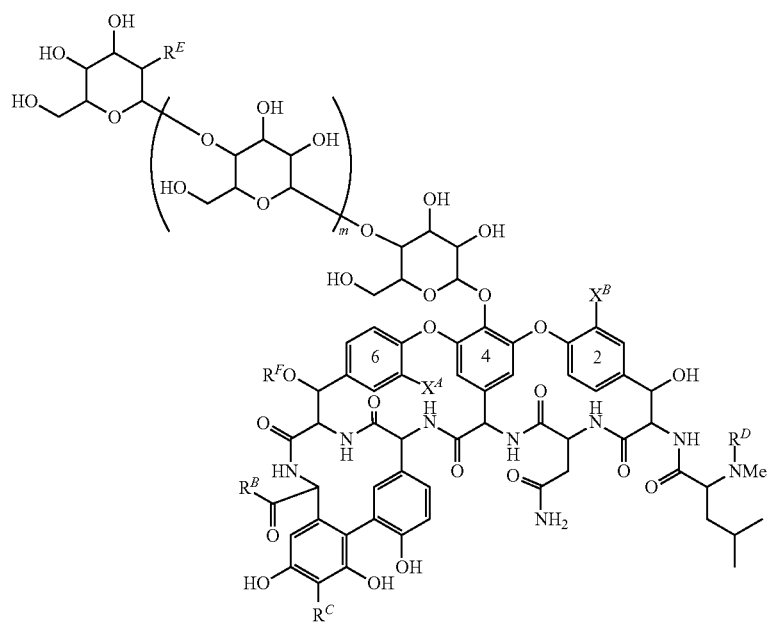
(VIII-2)
wherein $R^E$ is OH or NHAc; and other symbols are as defined above,
(step 2)
a step of subjecting the compound (VIII-2) or salt thereof to an oxidation reaction to obtain a compound (IX-2) or salt thereof represented by the formula:
[Chemical formula 32]
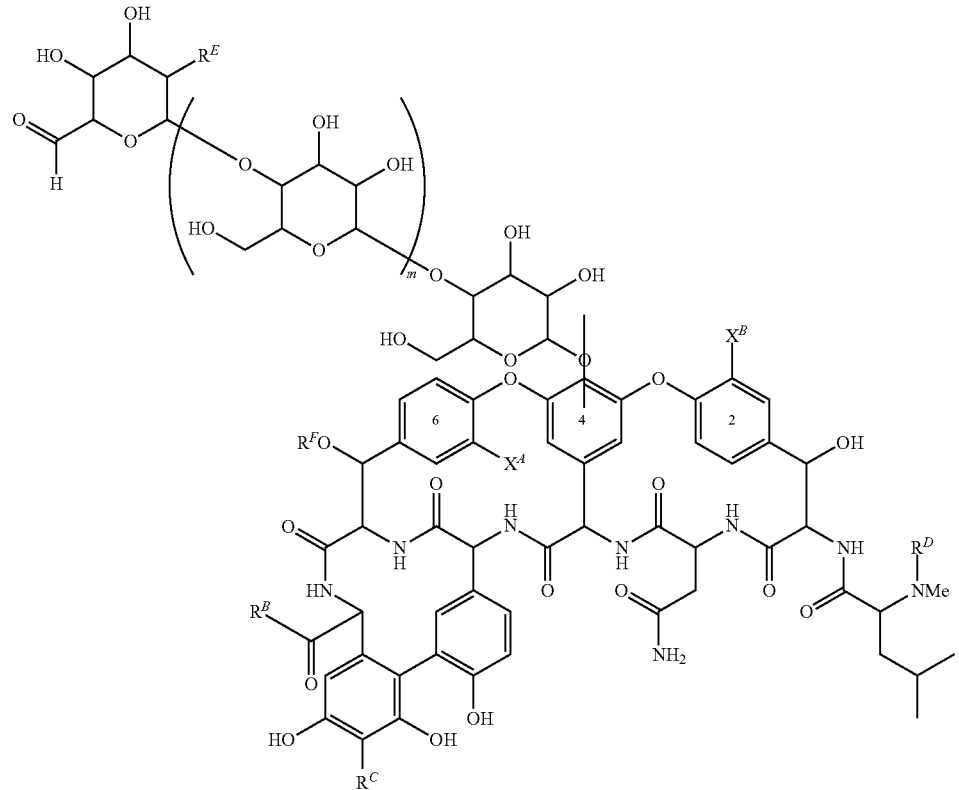
(IX-2)
wherein respective symbols are as defined above, and (step 3)
a step of subjecting the compound (IX-2) or salt thereof to a reductive amination reaction with a compound (A) represented by the formula: $R^{A1}NH_2$.

[Chemical formula 37]

35. A process for producing the compound (1V-2), or a pharmaceutically acceptable salt thereof, as defined in claim 17 represented by the formula:

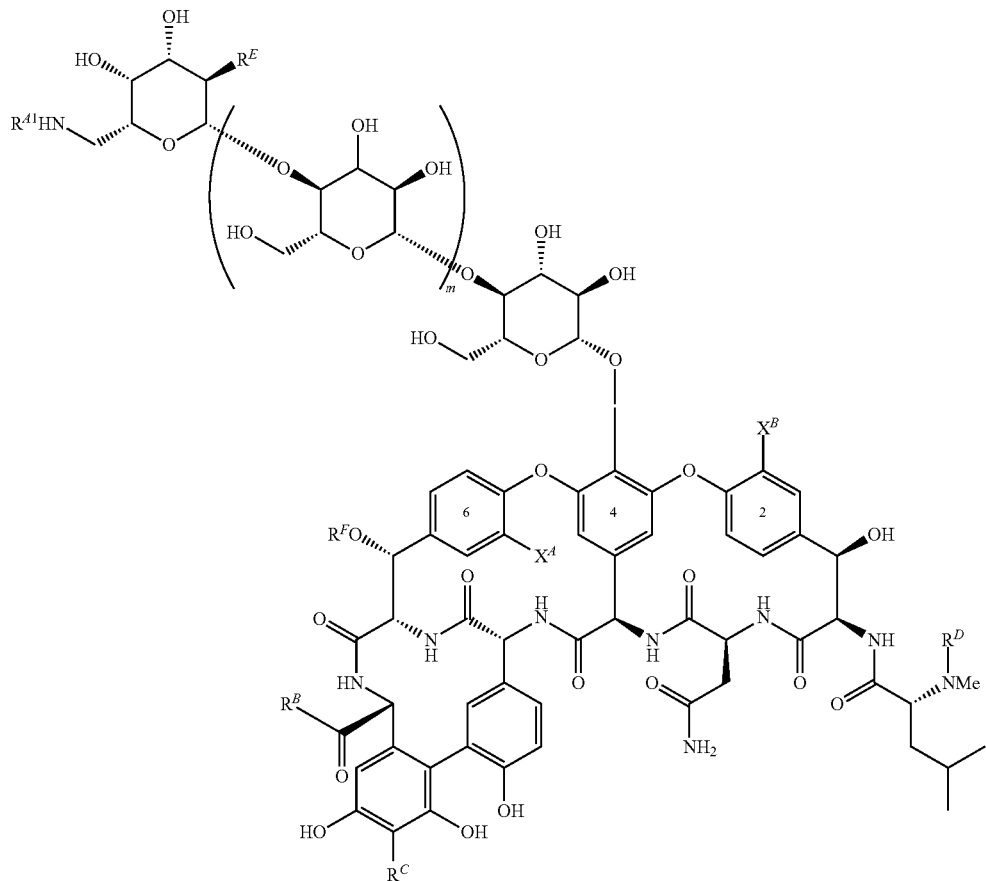

(IV-2)

wherein respective symbols are as defined below, comprising the following steps:
(step 1)
a step of reacting 1+m (m is an integer of 0 to 2) times of glycosylating reaction in the presence of glycosyltransferase and a sugar donor using a compound (VII-2) as a raw material represented by the formula:

[Chemical formula 34]

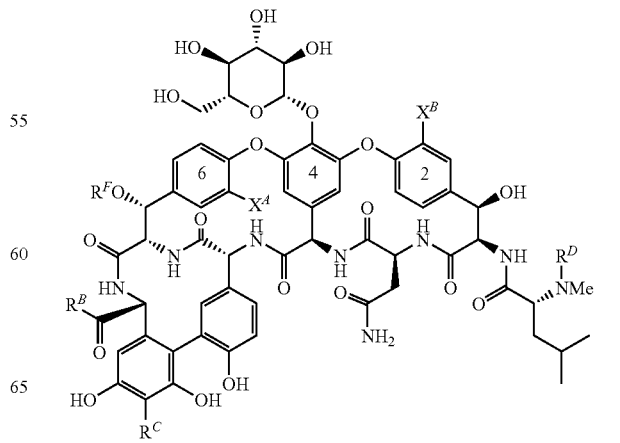

(VII-2)

to obtain a compound (VIII-3) or a salt thereof represented by the formula:

[Chemical formula 35]

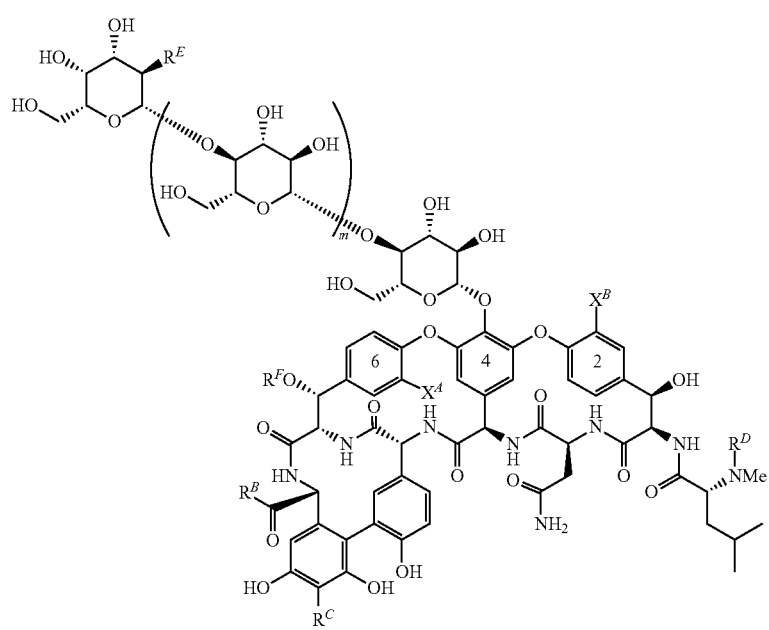

(VIII-3)

wherein $R^E$ is OH or NHAc; and other symbols are as defined above, (step 2)
a step of subjecting the compound (VIII-3) or salt thereof to an oxidation reaction to obtain a compound (IX-3) or a salt thereof represented by the formula:

[Chemical formula 36]

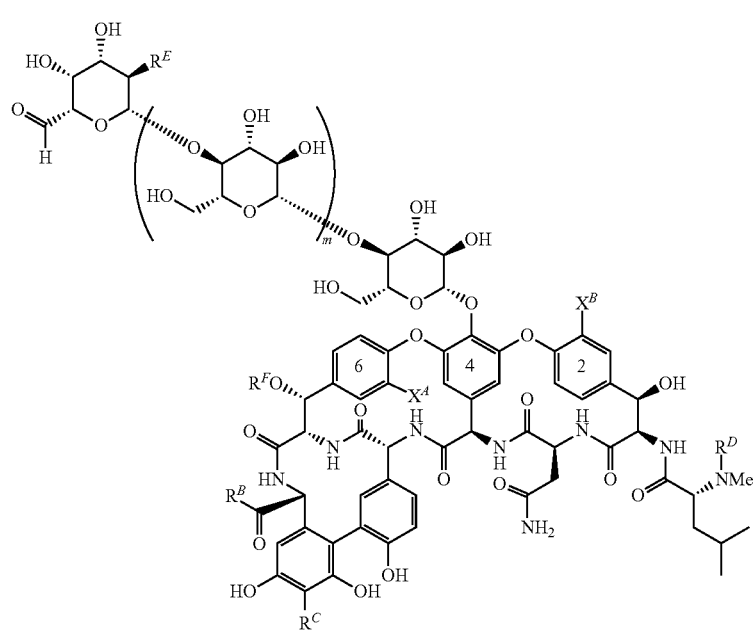

(IX-3)

wherein respective symbols are as defined above, and (step 3)

a step of subjecting the compound (IX-3) or salt thereof to a reductive amination reaction with a compound (A) represented by the formula: $R^{A1}NH_2$.

36. The process according to any one of claims 32 to 35, wherein in the step 1, the glycosyltransferase is galactosyltransferase; a sugar of the sugar donor is the same or different 1 to 3 sugars selected from glucose, galactose, N-acetylgalactosamine, deoxyglucose, and deoxygalactose; and, in the step 2, the oxidation reaction is performed with galactose oxidase.

37. The process according to any one of claims 32 to 35, wherein in the step 1, the glycosyltransferase is galactosyltransferase; and, after addition of glucose by an optional first glycosylating reaction, galactose is further added by a second glycosylating reaction; and, in the step 2, the oxidation reaction is performed with galactose oxidase.

38. The compound (VIII-I) or a salt thereof as defined in claim 33, wherein $R^D$ is lower alkyl.

39. The compound (IX-I) or a salt thereof as defined in claim 33.

* * * * *

UNITED STATES PATENT AND TRADEMARK OFFICE
CERTIFICATE OF CORRECTION

PATENT NO. : 8,481,696 B2
APPLICATION NO. : 12/810507
DATED : July 9, 2013
INVENTOR(S) : Kouhei Matsui et al.

Page 1 of 9

It is certified that error appears in the above-identified patent and that said Letters Patent is hereby corrected as shown below:

In the Claims

Claim 1, col. 397, line 62, "i to 5" should read --1 to 5--.

Claim 6, col. 398, line 42, "Rm and RE" should read --$R^{A1}$ and $R^E$--.

Claim 15, cols. 403-404, lines 33-67,

"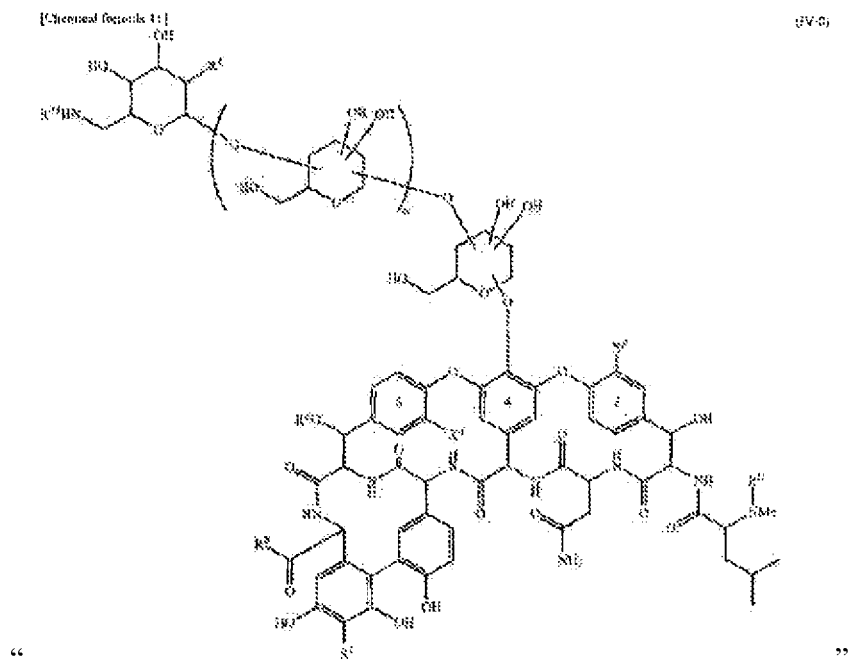"

Signed and Sealed this
Seventh Day of January, 2014

Margaret A. Focarino
Commissioner for Patents of the United States Patent and Trademark Office

CERTIFICATE OF CORRECTION (continued)
U.S. Pat. No. 8,481,696 B2 should read
  [Chemical formula 11]

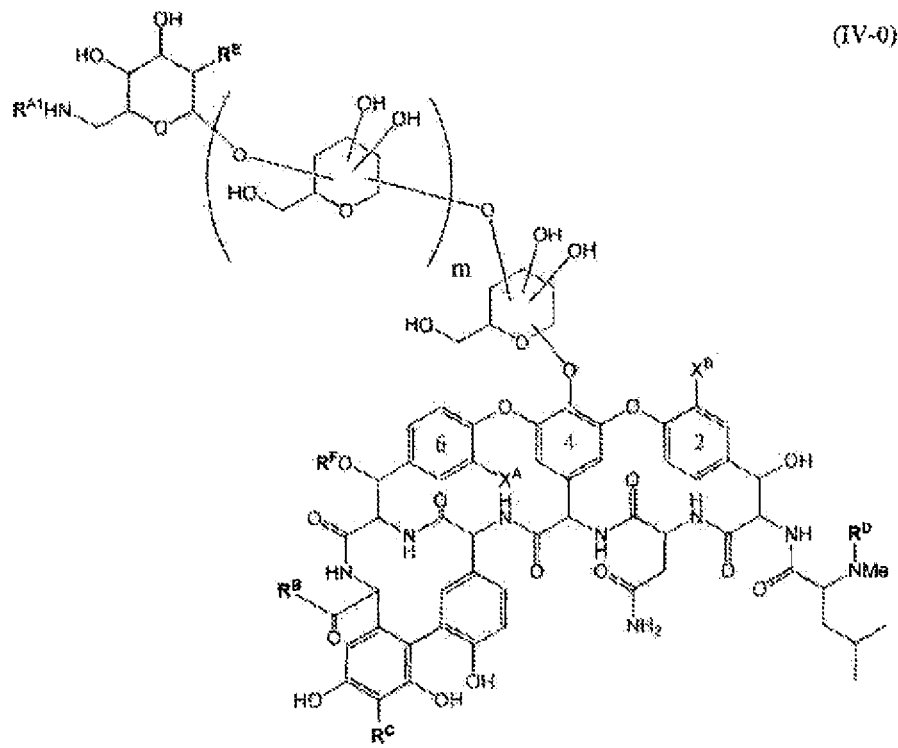

Claim 15, cols. 405-406, lines 4-43,

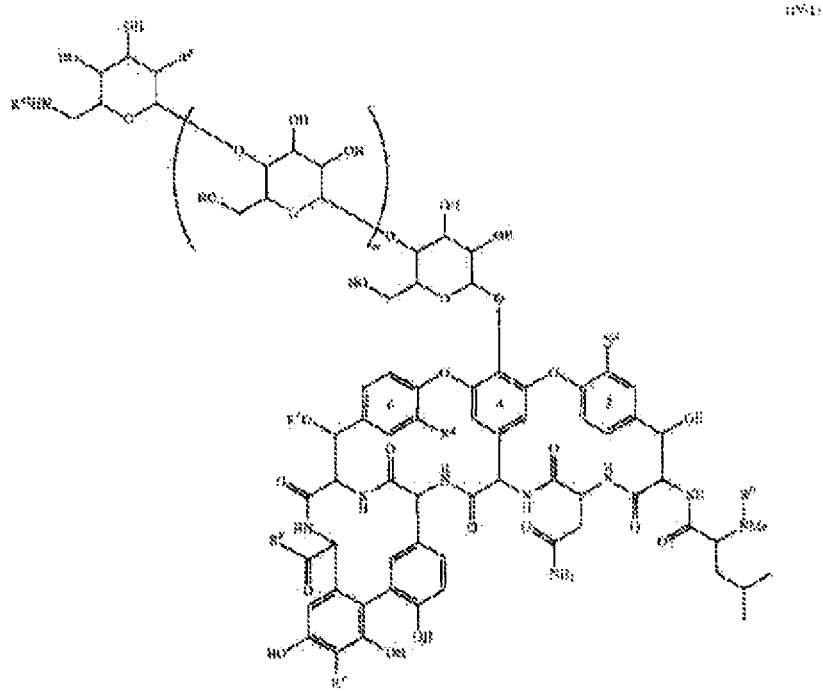

should read
[Chemical formula 12]
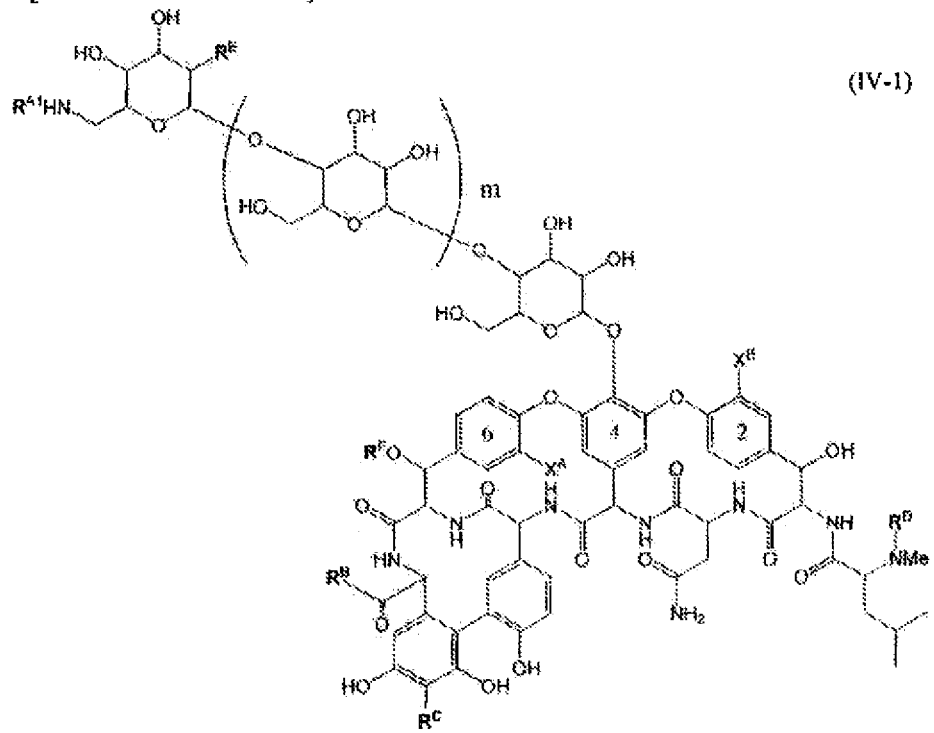
Claim 19, cols. 409-410, lines 1-40,
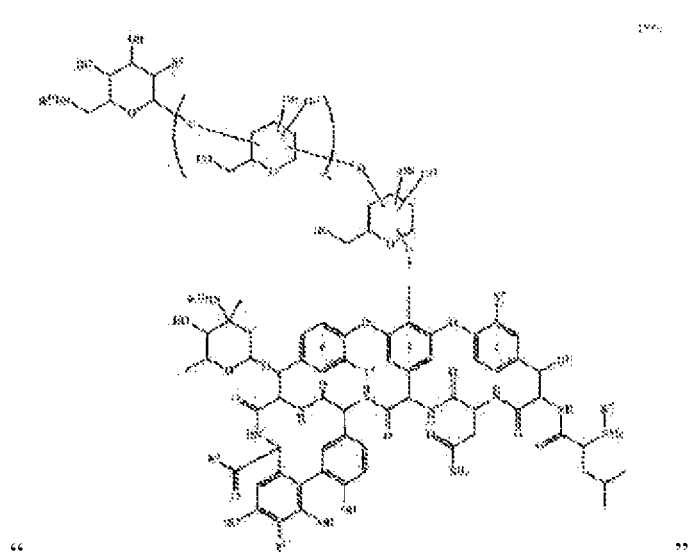

should read
 [Chemical formula 15]
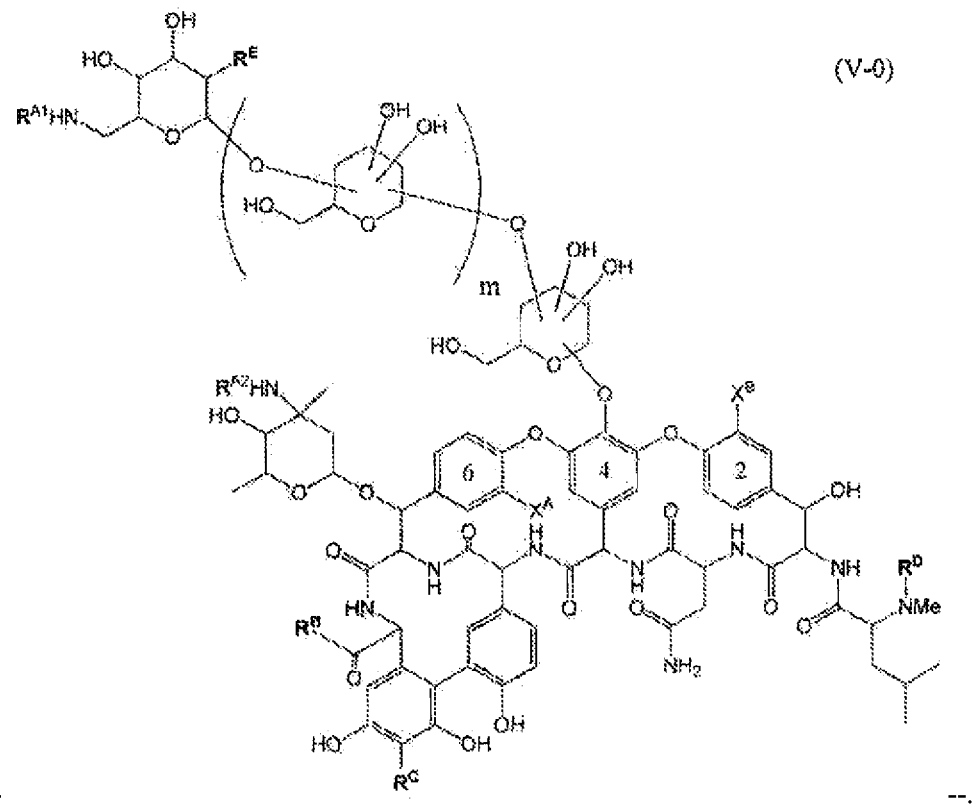
(V-0)
-- --.

Claim 23, cols. 413-414, lines 25-67,
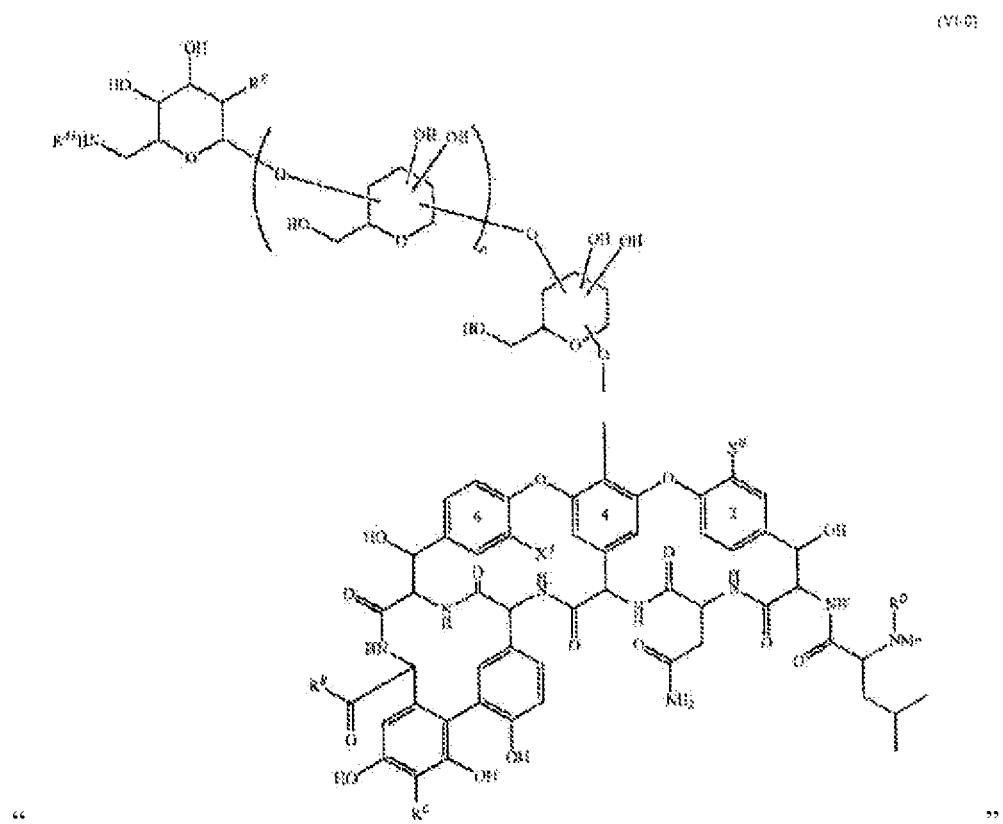

should read
[Chemical formula 19]
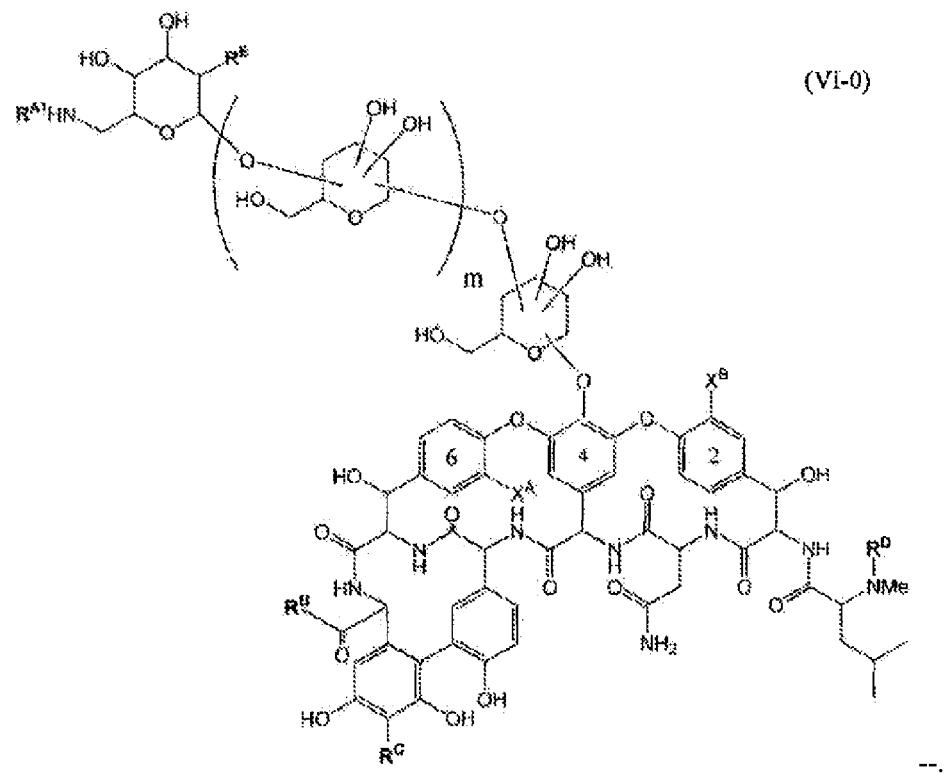
--                                                                              --.
Claim 24, cols. 415-416, lines 15-57,
[Chemical formula 18]
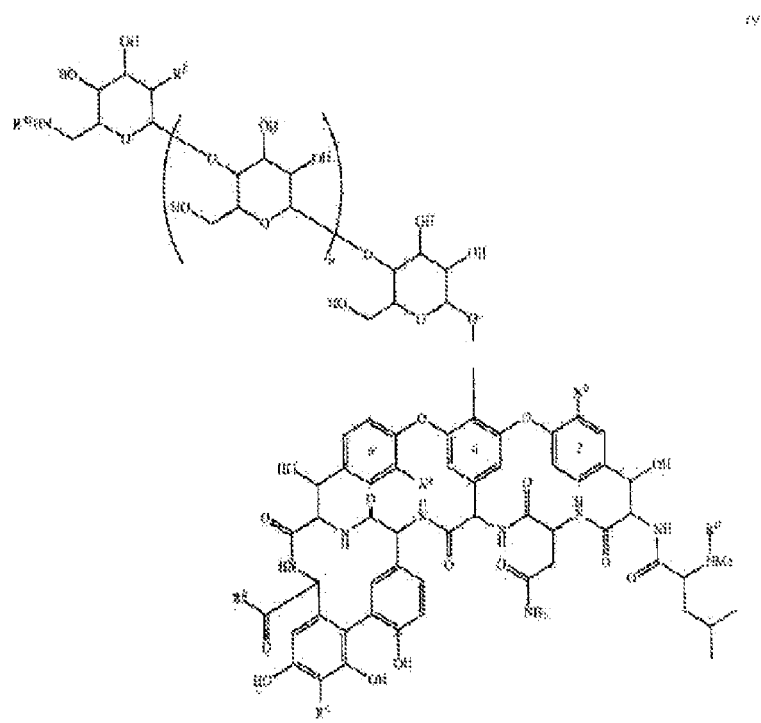
"                                                                              "

should read
[Chemical formula 20]
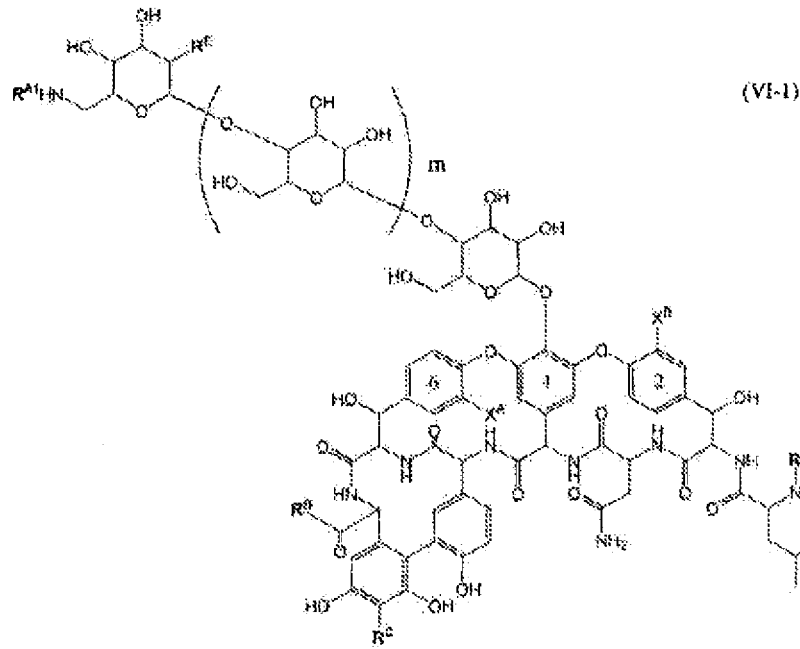
Claim 34, col. 425, line 1, "compound (IV1)" should read --compound (IV-1)--.
Claim 34, cols. 427-428, lines 35-66,
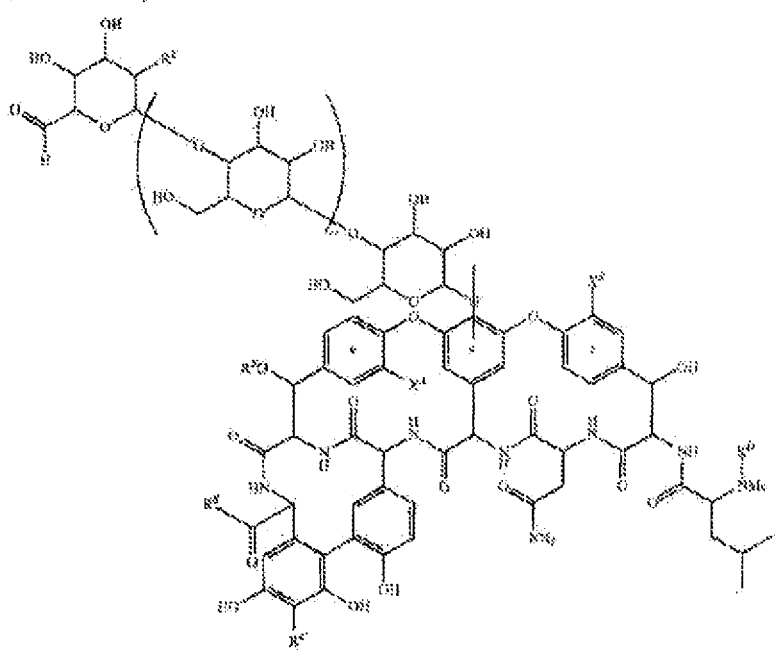

CERTIFICATE OF CORRECTION (continued)
U.S. Pat. No. 8,481,696 B2 should read

[Chemical formula 32]

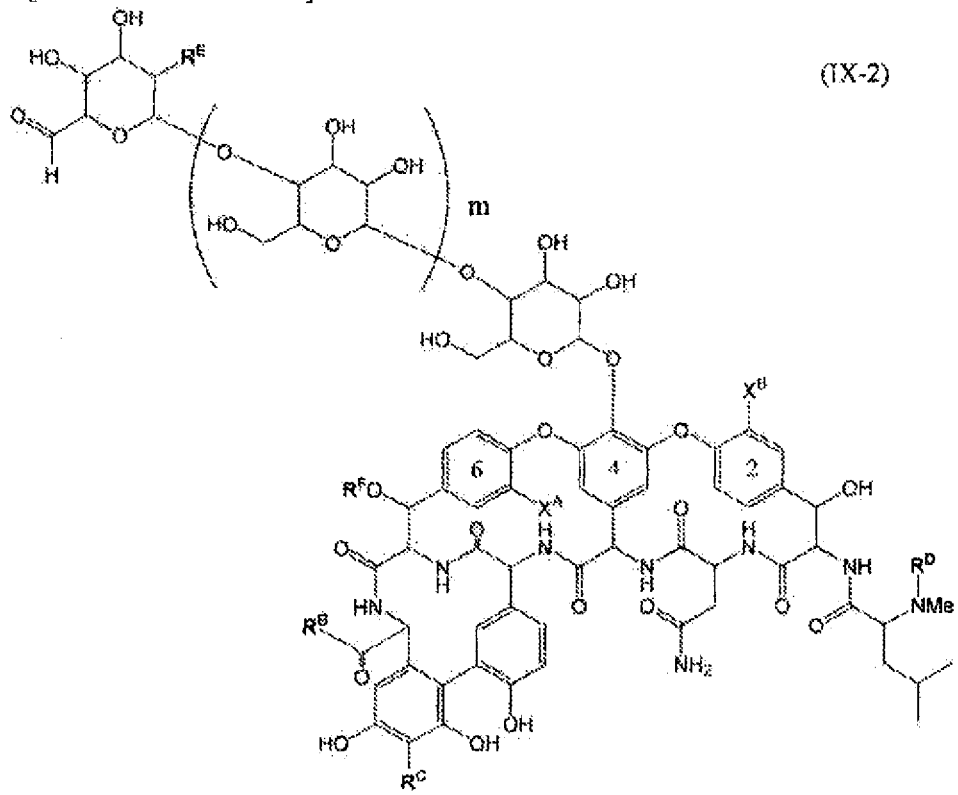

(IX-2)

--                                          --.

Claim 35, cols. 429-430, lines 4-39,

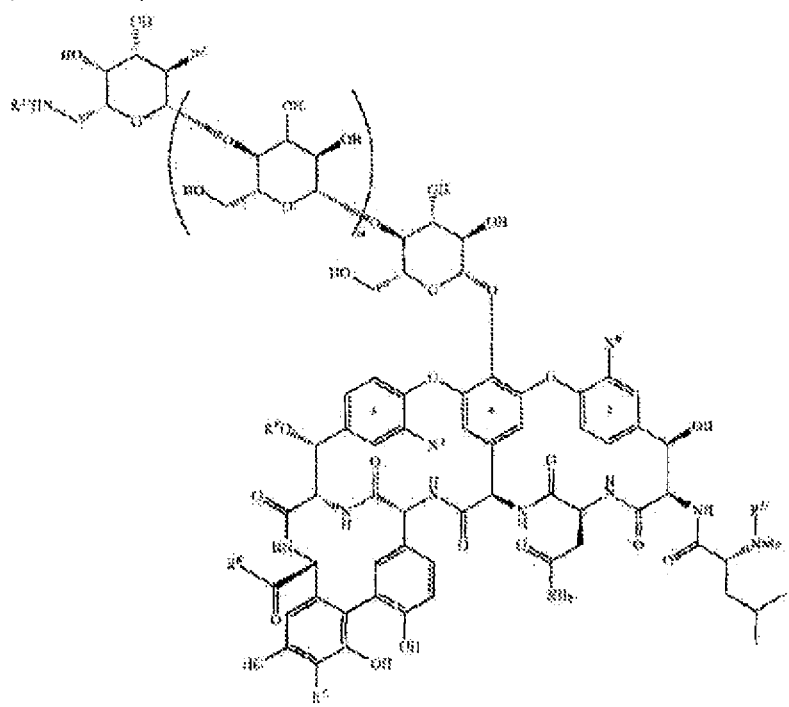

"                                          "

should read
[Chemical formula 37]
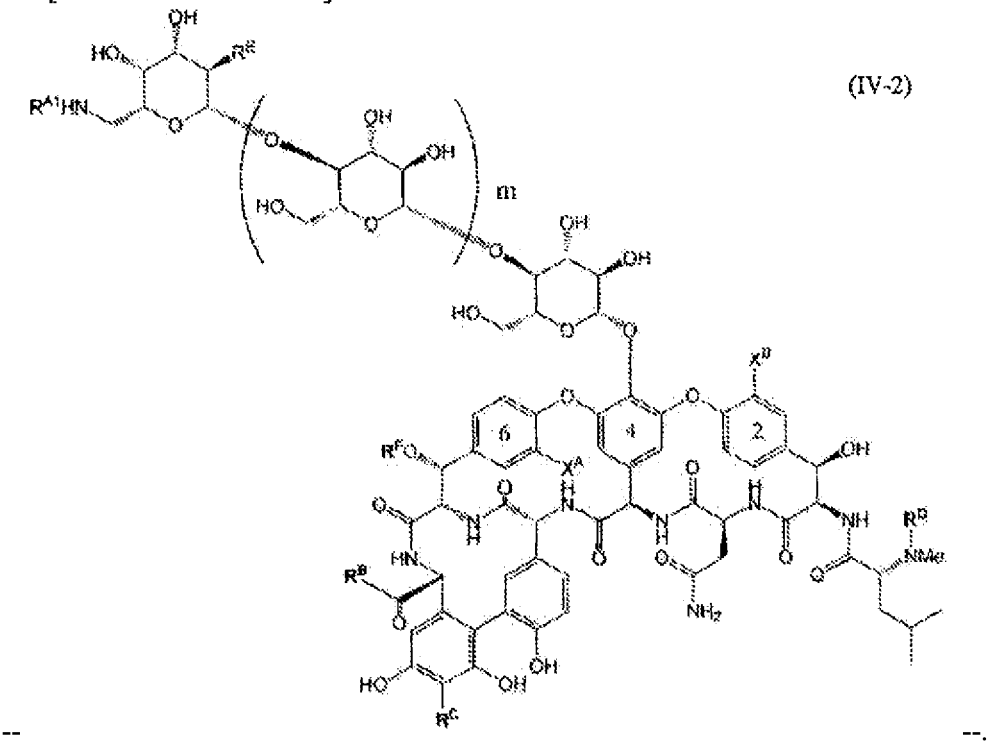
(IV-2)
-- --.